(12) United States Patent
Sookraj et al.

(10) Patent No.: US 10,703,702 B2
(45) Date of Patent: Jul. 7, 2020

(54) PRODUCTION SYSTEM/PRODUCTION PROCESS FOR ACRYLIC ACID AND PRECURSORS THEREOF

(71) Applicant: Novomer, Inc., Boston, MA (US)

(72) Inventors: Sadesh H Sookraj, Waltham, MA (US); Jay J. Farmer, Ithaca, NY (US)

(73) Assignee: Novomer, Inc., Rochester, NY (US)

( * ) Notice: Subject to any disclaimer, the term of this patent is extended or adjusted under 35 U.S.C. 154(b) by 243 days.

(21) Appl. No.: 15/223,178

(22) Filed: Jul. 29, 2016

(65) Prior Publication Data

US 2017/0029352 A1 Feb. 2, 2017

Related U.S. Application Data

(60) Provisional application No. 62/199,918, filed on Jul. 31, 2015.

(51) Int. Cl.
| | |
|---|---|
| *C07C 51/09* | (2006.01) |
| *C08G 63/78* | (2006.01) |
| *C08G 63/08* | (2006.01) |
| *B01J 19/18* | (2006.01) |

(52) U.S. Cl.
CPC .......... *C07C 51/09* (2013.01); *B01J 19/1862* (2013.01); *C08G 63/08* (2013.01); *C08G 63/785* (2013.01); *Y02P 20/582* (2015.11)

(58) Field of Classification Search
CPC .................................................. C07C 51/09
See application file for complete search history.

(56) References Cited

U.S. PATENT DOCUMENTS

| | | | |
|---|---|---|---|
| 2,361,036 | A | 10/1944 | Kung |
| 3,128,163 | A | 4/1964 | Weittenhiller et al. |
| 3,169,945 | A | 2/1965 | Fritz et al. |
| 3,678,069 | A | 7/1972 | Buster |
| 3,885,155 | A | 5/1975 | Anbar |

(Continued)

FOREIGN PATENT DOCUMENTS

| | | |
|---|---|---|
| EP | 0887334 A1 | 12/1998 |
| SU | 1169528 A | 7/1985 |

(Continued)

OTHER PUBLICATIONS

Abe et al., "Effects of Residual Zinc Compounds and Chain-End Structure on Thermal Degradation of Poly(ω-caprolactone)", Biomacromolecules, vol. 5, 2004, pp. 1480-1488.

(Continued)

*Primary Examiner* — Rachel Kahn
(74) *Attorney, Agent, or Firm* — Young Basile Hanlon & MacFarlane, P.C.

(57) ABSTRACT

Provided herein are systems, and methods of using such systems, for producing acrylic acid from ethylene oxide and carbon monoxide on an industrial scale. The production system/production process has various unit operations, including, for example, a β-propiolactone production system/production process configured to produce β-propiolactone from ethylene oxide and carbon monoxide; a polypropiolactone production system/production process configured to produce polypropiolactone from β-propiolactone; and a glacial acrylic acid production system/production process configured to produce acrylic acid with a high purity by thermolysis of polypropiolactone.

49 Claims, 24 Drawing Sheets

(56) References Cited

U.S. PATENT DOCUMENTS

| | | |
|---|---|---|
| 3,954,854 A | 5/1976 | Gehrmann et al. |
| 4,230,885 A | 10/1980 | Wu |
| 4,317,926 A | 3/1982 | Sato et al. |
| 4,427,884 A | 1/1984 | Anbar et al. |
| 4,759,313 A | 7/1988 | Dye |
| 4,973,841 A | 11/1990 | Purser |
| 5,310,948 A | 5/1994 | Drent et al. |
| 5,359,081 A | 10/1994 | Drent et al. |
| 5,438,194 A | 8/1995 | Koudijs et al. |
| 5,648,452 A | 7/1997 | Schechtman et al. |
| 5,661,299 A | 8/1997 | Purser |
| 5,705,688 A | 1/1998 | Fauconet et al. |
| 6,133,402 A | 10/2000 | Coates et al. |
| 6,252,110 B1 | 6/2001 | Uemura et al. |
| 6,316,590 B1 | 11/2001 | Coates et al. |
| 6,538,101 B2 | 3/2003 | Coates et al. |
| 6,541,665 B1 | 4/2003 | Bastiaensen et al. |
| 6,608,170 B1 | 8/2003 | Coates |
| 6,852,865 B2 | 2/2005 | Coates et al. |
| 6,887,380 B2 | 5/2005 | Lee et al. |
| 7,420,064 B2 | 9/2008 | Luinstra et al. |
| 8,246,915 B2 | 8/2012 | Boer et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,115,070 B2 | 8/2015 | Pazicky et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2002/0028909 A1 | 3/2002 | Kelsey et al. |
| 2005/0014977 A1 | 1/2005 | Drent et al. |
| 2007/0161806 A1 | 7/2007 | Preishuber-Pflugl et al. |
| 2009/0246430 A1 | 10/2009 | Kriegel et al. |
| 2011/0262669 A1 | 10/2011 | Kriegel et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0018574 A1 | 1/2014 | Raith et al. |
| 2014/0197580 A1 | 7/2014 | Poulat |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0126772 A1 | 5/2015 | Cao et al. |
| 2015/0141693 A1 | 5/2015 | Allen et al. |
| 2015/0183708 A1 | 7/2015 | Harris et al. |
| 2015/0299083 A1 | 10/2015 | Porcelli et al. |
| 2015/0368394 A1 | 12/2015 | Allen et al. |
| 2016/0016876 A1* | 1/2016 | Mahoney ............... C07C 51/09 562/599 |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354882 A1 | 12/2018 | Sookraj |
| 2019/0002385 A1 | 1/2019 | Sookraj et al. |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| WO | 2009/155086 A2 | 12/2009 |
| WO | 2010/118128 A1 | 10/2010 |
| WO | 2011/100608 A1 | 8/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

Abe, Hideki, "Thermal Degradation of Environmentally Degradable Poly(Hydroxyalkanoic Acid)s", Macromolecular Bioscience, vol. 6, 2006, pp. 469-486.

Agostini et al., "Synthesis and Characterization of Poly-β-Hydroxybutyrate. I. Synthesis of Crystalline DL-Poly-β-Hydroxybutyrate from DL-β-Butyrolactone", Journal of Polymer Science, Part A-1, vol. 9, No. 10, 1971, pp. 2775-2787.

(56) References Cited

OTHER PUBLICATIONS

Billingham et al., "Polymerization and Copolymerization of β-Butyrolactone by Aluminium Compounds", Journal of Organometallic Chemistry, vol. 341, No. 1-3, 1988, pp. 83-93.
Church et al., "Carbonylation of Heterocycles by Homogeneous Catalysts", Chemical Communications, vol. 21, No. 7, 2007, pp. 657-674.
Collias et al., "Biobased Terephthalic Acid Technologies: A Literature Review", Industrial Biotechnology, vol. 10, No. 2, Apr. 2014, pp. 91-105.
Dunn, Erin Whitfield., "Synthesis of Poly(Hydroxyalkanoates): Routes to Poly(3-Hydroxybutyrate) and Poly(3-Hydroxypropionate) from the Carbonylation and Ring-Opening Polymerization of Epoxides", A Dissertation Presented to the Faculty of the Graduate School of Cornell University, Aug. 2012, pp. 1-139.
Garozzo et al., "Primary Thermal Decomposition Processes in Aliphatic Polyesters Investigated by Chemical Ionization Mass Spectrometry", Macromolecules, vol. 19, No. 6, 1986, pp. 1643-1649.
Getzler et al., "Catalytic Carbonylation of β-Lactones to Succinic Anhydrides", Journal of the American Chemical Society, vol. 126, No. 22, 2004, pp. 6842-6843.
Gresham et al., "β-Propiolactone I. Polymerization Reactions", J. Am. Chem. Soc., vol. 70, Mar. 1948, pp. 998-999.
Gresham et al., "3-Propiolactone II. Reactions with Salts of Inorganic Acids", J. Am. Chem. Soc., vol. 70, Mar. 1948, pp. 999-1001.
Gresham et al., "β-Propiolactone III. Reactions with Dithiocarbamic Acids, their Salts and Thiourea", J. Am. Chem. Soc., vol. 70, Mar. 1948, pp. 1001-1002.
Gresham et al., "β-Propiolactone IV. Reactions with Salts of Carboxylic Acids", J. Am. Chem. Soc., vol. 70, Mar. 1948, pp. 1003-1004.
Gresham et al., "β-Propiolactone V. Reaction with Alcohols", J. Am. Chem. Soc., vol. 70, Mar. 1948, pp. 1004-1006.
Gross et al., "Polymerization of β-Monosubstituted-β-Propiolactones using Trialkylaluminum-Water Catalytic Systems and Polymer Characterization", Macromolecules, vol. 21, No. 9, 1988, pp. 2657-2668.
Hori et al., "Ring-Opening Polymerization of Optically Active β-Butyrolactone using Distannoxane Catalysts: Synthesis of High-Molecular-Weight Poly (3-Hydroxybutyrate)", Macromolecules, vol. 26, No. 20, 1993, pp. 5533-5534.
International Preliminary Report on Patentability received for PCT Patent Application No. PCT/US2016/044772, dated Feb. 15, 2018, 13 pages.
International Preliminary Report on Patentability received for PCT Patent Application No. PCT/US2016/044927, dated Feb. 15, 2018, 13 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
Iwabuchi et al., "The Thermal Degradation of Poly(Oxycarbonylethylene) (Poly-β-Propiolactone)", Die Makromolekulare Chemie, vol. 165, 1973, pp. 59-72.
Jacobi et al., "Strukturuntersuchung von Polyestern durch direkten Abbau im Massenspektrometer, 4. Polyester und Copolyester der Milchsäure und Glykolsäure", Macromolecular Chemistry and Physics, vol. 179, 1978, pp. 429-436 (with English Abstract).
Kim et al., "Effect of Metal Compounds on Thermal Degradation Behavior of Aliphatic Poly(Hydroxyalkanoic Acid)s", Polymer Degradation and Stability, vol. 93, 2008, pp. 776-785.

Kim et al., "Effects of Residual Metal Compounds and Chain-End Structure on Thermal Degradation of Poly(3-Hydroxybutyric Acid)", Polymer Degradation and Stability, vol. 91, 2006, pp. 769-777.
Kim et al., "Thermal Degradation Behavior of Poly(4-Hydroxybutyric Acid)", Polymer Degradation and Stability, vol. 91, 2006, pp. 2333-2341.
Kopinke et al., "Thermal Decomposition of Biodegradable Polyesters-I: Poly(β- Hydroxybutyric Acid)", Polymer Degradation and Stability, vol. 52, 1996, pp. 25-38.
Kricheldorf et al., "Strukturuntersuchung von Polyestern durch direkten Abbau im Massenspektrometer, 3. Poly-β-Propiolacton, poly-β-Pivalolacton und poly-δ-Valerolacton", Macromolecular Chemistry and Physics, vol. 179, 1978, pp. 421-427 (with English Abstract).
Liu et al., "Reducing the Formation of Six-Membered Ring Ester during Thermal Degradation of Biodegradable PHBV to Enhance its Thermal Stability", Polymer Degradation and Stability, vol. 94, 2009, pp. 18-24.
Luderwald et al., "Strukturuntersuchung von Polyestern durch direkten Abbau im Massenspektrometer, 2. Aliphatische Polyester", 2. Makromol. Chem. vol. 177, 1976, pp. 2093-2111 (with English Abstract).
Mahmoud et al., "Production of Benzoic Acid from Biomass-Derived Furan and Methyl Acrylate Using Lewis-Acidic Zeolites", Catalysis at the Confluence of Science and Technology, Jun. 15, 2015, pp. 1-2.
Nguyen et al., "Thermal Degradation of Poly(3-Hydroxyalkanoates): Preparation of Well-Defined Oligomers", Biomacromolecules, vol. 3, 2002, pp. 219-224.
Rieth et al., "Single-Site β-Diiminate Zinc Catalysts for the Ring-Opening Polymerization of β-Butyrolactone and β-Valerolactone to Poly (3-Hydroxyalkanoates)." Journal of the American Chemical Society, vol. 124, No. 51, 2002, pp. 15239-15248.
Schechtman et al., "Chemical Synthesis of Isotactic Poly(3-Hydroxyalkanoates)", Polymer Preprints, Division of Polymer Chemistry, Inc., vol. 40, No. 1, 1999, pp. 508-509.
Slowik et al., "Catalytic Conversion of Waste Carbon Monoxide to Valuable Chemicals & Materials", Technical Proceedings of the Clean Technology Conference and Trade Show, 2010, pp. 283-286.
Smith et al., "March's Advanced Organic Chemistry: Reactions, Mechanisms and Structure", Sixth Edition, A John Wiley & Sons, Inc., 2007, 2374 pages.
Sorrell, Thomas N., "Organic Chemistry", Second Edition, University Science Books, 1999, 24 pages.
Tachibana et al., "Synthesis and Verification of Biobased Terephthalic Acid from Furfural", Scientific Reports, vol. 5, No. 8249, 2015, pp. 1-5.
Tanahashi et al., "Thermal Properties and Stereoregularity of Poly (3-Hydroxybutyrate) Prepared from Optically Active β-Butyrolactone with a Zinc-based Catalyst", Macromolecules, vol. 24, No. 20, 1991, pp. 5732-5733.
Varma-Nair et al., "Heat Capacity and other Thermodynamic Properties of Linear Macromolecules: X. Update of the ATHAS 1980 Data Bank", Journal of Physical and Chemical Reference Data, vol. 20, No. 2, 1991, pp. 349, 375 & 400.
Vera et al., "Synthesis and Crystal Structure of Dimethyl-7-oxabicyclo[2.2.1]hept-5-ene exo,exo-2,3-dicarboxylate", Journal of Chemical Crystallography, vol. 37, 2007, pp. 543-548.
Zhang et al., "Stereochemistry of the Ring-Opening Polymerization of (S)-β-Butyrolactone", Macromolecules, vol. 23, No. 13, 1990, pp. 3206-3212.
Zhu et al., "Polymorphic Crystallization and Melting-Recrystallization Behavior of Poly(3-Hydroxypropionate)", Macromolecules, vol. 38, 2005, pp. 6455-6465.

\* cited by examiner

PRODUCTION SYSTEM/PRODUCTION PROCESS FOR ACRYLIC ACID AND PRECURSORS THEREOF

CROSS REFERENCE TO RELATED APPLICATIONS

The present application claims benefit from U.S. Ser. 62/199,918 filed Jul. 31, 2015, which is hereby incorporated by reference in its entirety as if fully restated herein.

FIELD

The present disclosure relates generally to systems and methods for producing acrylic acid and precursors thereof, including β-propiolactone and polypropiolactone, from ethylene oxide and carbon monoxide.

BACKGROUND

Polypropiolactone is a biodegradable polymer that can be used in many packaging and thermoplastic applications. Polypropiolactone is also a useful precursor for the production of acrylic acid. Polypropiolactone may serve as a precursor for glacial acrylic acid, which is in high demand for the production of polyacrylic acid-based superabsorbent polymers, detergent co-builders, dispersants, flocculants and thickeners. One advantage of polypropiolactone is that it can be safely transported and stored for extended periods of time without the safety or quality concerns associated with shipping and storing glacial acrylic acid. There additionally is interest in glacial acrylic acid which can be produced from biomass-derived feedstock, petroleum-derived feedstock, or combinations thereof. Given the size of the acrylic acid market and the importance of downstream applications of acrylic acid, there is a need for industrial systems and methods to produce acrylic acid and precursors thereof.

BRIEF SUMMARY OF THE INVENTION

Provided herein are systems and processes for the production of acrylic acid and precursors thereof, including β-propiolactone and polypropiolactone, and methods of using such production system/production process. In some aspects, provided is a production system/production process and a production process for glacial acrylic acid from ethylene oxide and carbon monoxide that includes a β-propiolactone production system/production process, a carbonylation catalyst recycling apparatus, a β-propiolactone purification system, a polypropiolactone production system/production process, and a glacial acrylic acid production system/production process.

In some embodiments, the β-propiolactone production system/production process includes a carbon monoxide source, an ethylene oxide source, a carbonylation catalyst source, a solvent source, and a carbonylation reactor. In certain variations, the carbonylation reactor has at least one inlet to receive carbon monoxide from the carbon monoxide source, ethylene oxide from the ethylene oxide source, carbonylation catalyst from the carbonylation catalyst source, and solvent from the solvent source; and an outlet to output a first β-propiolactone stream, wherein the first β-propiolactone stream comprises β-propiolactone, solvent, ethylene oxide, carbonylation catalyst, acetaldehyde, and succinic anhydride.

In some embodiments, the carbonylation catalyst recycling apparatus is configured to separate at least a portion of the catalyst from the first β-propiolactone stream and produce a recycle catalyst stream and a second β-propiolactone stream. In some variations, the recycle catalyst stream includes separated carbonylation catalyst. In some variations, the second β-propiolactone stream includes β-propiolactone, solvent, ethylene oxide, catalyst, acetaldehyde, and succinic anhydride. In other embodiments, the carbonylation catalyst recycling apparatus has an inlet to receive the first β-propiolactone stream from the β-propiolactone production system/production process; a recycle outlet to output the recycle catalyst stream to the carbonylation reactor; and a β-propiolactone outlet to output the second β-propiolactone stream.

In other embodiments, the β-propiolactone purification system includes an evaporator, a stripper, and a vacuum column. In some variations, the evaporator is configured to receive the second β-propiolactone stream from the carbonylation catalyst recycling apparatus, and separate the second β-propiolactone stream into:

a first overhead stream that includes (i) at least 75 wt % of solvent, (ii) less than 20 wt % of β-propiolactone, and (iii) less than 5 wt % of ethylene oxide and acetaldehyde, and a first bottoms stream that includes: (i) at least 75 wt % of β-propiolactone, (ii) less than 20 wt % of solvent, and (iii) less than 5 wt % of catalyst, acetaldehyde, and succinic anhydride.

In some variations, the stripper is configured to receive the first overhead stream from the evaporator, and separate the first overhead stream into:

a second overhead stream that includes (i) at least 25 wt % of ethylene oxide and acetaldehyde, and (ii) less than 75 wt % of solvent, a side stream comprising solvent, and a second bottoms stream comprising β-propiolactone.

In some variations, the vacuum column is configured to receive the first bottoms stream from the evaporator, and the second bottoms stream from the stripper and mix the first bottoms stream and the second bottoms stream to produce a mixed bottoms stream, separate the first bottoms stream and second bottoms stream into: a third overhead stream comprising solvent, and a third bottoms stream comprising β-propiolactone.

In some embodiments, the polypropiolactone production system/production process includes:

a polymerization initiator or catalyst source;

at least one polymerization reactor to receive the third bottoms stream from the β-propiolactone purification system and the polymerization initiator or catalyst from the polymerization initiator or catalyst source, and to output a polypropiolactone stream, wherein the polypropiolactone stream comprises polypropiolactone and β-propiolactone.

In other embodiments, the glacial acrylic acid production system/production process includes a thermolysis reactor, which has an inlet to receive the polypropiolactone stream from the polypropiolactone production system/production process, and an outlet to output a glacial acrylic acid stream, wherein the glacial acrylic acid stream comprises glacial acrylic acid.

In other aspects, provided is a polypropiolactone production system/production process that includes: a β-propiolactone source; a polymerization initiator or catalyst source; a first polymerization reactor; and a second polymerization reactor.

In some variations, the first polymerization reactor includes: a β-propiolactone inlet to receive β-propiolactone from the β-propiolactone source; a first catalyst inlet to receive catalyst from the polymerization catalyst source; and a first mixture outlet to output a first mixture. In one variation, the first mixture comprises polypropiolactone, β-propiolactone, and polymerization catalyst.

In other variations, the second polymerization reactor positioned after the first polymerization reactor, and includes: a mixture inlet to receive the first mixture from the first polymerization reactor; a second catalyst inlet to receive additional polymerization catalyst from the carbonylation catalyst source; and a second mixture outlet to output a second mixture. In one variation, the second mixture comprises polypropiolactone, β-propiolactone, and polymerization catalyst.

In certain aspects, provided is a β-propiolactone polymerizer that includes: a mixing zone configured to mix β-propiolactone and a catalyst; and a plurality of cooling zones positioned after the mixing zone. In some variations, the β-propiolactone polymerizer has a reaction length. In certain variations, up to 95% of the β-propiolactone is polymerized in the presence of the initiator or catalyst to form polypropiolactone in the first 25% of the reaction length.

In other aspects, provided is a method for continuously producing polypropiolactone, that includes:

continuously feeding β-propiolactone into a first reactor;
continuously feeding catalyst into the first reactor;
producing a first mixture comprising polypropiolactone, unreacted β-propiolactone, and residual catalyst in the first reactor;
transferring the first mixture from the first reactor to a second reactor;
feeding additional catalyst from the catalyst source to the second reactor;
producing a second mixture comprising polypropiolactone, unreacted β-propiolactone, and residual catalyst in the second reactor.

In some variations of the method, the first reactor has: a β-propiolactone inlet to receive the β-propiolactone from a β-propiolactone source; a first catalyst inlet to receive the catalyst from a catalyst source; and a first mixture outlet to output the first mixture. In other variations of the method, the second reactor has: a mixture inlet to receive the first mixture from the first reactor; a second catalyst inlet to receive the additional catalyst from the catalyst source; and a second mixture outlet to output the second mixture.

In yet other aspects, provided is a polypropiolactone production system/production process that includes: a β-propiolactone source; a first reactor; and a second reactor. In some embodiments, the first reactor has: a β-propiolactone inlet to receive β-propiolactone from the β-propiolactone source, a bed of supported catalyst or supported catalyst precursor, and a first mixture outlet to output a first mixture. In one variation, the first mixture comprises polypropiolactone and unreacted β-propiolactone. In other embodiments, the second reactor is positioned after the first reactor. In some variations, the mixture inlet is configured to receive the first mixture from the first reactor, a second bed of supported catalyst or supported catalyst precursor, and a second mixture outlet to output a second mixture. In one variation, the second mixture comprises polypropiolactone and unreacted β-propiolactone.

In yet other aspects, provided is a solid transportable polymer composition that includes: at least 95 wt % of β-propiolactone; less than 10 ppm of cobalt or ions thereof; less than 10 ppm of aluminum or ions thereof; less than 10 ppm acetic acid; and less than 10 ppm of tetrahydrofuran.

In another aspect, provided is a β-propiolactone purification system that includes: an evaporator; a first column, and a second column. In some embodiments, the evaporator configured to receive a feed stream, wherein the feed stream comprises β-propiolactone, solvent, and separate the feed stream into: a first overhead stream comprising: (i) at least 75 wt % solvent, and (ii) at most 20 wt % β-propiolactone; and a first bottoms stream comprising: (i) at least 75 wt % β-propiolactone, and (ii) at most 20 wt % solvent.

In some variations, the first column is configured to receive the first overhead stream from the evaporator, and separate the first overhead stream into: a second overhead stream comprising: (i) at least 35 wt % ethylene oxide, and (ii) at most 60 wt % solvent; a side stream comprising solvent; and a second bottoms stream comprising at least 75 wt % β-propiolactone.

In other variations, the second column is configured to receive the first bottoms stream from the evaporator, and the second bottoms stream from the first column, and separate the first bottoms stream and second bottoms stream into: a third overhead stream comprising at least 95 wt % solvent; and a third bottoms stream comprising at least 95 wt % β-propiolactone.

In one aspect, provided is a β-propiolactone composition that includes at least 95 wt % of β-propiolactone; less than 10 ppm of cobalt or ions thereof; less than 10 ppm of aluminum or ions thereof; less than 10 ppm acetic acid; and less than 10 ppm of tetrahydrofuran.

In yet other aspects, provided is a β-propiolactone production system/production process that includes: a carbon monoxide source; an ethylene oxide source; a carbonylation catalyst source; a solvent source; a recycled solvent storage tank; a reactor; and a purification apparatus. In some embodiments, the reactor has: at least one inlet to receive carbon monoxide from the carbon monoxide source, ethylene oxide from the ethylene oxide source, carbonylation catalyst from the carbonylation catalyst source, and solvent from the solvent source and the recycled solvent storage tank; and an outlet to output a mixture, wherein the mixture comprises β-propiolactone, solvent, unreacted carbon monoxide, unreacted ethylene oxide, and carbonylation catalyst. In other embodiments, the purification apparatus is configured to: separate solvent from the mixture, and transfer the separated solvent to the recycled solvent reservoir.

In one aspect, provided is a glacial acrylic acid production system/production process that includes: a polypropiolactone source; and a reactor. In some embodiments, the polypropiolactone source includes: at least 95 wt % of polypropiolactone; less than 10 ppm of cobalt or ions thereof; less than 10 ppm of aluminum or ions thereof; less than 10 ppm acetic acid; and less than 10 ppm of tetrahydrofuran. In other embodiments, the reactor has: an inlet configured to receive the polypropiolactone from the polypropiolactone source; and an outlet configured to output a mixture, wherein the mixture comprises glacial acrylic acid.

In yet other aspects, provided is a separation system that includes: a feed source; a membrane; a first pump; and a second pump. In some embodiments, the membrane has: an inlet to receive a feed stream from the feed source, wherein the feed stream comprises β-propiolactone, catalyst and solvent; a catalyst outlet to output a catalyst recycling stream comprising catalyst and solvent; and a β-propiolactone outlet to output a β-propiolactone stream comprising β-propiolactone and solvent. In other embodiments, the first pump is configured to pump the feed stream from the feed source to the membrane. In yet other embodiments, the second pump is configured to pump the catalyst recycling stream to a β-propiolactone production system/production process.

DESCRIPTION OF THE FIGURES

The present application can be best understood by reference to the following description taken in conjunction with the accompanying figures, in which like parts may be referred to by like numerals.

DETAILED DESCRIPTION

Figure 1:
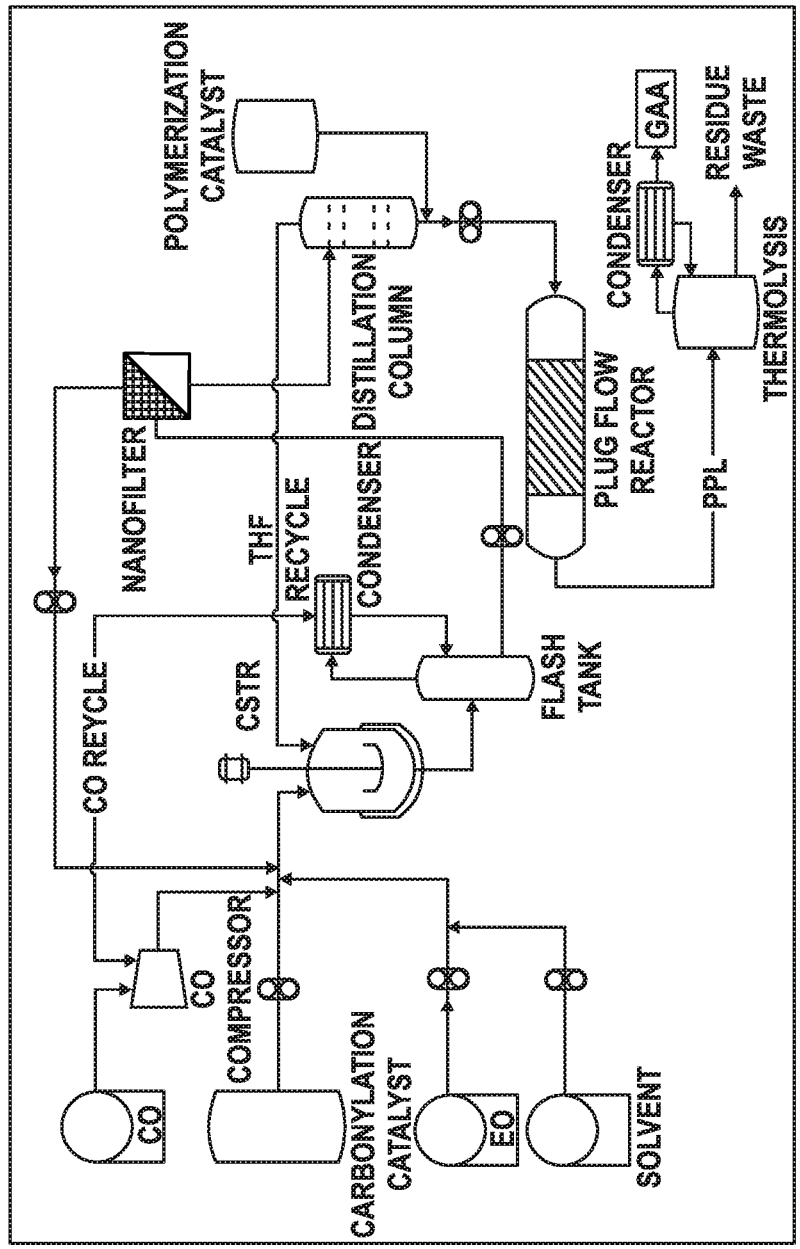
FIG. 1 is a schematic illustration of a system to produce acrylic acid from carbon monoxide and ethylene oxide.

The following description sets forth exemplary methods, parameters and the like. It should be recognized, however, that such description is not intended as a limitation on the scope of the present disclosure but is instead provided as a description of exemplary embodiments.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In some embodiments, aliphatic groups contain 1-12 carbon atoms. In some embodiments, aliphatic groups contain 1-8 carbon atoms. In some embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In some embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetitions of units derived, actually or conceptually, from molecules of low relative molecular mass. In some embodiments, a polymer is comprised of only one monomer species (e.g., polyethylene oxide). In some embodiments, a polymer is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In some embodiments, alkyl groups contain 1-8 carbon atoms. In some embodiments, alkyl groups contain 1-6 carbon atoms. In some embodiments, alkyl groups contain 1-5 carbon atoms, in some embodiments, alkyl groups contain 1-4 carbon atoms, in yet other embodiments, alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In some embodiments, alkenyl groups contain 2-8 carbon atoms. In some embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments, alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In some embodiments, alkynyl groups contain 2-8 carbon atoms. In some embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some embodiments, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-4}$C(O)N(R°)$_2$; —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R•, -(haloR•), —OH, —OR•, —O(haloR*), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^†$ are independently halogen, —R*, —(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

As used herein, the term "about" preceding one or more numerical values means the numerical value±5%. It should be understood that reference to "about" a value or parameter herein includes (and describes) embodiments that are directed to that value or parameter per se. For example, description referring to "about x" includes description of "x" per se.

Further, it should be understood that reference to "between" two values or parameters herein includes (and describes) embodiments that include those two values or parameters per se. For example, description referring to "between x and y" includes description of "x" and "y" per se.

The mass fractions disclosed herein can be converted to wt % by multiplying by 100.

Glacial Acrylic Acid Production System/Production Process

Glacial acrylic acid can be produced from ethylene oxide and carbon monoxide according to the following general reaction scheme:

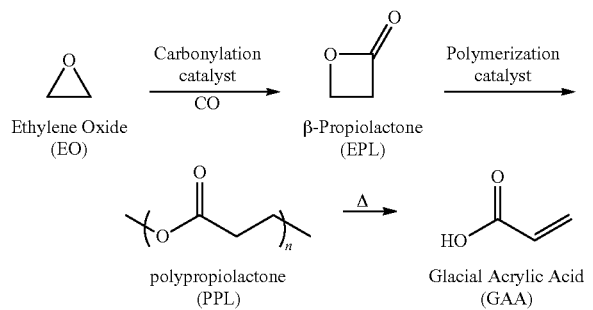

Ethylene oxide ("EO") may undergo a carbonylation reaction, e.g., with carbon monoxide ("CO"), in the present of a carbonylation catalyst to produce β-propiolactone ("bPL"). The β-propiolactone may undergo polymerization in the presence of a polymerization catalyst to produce polypropiolactone ("PPL"). The polypropiolactone may undergo thermolysis to produce glacial acrylic acid ("GAA").

PPL may undergo thermolysis by one of two primary reaction mechanisms as disclosed by (Iwabuchi, S., Jaacks, V., Galil, F. and Kern, W. (1973), The thermal degradation of poly(oxycarbonylethylene) (poly-β-propiolactone). Makromol. Chem., 165: 59-72). The desired mechanism is referred to as unzipping and it converts a PPL polymer with a chain length of "n" into one molecule of acrylic acid and reduces the PPL polymer chain length to n−1. The other method is referred to as chain scission; chain scission converts a PPL polymer of chain length n into a PPL polymer of chain length of less than n−2 and a PPL polymer of chain length of at least 2.

Product acrylic acid is susceptible to auto-polymerization via two mechanisms, either Michael addition or radical polymerization. Michael addition forms a product of two molecules of acrylic acid which is a di-acrylic acid ester and identical to a PPL of chain length 2. There is no known inhibitor of Michael addition of acrylic acid, but under thermolysis conditions this reaction is reversible and can decompose back into two molecules of acrylic acid. The product of Radical polymerization of acrylic acid produces polyacrylic acid, and will not normally convert back into acrylic acid under thermolysis conditions. There are many known inhibitors for radical polymerization of acrylic acid, including but not limited to phenothiazine (PTZ) and 4-methoxyphenol (MEHQ). Under many circumstances, a stream of radical polymerization inhibitor (either neat or in appropriate solvent) is added in batch or continuous mode to the primary thermolysis reactor or mixed with PPL stream before introduction to reactor to combat losses of acrylic acid to polyacrylic acid in thermolysis reactor.

Thermolysis of PPL may be catalyzed by the presence of a depolymerization catalyst. Depolymerization catalyst (either neat or in appropriate solvent) may be added in batch or continuous mode to the primary thermolysis reactor or mixed with PPL stream before introduction to reactor to reduce severity of thermolysis reaction conditions (which reduces conversion of acrylic acid to polyacrylic acid). Optimally, the catalyst employed for bPL polymerization can be used as a depolymerization catalyst as well. The thermolysis reactor can be designed (see below) such that the concentrations of the polymerization catalyst species in the PPL inlet stream and in the thermolysis reactor, which along with the difference in reactor conditions and stream compositions accounts for the seemingly divergent functions.

Provided herein are systems and methods for the production of glacial acrylic acid from ethylene oxide and carbon monoxide on an industrial scale. For example, in some aspects, the systems and methods described herein are suitable for the production of glacial acrylic acid on a scale of 25 kilo tons per annum ("KTA"). In some variations, the systems provided herein are configured to produce glacial acrylic acid in a continuous process, and further feedback loops to continually produce acrylic acid.

Further, in some variations, the systems provided herein further include various purification systems to produce glacial acrylic acid of high purity. For example, the systems provided herein may be configured to remove residual carbonylation catalyst, carbonylation solvent, and by-products (e.g., acetaldehyde, succinic anhydride, and acrylic acid dimer) to achieve glacial acrylic acid with a purity of at least 99.5%, at least 99.6%, at least 99.7%, at least 99.8%, or at least 99.9%.

In other variations, the systems provided herein are also configured to recycle various starting materials and glacial acrylic acid precursors, such as poly-propiolactone. For example, the systems may include one or more recycle systems to isolate unreacted ethylene oxide, unreacted carbon monoxide, carbonylation solvent, and catalyst.

In yet other variations, the systems provided herein are also configured to manage and integrate heat produced. The carbonylation reaction to produce β-propiolactone and the polymerization reaction to produce polypropiolactone are exothermic. Thus, the heat generated from the exothermic unit operations, such as the carbonylation reactor and polymerization reactor can be captured and used for cooling in endothermic unit operations, such as the distillation apparatus and thermolysis reactor. For example, in some variations of the systems and methods provided herein, steam may be generated in heat transfer equipment (e.g., shell and tube heat exchanger and reactor cooling jacket) via a temperature gradient between process fluid and water/steam. This steam can be used for heat integration between exothermic and endothermic unit operations. In other variations of the systems and methods provided herein, other suitable heat transfer fluids may be used.

In other variations, heat integration may be achieved by combining certain unit operations. For example, heat integration may be achieved by combining polymerization of β-propiolactone and vaporization of the solvent (e.g., THF) from the distillation column within a single unit operation. In such a configuration, the heat liberated from the β-propiolactone polymerization reaction is used directly to vaporize the solvent in the distillation apparatus, and the output of the unit produces polypropiolactone. In other variations, the heat liberated from the polymerization reaction can be exported to other systems at the same production site.

With reference to FIG. 1, an exemplary system to produce acrylic acid from carbon monoxide and ethylene oxide is depicted. Carbon monoxide (CO), a carbonylation catalyst, ethylene oxide (EO) and carbonylation solvent are fed into a β-propiolactone production system/production process, depicted as a continuous stirred tank reactor (CSTR) in FIG. 1. Such β-propiolactone production system/production process is typically configured to produce a liquid product stream of β-propiolactone. This β-propiolactone product stream is fed to an EO/CO separator, depicted as the flash tank in FIG. 1, where unreacted ethylene oxide and unreacted carbon monoxide may be separated and recycled for use in the CSTR. The β-propiolactone product stream is then fed from the EO/CO separator to a carbonylation catalyst recycle system, depicted as a nanofilter in FIG. 1. The carbonylation catalyst recycle system is configured to separate residual carbonylation catalyst present in the β-propiolactone product stream, and such separated carbonylation catalyst may be recycled for use in the CSTR. The nanofilter depicted in FIG. 1 may be any suitable membrane, such as a polymeric membrane or a ceramic membrane, and produces a retentate stream typically made up of β-propiolactone, carbonylation solvent, residual carbonylation catalyst, small amounts of ethylene oxide, carbon monoxide, and by-products (such as acetaldehyde and succinic anhydride), and a permeate stream typically made up of β-propiolactone, carbonylation solvent, small amounts of ethylene oxide, carbon monoxide, by-products (such as acetaldehyde and succinic anhydride) and trace amounts of carbonylation catalyst. In some embodiments, trace amount is less than 1% by wt, less than 0.5% by wt, less than 0.01% by wt, less than 0.005% by wt, less than 0.001% by wt, or less than 0.0001% by wt. In certain embodiments, trace amount is below the detection threshold of the measurement method being used.

The permeate is fed into a β-propiolactone purification system, depicted as a distillation column in FIG. 1, which is configured to separate ethylene oxide, carbon monoxide, and by-products from the solvent recycle stream, which is depicted as a tetrahydrofuran (THF) recycle stream. The system in FIG. 1 depicts the use of THF as the carbonylation solvent, but it should be understood that in other variations, other suitable solvents may be used. The purified β-propiolactone stream from the β-propiolactone purification system and polymerization catalyst are fed into a polypropiolactone production system/production process, depicted as a plug flow reactor in FIG. 1. The polypropiolactone production system/production process is configured to produce a polypropiolactone product stream, which can be fed into a thermolysis reactor to produce glacial acrylic acid.

It should be understood, however, that while FIG. 1 depicts an exemplary glacial acrylic acid production system/production process, variations of this productions system are envisioned. For example, while a CSTR is depicted as the reactor in the β-propiolactone production system/production process, other reactors and reactor configurations may be employed. In another example, while a distillation column and a plug flow reactor are depicted in FIG. 1 in the β-propiolactone purification system and polypropiolactone productions system, respectively, other separation apparatuses and other reactors and reactor configurations may be employed.

Additionally, in other exemplary embodiments of the systems described herein, various unit operations depicted in FIG. 1 may be combined or omitted. In some variations, the β-propiolactone production system/production process and membrane unit operations may be combined (e.g. membrane reactor) or polymerization and depolymerization may be combined (e.g. catalytic or reactive distillation) may be combined, or the EO/CO separator may be omitted.

Further, it should be understood that in other exemplary embodiments of systems described herein, additional unit operations may be employed. For example, in some embodiments it may be possible to incorporate one or more ion exchange resins into the systems to remove various cationic and anionic catalyst species that may result from the use of the carbonylation catalyst. In other embodiments, one or more heat exchangers may be incorporated into the systems to manage and integrate heat produced in the system.

In yet other embodiments the process and/or system by which it is practiced may employ a variety of sensors and control equipment to automate control of the process and any related system. For example, the various reactors, in particular a β-propiolactone reactor, used in the process and any related system may employ a sensor to detect amounts of water and oxygen in the reactor or that enters the reactor. Such sensor may be connected to a control that can adjust parameters to maintain water and oxygen content under a predefined amount. Such sensor may monitor the carbonylation catalyst to detect amounts of water and oxygen in the reactor and may be connected to a control that can control the amount of carbonylation catalyst from the carbonylation catalyst source. In addition, or alternatively the carbon monoxide source may comprise a sensor configured to detect amounts of water and oxygen in the reactor and such sensor may be connected to a control that can control the amount of carbon monoxide from the carbon monoxide source. In addition, or alternatively the ethylene oxide source may comprises a sensor configured to detect amounts of water and oxygen in the reactor and such sensor may be connected to a control that can control the amount of ethylene oxide from the ethylene oxide source.

Provided herein are various systems configured for the commercial production of polypropiolactone (PPL) and glacial acrylic acid (GAA). In some configurations, PPL and GAA are produced at the same geographical location. In other configurations, PPL is produced in one location and shipped to a second location where GAA is produced.

In other variations of such configurations, the residual carbonylation catalyst (which may include cationic and anionic species) may be removed at various points in the production system/production process. For example, in certain configurations, the residual carbonylation catalyst may be removed from the PPL product stream prior to thermolysis to produce GAA. In other configurations, the residual carbonylation catalyst may be removed, if desired to do so, after thermolysis by distillation or other separation means.

In yet other variations, β-propiolactone (bPL) may be polymerized to produce PPL by way of complete conversion of bPL. In such a variation, there may not be a need for additional apparatus in the system to isolate and recycle bPL to the polymerization reactor. In other variations, the conversion of bPL is not complete. Unreacted bPL may be separated from the PPL product stream and the recovered bPL may be recycled back to the polymerization reactor.

Figure 6:
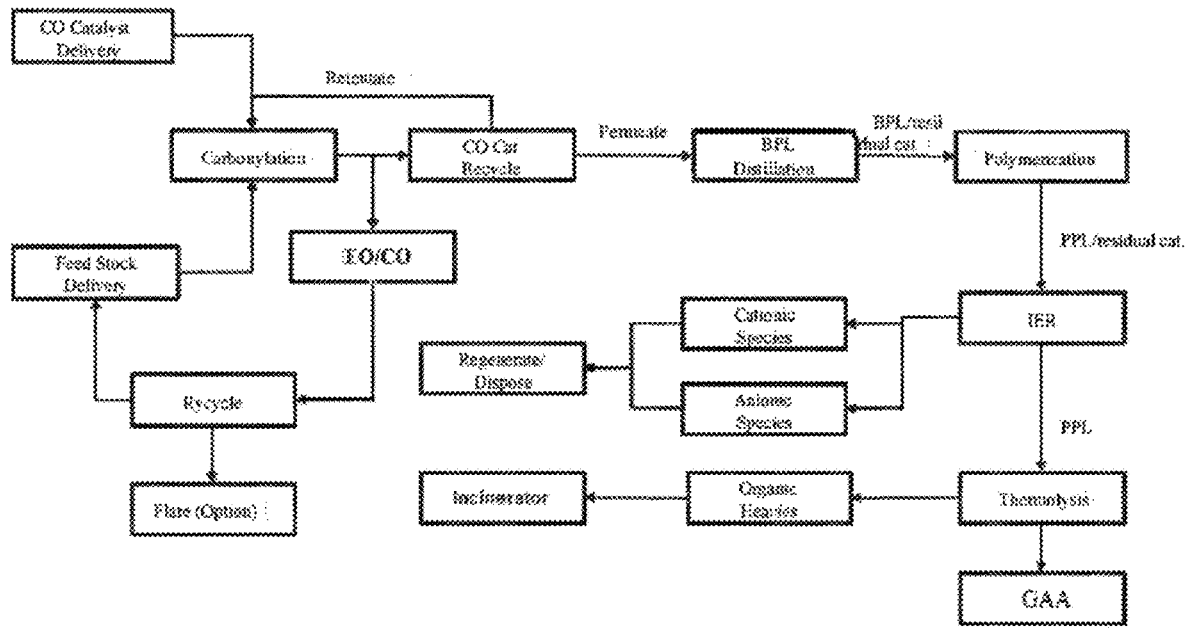
FIGS. 6-13 depict various configurations of production system/production process to produce glacial acrylic acid from ethylene oxide and carbon monoxide, via the production of β-propiolactone and polypropiolactone.

These variations in the configurations of the systems are described in further detail with respect to FIGS. 6-13. FIG. 6 depicts an exemplary system wherein the PPL product stream and the GAA product stream are produced at the same location, at least a portion of the carbonylation catalyst or components thereof are removed from the PPL product stream prior to entering the thermolysis reactor, and the polypropiolactone production system/production process is configured to achieve complete conversion of bPL to PPL.

Carbonylation catalyst components may include, for example, compounds produced by degradation of the catalyst, compounds used to produce the catalyst, metals or metal ions which were part of the catalyst, any organic compounds which were part of the catalyst, metal carbonyls or metal complexes which were part of the catalyst. For example, in some embodiments, carbonylation catalyst components are carbonyl cobaltate, aluminum salen compounds, aluminum porphyrin compounds, aluminum salophen compounds, cobalt or cobalt ions, or aluminum or aluminum ions, or any combinations thereof.

The BPL production system/production process (labeled 'Carbonylation' in FIG. 6) typically includes a carbon monoxide (CO) source, an ethylene oxide (EO) source, a carbonylation catalyst source, a solvent source, and a carbonylation reactor. In certain variations, the carbonylation reactor is configured to receive carbon monoxide (CO), ethylene oxide (EO), and solvent from a CO source, an EO source, and a solvent source (collectively labeled 'Feed Stock Delivery' in FIG. 6). The carbonylation reactor is further configured to receive a carbonylation catalyst from a carbonylation catalyst source (labeled 'CO Catalyst Delivery' in FIG. 6). The carbon monoxide, ethylene oxide, carbonylation solvent, and carbonylation catalyst may be obtained by any commercially available sources, or any commercially available methods and techniques known in the art.

In some variations, the CO, EO, and solvent are essentially water and oxygen free. In one variation, the solvent from the solvent source, the EO from the EO source, and the CO from the CO source have a concentration of water and oxygen less than about 500 ppm, less than about 250 ppm, less than about 100 ppm, less than about 50 ppm, less than about 10 ppm, less than about 2 ppm, or less than 1 ppm.

Any suitable carbonylation solvents may be used. In some embodiments, the carbonylation solvent comprises tetrahydrofuran, hexane, or a combination thereof. In other embodiments, the carbonylation solvent comprises an ether, a hydrocarbon, or a combination thereof. In yet other embodiments, the carbonylation solvent comprises tetrahydrofuran, tetrahydropyran, 2,5-dimethyl tetrahydrofuran, sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, propyl acetate, butyl acetate, 2-butanone, cyclohexanone, toluene, difluorobenzene, dimethoxy ethane, acetone, or methylethyl ketone, or any combination thereof. In one variation, the carbonylation solvent comprises tetrahydrofuran.

The carbonylation catalyst used herein may be made on-site and/or off-site. In some embodiments, the carbonylation catalyst is a cobalt-aluminum catalyst. In certain embodiments, the carbonylation catalyst comprises a carbonyl cobaltate in combination with an aluminum porphyrin compound, a carbonyl cobaltate in combination with an aluminum salen compound, or a carbonyl cobaltate in combination with an aluminum salophen compound. In one variation, the carbonylation catalyst is (Al(TPP)Co(CO)$_4$).

The carbonylation reactor may be a continuous reactor, such as a continuous stirred tank reactor (CSTR). Other reactors described herein, such as batch reactors, plug flow reactors (PFR), and semi-batch reactors may also be employed.

With reference again to the exemplary system in FIG. 6, the carbonylation reactor may be configured to receive EO from the EO source at any rate, temperature, or pressure described herein. For example, in some embodiments, the inlet to the carbonylation reactor receives EO from an EO source at about 1000 kg/hr to 25000 kg/hr. In some embodiments, the inlet to the carbonylation reactor receives EO from an EO source at about 30 kmol/hr to about 500 kmol/hr. In some embodiments, the inlet to the carbonylation reactor is configured to receive EO from an EO source at a temperature between about 10° C. to about 30° C. In some embodiments, the inlet to the carbonylation reactor is configured to receive EO from an EO source at a pressure between about 20 bar to about 100 bar and in a more narrow range 50 bar to 70 bar.

With reference again to the exemplary system in FIG. 6, the carbonylation reactor may be configured to receive CO from the CO source at any rate, temperature, or pressure described herein. For example, in some embodiments, the inlet to the carbonylation reactor is configured to receive CO from a CO source at a temperature between about 10° C. to about 170° C. and more narrowly between 10° C. to about 70° C. In some embodiments, the inlet to the carbonylation reactor is configured to receive CO from a CO source at a pressure between about 20 bar to about 100 bar and more narrowly 50 and 70 bar. In some embodiments, the CO source that supplies CO to the carbonylation reactor is a fresh carbon monoxide source (i.e., main CO feed), or recycled carbon monoxide from the β-propiolactone production system/production process, or a combination thereof. In some embodiments, the fresh CO source is configured to provide between about 1000 kg/hr CO to about 16000 kg/hr CO. In some embodiments, the fresh CO source is configured to provide between about 30 kmol/hr CO to about 600 kmol/hr CO. In some embodiments, the recycled CO from the β-propiolactone production system/production process can provide between about 100 kg/hr CO to about 3500 kg/hr CO. In some embodiments, the recycled CO source is configured to provide between about 3 kmol/hr CO to about 150 kmol/hr CO.

With reference again to the exemplary system in FIG. 6, the carbonylation reactor may be configured to receive solvent at any rate, temperature, or pressure described herein. For example, in some embodiments, the inlet to the carbonylation reactor is configured to receive solvent from a solvent feed at a rate of between about 10000 kg/hr to about 130000 kg/hr. In some embodiments, the inlet to the carbonylation reactor is configured to receive solvent from a solvent feed at rate of between about 150 kmol/hr to about 1900 kmol/hr. In some embodiments, the inlet to the carbonylation reactor is configured to receive solvent from a solvent feed at a temperature between about 10° C. to about 160° C. and more narrowly 10° C. to about 60° C. In some embodiments, the inlet to the carbonylation reactor is configured to receive solvent from a solvent feed at a pressure of between about 20 bar to about 100 bar and more narrowly 50 bar to 65 bar. In some embodiments, the solvent feed that supplies solvent to the carbonylation reactor can include solvent from a fresh solvent source, recycled solvent from the BPL purification system (e.g., BPL distillation system), and/or solvent in the recycled carbonylation catalyst stream from the carbonylation catalyst recycle system.

In some embodiments, the pressure in the carbonylation reactor is about 900 psig, and the temperature is about 70° C. In certain variations, the reactor is equipped with an external cooler (heat exchanger). In some variations, the carbonylation reaction achieves a selectivity of bPL above 99%.

With reference again to the exemplary system in FIG. 6, a β-propiolactone product stream exits the outlet of the carbonylation reactor. The β-propiolactone product stream comprises bPL, solvent, unreacted EO and CO, carbonylation catalyst, and by-products, such as acetaldehyde by-product (ACH) and succinic anhydride (SAH). The β-propiolactone product stream may have any concentration of bPL, solvent, EO, CO carbonylation catalyst, ACH, and SAH described herein. For example, in some embodiments, the β-propiolactone product stream includes between about 2000 kg/hr bPL to about 40000 kg/hr bPL. In some embodiments, the β-propiolactone product stream includes between about 30 kmol/hr bPL to about 550 kmol/hr bPL. In some embodiments, the mass fraction of bPL in the β-propiolactone product stream can be about 0.1 to about 0.4. In some embodiments, the mole fraction of bPL in the β-propiolactone product stream can be about 0.1 to about 0.6. and more narrowly 0.1 to 0.4. The β-propiolactone product stream can also include other components including unreacted ethylene oxide (in mass fraction of about 0.005 to 0.15, or at most about 0.1), unreacted carbon monoxide (in mass fraction of about 0.0005 to 0.04, or at most about 0.02), acetaldehyde (in mass fraction of about 0.0005 to 0.01, or at most about 0.02), succinic anhydride (in mass fraction of about 0.0005 to 0.005, or at most about 0.01), carbonylation catalyst (in about 40 to 640 kg/hr, or at most about 600 kg/hr; or a mass fraction of about 0.001 to 0.005, or at most about 0.004), and the remainder solvent. In some embodiments, the β-propiolactone product stream comprises carbonylation catalyst components (in about 40 to 640 kg/hr, or at most about 600 kg/hr; or a mass fraction of about 0.001 to 0.005, or at most about 0.004). In some embodiments, the β-propiolactone product stream from the β-propiolactone production system/production process can have a temperature of about 40° C. or 50° C. to about 100° C., and a pressure of about 1 bar to about 15 bar or more narrowly to 5 bar.

With reference again to the exemplary system in FIG. 6, the β-propiolactone product stream is output from an outlet of the carbonylation reactor and enters an inlet of the ethylene oxide and carbon monoxide separator (labeled 'EO/CO' in FIG. 6). In one embodiment, the ethylene oxide and carbon monoxide separator is a flash tank. The majority of the ethylene oxide and carbon monoxide is recovered from the carbonylation reaction stream and can be recycled back to the carbonylation reactor as a recycled ethylene oxide stream and a recycled carbon monoxide stream (labeled 'Recycle' in FIG. 6), or sent for disposal (labeled 'Flare' in FIG. 6). In some embodiments, at least 10% of the ethylene oxide and 80% of the carbon monoxide in the carbonylation reaction stream is recovered. The recycled carbon monoxide stream can also include unreacted ethylene oxide (in about at most 250 kg/hr or a mass fraction of between about 0.05 to about 0.075), secondary reaction product acetaldehyde (in at most about 13 kg/hr or a mass fraction of about 0.001 to about 0.009), bPL (in at most about 0.19 kg/hr), and the remainder solvent (e.g., THF).

With reference again to the exemplary system in FIG. 6, the β-propiolactone product stream is pumped into the carbonylation catalyst recycle system. In some variations, the ethylene oxide and carbon monoxide are disposed of using a method other than flare. For example, in one embodiment, the ethylene oxide and carbon monoxide recovered from the β-propiolactone product stream are disposed of using incineration.

With reference again to the exemplary system in FIG. 6, the β-propiolactone product stream enters an inlet of the carbonylation catalyst recycling system. The carbonylation catalyst recycling system may be configured to isolate at least a portion of the carbonylation catalyst from the β-propiolactone product stream using any of the methods described herein, including, for example distillation, liquid-liquid extraction, ionic liquids, nanofiltration, ion exchange, or adsorption, or any combinations thereof. In some variations, the carbonylation catalyst recycling system includes a membrane separator. In certain variations, the membrane separator comprises a polymeric membrane, while in other variations the membrane separator comprises a ceramic membrane. In some variations, the membrane of the catalyst recycle system is configured to achieve between 90% and 100% rejection of the catalyst, and have permeability greater than 1. In some embodiments the membrane is achieves greater than 90%, 92%, 95%, 98%, or 99% rejection of the catalyst.

The carbonylation catalyst recycling system is configured to produce a recycled carbonylation catalyst stream (labeled 'Retentate' in FIG. 6) comprising bPL, solvent, ethylene oxide, carbon monoxide, by-products (such as acetaldehyde and carbonylation catalyst) and carbonylation catalyst, and a post-isolation β-propiolactone product stream (labeled 'Permeate' in FIG. 6) comprising bPL, solvent, ethylene oxide, carbon monoxide, by-products (such as acetaldehyde and succinic anhydride) and trace amounts of carbonylation catalyst. In some embodiments, the post-isolation β-propiolactone product stream comprises trace amounts of carbonylation catalyst components. In some embodiments, trace amount is less than 1% by wt, less than 0.5% by wt, less than 0.01% by wt, less than 0.005% by wt, less than 0.001% by wt, or less than 0.0001% by wt. In certain embodiments, trace amount is below the detection threshold of the measurement method being used.

The recycled carbonylation catalyst stream may comprise any concentration of carbonylation catalyst, carbonylation catalyst components, and solvent disclosed herein. For example, in some embodiments, the mass fraction of carbonylation catalyst in the recycled carbonylation catalyst stream is about 0.005 to about 0.05. In some embodiments, the mass fraction of carbonylation catalyst components in the recycled carbonylation catalyst stream is about 0.0051 to about 0.05. In some embodiments, the mole fraction of carbonylation catalyst in the recycled carbonylation catalyst stream is about 0.0005 to about 0.05. In some embodiments, the mole fraction of carbonylation catalyst components in the recycled carbonylation catalyst stream is about 0.0005 to about 0.05. In some embodiments, the mass fraction of solvent in the recycled carbonylation catalyst stream is between 0.60 to about 0.99. In some embodiments, the mole fraction of solvent in the recycled carbonylation catalyst stream is between about 0.60 to about 0.99. In some embodiments, the recycled carbonylation catalyst stream can also include unreacted carbon monoxide (in at most about 15 kg/hr or a mass fraction of at most about 0.001), unreacted ethylene oxide (in at most about 330 kg/hr or a mass fraction of between 0.005 to 0.01), secondary reaction product acetaldehyde (in at most about 33 kg/hr or a mass fraction of at most about 0.001), secondary reaction product succinic anhydride (in at most about 30 kg/hr or a mass fraction of at most about 0.001), bPL (in at most about 5450 kg/hr or a mass fraction of at most about 0.25). The recycled carbonylation catalyst stream is recycled back to the carbonylation reactor.

The post-isolation β-propiolactone product stream may have any concentration of bPL, solvent, ethylene oxide, carbon monoxide, by-products (such as acetaldehyde and succinic anhydride), carbonylation catalyst, or carbonylation catalyst components described herein. For example, in some embodiments, the post-isolation β-propiolactone product stream includes about 2000 kg/hr bPL to about 35000 kg/hr bPL. In some embodiments, the post-isolation β-propiolactone product stream includes about 30 kmol/hr bPL to about 450 kmol/hr bPL. In some embodiments, the mass fraction of bPL in the post-isolation β-propiolactone product stream can be about 0.1 to 0.4, or the mole fraction of bPL in the post-isolation β-propiolactone product stream can be about 0.1 to about 0.4. The post-isolation β-propiolactone product stream can also include other components including unreacted ethylene oxide (in mass fraction of about 0.005 to 0.1), unreacted carbon monoxide (in mass fraction of about 0.0005 to 0.001, or at most about 0.002), acetaldehyde (in mass fraction of about 0.0005 to 0.001, or at most about 0.002), succinic anhydride (in mass fraction of about 0.0005 to 0.01, or at most about 0.02), carbonylation catalyst (in about 0 to 50 kg/hr, or at most about 20 kg/hr), carbonylation catalyst components (in about 0 to 50 kg/hr, or at most about 20 kg/hr) and the remainder solvent. In some embodiments, the post-isolation β-propiolactone product stream from the carbonylation catalyst recycling system can have a temperature of about 20° C. to about 60° C. In some embodiments, the post-isolation β-propiolactone product stream can have a pressure of about 1 to about 5 bar.

With reference again to the exemplary system in FIG. 6, the post-isolation β-propiolactone product stream may enter the inlet of the BPL purification system (labeled 'BPL Distillation' in FIG. 6). In one variation, the BPL purification system comprises one or more distillation columns operating at or below atmospheric pressure configured to produce a recovered solvent stream, and a production stream comprising purified bPL and trace amounts of carbonylation catalyst (labeled 'BPL/residual cat.' in FIG. 6). The pressure is selected in such a way to achieve the temperature that reduces the decomposition of bPL. In some embodiments, the one or more distillation columns are operated at a pressure of about 0.15 bara and a temperature between about 80° C. and about 120° C. In some embodiments, the distillation system is configured to produce a recycled solvent stream essentially free of ethylene oxide, carbon monoxide, acetaldehyde, and succinic anhydride.

With reference again to the exemplary system in FIG. 6, the recovered solvent stream exits an outlet of the BPL purification system and may be fed back to the carbonylation reactor. In some variations, the concentration of $H_2O$ and $O_2$ is reduced in the recycled solvent stream prior to being fed to the carbonylation reactor. The recovered solvent stream may have any concentration of $H_2O$ and $O_2$ described herein when fed back to the carbonylation reactor. For example, in some embodiments, the concentration of $H_2O$ and $O_2$ is less than about 500 ppm, less than about 250 ppm, less than about 100 ppm, less than about 50 ppm, less than about 20 ppm, less than about 10 ppm, less than about 2 ppm, or less than about 1 ppm when fed back into the carbonylation reactor.

With reference again to the exemplary system in FIG. 6, the production stream comprising purified bPL exits the outlet of the BPL purification system. The production stream may contain trace amounts of carbonylation catalyst, but is essentially free of solvent, ethylene oxide, carbon monoxide, acetaldehyde, and succinic anhydride. In some embodiments, the production stream contains a mass fraction of bPL of about 0.90 to 1.0. In some embodiments, the mole fraction of bPL in the production stream is about 0.90 to 1.0. In some embodiments, the remainder of the production stream includes secondary reaction products such as succinic anhydride (in mole fraction of at most about 0.015, or from 0 to 0.0015), leftover solvent (e.g., THF) and leftover carbonylation catalyst (in at most about 1000 ppm). In some embodiments, the remainder of the production stream includes carbonylation catalyst components (in at most about 1000 ppm).

The production stream enters an inlet of the polypriolactone production system/production process. In the exemplary system depicted in FIG. 6, the polypriolactone production system/production process comprises a polymerization reactor (labeled 'Polymerization' in FIG. 6). The polypriolactone production system/production process is configured to receive and output streams at any rate, concentration, temperature, or pressure described herein. For example, in one embodiment, the inlet to the polymerization process can include about 2000 kg/hr bPL to about 35000 kg/hr bPL. In some embodiments, the inlet to the polymerization process can include about 25 kmol/hr bPL to about 500 kmol/hr bPL. In some embodiments, the mass fraction of bPL in the inlet to the polymerization process can be about 0.90 to 1.0. In some embodiments, the mole fraction of bPL in the inlet to the polymerization process can be from about 0.90 to 1.0. The remainder of the production stream entering the polymerization process can include secondary reaction products such as succinic anhydride (in mole fraction of at most about 0.015, or from 0 to about 0.015), leftover solvent (e.g., THF) and leftover carbonylation catalyst (in at most about 1000 ppm). The remainder of the production stream entering the polymerization process can include carbonylation catalyst components (in at most about 1000 ppm). In some embodiments, the inlet to the polymerization process can also include a polymerization catalyst, for example, if the polymerization reaction is a homogenous polymerization reaction. In some embodiments, the production stream entering the polymerization process can have a temperature between about 80° C. to 120° C. In some embodiments, the production stream exiting the distillation process can be at a pressure of about 0.05 bar to about 0.15 bar. In some embodiments, the production stream entering the polymerization process can be at a pressure of at least about 0.05 bar, at least about 1 bar, or at least about 5 bar, or between about 0.05 bar and about 20 bar.

With reference again to the exemplary system in FIG. 6, the polypropiolactone production system/production process is configured to operate in a continuous mode and achieves complete conversion of bPL in the production stream to PPL. A PPL product stream (labeled 'PPL/residual cat.' in FIG. 6) exits an outlet of the polypropiolactone production system/production process, and comprises PPL with trace amount of carbonylation catalyst. In some embodiments, the PPL product stream comprises trace amount of carbonylation catalyst components.

In some embodiments, the polymerization process is configured to produce about 2000 kg/hr PPL to about 35000 kg/hr PPL. In some embodiments, the polymerization process is configured to produce about 25 kmol/hr PPL to about 500 kmol/hr PPL.

In some embodiments, the mass fraction of PPL in the PPL product stream can be about 0.90 to 1.0. In some embodiments, the mole fraction of PPL in the PPL product stream can be about 0.90 to 1.0. The remainder of the PPL product stream can include unreacted bPL (in mole fraction of at most about 0.02, or between 0 and 0.02), secondary reaction products such as succinic anhydride (in mole fraction of at most about 0.01, or between 0 and 0.01) and left over solvent (e.g., THF) and leftover carbonylation catalyst (in at most about 1000 ppm). In some embodiments, the remainder of the PPL product stream can include carbonylation catalyst components (in at most about 1000 ppm). In some embodiments, the PPL product stream can have a temperature between about 100° C. to 140° C. In some embodiments, the PPL product stream can be at a pressure of at least about 0.001 bar.

With reference again to the exemplary system in FIG. 6, the PPL product stream enters an inlet of the PPL purification system (labeled 'IER' in FIG. 6). The PPL purification system can comprises and ion exchange resin (IER) configured to reduce the concentration of carbonylation catalyst in the PPL product stream. The cationic and anionic carbonylation catalyst species are recovered from the IER in the PPL purification system and can be regenerated to obtain catalyst available for recycle to the carbonylation reactor or be disposed of (labeled 'Regenerate/Dispose' in FIG. 6). A post-purification PPL product stream exits an outlet of the PPL purification system and enters an inlet of the thermolysis reactor. The post-purification PPL product stream may have any concentration of compounds, temperature, or pressure described herein. For example, in some embodiments, the mass fraction of PPL in the post-purification PPL product stream can be about 0.90 to 1.0. In some embodiments, the mole fraction of PPL in the post-purification PPL product stream can be about 0.90 to 1.0. In some embodiments, the post-purification PPL product stream can have a temperature between about 100° C. to 140° C. In some embodiments, the post-purification PPL product stream can be at a pressure of at least about 0.001 bar.

With reference again to the exemplary system in FIG. 6, a thermolysis reactor is configured to convert the post-purification PPL stream to a GAA product stream. In some embodiments, the temperature of the thermolysis reactor is between 140° C. or 160° C. and 300° C. and the pressure is between 0.1 bara and 5 bara.

Traces of high boiling organic impurities (labeled 'Organic Heavies' in FIG. 6) are separated from the GAA stream, exit an outlet of the thermolysis reactor, and sent to the incinerator for disposal (labeled 'Incinerator' in FIG. 6).

A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 50° C. In some embodiments, the GAA product stream can be at a pressure of about 0.5 bar to about 1.5 bar.

The exemplary production system/production process depicted in FIG. 6 may produce GAA at any rate described herein. For example, in some embodiments, the system produces at least about 25 kilo tons per annum ("KTA") to about 250 KTA for annual production operation of about 8000 hours. In some embodiments, the production system/production process can produce at least about 2000 kg/hr GAA to about 35000 kg/hr GAA. In some embodiments, the production system/production process can produce about 25 kmol/hr GAA to about 500 kmol/hr GAA.

Figure 7:
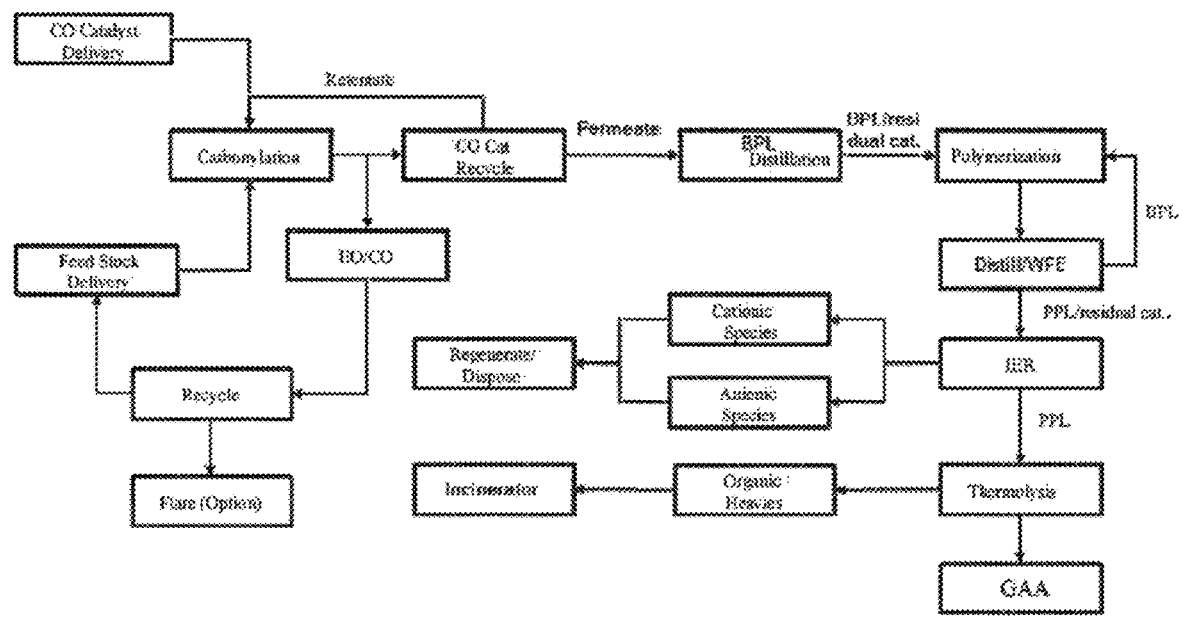

FIG. 7 provides an exemplary production system/production process where the PPL product stream and the GAA product stream are produced at the same location, at least a portion of the carbonylation catalyst or components thereof are removed from the PPL product stream prior to entering the thermolysis reactor, and the conversion of bPL in the production stream to PPL in the polymerization reactor is incomplete, with recycling of bPL back to the polymerization reactor. The production system/production process shown in FIG. 7 has the same configuration of carbonylation reactor, CO catalyst recycling, EO/CO recycling and BPL purification system as shown in FIG. 6.

With reference again to the exemplary system in FIG. 7, the production stream comprising purified bPL exits the outlet of the BPL purification system. The production stream may contain trace amounts of carbonylation catalyst, but is essentially free of solvent, ethylene oxide, carbon monoxide, acetaldehyde, and succinic anhydride. In some embodiments, the production stream contains a mass fraction of bPL of about 0.90 to 1.0. In some embodiments, the mole fraction of bPL in the production stream is about 0.90 to 1.0. In some embodiments, the remainder of the production stream includes secondary reaction products such as succinic anhydride (in mole fraction of at most about 0.015) and left over solvent (e.g., THF) and leftover carbonylation catalyst (in at most about 1000 ppm). In some embodiments, the remainder of the production stream includes carbonylation catalyst components (in at most about 1000 ppm).

With reference again to the exemplary system in FIG. 7, the polypropiolactone production system/production process comprises a polymerization reactor (labeled 'Polymerization' in FIG. 7) and a BPL recycling system (labeled 'Distill/WFE' in FIG. 7). The polypropiolactone production system/production process may be configured to receive and output streams at any rate, concentration, temperature, or pressure of production stream described herein. For example, in one embodiment, the inlet to the polymerization process can include about 2000 kg/hr bPL to about 35000 kg/hr bPL. In some embodiments, the inlet to the polymerization process can include about 25 kmol/hr bPL to about 500 kmol/hr bPL. In some embodiments, the mass fraction of bPL in the inlet to the polymerization process can be about 0.90 to 1.0. In some embodiments, the mole fraction of bPL in the inlet to the polymerization process can be from about 0.90 to 1.0. The remainder of the production stream entering the polymerization process can include secondary reaction products such as succinic anhydride (in mole fraction of at most about 0.015, or 0 to 0.015) and left over solvent (e.g., THF) and leftover carbonylation catalyst (in at most about 1000 ppm). In some embodiments, the remainder of the production stream entering the polymerization process can include carbonylation catalyst components (in at most about 1000 ppm). In some embodiments, the inlet to the polymerization process can also include a polymerization catalyst, for example, if the polymerization reaction is a homogenous polymerization reaction. In some embodiments, the production stream entering the polymerization process can have a temperature between about 80 to 120° C. In some embodiments, the production stream entering the polymerization process can be at a pressure of about 0.05 bar to about 20 bar.

With reference again to the exemplary system in FIG. 7, the PPL production system/production process is configured to operate in a continuous mode, achieving partial conversion of bPL to PPL. The PPL production system/production process may be configured to achieve various levels of bPL conversion. For example, in some embodiments, at least 40%, at least 50%, at least 60%, at least 70%, at least 80%, or at least 90% of the bPL in the production stream is converted to PPL. In some embodiments, about 50% to about 99% of the bPL in the production stream is converted to PPL. The partial polymerization stream exits the outlet of the polymerization reactor and enters the inlet of the BPL recycling system. The BPL recycling system is configured to separate unreacted bPL from the partial polymerization stream and recycle the bPL back into the polymerization reactor (labeled 'bPL' in FIG. 7). In some embodiments, the BPL recycling system comprises one or more distillation columns, while in other embodiments the BPL recycling system comprises one or more wiped-film evaporators (WFE). A PPL product stream (labeled 'PPL/residual cat.' in FIG. 7) exits the outlet of the BPL recycling system, and comprises PPL with trace amount of carbonylation catalyst. In some embodiments, the PPL product stream comprises PPL with trace amount of carbonylation catalyst components. In some embodiments, the polymerization process can produce about 2000 kg/hr PPL to about 35000 kg/hr PPL. In some embodiments, the polymerization process can produce about 25 kmol/hr PPL to about 500 kmol/hr PPL.

In some embodiments, the mass fraction of PPL in the PPL product stream can be about 0.90 to 1.0. In some embodiments, the mole fraction of PPL in the PPL product stream can be about 0.90 to 1.0. The remainder of the PPL product stream can include unreacted bPL (in mole fraction of at most about 0.02, or 0 to 0.02), secondary reaction products such as succinic anhydride (in mole fraction of at most about 0.01, or from 0 to 0.01) and left over solvent (e.g., THF) and leftover carbonylation catalyst (in at most about 1000 ppm). In some embodiments, the remainder of the PPL product stream can include carbonylation catalyst components (in at most about 1000 ppm). In some embodiments, the PPL product stream can have a temperature between about 100° C. to 140° C. In some embodiments, the PPL product stream can be at a pressure of at least about 0.001 bar.

The PPL product stream enters the inlet of the PPL purification system (labeled 'IER' in FIG. 7). In some variations, the PPL purification system may use an ion exchange resin (IER) to reduce the concentration of carbonylation catalyst in the PPL product stream. The cationic and anionic carbonylation catalyst species are recovered from the IER in the PPL purification system and can be regenerated to obtain catalyst available for recycle to the carbonylation reactor or be disposed of (labeled 'Regenerate/Dispose' in FIG. 7). A post-purification PPL product stream exits an outlet of the PPL purification system and enters an inlet of the thermolysis reactor. The post-purification PPL product stream may have any concentration of compounds, temperature, or pressure described herein. For example, in some embodiments, the mass fraction of PPL in the post-purification PPL product stream can be about 0.90 to 1.0. In some embodiments, the mole fraction of PPL in the post-purification PPL product stream can be about 0.90 to 1.0. In some embodiments, the post-purification PPL product stream can have a temperature between about 100° C. to about 140° C. In some embodiments, the post-purification PPL product stream can be at a pressure of at least about 0.001 bar.

With reference again to the exemplary system in FIG. 7, the glacial acrylic acid production system/production process is configured to convert the post-purification PPL stream to a GAA stream. Traces of high boiling organic impurities (labeled 'Organic Heavies' in FIG. 7) are output via an outlet of the thermolysis reactor, and are sent to the incinerator for disposal (labeled 'Incinerator' in FIG. 7). A GAA product stream exits an outlet of the thermolysis reactor, and may be condensed, further processed or stored. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 bar to about 1.5 bar.

The exemplary production system/production process depicted in FIG. 7 may produce GAA at any rate described herein. For example, in some embodiments, the system produces at least about 25 kilo tons per annum ("KTA") to about 400 KTA for annual production operation of about 8000 hours. In some embodiments, the production system/production process can produce at least about 2000 kg/hr GAA, or between about 2000 kg/hr GAA and about 35000 kg/hr GAA. In some embodiments, the production system/production process can produce about 25 kmol/hr GAA to about 500 kmol/hr GAA.

Figure 8:
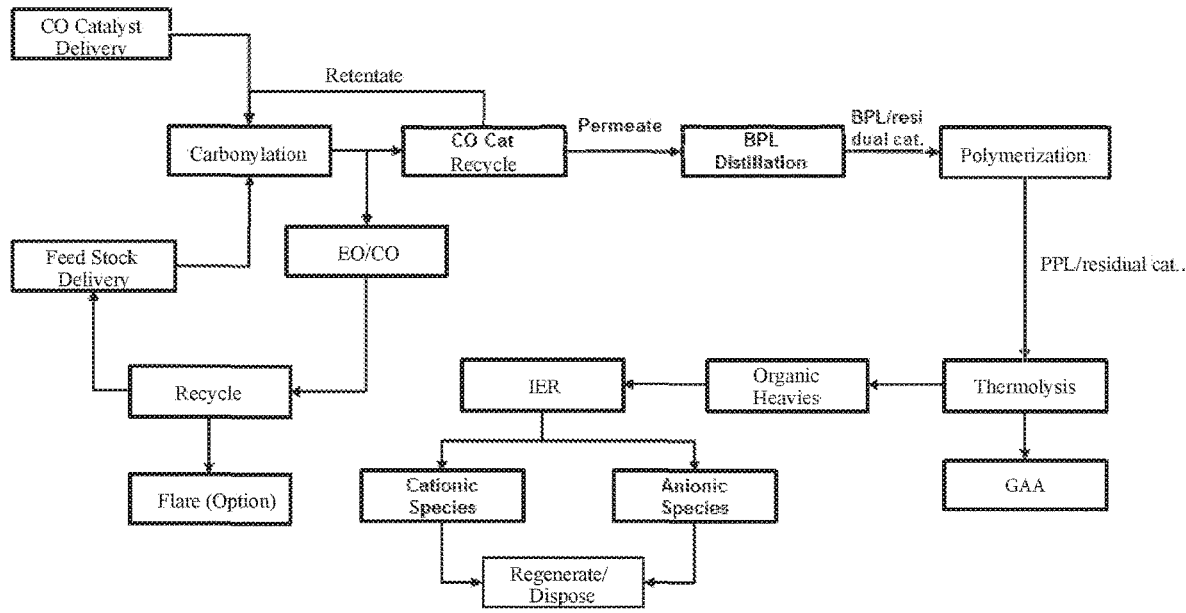

FIG. 8 depicts an exemplary production system/production process where the PPL product stream and the GAA product stream are produced at the same location, carbonylation catalyst or components thereof are not removed from the PPL product stream prior to entering the thermolysis reactor, the conversion of bPL to PPL in the polymerization process is complete with no recycling of bPL to the polymerization process, and carbonylation catalyst or components thereof are removed from the organic heavies produced by the thermolysis reactor. The production system/production process in FIG. 8 has the same configuration of carbonylation reactor, CO catalyst recycling, EO/CO recycling and BPL purification system as shown in FIG. 6.

With reference again to the exemplary system in FIG. 8, the production stream exits the outlet of the BPL purification system and enters the inlet of the polymerization process. In the production system/production process depicted in FIG. 8, the polymerization process comprises a polymerization reactor (labeled 'Polymerization' in FIG. 8). An inlet to the polymerization process may include any rate, concentration, temperature, or pressure of production stream described herein. For example, in one embodiment, the inlet to the polymerization process can include about 2000 kg/hr bPL to about 35000 kg/hr bPL. In some embodiments, the inlet to the polymerization process can include about 25 kmol/hr bPL to about 500 kmol/hr bPL. In some embodiments, the mass fraction of bPL in the inlet to the polymerization process can be about 0.90 to 1.0. In some embodiments, the mole fraction of bPL in the inlet to the polymerization process can be from about 0.90 to 1.0. The remainder of the production stream entering the polymerization process can include secondary reaction products such as succinic anhydride (in mole fraction of at most about 0.015, or 0 to 0.015), leftover solvent (e.g., THF) and leftover carbonylation catalyst (in at most about 1000 ppm). In some embodiments, the remainder of the production stream entering the polymerization process can include carbonylation catalyst components (in at most about 1000 ppm). In some embodiments, the inlet to the polymerization process can also include a polymerization catalyst, for example, if the polymerization reaction is a homogenous polymerization reaction. In some embodiments, the production stream entering the polymerization process can have a temperature between about 80° C. to about 120° C. In some embodiments, the production stream entering the polymerization process can be at a pressure of about 0.05 bar to about 0.15 bar.

With reference again to the exemplary system in FIG. 8, the polypropiolactone production system/production process is configured to operate in a continuous mode, achieving complete conversion of bPL in the production stream to PPL. A PPL product stream (labeled 'PPL/residual cat.' in FIG. 8) exits the polymerization process outlet, and comprises PPL with trace amount of carbonylation catalyst. In some embodiments, the PPL product stream comprises PPL with trace amount of carbonylation catalyst components.

In some embodiments, the polymerization process can produce about 2000 kg/hr PPL to about 35000 kg/hr PPL. In some embodiments, the polymerization process can produce about 25 kmol/hr PPL to about 500 kmol/hr PPL.

In some embodiments, the mass fraction of PPL in the PPL product stream can be about 0.90 to 1.0. In some embodiments, the mole fraction of PPL in the PPL product stream can be about 0.90 to 1.0. The remainder of the PPL product stream can include unreacted bPL (in mole fraction of at most about 0.02, or from 0 to 0.02), secondary reaction products such as succinic anhydride (in mole fraction of at most about 0.01, or from 0 to 0.01), leftover solvent (e.g., THF) and leftover carbonylation catalyst (in at most about 1000 ppm). In some embodiments, the PPL product stream can have a temperature between about 100° C. to about 140° C. In some embodiments, the PPL product stream can be at a pressure of at least about 0.001 bar.

With reference again to the exemplary system in FIG. 8, the PPL product stream enters the inlet of the thermolysis reactor. The thermolysis reactor is configured to convert the PPL product stream to a GAA stream. Traces of high boiling organic impurities (labeled 'Organic Heavies' in FIG. 8) are output via an outlet of the thermolysis reactor. The stream of high boiling organic impurities enters a purification system (labeled 'IER' in FIG. 8) comprising ion exchange resin (IER) which may be used in some embodiments may be useful. The IER is configured to reduce the concentration of carbonylation catalyst in the stream of high boiling organic impurities. In some embodiments, the concentration of carbonylation catalyst in the stream of high boiling organic impurities is between 100 ppm to 1000 ppm before entering the purification system, and is less than 50 ppm, less than 20 ppm, or less than 5 ppm after exiting the purification system.

The cationic and anionic carbonylation catalyst species are recovered from the IER and can be regenerated to obtain catalyst available for recycle to the carbonylation reactor or be disposed of (labeled 'Regenerate/Dispose' in FIG. 8). A GAA product stream exits an outlet of the thermolysis reactor for storage or further processing. The GAA product stream comprises essentially pure GAA. A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 8 may produce GAA at any rate described herein. For example, in some embodiments, the system produces at least about 25 kilo tons per annum ("KTA"), or between about 25 KTA to about 400 KTA for annual production operation of about 8000 hours. In some embodiments, the production system/production process can produce at least about 2000 kg/hr GAA, or between about 2000 kg/hr GAA to about 35000 kg/hr GAA. In some embodiments, the production system/production process can produce about 25 kmol/hr GAA to about 500 kmol/hr GAA.

Figure 9:
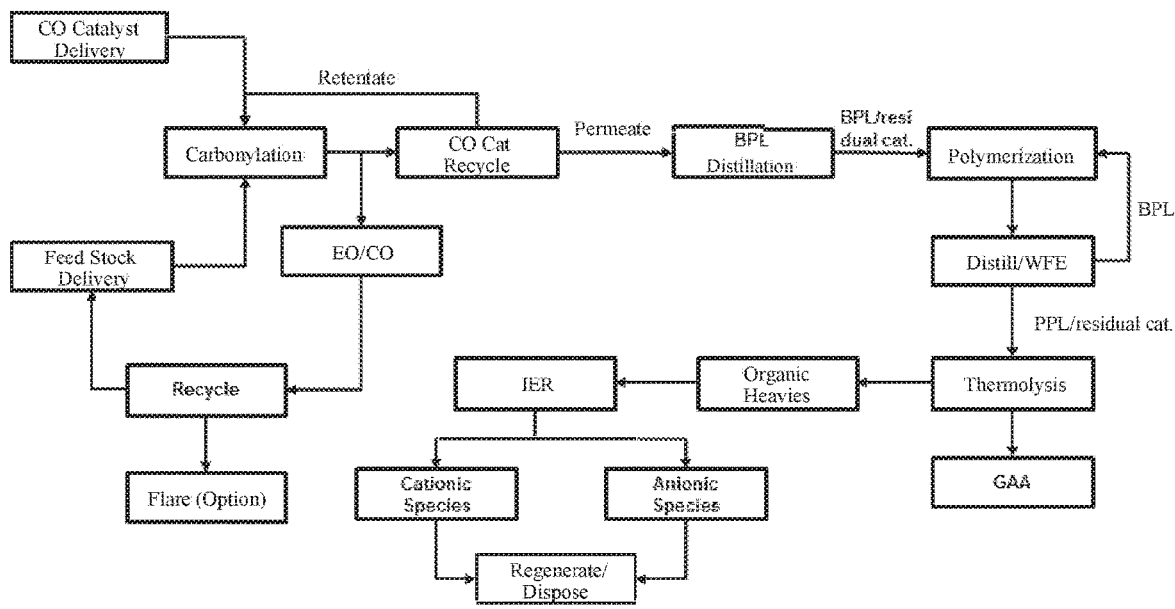

FIG. 9 depicts an exemplary production system/production process where the PPL product stream and the GAA product stream are produced at the same location, carbonylation catalyst or components thereof are not removed from the PPL product stream prior to entering the thermolysis reactor, the conversion of bPL to PPL in the polymerization process is in complete and bPL is recycled back to the polymerization process, and carbonylation catalyst or components thereof are removed from the organic heavies produced by the thermolysis reactor. The production system/production process in FIG. 9 has the same configuration of carbonylation reactor, CO catalyst recycling, EO/CO recycling and BPL purification system as shown in FIG. 6.

With reference again to the exemplary system in FIG. 9, the production stream comprising purified bPL exits the outlet of the BPL purification system. The production stream contains trace amounts of carbonylation catalyst, but is essentially free of THF, EO, CO, ACH, and SAH. The production stream is fed forward and enters an inlet of the polymerization process. The polymerization process comprises a polymerization reactor (labeled 'Polymerization' in FIG. 9) and a BPL recycling system (labeled 'Distill/WFE' in FIG. 9). An inlet to the polymerization process may include any rate, concentration, temperature, or pressure of production stream described herein. For example, in one embodiment, the inlet to the polymerization process can include about 2000 kg/hr bPL to about 35000 kg/hr bPL. In some embodiments, the inlet to the polymerization process can include about 25 kmol/hr bPL to about 500 kmol/hr bPL. In some embodiments, the mass fraction of bPL in the inlet to the polymerization process can be about 0.90 to 1.0. In some embodiments, the mole fraction of bPL in the inlet to the polymerization process can be from about 0.90 to 1.0. The remainder of the production stream entering the polymerization process can include secondary reaction products such as succinic anhydride (in mole fraction of at most about 0.015, or from 0 to 0.015) and left over solvent (e.g., THF) and leftover carbonylation catalyst (in at most about 1000 ppm). In some embodiments, the inlet to the polymerization process can also include a polymerization catalyst, for example, if the polymerization reaction is a homogenous polymerization reaction. In some embodiments, the production stream entering the polymerization process can have a temperature between about 80° C. to 120° C. In some embodiments, the production stream entering the polymerization process can be at a pressure of about 0.05 bar to about 20 bar.

With reference again to the exemplary system in FIG. 9, the polypropiolactone production system/production process is configured to operate in a continuous mode, achieving partial conversion of bPL in the production stream to PPL. The polypropiolactone production system/production process may be configured to achieve various levels of bPL conversion. For example, in some embodiments, at least 40%, at least 50%, at least 60%, at least 70%, at least 80%, or at least 90% of the bPL in the production stream is converted to PPL. In some embodiments, about 50% to about 95% of the bPL in the production stream is converted to PPL. In some embodiments, about 50% to about 99% of the bPL in the production stream is converted to PPL. The partial polymerization stream exits the outlet of the polymerization reactor and enters the inlet of the BPL recycling system. The BPL recycling system is configured to separate unreacted bPL from the partial polymerization stream and recycle the bPL back into the polymerization reactor (labeled 'bPL' in FIG. 9). In some embodiments, the BPL recycling system comprises one or more distillation columns, while in other embodiments the BPL recycling system comprises one or more wiped-film evaporators (WFE). A PPL product stream (labeled 'PPL/residual cat.' in FIG. 9) exits the outlet of the BPL recycling system, and comprises PPL with trace amount of carbonylation catalyst. In some embodiments, the PPL product stream comprises PPL with trace amount of carbonylation catalyst components. In some embodiments, the polymerization process is configured to produce about 2000 kg/hr PPL to about 35000 kg/hr PPL. In some embodiments, the polymerization process is configured to produce from about 25 kmol/hr PPL to about 500 kmol/hr PPL.

In some embodiments, the mass fraction of PPL in the PPL product stream can be about 0.90 to 1.0. In some embodiments, the mole fraction of PPL in the PPL product stream can be about 0.90 to 1.0. The remainder of the PPL product stream can include unreacted bPL (in mole fraction of at most about 0.02, or from 0 to 0.02), secondary reaction products such as succinic anhydride (in mole fraction of at most about 0.01, or from 0 to 0.01), leftover solvent (e.g., THF) and leftover carbonylation catalyst (in at most about 1000 ppm). In some embodiments, the PPL product stream can have a temperature between about 100° C. to 140° C. In some embodiments, the PPL product stream can be at a pressure of at least about 0.001 bar.

With reference again to the exemplary system in FIG. 9, the PPL product stream enters the inlet of the thermolysis reactor. The thermolysis reactor is configured to convert the PPL product stream to a GAA stream. Traces of high boiling organic impurities (labeled 'Organic Heavies' in FIG. 9) are output via an outlet of the thermolysis reactor. The stream of high boiling organic impurities enters a purification system (labeled 'IER' in FIG. 9) comprising ion exchange resin (IER). The IER is configured to reduce the concentration of carbonylation catalyst (or components thereof) in the stream of high boiling organic impurities. The cationic and anionic carbonylation catalyst species are recovered from the IER and can be regenerated to obtain catalyst available for recycle to the carbonylation reactor or be disposed of (labeled 'Regenerate/Dispose' in FIG. 9). A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and leftover solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 9 may produce GAA at any rate described herein. For example, in some embodiments, the system produces at least about 25 kilo tons per annum ("KTA"), or between about 25 KTA and about 400 KTA for annual production operation of about 8000 hours. In some embodiments, the production system/production process can produce at least about 2000 kg/hr GAA, or between about 2000 kg/hr GAA and about 35000 kg/hr GAA. In some embodiments, the production system/production process can produce about 25 kmol/hr GAA to about 500 kmol/hr GAA.

Figure 10:
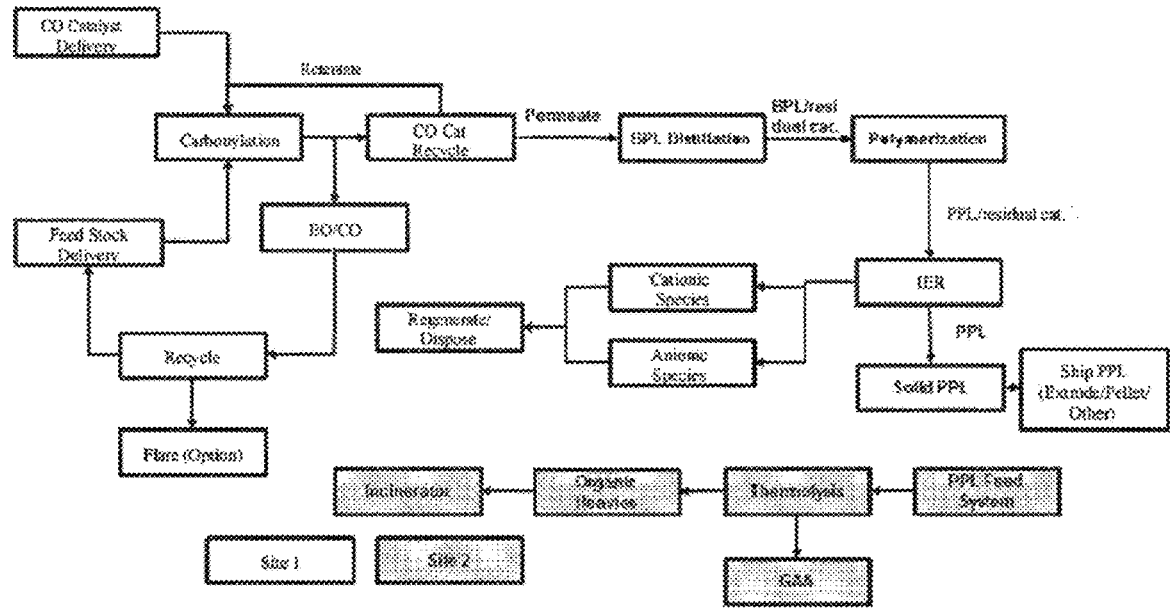

FIG. 10 depicts another exemplary production system/production process where the PPL product stream is produced at a first location, then isolated, packaged, and shipped to a second location where the GAA product stream is produced; carbonylation catalyst or components thereof are removed from the PPL product stream prior to entering the thermolysis reactor, the polymerization reactor achieves complete conversion of bPL in the production stream to PPL and bPL is not recycled back to the polymerization reactor. The production system/production process in FIG. 10 has the same configuration of carbonylation reactor, CO catalyst recycling, EO/CO recycling and BPL purification system, polymerization process, PPL purification system, and regeneration or disposal of carbonylation catalyst components as shown in FIG. 6.

With reference again to the exemplary system in FIG. 10, the post-purification PPL product stream exits an outlet of the PPL purification system and is pelletized, extruded, flaked, powdered, or granulated by any means known in the art in essentially dry atmosphere. The solid post-purification PPL product stream is then fed forward to packaging, and becomes ready to be shipped to the location of the GAA production system/production process. The packaging used to ship the solid post-purification PPL product stream is selected to minimize the moisture absorption by solid PPL. At the location of the GAA production system/production process, the essentially pure, essentially dry solid post-purification PPL product stream is unpackaged in a way to minimize introduction of moisture, and then fed in a solid or molten form to the inlet of the thermolysis reactor. The thermolysis reactor is configured to convert the post-isolation PPL product stream to a GAA stream. Traces of high boiling organic impurities (labeled 'Organic Heavies' in FIG. 10) are output via an outlet of the thermolysis reactor and sent to an incinerator for disposal (labeled 'Incinerator' in FIG. 10). A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 10 may produce GAA at any rate described herein. For example, in some embodiments, the system produces at least about 25 kilo tons per annum ("KTA"), or between about 25 KTA and about 400 KTA for annual production operation of about 8000 hours. In some embodiments, the production system/production process can produce at least about 2000 kg/hr GAA, or between about 2000 kg/hr GAA and about 35000 kg/hr GAA. In some embodiments, the production system/production process can produce about 25 kmol/hr GAA to about 500 kmol/hr GAA.

Figure 11:
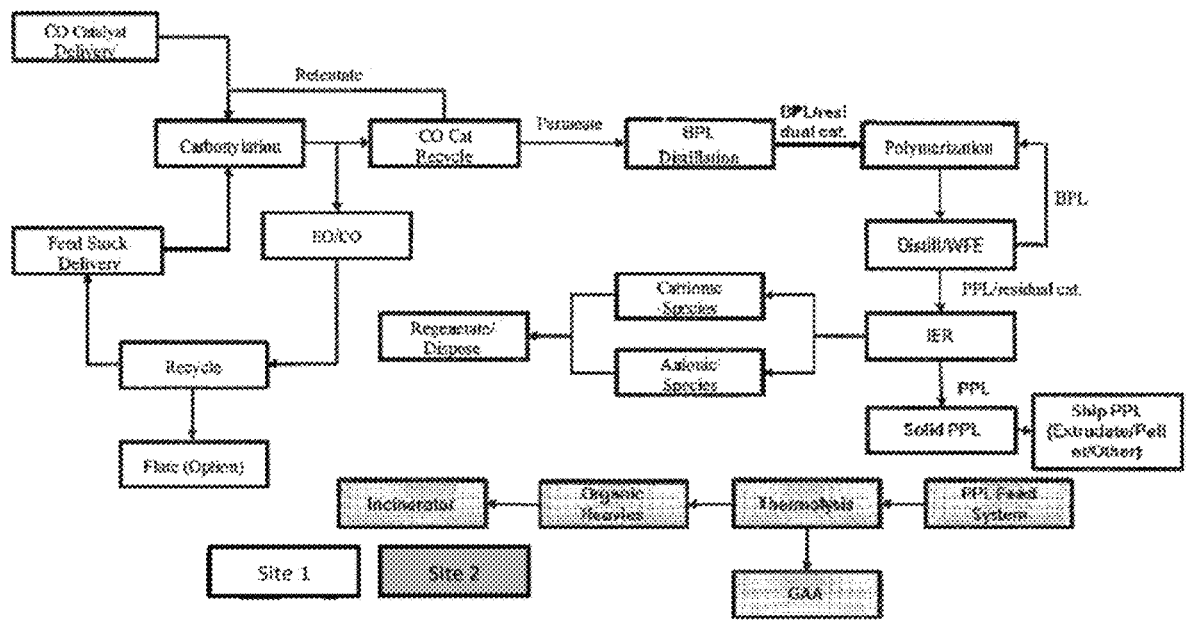

FIG. 11 depicts an exemplary production system/production process where the PPL product stream is produced at a first location, then isolated, packaged, and shipped to a second location where the GAA product stream is produced; carbonylation catalyst or components thereof are removed from the PPL product stream prior to entering the thermolysis reactor, the polymerization reactor achieves incomplete conversion of bPL in the production stream to PPL and bPL is recycled back to the polymerization reactor. The production system/production process in FIG. 11 has the same configuration of carbonylation reactor, CO catalyst recycling, EO/CO recycling and BPL purification system, polymerization process, PPL purification system, and regeneration or disposal of carbonylation catalyst components as shown in FIG. 7.

With reference again to the exemplary system in FIG. 11, the post-purification PPL product stream exits an outlet of the PPL purification system and is pelletized, extruded, flaked, powdered, or granulated by means known in the art in essentially dry atmosphere. The solid post-purification PPL product stream is then fed forward to packaging, and becomes ready to be shipped to the location of the GAA production system/production process. The packaging used to ship the solid post-purification PPL product stream is selected to minimize the moisture absorption by solid PPL. At the location of the GAA production system/production process, the essentially pure, essentially dry solid post-purification PPL product stream is unpackaged in a way to minimize introduction of moisture, and then fed in a solid or molten form to the inlet of the thermolysis reactor. The thermolysis reactor is configured to convert the post-isolation PPL product stream to a GAA stream. Traces of high boiling organic impurities (labeled 'Organic Heavies' in FIG. 11) are output via an outlet of the thermolysis reactor and sent to an incinerator for disposal (labeled 'Incinerator' in FIG. 11). A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 11 may produce GAA at any rate described herein. For example, in some embodiments, the system produces at least about 25 kilo tons per annum ("KTA"), or between about 25 KTA to about 250 KTA for annual production operation of about 8000 hours. In some embodiments, the production system/production process can produce at least about 2000 kg/hr GAA, or between about 2000 kg/hr GAA to about 35000 kg/hr GAA. In some embodiments, the production system/production process can produce about 25 kmol/hr GAA to about 500 kmol/hr GAA.

Figure 12:
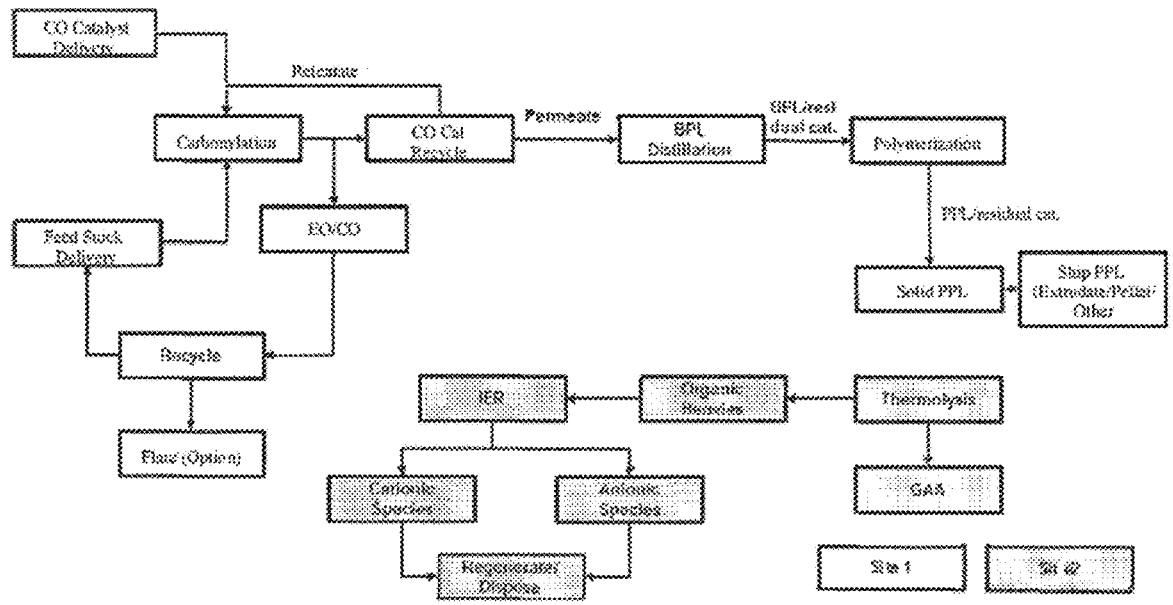

FIG. 12 depicts another exemplary production system/production process where the PPL product stream is produced at a first location, then isolated, packaged, and shipped to a second location where the GAA product stream is produced; carbonylation catalyst or components thereof are not removed from the PPL product stream prior to entering the thermolysis reactor; the polymerization reactor achieves complete conversion of bPL in the production stream to PPL and bPL is not recycled back to the polymerization reactor; and carbonylation catalyst or components thereof are removed from the organic heavies produced by the thermolysis reactor. The production system/production process in FIG. 12 has the same configuration of carbonylation reactor, CO catalyst recycling, EO/CO recycling and BPL purification system, and polymerization process as shown in FIG. 8.

With reference again to the exemplary system in FIG. 12, the PPL product stream exits an outlet of the polymerization process and is pelletized, extruded, flaked, powdered, or granulated by means known in the art in essentially dry atmosphere. The solid PPL product stream is then fed forward to packaging, and becomes ready to be shipped to the location of the GAA production system/production process. The packaging used to ship the solid PPL product stream is selected to minimize the moisture absorption by solid PPL. At the location of the GAA production system/production process, the essentially pure, essentially dry solid PPL product stream is unpackaged in a way to minimize introduction of moisture, and then fed in a solid or molten form to the inlet of the thermolysis reactor. The thermolysis reactor is configured to convert the PPL product stream to a GAA stream. Traces of high boiling organic impurities (labeled 'Organic Heavies' in FIG. 12) are output via an outlet of the thermolysis reactor. The stream of high boiling organic impurities enters a purification system (labeled 'IER' in FIG. 12) comprising ion exchange and which is an example of one separation the may be employed. The IER is configured to reduce the concentration of carbonylation catalyst (or components thereof) in the stream of high boiling organic impurities. The cationic and anionic carbonylation catalyst species are recovered from the IER and can be regenerated to obtain catalyst available for recycle to the carbonylation reactor or be disposed of (labeled 'Regenerate/Dispose' in FIG. 12). A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. In preferred embodiment the temperature is controlled to limit the risk of autopolymerization of acrylic acid. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 12 may produce GAA at any rate described herein. For example, in some embodiments, the system produces at least about 25 kilo tons per annum ("KTA"), or between about 25 KTA and about 400 KTA for annual production operation of about 8000 hours. In some embodiments, the production system/production process can produce at least about 2000 kg/hr GAA, or between about 2000 kg/hr GAA to about 35000 kg/hr GAA. In some embodiments, the production system/production process can produce about 25 kmol/hr GAA to about 500 kmol/hr GAA.

Figure 13:
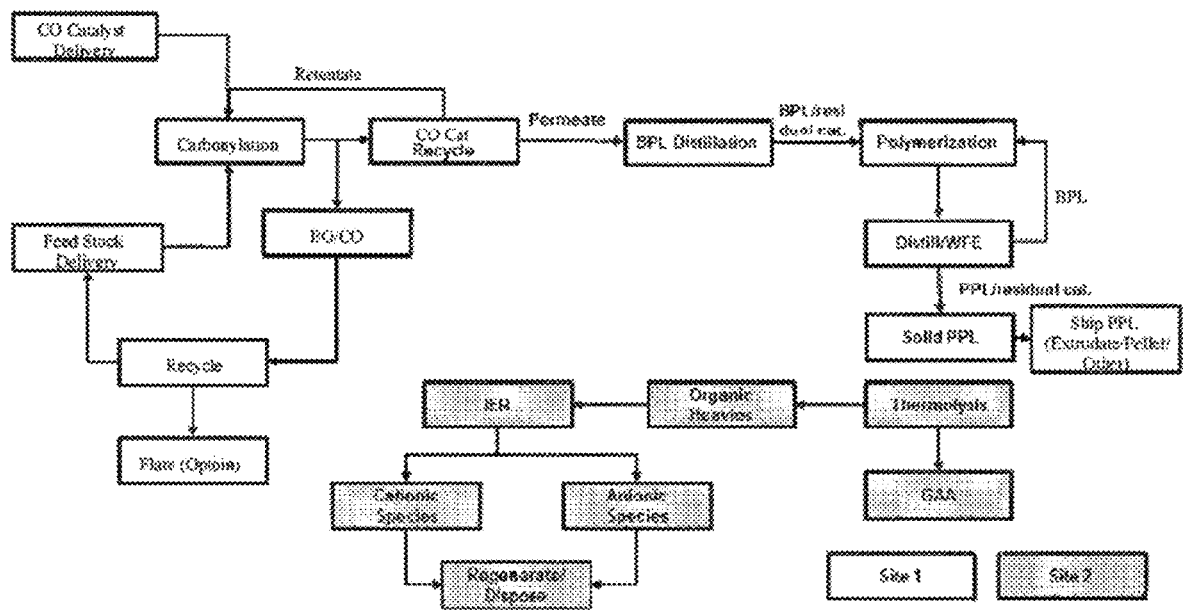

FIG. 13 depicts an exemplary production system/production process where the PPL product stream is produced at a first location, then isolated, packaged, and shipped to a second location where the GAA product stream is produced; carbonylation catalyst or components thereof are not removed from the PPL product stream prior to entering the thermolysis reactor; the polymerization reactor achieves incomplete conversion of bPL in the production stream to PPL and bPL is recycled back to the polymerization reactor; and carbonylation catalyst or components thereof are removed from the organic heavies produced by the thermolysis reactor. The production system/production process in FIG. 13 has the same configuration of carbonylation reactor, CO catalyst recycling, EO/CO recycling and BPL purification system, and polymerization process as shown in FIG. 9.

With reference again to the exemplary system in FIG. 13, the PPL product stream exits an outlet of the polymerization process and is pelletized, extruded, flaked, powdered, or granulated by means known in the art in essentially dry atmosphere. The solid PPL product stream is then fed forward to packaging, and becomes ready to be shipped to the location of the GAA production system/production process. The packaging used to ship the solid PPL product stream is selected to minimize the moisture absorption by solid PPL. At the location of the GAA production system/production process, the essentially pure, essentially dry solid PPL product stream is unpackaged in a way to minimize introduction of moisture, and then fed in a solid or molten form to the inlet of the thermolysis reactor. The thermolysis reactor is configured to convert the PPL product stream to a GAA stream. Traces of high boiling organic impurities (labeled 'Organic Heavies' in FIG. 13) are output via an outlet of the thermolysis reactor. The stream of high boiling organic impurities enters a purification system (labeled 'IER' in FIG. 13) comprising ion exchange resin (IER). The IER is configured to reduce the concentration of carbonylation catalyst (or components thereof) in the stream of high boiling organic impurities. The cationic and anionic carbonylation catalyst species are recovered from the IER and can be regenerated to obtain catalyst available for recycle to the carbonylation reactor or be disposed of (labeled 'Regenerate/Dispose' in FIG. 13). A GAA product stream exits an outlet of the thermolysis reactor for storage or further processing. The GAA product stream comprises essentially pure GAA. The GAA product stream may exit an outlet of the thermolysis reactor at any rate, concentration, temperature, or pressure described herein. The remainder of the GAA product stream can include secondary reaction products such as succinic anhydride and left over solvent such as THF. In some embodiments, the GAA product stream can have a temperature between about 15° C. to about 60° C. In some embodiments, the GAA product stream can be at a pressure of about 0.5 to about 1.5 bar.

The exemplary production system/production process depicted in FIG. 13 may produce GAA at any rate described herein. For example, in some embodiments, the system produces at least about 25 kilo tons per annum ("KTA"), at least about 100 KTA, at least about 110 KTA, at least about 120 KTA, at least about 130 KTA, at least about 140 KTA, at least about 150 KTA, at least about 160 KTA, at least about 170 KTA, at least about 180 KTA, at least about 190 KTA, at least about 200 KTA, at least about 250 KTA, at least about 300 KTA, at least about 350 KTA, at least about 400 KTA, and in some variations that may be combined with any of the preceding variations, up to about 400 KTA, for annual production operation of about 8000 hours. In some embodiments, the production system/production process can produce at least about 2000 kg/hr GAA, or between about 2000 kg/hr GAA and about 35000 kg/hr GAA. In some embodiments, the production system/production process can produce about 25 kmol/hr GAA to about 500 kmol/hr GAA.

It should be understood that while FIGS. 6-13 depict process configurations comprising certain steps and unit operations, in other embodiments of the methods described herein the process configuration contains fewer steps, more steps, fewer unit operations, or more unit operations. For example, in some variations, the permeate stream is treated to remove at least a portion of the trace carbonylation catalyst prior to the BPL purification train. In certain variations, it may be possible to remove of at least a portion of the trace carbonylation catalyst from the permeate with an ion exchange resin. Thus, in certain embodiments, the process configurations in FIGS. 6-13 includes the additional step of removing at least a portion of the trace carbonylation catalyst from the permeate using IER, before the permeate enters the BPL purification train. In some embodiments, the systems depicted in FIGS. 6-13 and described herein include a purification system with IER before prior to the BPL purification train. In other embodiments, the systems include a purification system with IER prior to the BPL purification train and use a heterogeneous polymerization catalyst in the polymerization process. In some embodiments, the systems do not have a purification system after the polymerization process.

Each of the unit operations in the production system/production process for acrylic acid and precursors thereof are described in further detail below.

β-Propiolactone Production System/Production Process (i.e., Carbonylation Reaction System)

Figure 14:
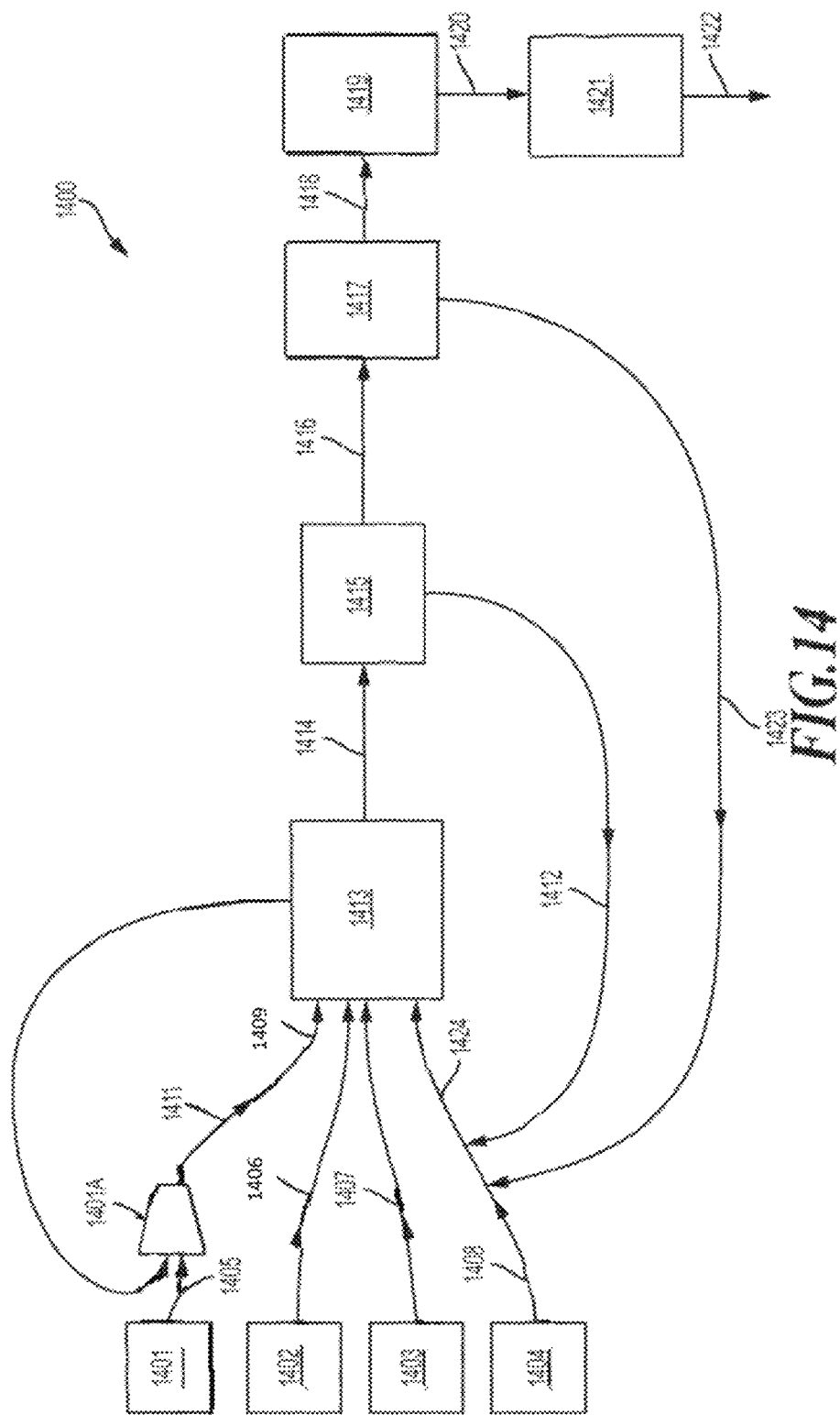
FIG. 14 illustrates an embodiment of an acrylic acid production system/production process described herein.

FIG. 14 illustrates an exemplary embodiment of the production system/production process disclosed herein. FIG. 14 contains carbonylation reaction system 1413 (i.e., β-propiolactone production system/production process), catalyst isolation system 1415, BPL purification system 1417, polymerization reaction system 1419, and thermolysis system 1421.

In the carbonylation reaction system, Ethylene oxide can be converted to β-propiolactone by a carbonylation reaction, as depicted in the reaction scheme below.

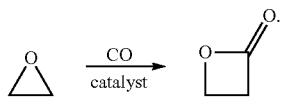

Water and oxygen can damage the carbonylation catalyst. The feed streams (i.e., EO, CO, solvent, carbonylation catalyst) to the carbonylation reaction system should be substantially dry (i.e., have a water content below 5 ppm) and be oxygen free (i.e., have an oxygen content below 5 ppm). As such, the feed streams and/or storage tanks and/or feed tank can have sensors on them in order to determine the composition of the stream/tank to make sure that they have a low enough oxygen and water content. In some embodiments, the feed streams can be purified such as by adsorption to reduce the water and oxygen content in the streams fed to the carbonylation reaction system. In some embodiments, prior to running the production system/production process, the tubes, apparatuses, and other flow paths can be purged with an inert gas or carbon monoxide to minimize exposure to oxygen or water in the production system/production process.

Ethylene Oxide Source

FIG. 14 includes ethylene oxide source 1402 that can feed fresh ethylene oxide in ethylene oxide stream 1406 to carbonylation reaction system inlet 1409. Inlet 1409 can be one inlet to the carbonylation reaction system or multiple inlets. Ethylene oxide can be fed as a liquid using a pump or any other means known to those of ordinary skill in the art. In addition, the ethylene oxide source can be maintained under an inert atmosphere. In some embodiments, the inlet to the carbonylation reaction system can receive ethylene oxide from an ethylene oxide source at least about 1000 kg/hr, at least about 1500 kg/hr, at least about 2000 kg/hr, at least about 2070 kg/hr, or at least about 2500 kg/hr. In some embodiments, the inlet to the carbonylation reaction system can receive ethylene oxide from an ethylene oxide source at about 1000 kg/hr to about 2500 kg/hr, at least about 1500 kg/hr to about 2500 kg/hr, at least about 2000 kg/hr to about 2500 kg/hr, or at least about 2070 kg/hr to about 2500 kg/hr. In some embodiments, the inlet to the carbonylation reaction system can receive ethylene oxide from an ethylene oxide source from about 1000 kg/hr to about 25000 kg/hr, about 1500 kg/hr to about 25000 kg/hr, about 2000 kg/hr to about 25000 kg/hr, about 2500 kg/hr to about 25000 kg/hr, about 5000 kg/hr to about 25000 kg/hr, about 7500 kg/hr to about 25000 kg/hr, about 10000 kg/hr to about 25000 kg/hr, about 12500 kg/hr to about 25000 kg/hr, about 15000 kg/hr to about 25000 kg/hr, about 17500 kg/hr to about 25000 kg/hr, about 20000 kg/hr to about 25000 kg/hr, or about 22500 kg/hr to about 25000 kg/hr. In some embodiments, the inlet to the carbonylation reaction system can receive ethylene oxide from an ethylene oxide source at about 1000 kg/hr, about 1500 kg/hr, about 2000 kg/hr, about 2070 kg/hr, about 2500 kg/hr, about 3000 kg/hr, about 3500 kg/hr, about 4000 kg/hr, about 4500 kg/hr, about 5000 kg/hr, 7500 kg/hr, about 10000 kg/hr, about 12500 kg/hr, about 15000 kg/hr, about 17500 kg/hr, about 20000 kg/hr, about 22500 kg/hr, or about 25000 kg/hr. In some embodiments, the inlet to the carbonylation reaction system can receive ethylene oxide from an ethylene oxide source at least about 30 kmol/hr, at least about 35 kmol/hr, at least about 40 kmol/hr, at least about 47 kmol/hr, at least about 50 kmol/hr, at least about 100 kmol/hr, at least about 200 kmol/hr, at least about 300 kmol/hr, at least about 400 kmol/hr, or at least about 500 kmol/hr. In some embodiments, the inlet to the carbonylation reaction system can receive ethylene oxide from an ethylene oxide source at about 30 kmol/hr to about 500 kmol/hr, about 35 kmol/hr to about 500 kmol/hr, about 40 kmol/hr to about 500 kmol/hr, about 47 kmol/hr to about 500 kmol/hr, about 50 kmol/hr to about 500 kmol/hr, about 100 kmol/hr to about 500 kmol/hr, about 200 kmol/hr to about 500 kmol/hr, about 300 kmol/hr to about 500 kmol/hr, or about 400 kmol/hr to about 500 kmol/hr. In some embodiments, the inlet to the carbonylation reaction system can receive ethylene oxide from an ethylene oxide source at about 30 kmol/hr, about 35 kmol/hr, about 40 kmol/hr, about 47 kmol/hr, about 50 kmol/hr, about 70 kmol/hr, about 80 kmol/hr about 90 kmol/hr, about 100 kmol/hr, about 150 kmol/hr, about 200 kmol/hr, about 250 kmol/hr, about 300 kmol/hr, about 350 kmol/hr, about 400 kmol/hr, about 450 kmol/hr, or about 500 kmol/hr. In some embodiments, the inlet to the carbonylation reaction system can receive ethylene oxide from an ethylene oxide source at a temperature between about 10-30° C., between about 15-25° C., or about 20° C. In some embodiments, the inlet to the carbonylation reaction system can receive ethylene oxide from an ethylene oxide source at a pressure of at least about 50 bar, about 60-70 bar, or at least about 65 bar.

Carbonylation Catalyst Source

Numerous carbonylation catalysts known in the art are suitable for (or can be adapted to) methods of the present invention. For example, in some embodiments, the carbonylation methods utilize a metal carbonyl-Lewis acid catalyst such as those described in U.S. Pat. No. 6,852,865. In other embodiments, the carbonylation step is performed with one or more of the carbonylation catalysts disclosed in U.S. patent application Ser. Nos. 10/820,958; and 10/586,826. In other embodiments, the carbonylation step is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In some embodiments, the carbonylation catalyst includes a metal carbonyl compound. Typically, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds. Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation.

In some embodiments, a provided metal carbonyl compound comprises an anionic metal carbonyl moiety. In other embodiments, a provided metal carbonyl compound comprises a neutral metal carbonyl compound. In some embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings of the present disclosure.

In some embodiments, the metal carbonyl compound comprises an anionic metal carbonyl species. In some embodiments, such anionic metal carbonyl species have the general formula $[Q_d M'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}[V(CO)_6]^-[Rh(CO)_4]^-$, $[Fe(CO)_4]^{2-}[Ru(CO)_4]^{2-}$, $[Os(CO)_4]^{2-}[Cr_2(CO)_{10}]^{2-}[Fe_2(CO)_8]^{2-}[Tc(CO)_5]^-[Re(CO)^5]^-$ and $[Mn(CO)_5]^-$. In some embodiments, the anionic metal carbonyl comprises $[Co(CO)_4]^-$. In some embodiments, a mixture of two or more anionic metal carbonyl complexes may be present in the carbonylation catalysts used in the methods.

The term "such as to provide a stable anionic metal carbonyl" for $[Q_dM'_e(CO)_{w'}]^{y-}$ is used herein to mean that $[Q_dM'_e(CO)_{w'}]^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. In some variations, no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments a cation associated with a provided anionic metal carbonyl compound is a simple metal cation such as those from Groups 1 or 2 of the periodic table (e.g., $Na^+$, $Li^+$, $K^+$, $Mg^{2+}$ and the like). In other embodiments a cation associated with a provided anionic metal carbonyl compound is a bulky non electrophilic cation such as an 'onium salt' (e.g., $Bu_4N^+$, $PPN^+$, $Ph_4P^+Ph_4As^+$, and the like). In other embodiments, a metal carbonyl anion is associated with a protonated nitrogen compound (e.g., a cation may comprise a compound such as $MeTBD-H^+$, $DMAP-H^+$, $DABCO-H^+$, $DBU-H^+$ and the like). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In some embodiments, a catalyst utilized in the methods described herein comprises a neutral metal carbonyl compound. In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, but are not limited to: $Ti(CO)_7$; $V_2(CO)_{12}$; $Cr(CO)_6$; $Mo(CO)_6$; $W(CO)_6Mn_2(CO)_{10}$, $Tc_2(CO)_{10}$, and $Re_2(CO)_{10}Fe(CO)_5$, $Ru(CO)_5$ and $Os(CO)_5Ru_3(CO)_{12}$, and $Os_3(CO)_{12}Fe_3(CO)_{12}$ and $Fe_2(CO)_9Co_4(CO)_{12}$, $Rh_4(CO)_{12}$, $Rh_6(CO)_{16}$, and $Ir_4(CO)_{12}Co_2(CO)_8Ni(CO)_4$.

The term "such as to provide a stable neutral metal carbonyl" for $Q_dM'_e(CO)_{w'}$ is used herein to mean that $Q_dM'_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the carbonylation catalyst utilized in the methods described above further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., $R_2BX$), a dihalo monoalkyl compound (e.g., $RBX_2$), an aryl halo boron compound (e.g., $Ar_2BX$ or $ArBX_2$), or a trihalo boron compound (e.g., $BCl_3$ or $BBr_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in systems and methods described herein include a cationic metal complex, the metal complex has the formula $[(L^c)_v M_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

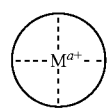

I wherein:

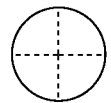

is a multidentate ligand;

M is a metal atom coordinated to the multidentate ligand;

a is the charge of the metal atom and ranges from 0 to 2; and

In some embodiments, provided metal complexes conform to structure II:

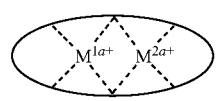

II

Where a is as defined above (each a may be the same or different), and $M^1$ is a first metal atom;

$M^2$ is a second metal atom;

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In some embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

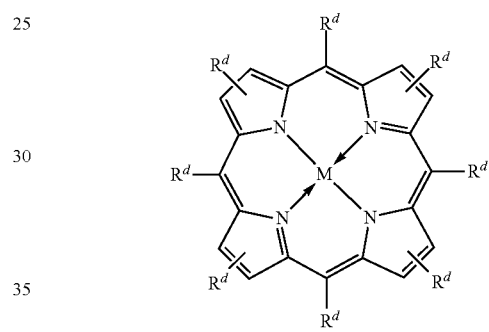

1

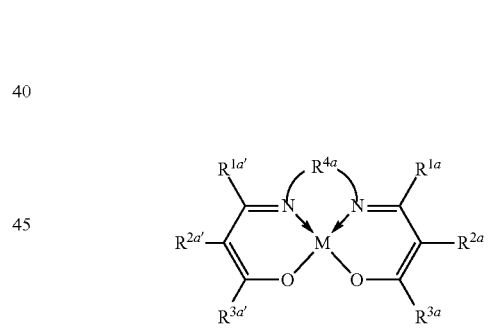

2

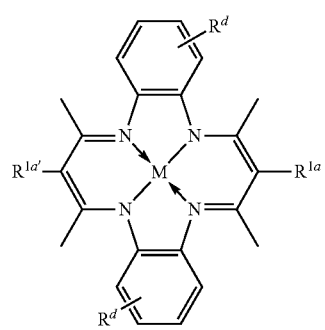

3

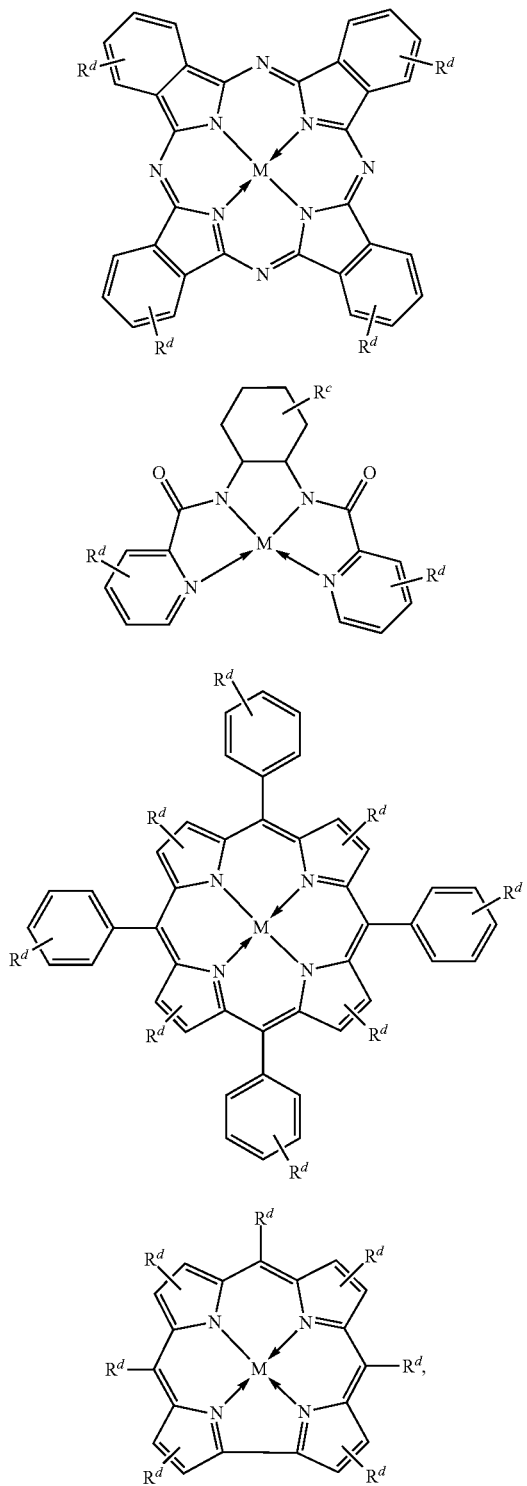

where each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided carbonylation catalysts used in systems and methods described herein comprise metal-porphinato complexes. In some embodiments, the moiety

has the structure:

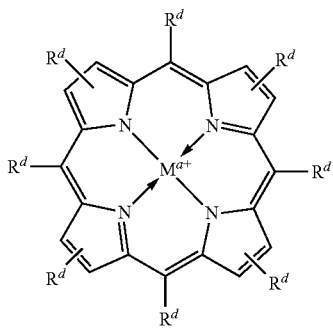

where each of M and a is as defined above and described in the classes and subclasses herein, and $R^d$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or R.

In some embodiments, the moiety

has the structure:

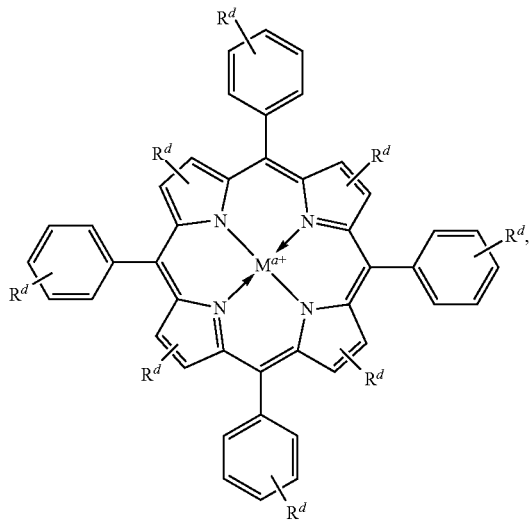

where M, a and $R^d$ are as defined above and in the classes and subclasses herein.

In some embodiments, the moiety

has the structure:

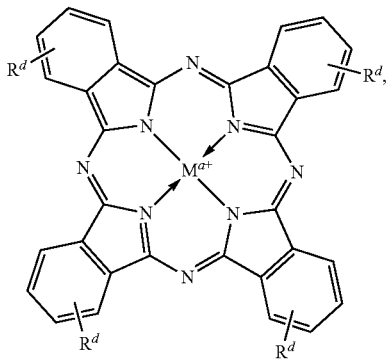

where M, a and $R^d$ are as defined above and in the classes and subclasses herein.

In some embodiments, Lewis acids included in carbonylation catalysts used in systems and methods described herein comprise metallo salenate complexes. In some embodiments, the moiety

has the structure:

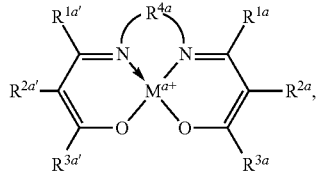

wherein:
M, and a are as defined above and in the classes and subclasses herein.

$R^{1a}$, $R^{1a'}$, $R^{2a}$, $R^{2a'}$, $R^{3a}$, and $R^{3a'}$ are independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

e)

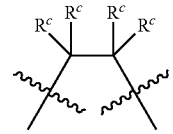

f)

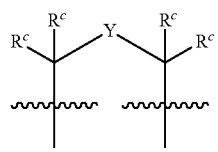

g)

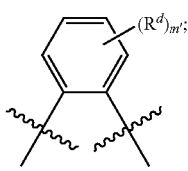

and h)

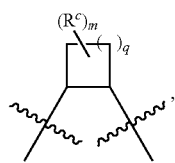

where
R$^c$ at each occurrence is independently hydrogen, halogen, —OR$^4$, —NR$^y_2$, —SR$^y$, —CN, —NO$_2$, —SO$_2$R$^y$, —SOR$^y$, —SO$_2$NR$^y_2$; —CNO, —NR$^y$SO$_2$R$^y$, —NCO, —N$_3$, —SiR$^y_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:
  two or more R$^c$ groups may be taken together with the carbon atoms to which they are attached and any intervening atoms to form one or more rings;
  when two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
where R$^4$ and R$^y$ are as defined above and in classes and subclasses herein;
Y is a divalent linker selected from the group consisting of: —NR$^y$—, —N(R$^y$)C(O)—, —C(O)NR$^y$—, —O—, —C(O)—, —OC(O)—, —C(O)O—, —S—, —SO—, —SO$_2$—, —C(=S)—, —C(=NR$^y$)—, —N=N—; a polyether; a C$_3$ to C$_8$ substituted or unsubstituted carbocycle; and a C$_1$ to C$_8$ substituted or unsubstituted heterocycle;
m' is 0 or an integer from 1 to 4, inclusive;
q is 0 or an integer from 1 to 4, inclusive; and
x is 0, 1, or 2.

In some embodiments, a provided Lewis acid comprises a metallo salen compound, as shown in formula Ia:

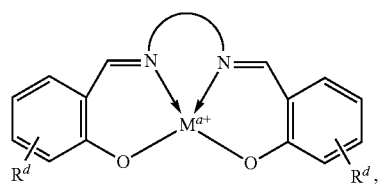

wherein each of M, R$^d$, and a, is as defined above and in the classes and subclasses herein, ⌒ represents is an optionally substituted moiety linking the two nitrogen atoms of the diamine portion of the salen ligand, where ⌒ is selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_{2-20}$ aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—.

In some embodiments metal complexes having formula Ia above, at least one of the phenyl rings comprising the salicylaldehyde-derived portion of the metal complex is independently selected from the group consisting of:

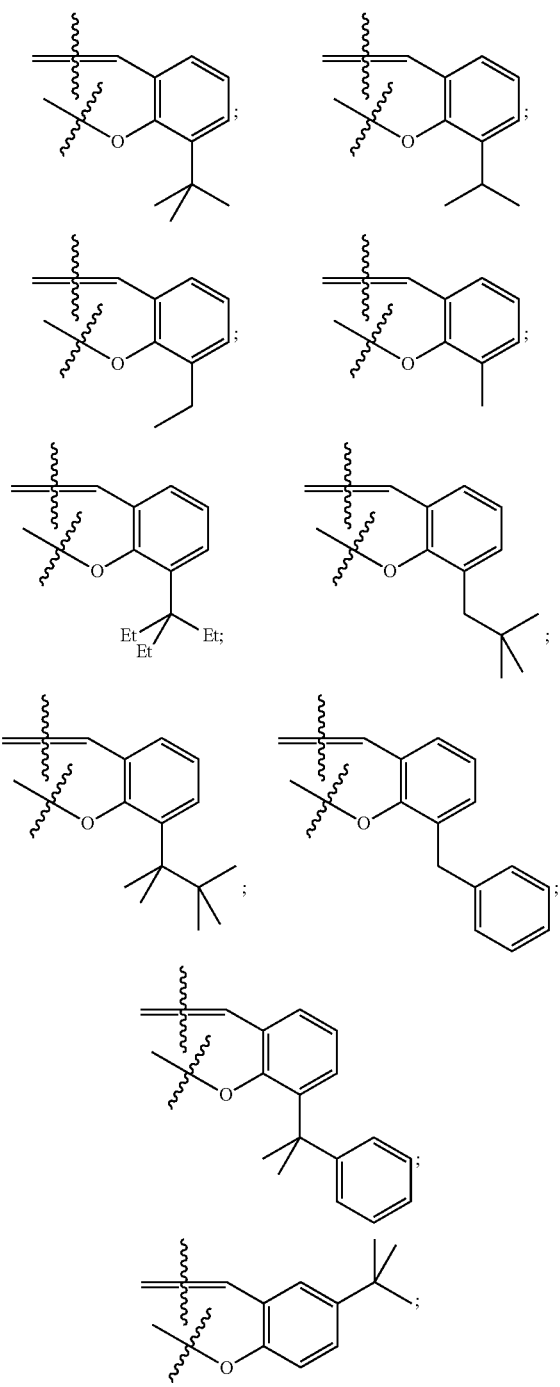

-continued
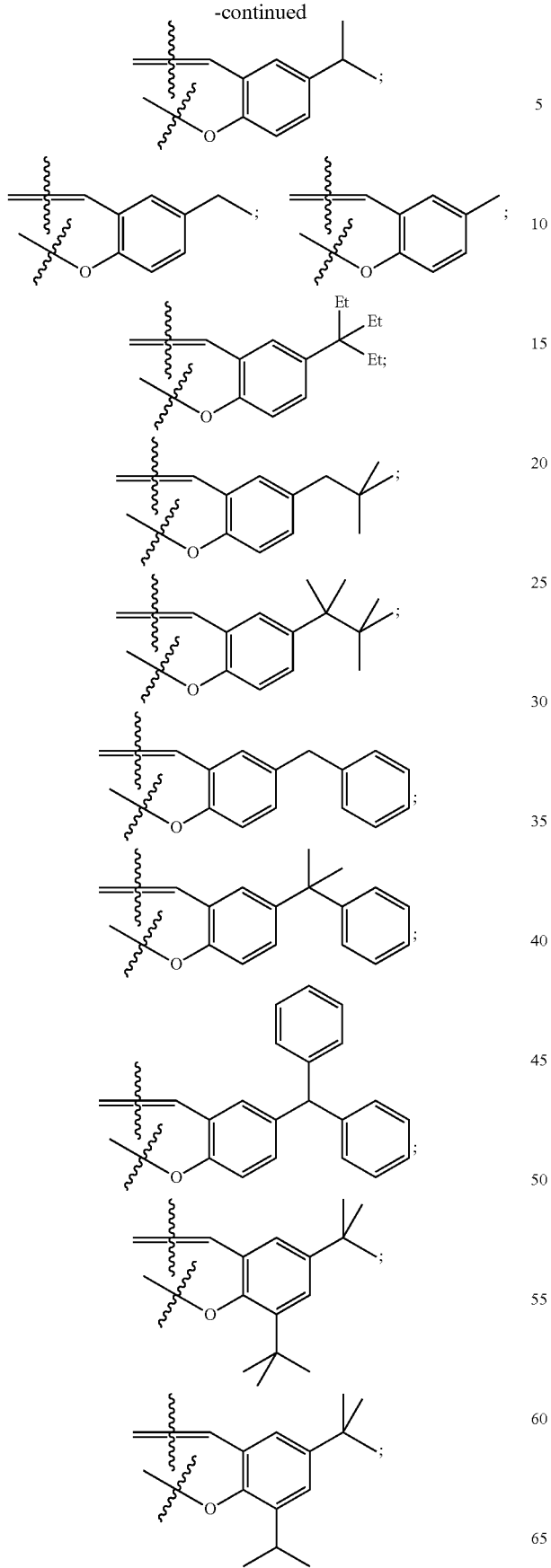
-continued
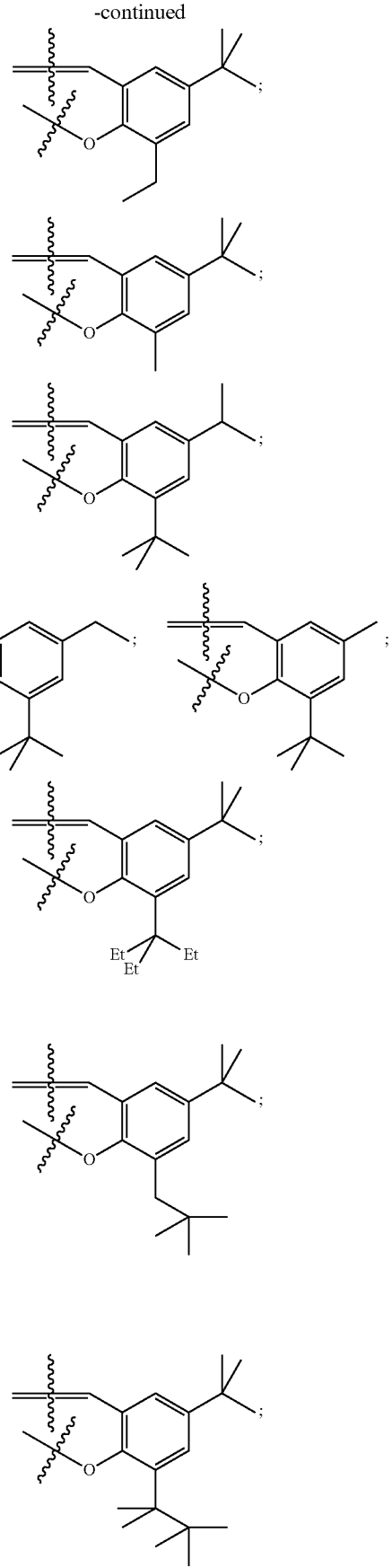

-continued

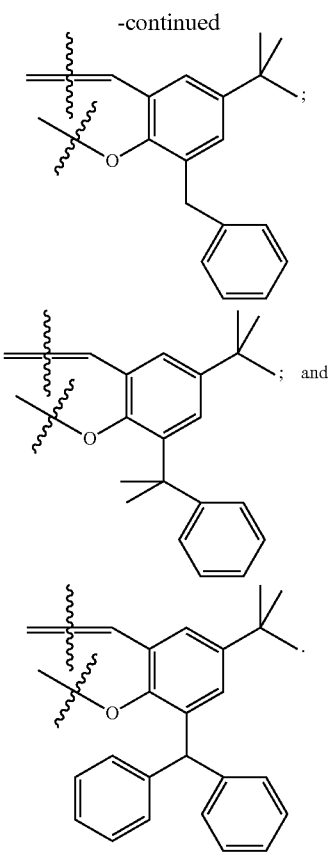

In some embodiments, a provided Lewis acid comprises a metallo salen compound, conforming to one of formulae Va or Vb:

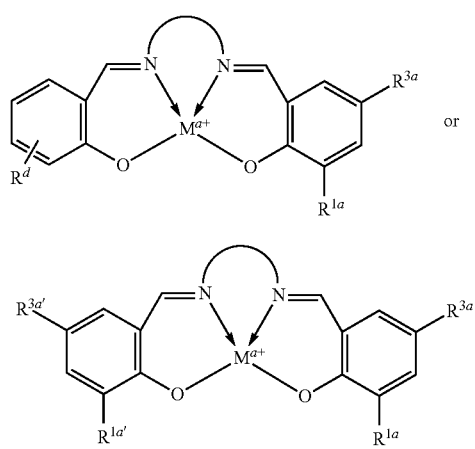

where M, a, $R^d$, $R^{1a}$, $R^{3a}$, $R^{1a'}$, $R^{3a'}$, and ⌒ are as defined above and in the classes and subclasses herein.

In some embodiments of metal complexes having formulae Va or Vb, each $R^{1a}$ and $R^{3a}$ is, independently, optionally substituted $C_1$-$C_{20}$ aliphatic.

In some embodiments, the moiety ⌒ comprises an optionally substituted 1,2-phenyl moiety.

In some embodiments, Lewis acids included in carbonylation catalysts used in systems and methods described herein comprise metal-tmtaa complexes. In some embodiments, the moiety

has the structure:

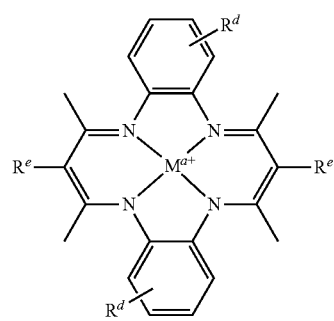

where M, a and $R^d$ are as defined above and in the classes and subclasses herein, and $R^e$ at each occurrence is independently hydrogen, halogen, —OR, —NR$^y_2$, —SR$^y$, —CN, —NO$_2$, —SO$_2$R$^y$, —SOR$^y$, —SO$_2$NR$^y_2$; —CNO, —NR$^y$SO$_2$R$^y$, —NCO, —N$_3$, —SiR$^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

has the structure:

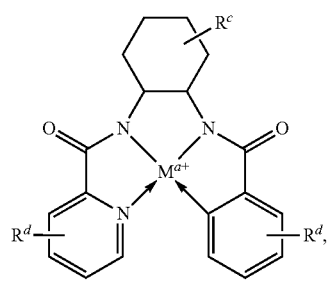

where each of M, a, $R^c$ and $R^d$ is as defined above and in the classes and subclasses herein.

In some embodiments, where carbonylation catalysts used in systems and methods described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

In some embodiments, the carbonylation catalyst includes a carbonyl cobaltate in combination with an aluminum porphyrin compound. In some embodiments, the carbonylation catalyst is [(TPP)Al(THF)$_2$][Co(CO)$_4$] where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

In certain embodiments, the carbonylation catalyst includes a carbonyl cobaltate in combination with an aluminum porphyrin compound. In certain embodiments, the carbonylation catalyst includes a carbonyl cobaltate in combination with a chromium porphyrin compound. In certain embodiments, the carbonylation catalyst includes a carbonyl cobaltate in combination with a chromium salen compound. In certain embodiments, the carbonylation catalyst includes a carbonyl cobaltate in combination with a chromium salophen compound. In certain embodiments, the carbonylation catalyst includes a carbonyl cobaltate in combination with an aluminum salen compound. In certain embodiments, the carbonylation catalyst includes a carbonyl cobaltate in combination with an aluminum salophen compound.

Biphasic Carbonylation Catalysts

In some embodiments, the carbonylation catalyst is biphasic. Thus, in certain variations, the carbonylation reaction product mixture comprises at least two phases, wherein one phase is a catalyst phase and a second phase is a product phase, wherein following the carbonylation reaction, the majority of the carbonylation catalyst is located in the catalyst phase, and the majority of the bPL produced is located in the product phase. For example, in some embodiments, between 50 wt % and 100 wt %, between 60 wt % and 100 wt %, between 70 wt % and 100 wt %, between 80 wt % and 100 wt %, between 90 wt % and 100 wt %, or between 95 wt % and 100 wt % of the carbonylation catalyst is located in the catalyst phase. In some embodiments, between 50 wt % and 100 wt %, between 60 wt % and 100 wt %, between 70 wt % and 100 wt %, between 80 wt % and 100 wt %, between 90 wt % and 100 wt %, or between 95 wt % and 100 wt % of the bPL produced is located in the product phase. In some embodiments, the biphasic carbonylation catalyst is any of the carbonylation catalysts described herein, provided the catalyst is at least partially immiscible with bPL. In other embodiments, the carbonylation catalyst is any of the carbonylation catalysts described herein modified to contain a substituent to make the modified catalyst at least partially immiscible with bPL.

In some embodiments, the carbonylation catalyst is at least partially immiscible with bPL under certain conditions, but miscible with bPL under other conditions. For example, in some variations, the biphasic catalyst is completely miscible with bPL in the carbonylation product stream at one temperature and at least partially immiscible with bPL in the carbonylation product stream at a lower temperature. In other variations, the biphasic catalyst comprises one or more ionizable functional groups which enable the catalyst to be miscible with bPL in the carbonylation product stream at one pH, and at least partially immiscible at a different pH. Thus, in some embodiments, the biphasic catalyst is combined with EO and CO at a first pH to produce bPL, wherein the biphasic catalyst is miscible with bPL, and then the pH of the reaction mixture is changed such that the biphasic catalyst is at least partially immiscible with bPL.

Monitoring and Replacing Catalyst

In one aspect, the production system/production process is configured for continuous carbonylation of an epoxide or lactone feedstock, the process comprising the steps of:

reacting an epoxide or lactone feedstock with carbon monoxide in the presence of a catalyst comprising a Lewis acid and a metal carbonyl in a carbonylation reaction vessel;

measuring one or more parameters selected from the group consisting of:

i) a concentration of the Lewis acid, or a decomposition product thereof, within the carbonylation reaction vessel;

ii) a concentration of the Lewis acid, or a decomposition product thereof, in a product stream downstream from the carbonylation reaction vessel;

iii) a concentration of the metal carbonyl, or a decomposition product thereof, within the carbonylation reaction vessel;

iv) a concentration of the metal carbonyl, or a decomposition product thereof, in a product stream downstream from the carbonylation reaction vessel; and v) a rate of the carbonylation reaction;

comparing the measured value of the one or more parameters to predetermined reference values for the one or more parameters; and where the measured value of any one of parameters i), iii), or v) is less than the reference value, or where the measured value of any one of parameters ii) or iv) is greater than the reference value, introducing to the carbonylation reaction vessel a catalyst replacement component which is different from the catalyst and comprises a species selected from the group consisting of the Lewis acid, a precursor to the Lewis acid, the metal carbonyl, and a precursor to the metal carbonyl.

In some embodiments, one of the one or more parameters measured is the concentration of the Lewis acid, or a decomposition product thereof, within the carbonylation reaction vessel. In some embodiments, the concentration of the Lewis acid within the carbonylation reaction vessel is measured. In some embodiments, the concentration of a decomposition product of the Lewis acid within the carbonylation reaction vessel is measured.

In some embodiments, one of the one or more parameters measured is the concentration of the metal carbonyl, or a decomposition product thereof, within the carbonylation reaction vessel. In some embodiments, the concentration of the metal carbonyl within the carbonylation reaction vessel is measured. In some embodiments, the concentration of a decomposition product of the metal carbonyl within the carbonylation reaction vessel is measured.

In some embodiments, one of the one or more parameters measured is the concentration of the Lewis acid, or a decomposition product thereof, in the product stream downstream from the carbonylation reaction vessel. In some embodiments, the concentration of the Lewis acid in the product stream downstream from the carbonylation reaction vessel is measured. In some embodiments, the concentration of a decomposition product of the Lewis acid in the product stream downstream from the carbonylation reaction vessel is measured.

In some embodiments, one of the one or more parameters measured is the concentration of the metal carbonyl, or a decomposition product thereof, in the product stream downstream from the carbonylation reaction vessel. In some embodiments, the concentration of the metal carbonyl in the product stream downstream from the carbonylation reaction vessel is measured. In some embodiments, the concentration of a decomposition product of the metal carbonyl in the product stream downstream from the carbonylation reaction vessel is measured.

In some embodiments, one of the one or more parameters measured is the rate of the carbonylation reaction. In some embodiments, the rate of the carbonylation reaction is measured by the change in concentration of a carbonylation product in the carbonylation reaction vessel over time. In some embodiments, the rate of the carbonylation reaction is measured by the change in concentration of a carbonylation product in the product stream downstream from the carbonylation reaction vessel over time. In some embodiments, the carbonylation product is a beta-propiolactone. In some embodiments, the carbonylation product is beta-propiolactone (bPL). In some embodiments, the carbonylation product is a succinic anhydride. In some embodiments the carbonylation product is succinic anhydride (SA).

In some embodiments, the product stream is separated from the carbonylation reaction vessel by a nanofiltration membrane. In some embodiments, the nanofiltration membrane is selected based on its ability to retain solutes having a molecular weight greater than the molecular weight of the epoxide or lactone carbonylation products, but less than the molecular weights of either the Lewis acid or the metal carbonyl. In some embodiments, the nanofiltration membrane is designed to retain solutes having a molecular weight greater than the molecular weight of the epoxide or lactone carbonylation products, but less than the molecular weights of either the Lewis acid or the metal carbonyl.

In some embodiments, the catalyst replacement component comprises the Lewis acid, or a precursor to the Lewis acid. In some embodiments, the catalyst replacement component comprises the Lewis acid. In some embodiments, the catalyst replacement component comprises a precursor to the Lewis acid.

In some embodiments, the catalyst replacement component comprises the metal carbonyl, or a precursor to the metal carbonyl. In some embodiments, the catalyst replacement component comprises the metal carbonyl. In some embodiments, the catalyst replacement component comprises a precursor to the metal carbonyl.

In some embodiments, where more than one catalyst replacement component is added, each of the one or more catalyst replacement components is added to the carbonylation reaction vessel separately. In some embodiments, where more than one catalyst replacement component is added, all of the one or more catalyst replacement components are added to the carbonylation reaction vessel together.

In some embodiments, each of the one or more catalyst replacement components is added individually to the carbonylation reaction vessel without solvent, as a solution in an organic solvent, or as a slurry. In some embodiments, each of the one or more catalyst replacement components is added to the carbonylation reaction vessel without solvent. In some embodiments, each of the one or more catalyst replacement components is added to the carbonylation reaction vessel as a solution in an organic solvent. In some embodiments, each of the one or more catalyst replacement components is added to the carbonylation reaction vessel as a slurry.

In certain embodiments, where more than one catalyst replacement component are added, each catalyst replacement component is dissolved in solution, and the solutions are combined enroute to the vessel, e.g., by using a mixing tee or flowing the combined solutions through a static mixer.

In certain embodiments, fresh catalyst may also be added to the reaction vessel at the same or different times as the one or more catalyst replacement components.

In certain embodiments, the catalyst replacement components are added under an atmosphere comprising CO. In certain embodiments, the CO is present at a pressure from about 1 atmosphere to about 400 atmospheres. In certain embodiments, the catalyst replacement components are added under an atmosphere comprising CO at a pressure between about 1 atmosphere and about 100 atmospheres, or between about 1 atmosphere and about 50 atmospheres, or between about 10 atmospheres and about 20 atmospheres, or between about 5 atmospheres and about 10 atmospheres, or between about 1 atmosphere and about 5 atmospheres.

In some embodiments, the amount of a given catalyst replacement component added to the carbonylation reaction vessel is proportional to one of the parameters being measured in step (a). In some embodiments, the amount of a given catalyst replacement component is directly proportional to changes in the concentration of the parameter measured in the product stream downstream from the carbonylation reaction vessel.

In some embodiments, if the concentration of the Lewis acid, or a decomposition product thereof, measured in step (a) is increased in the product stream downstream from the carbonylation reaction vessel, an amount of Lewis acid that is proportional to the increase in the concentration of Lewis acid, or a decomposition product thereof, measured in step (a) is added to the carbonylation reaction vessel. In some embodiments, if the concentration of the Lewis acid, or a decomposition product thereof, measured in step (a) is decreased within the carbonylation reaction vessel, an amount of Lewis acid, or a precursor to the Lewis acid, that is proportional to the decrease in the concentration of Lewis acid, or a decomposition product thereof, measured in step (a) is added to the carbonylation reaction vessel. For example, if the concentration of the Lewis acid has decreased by 5%, an amount of the Lewis acid or precursor to the Lewis acid that is equivalent to about 5% of the amount of the Lewis acid initially charged into the carbonylation reaction vessel is added.

In some embodiments, if the rate of the carbonylation reaction, measured in step (a) is decreased, an amount of Lewis acid, or a precursor to the Lewis acid, that is proportional to the decrease in the rate of the carbonylation reaction is added to the carbonylation reaction vessel. In some embodiments, if the rate of the carbonylation reaction measured in step (a) is decreased, an amount of the metal carbonyl or a precursor to the metal carbonyl that is proportional to the decrease in the rate of the carbonylation reaction is added to the carbonylation reaction vessel. For example, if the rate of the carbonylation reaction has decreased by 5%, an amount of Lewis acid, precursor to the Lewis acid, metal carbonyl, or precursor to the metal carbonyl that is equivalent to about 5% of the amount of the Lewis acid or metal carbonyl initially charged into the carbonylation reaction vessel is added.

In some embodiments, if the concentration of the metal carbonyl, measured in step (a) is increased in the product stream downstream from the carbonylation reaction vessel, an amount of metal carbonyl, or a precursor to the metal carbonyl that is proportional to the increase in the amount of metal carbonyl measured in step (a) is added to the carbonylation reaction vessel. In some embodiments, if the concentration of the metal carbonyl, or a decomposition product thereof, measured in step (a) is decreased within the carbonylation reaction vessel, an amount of metal carbonyl, or a precursor to the metal carbonyl, that is proportional to the decrease in the amount of metal carbonyl, or a decomposition product thereof, measured in step (a) is added to the carbonylation reaction vessel. For example, if the concentration of the metal carbonyl has decreased by 5%, an amount of the metal carbonyl or precursor to the metal carbonyl that is equivalent to about 5% of the amount of the metal carbonyl initially charged into the carbonylation reaction vessel is added.

FIG. 14 includes carbonylation catalyst source 1403 that can feed fresh carbonylation catalyst in carbonylation catalyst stream 1407 to carbonylation reaction system inlet 1409. Carbonylation catalyst can arrive to the carbonylation catalyst source as either solids (perhaps blanketed under CO or a suitable inert gas) or in solution of solvent such as hexane or THF. If solid catalysts, the solids can be unpacked and loaded into one or more hoppers under inert conditions (for example, CO or inert gas). The solids from the one or more hoppers can be metered into a suitable solvent before pumping. In some embodiments, the solid catalyst (or liquid catalyst) or catalyst precursors can be dispensed from a shipping vessel/container into an intermediate inert vessel to be mixed with solvent and then pumped. In some embodiments, the catalyst preparation system and connections are selected such that the catalyst/precursors are not exposed to the atmosphere. Carbonylation catalyst solutions can be suitable for direct pumping to the carbonylation reaction system. In some embodiments, the carbonylation catalyst feed is pumped under CO pressure to help ensure stability of the catalyst. Furthermore, carbonylation catalyst source and feed can be cooled below ambient temperature to ensure stability. In some embodiments, the inlet to the carbonylation reaction system can receive carbonylation catalyst from a carbonylation catalyst source at between about 0.01 to 50 kg/hr, between about 0.01 to 40 kg/hr, between about 0.01 to 30 kg/hr, between about 0.01 to 20 kg/hr, between about 0.01 to 10 kg/hr, between about 0.2-5 kg/hr, between about 0.5-4 kg/hr, between about 1-3 kg/hr, between about 1-2 kg/hr, or about 1.4 kg/hr. In some embodiments, the inlet to the carbonylation reaction system can receive carbonylation catalyst from a carbonylation catalyst source at between about 0.0001-10 kmol/hr, between about 0.0001-1 kmol/hr, between about 0.0001-0.1 kmol/hr, between about 0.0001-0.01 kmol/hr, between about 0.0005-0.001 kmol/hr, between about 0.0005-0.005 kmol/hr, or about 0.001 kmol/hr, or about 0.01 kmol/hr, or about 0.1 kmol/hr. In some embodiments, the carbonylation catalyst can be in a solvent such as THF so that the mass fraction of carbonylation catalyst in the stream from the carbonylation catalyst source can be between about 0.001-0.1, about 0.005-0.05, about 0.01-0.05, or about 0.02. In some embodiments, the inlet to the carbonylation reaction system can receive carbonylation catalyst from a carbonylation catalyst source at a temperature between about 10-30° C., between about 15-25° C., or about 20° C. In some embodiments, the inlet to the carbonylation reaction system can receive carbonylation catalyst from a carbonylation catalyst source at a pressure of at least about 50 bar, about 60-70 bar, or at least about 65 bar.

Carbon Monoxide Source

Carbon monoxide is fed into the β-propiolactone production system/production process at an amount sufficient to carbonylate ethylene oxide to produce β-propiolactone. In some variations, this may be achieved performing the carbonylation reaction under a superatmospheric pressure of carbon monoxide. In certain embodiments, the carbon monoxide is provided into the β-propiolactone production system/production process at a pressure in the range from about 50 psi (350 kPa) to about 5000 psi (35 MPa). In certain embodiments, the carbon monoxide is provided into the β-propiolactone production system/production process at a pressure from about 50 psi (350 kPa) to about 1000 psi (7 MPa). In certain embodiments, the carbon monoxide is provided into the β-propiolactone production system/production process at a pressure from about 50 psi (350 kPa) to about 500 psi (3.5 MPa). In certain embodiments, the carbon monoxide is provided into the β-propiolactone production system/production process at a pressure from about 100 psi (700 kPa) to about 400 psi (2.8 MPa). In certain embodiments, the carbon monoxide is provided into the β-propiolactone production system/production process at a pressure of about 200 psi (1.4 MPa). In certain embodiments, the carbon monoxide is provided into the β-propiolactone production system/production process under an atmosphere having a partial pressure of CO of about 200 psi (1.4 MPa). The superatmospheric pressure of carbon monoxide may be provided in the form of pure carbon monoxide, or by providing a gas mixture containing carbon monoxide. In certain embodiments, the carbon monoxide may be provided in the form of substantially pure carbon monoxide. In other embodiments, the carbon monoxide may be provided in the form of carbon monoxide mixed with one or more inert gases. In other embodiments, the carbon monoxide may be provided in the form of a mixture of carbon monoxide and hydrogen. In certain embodiments, the carbon monoxide may be provided in the form of a carbon monoxide-containing industrial process gas such as syngas, coal gas, wood gas, or the like.

FIG. 14 includes carbon monoxide source 1411 that can feed carbon monoxide to carbonylation reaction system inlet 1409. In some embodiments, the carbon monoxide source that supplies carbon monoxide to the carbonylation reaction system can include fresh carbon monoxide source 1401 (i.e., main CO feed) and recycled carbon monoxide stream 1410 from the carbonylation reaction system. In some embodiments, the carbon monoxide source can be only the fresh carbon monoxide source. In some embodiments, the carbon monoxide source can be only the recycled carbon monoxide. In some embodiments, fresh carbon monoxide stream 1405 and/or the recycled carbon monoxide streams can be fed into carbon monoxide compressor 1401A prior to the resultant stream from the carbon monoxide compressor (i.e., reactor carbon monoxide inlet stream) being fed into the carbonylation reaction system. In some embodiments, resultant stream from the carbon monoxide compressor 1411 (i.e., reaction system carbon monoxide inlet stream) can be the carbon monoxide source. The carbon monoxide source can be compressed to the pressure at or above the carbonylation reaction system pressure and then fed to the carbonylation system. In some embodiments, the fresh carbon monoxide source (i.e., main CO feed) and the recycled carbon monoxide can be compressed in separate compressors. One reason recycled carbon monoxide can be compressed separately from the fresh carbon monoxide feed (i.e., main CO feed) to reaction system pressure is to avoid contamination of the main compressor (i.e., fresh feed compressor) with hazardous components such as ethylene oxide and bPL that may be present in the carbon monoxide recycle stream. Some of these potentially hazardous components may be removed from the compressor as partially liquefied components as waste. In some embodiments, these potentially hazardous components can also be recycled to the carbonylation reaction system. In some embodiments, the compressed carbon monoxide from both compressors can be fed to the carbonylation reaction system as the reaction system carbon monoxide inlet stream.

In some embodiments, the fresh carbon monoxide source can provide at least about 1000 kg/hr CO, at least about 1200 kg/hr CO, at least about 1400 kg/hr CO, at least about 1500 kg/hr CO, at least about 1600 kg/hr CO, at least about 2000 kg/hr CO, at least about 4000 kg/hr CO, at least about 5000 kg/hr CO, at least about 10000 kg/hr CO, at least about 12000 kg/hr CO, at least about 14000 kg/hr CO, at least about 15000 kg/hr CO, or at least about 16000 kg/hr CO. In some embodiments, the fresh carbon monoxide source can provide at least about 30 kmol/hr CO, at least about 40 kmol/hr CO, at least about 50 kmol/hr CO, at least about 55 kmol/hr CO, or at least about 60 kg/hr CO. In some embodiments, the fresh carbon monoxide source can provide about 1000 kg/hr CO to about 16000 kg/hr CO, about 1200 kg/hr CO to about 16000 kg/hr CO, about 1400 kg/hr CO to about 16000 kg/hr CO, about 1500 kg/hr CO to about 16000 kg/hr CO, about 1600 kg/hr CO to about 16000 kg/hr CO, about 2000 kg/hr CO to about 16000 kg/hr CO, about 4000 kg/hr CO to about 16000 kg/hr CO, about 6000 kg/hr CO to about 16000 kg/hr CO, about 1000 kg/hr CO to about 16000 kg/hr CO, or about 1400 kg/hr CO to about 16000 kg/hr CO. In some embodiments, the fresh carbon monoxide source can provide about 1000 kg/hr CO, about 1200 kg/hr CO, about 1400 kg/hr CO, about 1500 kg/hr CO, about 1600 kg/hr CO, about 1800 kg/hr CO, about 2000 kg/hr CO, about 2400 kg/hr CO, about 2600 kg/hr CO, about 2800 kg/hr CO, about 3000 kg/hr CO, about 3200 kg/hr CO, about 4000 kg/hr CO, about 6000 kg/hr CO, about 8000 kg/hr CO, about 10000 kg/hr CO, about 12000 kg/hr CO, about 14000 kg/hr CO, or about 16000 kg/hr CO. In some embodiments, the fresh carbon monoxide source can provide at least about 30 kmol/hr CO, at least about 40 kmol/hr CO, at least about 50 kmol/hr CO, at least about 55 kmol/hr CO, at least about 60 kmol/hr CO, at least about 100 kmol/hr CO, at least about 150 kmol/hr CO, at least about 200 kmol/hr CO, at least about 250 kmol/hr CO, at least about 300 kg/hr CO, at least about 350 kmol/hr CO, at least about 400 kmol/hr CO, at least about 500 kmol/hr CO, at least about 550 kmol/hr CO, or at least about 600 kg/hr CO. In some embodiments, the fresh carbon monoxide source can provide about 30 kmol/hr CO to about 60 kmol/hr CO, about 40 kmol/hr CO to about 60 kmol/hr CO, about 50 kmol/hr CO to about 60 kmol/hr CO, about 30 kmol/hr CO to about 600 kmol/hr CO, about 40 kmol/hr CO to about 600 kmol/hr CO, about 50 kmol/hr CO to about 600 kmol/hr CO, about 55 kmol/hr CO to about 600 kmol/hr CO, about 100 kmol/hr CO to about 600 kmol/hr CO, about 200 kg/hr CO to about 600 kmol/hr CO, about 300 kmol/hr CO to about 600 kmol/hr CO, about 400 kmol/hr CO to about 600 kmol/hr CO, about 500 kmol/hr CO to about 600 kmol/hr CO, about 525 kmol/hr CO to about 600 kmol/hr CO, about 550 kg/hr CO to about 600 kmol/hr CO. In some embodiments, the fresh carbon monoxide from the fresh carbon monoxide source may have some impurities and thus may require additional purification steps such as adsorption. In some embodiments, the flow rate from the fresh carbon monoxide source is set to about the stoichiometric value for the carbonylation reaction, to about 5% higher than the stoichiometric value, to about 10% higher than the stoichiometric value, to about 15% higher than the stoichiometric value, or to about 20% higher than the stoichiometric value.

In some embodiments, the recycled carbon monoxide from the carbonylation reaction system can provide at least about 100 kg/hr CO, at least about 150 kg/hr CO, at least about 200 kg/hr CO, at least about 255 kg/hr CO, at least about 300 kg/hr CO, at least about 350 kg/hr CO, at least about 500 kg/hr CO, at least about 600 kg/hr CO, at least about 800 kg/hr CO, at least about 1000 kg/hr CO, at least about 1250 kg/hr CO, at least about 1500 kg/hr CO, at least about 1750 kg/hr CO, at least about 2000 kg/hr CO, at least about 2500 kg/hr CO, at least about 3000 kg/hr CO, or at least about 3500 kg/hr CO. In some embodiments, the recycled carbon monoxide from the carbonylation reaction system can provide from about 100 kg/hr CO to about 350 kg/hr CO, about 150 kg/hr CO to about 350 kg/hr CO, about 200 kg/hr CO to about 350 kg/hr CO, about 255 kg/hr CO to about 350 kg/hr CO, about 300 kg/hr CO to about 350 kg/hr CO, from about 100 kg/hr CO to about 3500 kg/hr CO, about 150 kg/hr CO to about 3500 kg/hr CO, about 200 kg/hr CO to about 3500 kg/hr CO, about 255 kg/hr CO to about 3500 kg/hr CO, about 300 kg/hr CO to about 3500 kg/hr CO, about 350 kg/hr CO to about 3500 kg/hr CO, about 1000 kg/hr CO to about 3500 kg/hr CO, about 1500 kg/hr CO to about 3500 kg/hr CO, about 2000 kg/hr CO to about 3500 kg/hr CO, about 2550 kg/hr CO to about 3500 kg/hr CO, about 3000 kg/hr CO to about 3500 kg/hr CO. In some embodiments, the recycled carbon monoxide from the carbonylation reaction system can provide about 100 kg/hr CO, about 150 kg/hr CO, about 200 kg/hr CO, about 255 kg/hr CO, about 300 kg/hr CO, about 350 kg/hr CO, about 500 kg/hr CO, about 750 kg/hr CO, about 1000 kg/hr CO, about 1250 kg/hr CO, about 1500 kg/hr CO, about 2000 kg/hr CO, about 2500 kg/hr CO, about 3000 kg/hr CO, or about 3500 kg/hr CO. In some embodiments, the recycled carbon monoxide source can provide at least about 3 kmol/hr CO, at least about 5 kmol/hr CO, at least about 7 kmol/hr CO, at least about 9 kmol/hr CO, at least about 10 kmol/hr CO, at least about 15 kmol/hr CO, at least 50 kmol/hr CO, at least 100 kmol/hr CO, or at least 150 kmol/hr CO. In some embodiments, the mass fraction of CO in the recycled carbon monoxide stream can be at least about 0.70, at least about 0.75, at least about 0.8, or at least about 0.85. In some embodiments, the mole fraction of CO in the recycled carbon monoxide stream can be at least about 0.70, at least about 0.75, at least about 0.8, at least about 0.85, at least about 0.896, at least about 0.9, or at least about 0.95. In some embodiments, the mole fraction of CO in the recycled carbon monoxide stream can be 0.70 to 1.0, 0.75 to 1.0, 0.8 to 1.0, 0.85 to 1.0, 0.896 to 1.0, 0.9 to 1.0, or 0.95 to 1.0. The recycled carbon monoxide stream from the carbonylation reaction system can also include unreacted ethylene oxide (in about at most 10 kg/hr, at most 15 kg/hr, at most 20 kg/hr, at most 25 kg/hr, at most 50 kg/hr, at most 75 kg/hr, at most 100 kg/hr, at most 150 kg/hr, at most 200 kg/hr, or at most 250 kg/hr or a mass fraction of between about 0.05-0.075, about 0.055-0.07, about 0.06-0.07, about at most 0.065, about at most 0.07, or about at most 0.075), secondary reaction product acetaldehyde (in about at most 0.5 kg/hr, at most about 1 kg/hr, at most about 1.3 kg/hr, at most about 2 kg/hr, at most about 4 kg/hr, at most about 6 kg/hr, at most about 10 kg/hr, at most about 13 kg/hr or a mass fraction of about 0.001-0.009, about 0.003-0.005, or about most 0.004, about at most 0.005, or about most 0.009), bPL (in about at most about 0.005 kg/hr, at most about 0.01 kg/hr, at most about 0.015 kg/hr, about at most about 0.019 kg/hr, at most about 0.05 kg/hr, at most about 0.1 kg/hr, at most about 0.15 kg/hr, or about at most about 0.19 kg/hr), and the remainder solvent (e.g., THF).

In some embodiments, the inlet to the carbonylation reaction system can receive carbon monoxide from a carbon monoxide source at least about 1000 kg/hr, at least about 1250 kg/hr, at least about 1500 kg/hr, at least about 1600 kg/hr, at least about 1655 kg/hr, at least about 1700 kg/hr, at least about 4000 kg/hr, at least about 5000 kg/hr, at least about 700 kg/hr, at least about 8500 kg/hr, at least about 10000 kg/hr, at least about 12500 kg/hr, at least about 15000 kg/hr, at least about 16000 kg/hr, at least about 16550 kg/hr, or at least about 17000 kg/hr. In some embodiments, the inlet to the carbonylation reaction system can receive carbon monoxide from a carbon monoxide source at about 1000 kg/hr to about 1700 kg/hr, about 1250 kg/hr to about 1700 kg/hr, about 1500 kg/hr to about 1700 kg/hr, about 1600 kg/hr to about 1700 kg/hr, about 1655 kg/hr to about 1700 kg/hr, 1000 kg/hr to about 17000 kg/hr, about 1250 kg/hr to about 17000 kg/hr, about 1500 kg/hr to about 17000 kg/hr, about 1600 kg/hr to about 17000 kg/hr, about 1655 kg/hr to about 17000 kg/hr, about 1700 kg/hr to about 17000 kg/hr, at about 2000 kg/hr to about 17000 kg/hr, about 3000 kg/hr to about 17000 kg/hr, about 4000 kg/hr to about 17000 kg/hr, about 6000 kg/hr to about 17000 kg/hr, about 8000 kg/hr to about 17000 kg/hr, about 1200 kg/hr to about 17000 kg/hr, about 1400 kg/hr to about 17000 kg/hr, about 1500 kg/hr to about 17000 kg/hr, or about 1600 kg/hr to about 17000 kg/hr. In some embodiments, the inlet to the carbonylation reaction system can receive carbon monoxide from a carbon monoxide source at about 1000 kg/hr, about 1250 kg/hr, about 1500 kg/hr, about 1600 kg/hr, about 1655 kg/hr, about 1700 kg/hr, about 2000 kg/hr, about 1900 kg/hr, about 2500 kg/hr, about 3000 kg/hr, about 4000 kg/hr, about 6000 kg/hr, about 8000 kg/hr, about 10000 kg/hr, about 12000 kg/hr, about 13000 kg/hr, about 14000 kg/hr, about 15000 kg/hr, about 16000 kg/hr, or about 17000 kg/hr. In some embodiments, the inlet to the carbonylation reaction system can receive carbon monoxide from a carbon monoxide source at least about 35 kmol/hr, at least about 45 kmol/hr, at least about 50 kmol/hr, at least about 55 kmol/hr, or at least about 59 kmol/hr. As previously discussed, in some embodiments, the carbon monoxide source can include some recycled carbon monoxide from the carbonylation reaction system. Accordingly, in some embodiments, the inlet to the carbonylation reaction system can also receive ethylene oxide (in about 5-300 kg/hr, about 10-200 kg/hr, about 10-100 kg/hr, about 10-50 kg/hr, about 10-30 kg/hr, about 10-20 kg/hr, or at most about 15 kg/hr, at most about 50 kg/hr, at most about 100 kg/hr, at most about 150 kg/hr, at most about 200 kg/hr, at most about 300 kg/hr, or a mass fraction of about 0.001-0.05, about 0.005-0.02, or at most about 0.009, at most about 0.02, or at most about 0.05), acetaldehyde (in about 0.25-15 kg/hr, about 0.5-12.5 kg/hr, about 0.25-10 kg/hr, about 0.5-5 kg/hr, about 0.25-1.5 kg/hr, about 0.5-1.25 kg/hr, or at most about 0.9 kg/hr, at most about 1.5 kg/hr, at most about 3 kg/hr, at most about 6 kg/hr, at most about 12 kg/hr, at most about 15 kg/hr, or a mass fraction of about 0.001-0.05, about 0.005-0.02, or at most about 0.009, at most about 0.02, or at most about 0.05), and the remainder solvent from the carbon monoxide source. In some embodiments, the mass fraction of CO from the carbon monoxide source can be at least about 0.9, at least about 0.95, at least about 0.985, or at least about 0.99. In some embodiments, the mole fraction of CO from the carbon monoxide source can be at least about 0.9, at least about 0.95, at least about 0.98, at least about 0.99, or at least about 0.995. In some embodiments, the mole fraction of CO from the carbon monoxide source can be 0.9 to 1.0, 0.95 to 1.0, 0.98 to 1.0, 0.99 to 1.0, or 0.995 to 1.0.

In some embodiments, the inlet to the carbonylation reaction system can receive carbon monoxide from a carbon monoxide source at a temperature between about 10-170° C., between about 30-70° C., between about 40-60° C., between about 45-55° C., or about 50° C. In some embodiments, the inlet to the carbonylation reaction system can receive carbon monoxide from a carbon monoxide source at a pressure of at least about 50 bar, about 60-70 bar, or at least about 65 bar.

Solvent Source

The solvent may be selected from any solvents described herein, and mixtures of such solvents. In some variations, the solvent is an organic solvent. In certain variations, the solvent is an aprotic solvent.

In some embodiments, the solvent includes dimethylformamide, N-methyl pyrrolidone, tetrahydrofuran, toluene, xylene, diethyl ether, methyl-tert-butyl ether, acetone, methylethyl ketone, methyl-iso-butyl ketone, butyl acetate, ethyl acetate, dichloromethane, and hexane, and mixtures of any two or more of these. In general polar aprotic solvents or hydrocarbons are suitable for this step.

Additionally, in one variation, β-lactone may be utilized as a co-solvent. In other variations, the solvent may include ethers, hydrocarbons and non protic polar solvents. In some embodiments, the solvent includes tetrahydrofuran ("THF"), sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, dimethoxy ethane, acetone, and methylethyl ketone. In other embodiments, the solvent includes tetrahydrofuran, tetrahydropyran, 2,5-dimethyl tetrahydrofuran, sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, propyl acetate, butyl acetate, 2-butanone, cyclohexanone, toluene, difluorobenzene, dimethoxy ethane, acetone, and methylethyl ketone. In certain variations, the solvent is a polar donating solvent. In one variation, the solvent is THF.

In some embodiments, the catalyst and/or solvent stream is recycled to the feed stream or to the carbonylation reaction system. In some embodiments, the portion of the solvent and/or catalyst from the reaction product stream recycled to the carbonylation reactor or feed stream ranges from about 0% to about 100%. In some embodiments, the portion of the solvent and/or catalyst from the reaction product stream recycled to the carbonylation reactor or feed stream is about 100%, about 90%, about 80%, about 70%, about 60%, about 50%, about 40%, about 30%, about 20%, about 10%, or about 0%. In some embodiments, a different percentage of the catalyst, as compared to the solvent is recycled, i.e., the proportions of either the catalyst or solvent component do not need to be equal.

Referring again to the exemplary system depicted in FIG. 14, in some embodiments, solvent feed 1424 can supply solvent to the carbonylation reaction system inlet 1409. Solvent can be fed to the carbonylation reaction system suing a pump. In addition, the solvent streams, sources, storage tanks, etc, can be maintained under an inert or CO atmosphere. In some embodiments, the solvent feed that supplies solvent to the carbonylation reaction system can include solvent 1408 from fresh solvent source 1404, recycled solvent 1423 from the BPL purification system, and/or solvent in recycled carbonylation catalyst stream 1412 from the carbonylation catalyst isolation system. In some embodiments, the recycled solvent from the BPL purification system can be stored in a make-up solvent reservoir. In some embodiments, the solvent feed that supplies solvent to the carbonylation reaction system can include solvent from the make-up solvent reservoir. In some embodiments, solvent can be purged from the system. In some embodiments, the purged solvent can be solvent from the recycled solvent of the BPL purification system. In some embodiments, solvent from the fresh solvent source is also stored into the make-up solvent reservoir to dilute the recycled solvent from the BPL purification system with fresh solvent. In some embodiments, fresh solvent is fed from the fresh solvent source to the make-up solvent reservoir prior to entering the carbonylation reaction system. In some embodiments, solvent from the fresh solvent source, the BPL purification system, and the carbonylation catalyst isolation system can be purified by operations such as adsorption to remove oxygen and water that can inhibit the carbonylation catalyst. In some embodiments, the amount of oxygen and/or water in all streams entering the carbonylation reaction system is less than about 500 ppm, less than about 250 ppm, less than about 100 ppm, less than about 50 ppm, less than about 20 ppm, less than about 10 ppm, less than about 5 ppm, less than about 2 ppm, or less than about 1 ppm.

In some embodiments, the fresh solvent source can provide at least about 50 kg/hr solvent, at least about 100 kg/hr solvent, at least about 150 kg/hr solvent, at least about 188 kg/hr solvent, at least about 200 kg/hr solvent, at least about 250 kg/hr solvent, at least about 500 kg/hr solvent, at least about 1000 kg/hr solvent, at least about 1500 kg/hr solvent, at least about 1880 kg/hr solvent, at least about 2000 kg/hr solvent, or at least about 2500 kg/hr solvent. In some embodiments, the fresh solvent source can provide about 50 kg/hr to about 250 kg/hr solvent, about 100 kg/hr to about 250 kg/hr solvent, about 150 kg/hr to about 250 kg/hr solvent, about 188 kg/hr to about 250 kg/hr solvent, about 200 kg/hr to about 250 kg/hr solvent, about 50 kg/hr to about 2500 kg/hr solvent, about 100 kg/hr to about 2500 kg/hr solvent, about 150 kg/hr to about 2500 kg/hr solvent, about 188 kg/hr to about 2500 kg/hr solvent, about 200 kg/hr to about 2500 kg/hr solvent, about 250 kg/hr to about 2500 kg/hr solvent, about 500 kg/hr to about 2500 kg/hr solvent, about 1000 kg/hr to about 2500 kg/hr solvent, about 1500 kg/hr to about 2500 kg/hr solvent, about 1880 kg/hr to about 2500 kg/hr solvent, about 2000 kg/hr to about 2500 kg/hr solvent, or about 2250 kg/hr to about 2500 kg/hr solvent. In some embodiments, the fresh solvent source can provide about 50 kg/hr solvent, about 100 kg/hr solvent, about 150 kg/hr solvent, about 188 kg/hr solvent, about 200 kg/hr solvent, about 250 kg/hr solvent, about 500 kg/hr solvent, about 1000 kg/hr solvent, about 1500 kg/hr solvent, about 1880 kg/hr solvent, about 2000 kg/hr solvent, or about 2500 kg/hr solvent. In some embodiments, the fresh solvent source can provide at least about 1 kmol/hr solvent, at least about 2 kmol/hr solvent, at least about 2.6 kmol/hr solvent, at least about 3 kmol/hr solvent, at least about 50 kmol/hr solvent, at least about 100 kmol/hr solvent, at least about 150 kmol/hr solvent, at least about 250 kmol/hr solvent, at least about 400 kmol/hr solvent, or at least about 500 kmol/hr solvent.

In some embodiments, the recycled solvent from the BPL purification system can provide at least about 8000 kg/hr solvent, at least about 9000 kg/hr solvent, at least about 10000 kg/hr solvent, at least about 10444 kg/hr solvent, at least about 12000 kg/hr solvent, at least about 80000 kg/hr solvent, at least about 90000 kg/hr solvent, at least about 100000 kg/hr solvent, at least about 104440 kg/hr solvent, or at least about 120000 kg/hr solvent. In some embodiments, the recycled solvent from the BPL purification system can provide between about 8000 kg/hr to about 12000 kg/hr solvent, between about 9000 kg/hr to about 12000 kg/hr solvent, between about 10000 kg/hr to about 12000 kg/hr solvent, between about 10444 kg/hr to about 12000 kg/hr solvent, about 8000 kg/hr to about 120000 kg/hr solvent, between about 9000 kg/hr to about 120000 kg/hr solvent, between about 10000 kg/hr to about 120000 kg/hr solvent, between about 10444 kg/hr to about 120000 kg/hr solvent, between about 12000 kg/hr to about 120000 kg/hr solvent, about 40000 kg/hr to about 120000 kg/hr solvent, about 60000 kg/hr to about 120000 kg/hr solvent, about 80000 kg/hr to about 120000 kg/hr solvent, between about 90000 kg/hr to about 120000 kg/hr solvent, between about 100000 kg/hr to about 120000 kg/hr solvent, between about 104440 kg/hr to about 120000 kg/hr solvent, or between about 120000 kg/hr to about 120000 kg/hr solvent. In some embodiments, the recycled solvent from the BPL purification system can provide about 8000 kg/hr solvent, about 9000 kg/hr solvent, about 10000 kg/hr solvent, about 10444 kg/hr solvent, or about 12000 kg/hr solvent. In some embodiments, the recycled solvent from the BPL purification system can provide at least about 100 kmol/hr solvent, at least about 120 kmol/hr solvent, at least about 140 kmol/hr solvent, at least about 145 kmol/hr solvent, at least about 150 kmol/hr solvent, at least 250 kmol/hr solvent, at least 350 kmol/hr solvent, or at least 500 kmol/hr solvent. In some embodiments, the mass fraction of solvent in the recycled solvent stream can be at least about 0.85, at least about 0.90, at least about 0.95, or at least about 0.995. In some embodiments, the mole fraction of solvent in the recycled solvent stream can be at least about 0.85, at least about 0.90, at least about 0.95, at least about 0.98, at least about 0.99, or at least about 0.993. In some embodiments, the mole fraction of solvent in the recycled solvent stream can be 0.85 to 1.0, 0.90 to 1.0, 0.95 to 1.0, 0.98 to 1.0, 0.99 to 1.0, or 0.993 to 1.0. In some embodiments, the mole fraction of solvent in the recycled solvent stream can be about 0.85, about 0.90, about 0.95, about 0.98, about 0.99, or about 0.993. The recycled solvent stream from the BPL purification system can also include unreacted carbon monoxide (in about at most 0.001 kg/hr, at most about 0.0025 kg/hr, at most about 0.005 kg/hr, at most about 0.01 kg/hr, at most 0.02 kg/hr, at most about 0.025 kg/hr, at most about 0.05 kg/hr, or at most about 0.01 kg/hr or between 0 and 0.005 kg/hr, or between 0 and 0.05 kg/hr) unreacted ethylene oxide (in about at most about 10 kg/hr, at most about 20 kg/hr, at most about 30 kg/hr, at most about 33 kg/hr, at most about 50 kg/hr, at most about 100 kg/hr, at most about 200 kg/hr, or at most about 330 kg/hr, or a mass fraction of between about 0.001-0.005, about 0.02-0.004, or at most about 0.003, at most about 0.004, or at most about 0.005), secondary reaction product acetaldehyde (in about at most 3 kg/hr, at most about 5 kg/hr, at most about 8.2 kg/hr, at most about 10 kg/hr, at most about 15 kg/hr, at most 30 kg/hr, at most about 50 kg/hr, or at most about 82 kg/hr or a mass fraction of at most about 0.001, or between 0 and 8.2 kg/hr), and bPL (in at most about 2 kg/hr, at most about 3 kg/hr, at most about 5 kg/hr, at most about 7 kg/hr, at most about 10 kg/hr, at most about 25 kg/hr, at most about 50 kg/hr, or at most about 70 kg/hr or a mass fraction of at most about 0.001, or between 0 and 7 kg/hr, or between 0 and 70 kg/hr).

In some embodiments, the recycled carbonylation catalyst stream from the carbonylation catalyst isolation system can provide at least about 1000 kg/hr solvent, at least about 1500 kg/hr solvent, at least about 1700 kg/hr solvent, at least about 1840 kg/hr solvent, at least about 2000 kg/hr solvent, at least about 5000 kg/hr solvent, at least about 10000 kg/hr solvent, at least about 15000 kg/hr solvent, at least about 17000 kg/hr solvent, at least about 18400 kg/hr solvent, or at least about 20000 kg/hr solvent. In some embodiments, the recycled carbonylation catalyst stream from the carbonylation catalyst isolation system can provide about 1000 kg/hr to about 2000 kg/hr solvent, about 1500 kg/hr to about 2000 kg/hr solvent, about 1700 kg/hr to about 2000 kg/hr solvent, about 1840 kg/hr to about 2000 kg/hr solvent, about 1000 kg/hr to about 20000 kg/hr solvent, about 1500 kg/hr to about 20000 kg/hr solvent, about 1700 kg/hr to about 20000 kg/hr solvent, about 1840 kg/hr to about 20000 kg/hr solvent, about 2000 kg/hr to about 20000 kg/hr solvent, about 5000 kg/hr to about 20000 kg/hr solvent, about 7500 kg/hr to about 20000 kg/hr solvent, about 12500 kg/hr to about 20000 kg/hr solvent, about 15000 kg/hr to about 20000 kg/hr solvent, or about 17500 kg/hr to about 20000 kg/hr solvent. In some embodiments, the recycled carbonylation catalyst stream from the carbonylation catalyst isolation system can provide about 1000 kg/hr solvent, about 1500 kg/hr solvent, about 1700 kg/hr solvent, about 1840 kg/hr solvent, about 2000 kg/hr solvent, about 2500 kg/hr solvent, about 3000 kg/hr solvent, about 5000 kg/hr solvent, about 7000 kg/hr solvent, about 10000 kg/hr solvent, about 12500 kg/hr solvent, about 15000 kg/hr solvent, or about 20000 kg/hr solvent. In some embodiments, the recycled carbonylation catalyst stream from the carbonylation catalyst isolation system can provide at least about 10 kmol/hr solvent, at least about 15 kmol/hr solvent, at least about 20 kmol/hr solvent, at least about 25 kmol/hr solvent, at least about 30 kmol/hr solvent, at least about 50 kmol/hr solvent, at least about 75 kmol/hr solvent, at least about 100 kmol/hr solvent, at least about 150 kmol/hr solvent, at least about 175 kmol/hr solvent, at least about 200 kmol/hr solvent, at least about 250 kmol/hr solvent, or at least about 300 kmol/hr solvent In some embodiments, the mass fraction of solvent in the recycled carbonylation catalyst stream can be at least about 0.60, at least about 0.65, at least about 070, or at least about 0.74. In some embodiments, the mole fraction of solvent in the recycled carbonylation catalyst stream can be at least about 0.60, at least about 0.65, at least about 0.70, at least about 0.75, at least about 0.80, or at least about 0.85. In some embodiments, the recycled carbonylation catalyst stream from the carbonylation catalyst isolation system can also include unreacted carbon monoxide (in about at most 0.5 kg/hr, at most about 1 kg/hr, at most about 1.2 kg/hr, at most about 1.5 kg/hr, at most 5 kg/hr, at most about 10 kg/hr, at most about 12 kg/hr, or at most about 15 kg/hr, or a mass fraction of at most about 0.001), unreacted ethylene oxide (in about at most about 10 kg/hr, at most about 20 kg/hr, at most 30 kg/hr, at most 33 kg/hr, at most about 100 kg/hr, at most about 200 kg/hr, at most 300 kg/hr, or at most 330 kg/hr or a mass fraction of between about 0.005-0.01, about 0.01-0.05, or at most about 0.014, or at most about 0.10), secondary reaction product acetaldehyde (in about at most 1 kg/hr, at most about 2 kg/hr, at most about 3.3 kg/hr, at most 10 kg/hr, at most about 20 kg/hr, or at most about 33 kg/hr or a mass fraction of at most about 0.01), secondary reaction product succinic anhydride (in about at most 1 kg/hr, at most about 2 kg/hr, at most about 3 kg/hr, at most 10 kg/hr, at most about 20 kg/hr, or at most about 30 kg/hr or a mass fraction of at most about 0.01), bPL (in about at most about 250 kg/hr, at most about 400 kg/hr, at most about 500 kg/hr, at most about 545 kg/hr, at most about 1000 kg/hr, at most about 2500 kg/hr, at most about 4000 kg/hr, or at most about 5450 kg/hr or a mass fraction of at most about 0.1, at most about 0.15, at most about 0.2, at most about 0.22, or at most about 0.23), and carbonylation catalyst or components thereof.

Carbonylation catalyst components may include, for example, compounds produced by degradation of the catalyst, compounds used to produce the catalyst, metals or metal ions which were part of the catalyst, any organic compounds which were part of the catalyst, metal carbonyls or metal complexes which were part of the catalyst. For example, in some embodiments, carbonylation catalyst components are carbonyl cobaltate, aluminum salen compounds, aluminum porphyrin compounds, aluminum salophen compounds, cobalt or cobalt ions, or aluminum or aluminum ions, or any combinations thereof.

In some embodiments, the recycled carbonylation catalyst stream from the carbonylation catalyst isolation system can provide at least about 25 kg/hr carbonylation catalyst, at least about 35 kg/hr carbonylation catalyst, at least about 45 kg/hr carbonylation catalyst, at least about 50 kg/hr carbonylation catalyst, at least about 53 kg/hr carbonylation catalyst, at least about 100 kg/hr carbonylation catalyst, at least about 250 kg/hr carbonylation catalyst, at least about 350 kg/hr carbonylation catalyst, at least about 450 kg/hr carbonylation catalyst, at least about 500 kg/hr carbonylation catalyst, at least about 530 kg/hr carbonylation catalyst. In some embodiments, the recycled carbonylation catalyst stream from the carbonylation catalyst isolation system can provide at least about 0.01 kmol/hr carbonylation catalyst, at least about 0.025 kmol/hr carbonylation catalyst, at least about 0.04 kmol/hr carbonylation catalyst, at least about 0.05 kmol/hr carbonylation catalyst, at least about 0.056 kmol/hr carbonylation catalyst, at least about 0.1 kmol/hr carbonylation catalyst, at least about 0.25 kmol/hr carbonylation catalyst, at least about 0.4 kmol/hr carbonylation catalyst, at least about 0.5 kmol/hr carbonylation catalyst, or at least about 0.56 kmol/hr carbonylation catalyst. In some embodiments, the mass fraction of carbonylation catalyst in the recycled carbonylation catalyst stream can be at least about 0.002, at least about 0.015, at least about 0.02, or at least about 0.022. In some embodiments, the mole fraction of carbonylation catalyst in the recycled carbonylation catalyst stream can be at least about 0.0002, at least about 0.0015, at least about 0.002, at least about 0.003, at least about 0.004, or at least about 0.005.

In some embodiments, the inlet to the carbonylation reaction system can receive solvent from solvent feed 1424 at least about 10000 kg/hr, at least about 11000 kg/hr, at least about 12000 kg/hr, at least about 12250 kg/hr, at least about 13000 kg/hr, at least about 25000 kg/hr, at least about 50000 kg/hr, at least about 100000 kg/hr, at least about 110000 kg/hr, at least about 120000 kg/hr, at least about 122500 kg/hr, or at least about 130000 kg/hr. In some embodiments, the inlet to the carbonylation reaction system can receive solvent from a solvent feed at least about 150 kmol/hr, at least about 160 kmol/hr, at least about 170 kmol/hr, at least about 180 kmol/hr, at least about 190 kmol/hr, at least about 500 kmol/hr, at least about 1000 kmol/hr, at least about 1500 kmol/hr, at least about 1600 kmol/hr, at least about 1700 kmol/hr, at least about 1800 kmol/hr, or at least about 1900 kmol/hr In some embodiments, the amount of solvent in the solvent feed to the carbonylation reaction system can be fixed to ensure the residence time in the carbonylation reaction system is at a set time. For example, the residence time can be about 1-500 minutes, about 20-450 minutes, about 30-300 minutes, about 35-200 minutes, or about 40-80 minutes. As previously discussed, in some embodiments, the solvent introduced to the carbonylation reaction system can include some recycled solvents from the carbonylation catalyst isolation system and the BPL purification system. Accordingly, in some embodiments, the inlet to the carbonylation reaction system can also receive carbon monoxide (in about 0.1-10 kg/hr, about 0.5-5 kg/hr, about 0.1-10 kg/hr, about 0.1-50 kg/hr, about 0.1-100 kg/hr, about 0.5-50 kg/hr, at most about 50 kg/hr, at most about 10 kg/hr, at most about 5 kg/hr, at most about 3 kg/hr, or at most about 1.3 kg/hr), ethylene oxide (in about 40-80 kg/hr, about 50-70 kg/hr, about 40-150 kg/hr, about 40-250 kg/hr, about 50-500 kg/hr, about 50-800 kg/hr, at most about 800 kg/hr, at most about 500 kg/hr, about most about 250 kg/hr, 80 kg/hr, at most about 70 kg/hr, or at most about 66 kg/hr or a mass fraction of about 0.001-0.01, about 0.002-0.007, or most about 0.01, at most about 0.005), acetaldehyde (in about 1-200 kg/hr, about 1-150 kg/hr, about 1-100 kg/hr, about 1-50 kg/hr, about 1-20 kg/hr, about 5-15 kg/hr, or at most about 200 kg/hr, at most about 150 kg/hr, at most about 100 kg/hr, at most about 50 kg/hr, at most about 20 kg/hr, at most about 15 kg/hr, or at most about 11 kg/hr or a mass fraction of at most about 0.001), succinic anhydride (in about 1-100 kg/hr, about 1-50 kg/hr, 1-10 kg/hr, about 1-5 kg/hr, or at most about 50 kg/hr, at most about 10 kg/hr, 5 kg/hr, or at most about 3 kg/hr), bPL (in about at most 2000 kg/hr, at most about 1500 kg/hr, at most about 1000 kg/hr, at most about 500 kg/hr, 200 kg/hr, at most about 300 kg/hr, at most about 500 kg/hr, at most about 550 kg/hr, or at most about 600 kg/hr, or a mass fraction of at most 0.1, at most about 0.075, at most about 0.05, or at most about 0.043), and carbonylation catalyst or components thereof from the solvent feed. In some embodiments, the mass fraction of solvent from the solvent feed can be at least about 0.85, at least about 0.9, at least about 0.94, or at least about 0.95. In some embodiments, the mole fraction of solvent from the solvent feed can be at least about 0.85, at least about 0.9, at least about 0.94, or at least about 0.95.

In some embodiments, the inlet to the carbonylation reaction system can receive carbonylation catalyst from a solvent feed at least about 1000 kg/hr, at least about 750 kg/hr, at least about 600 kg/hr, at least about 530 kg/hr, at least about 500 kg/hr, at least about 250 kg/hr, at least about 100 kg/hr, at least about 75 kg/hr, at least about 60 kg/hr, at least about 53 kg/hr, or at least about 50 kg/hr. In some embodiments, the inlet to the carbonylation reaction system can receive carbonylation catalyst from a solvent feed at least about 1 kmol/hr, at least about 0.8 kmol/hr, at least about 0.75 kmol/hr, at least about 0.56 kmol/hr, or at least about 0.5 kmol/hr, at least about 0.25 kmol/hr, at least about 0.1 kmol/hr, at least about 0.1 kmol/hr, at least about 0.075 kmol/hr, at least about 0.056 kmol/hr, or at least about 0.05 kmol/hr. In some embodiments, the mass fraction of carbonylation catalyst from the solvent feed can be at least about 0.0002, at least about 0.002, at least about 0.003, or at least about 0.004.

In some embodiments, the inlet to the carbonylation reaction system can receive a solvent feed at a temperature between about 10-100° C., between about 20-50° C., between about 25-45° C., between about 30-40° C., or about 36.6° C. In some embodiments, the inlet to the carbonylation reaction system can receive a solvent feed at a pressure of at least about 50 bar, about 60-70 bar, or at least about 65 bar.

Other Feed Sources

The β-propiolactone production system/production process may further include other feed sources. For example, in one variation, the β-propiolactone production system/production process further includes a Lewis base additive source.

In some embodiments, a Lewis base additive may be added to the carbonylation reactor. In certain embodiments, such Lewis base additives can stabilize or reduce deactivation of the catalysts. In some embodiments, the Lewis base additive is selected from the group consisting of phosphines, amines, guanidines, amidines, and nitrogen-containing heterocycles. In some embodiments, the Lewis base additive is a hindered amine base. In some embodiments, the Lewis base additive is a 2,6-lutidine; imidazole, 1-methylimidazole, 4-dimethylaminopyridine, trihexylamine and triphenylphosphine.

The exemplary system depicted in FIG. 14 also includes carbonylation product stream 1414, post-isolation carbonylation product stream 1416, BPL purified stream 1418, PPL product stream 1420, and GAA product stream 1422.

Reactor

In some embodiments, the carbonylation reaction system can include at least one reactor for the carbonylation reaction. In some embodiments, the carbonylation system can include multiple reactors in series and/or parallel for the carbonylation reaction. In some embodiments, the reactor(s) can be a continuous reactor(s). Examples of suitable continuous reactors include but are not limited to tubular reactors (i.e., plug flow-type reactors), fixed bed reactors, fluid bed reactors, continuous stirred tank reactors ("CSTR"), heat exchanger reactors (e.g., shell and tube type reactor), loop reactors (e.g., Buss, jet, etc.), membrane reactors, or other reactors known to those of ordinary skill in the art. In some embodiments, the carbonylation reaction system includes one or more CSTRs. All inlets and outlets to the carbonylation reaction system can include sensors that can determine the flowrate, composition (especially water and/or oxygen content), temperature, pressure, and other variables known to those of ordinary skill in the art. In addition, the sensors can be connected to control units that can control the various streams (i.e., feed controls) in order to adjust the process based on the needs of the process determined by the sensor units. Such control units can adjust the quality as well as the process controls of the system.

In some variations, the reactor in the β-propiolactone production system/production process is configured to receive the catalyst, ethylene oxide and carbon monoxide in certain ratios. In some embodiments, the ratio of catalyst to ethylene oxide is selected, based on other reaction conditions, so that the reaction proceeds in an economical and time-feasible manner. In some embodiments, the ratio of catalyst to ethylene oxide is about 1:10000 on a molar basis. In some embodiments, the molar ratio of catalyst to ethylene oxide is about 1:5000, is about 1:2500, is about 1:2000, is about 1:1500, is about 1:1000, is about 1:750, is about 1:500, is about 1:250, is about 1:200, is about 1:150, or is about 1:100. In some embodiments, the concentration of the ethylene oxide is in the range between about 0.1 M and about 5.0 M. In some embodiments, the concentration of the ethylene oxide is in the range between about 0.5 M and about 3.0 M.

In certain embodiments, the molar ratio of carbon monoxide to ethylene oxide in the reaction stream ranges from about 0.1:1 to about 100:1. In certain embodiments, the molar ratio of carbon monoxide to ethylene oxide in the reaction stream is about 50:1, is about 20:1, is about 10:1, is about 5:1 or is about 1:1, or within a range including any two of these ratios. In some embodiments, the ratio of carbon monoxide to ethylene oxide is selected based on other reaction conditions so that the reaction proceeds in an economical and time-feasible manner.

In some variations, the reactor in the β-propiolactone production system/production process is configured to further receive one or more additional components. In certain embodiments, the additional components comprise diluents which do not directly participate in the chemical reactions of ethylene oxide. In certain embodiments, such diluents may include one or more inert gases (e.g., nitrogen, argon, helium and the like) or volatile organic molecules such as hydrocarbons, ethers, and the like. In certain embodiments, the reaction stream may comprise hydrogen, carbon monoxide of carbon dioxide, methane, and other compounds commonly found in industrial carbon monoxide streams. In certain embodiments, such additional components may have a direct or indirect chemical function in one or more of the processes involved in the conversion of ethylene oxide to β-propiolactone and various end products. Additional reactants can also include mixtures of carbon monoxide and another gas. For example, as noted above, in certain embodiments, carbon monoxide is provided in a mixture with hydrogen (e.g., Syngas).

Because the carbonylation reaction is exothermic, the reactors used can include an external circulation loop for reaction mass cooling. In some embodiments, the reactors can also include internal heat exchangers for cooling. For example, in the case of a shell and tube type reactor, the reactors can flow through the tube part of the reactor and a cooling medium can flow through the shell of the reactor or vice versa. Heat exchanger systems can vary depending on layout, reactor selection, as well as physical location of the reactor. The reactors can employ heat exchangers outside of the reactors in order to do the cooling/heating or the reactors can have an integrated heat exchanger such as a tube and shell reactor. For example, a CSTR can utilize a layout for heat rejection by pumping a portion of the reaction fluid through an external heat exchanger or a plug flow-type reactor can be an integrated unit that combines the reactor and the heat exchanger into a single unit. Additional reactor/heat exchanger systems and heat management systems can be found in U.S. Pat. Nos. 3,128,163; 4,759,313; 8,246,915, which are hereby incorporated by reference in their entirety. In some embodiments, heat can be removed from a CSTR by using a coolant in a reactor jacket, one or more internal cooling coils, lower temperature feeds and/or recycle streams, an external heat exchange with pump around loop, and/or other methods known by those of ordinary skill in the art. In some embodiments, heat can be removed from a plug flow type reactor or a loop reaction by using a coolant in the reactor jacket and/or internal cooling coils. Furthermore, the reaction can occur on the tube side or the shell side of a shell and tube reactor and the other side can have the cooling medium. In addition, the reactors may have multiple cooling zones with varying heat transfer areas and/or heat transfer fluid temperatures and flows.

The type of reactor employed and the type of heat exchanger employed (either external or integrated) can be a function of various chemistry considerations (e.g., reaction conversions, by-products, etc.), degree of exotherm produced, and the mixing requirements for the reaction.

Since carbonylation reactions are exothermic reactions and the BPL purification system and thermolysis requires energy, it is possible to integrate at least some of the components between the carbonylation reaction system and the BPL purification system and/or thermolysis system. For example, steam or tempered water or other appropriate heat transfer media can be produced in a heat exchanger of the carbonylation reaction system and transported to the BPL purification system for heating a distillation column for example. In addition, the BPL purification system and the carbonylation reaction system may be integrated into a single system or unit so that the heat produced from the carbonylation reaction can be used in the BPL purification system (in an evaporator or distillation column). The steam can be generated in a heat exchanger (e.g., shell and tube heat exchanger, reactor's cooling jacket, etc) via a temperature gradient between reaction fluids and water/steam of the heat exchanger. Steam can be used for heat integration between exothermic units (carbonylation reaction, polymerization reaction) and endothermic units (BPL purification system's columns/evaporators and thermolysis reaction). In some embodiments, steam is only used for heat management and integration and will not be introduced directly into the production processes.

As previously described, water and oxygen can damage the carbonylation catalyst. As such, oxygen and water intrusion into the carbonylation system should also be minimized. As such, the reactor seals may utilize a magnetic drive, a double mechanical seal, and/or materials of construction that are compatible with the reactants and products of the carbonylation reaction but not permeable to atmosphere. In some embodiments, the materials of construction of the reactor include metals. In some embodiments, the metals can be stainless steel. In some embodiments, the metals can be carbon steel. In some embodiments, the metals can be metal alloys such as nickel alloys. In some embodiments, the metals are chosen when compatibility or process conditions dictate, e.g., high chloride content or if carbon steel catalyzes EO decomposition. In some embodiments, everything up until the polymerization reaction system can include carbon steel. One of the benefits of carbon steel over stainless steel is its cost. In some embodiments, the metals can have a surface finish so as to minimize polymer nucleation sites. The materials of construction of the reactor can also include elastomer seals. In some embodiments, the elastomer seals are compatible with the reactants and products of the carbonylation reaction but not permeable to the atmosphere. Examples of elastomer seals include but are not limited to Kalrez 6375, Chemraz 505, PTFE-encapsulated Viton, and PEEK. The materials of construction of external parts of the carbonylation reaction system can be compatible with the environment, for example, compatible with sand, salty water, not heat absorbing, and can protect the equipment from the environment.

In some embodiments, the carbonylation reaction system is operated so as to minimize or mitigate PPL and polyethylene oxide formation prior to the polymerization reaction system. In some embodiments, the carbonylation reaction system is operated so as to avoid catalyst decomposition.

In some embodiments, the carbonylation reactor(s) can have a downstream flash tank with a reflux condenser to separate unreacted carbon monoxide as a recycled carbon monoxide stream from the carbonylation reaction system. As previously described, the recycled carbon monoxide stream can be sent to a CO compressor and/or combined with a fresh carbon monoxide feed prior to being sent back into the carbonylation reaction system. The flash tank can separate most of the CO to avoid its separation downstream, especially in the carbonylation catalyst isolation system. In some embodiments, excess gas is removed or purged from the reactor itself and thus a flash tank is not necessary.

In some embodiments, the carbonylation reactor(s) can operate at a temperature of about 40-100° C., about 50-90° C., about 60-80° C., about 65-75° C., or about 70° C. In some embodiments, the reaction temperature can range from between about −20° C., to about 600° C. In some embodiments, the reaction temperature is about −20° C., about 0° C., about 20° C., about 40° C., about 60° C., about 80° C., about 100° C., about 200° C., about 300° C., about 400° C., about 500° C. or about, about 600° C. In some embodiments, the temperature is in a range between about 40° C. and about 120° C. In some embodiments, the temperature is in a range between about 60° C. and about 140° C. In some embodiments, the temperature is in a range between about 40° C. and about 80° C. In some embodiments, the temperature is in a range between about 50° C. and about 70° C. In some embodiments, the reactants, catalyst and solvent are supplied to the reactor at standard temperature, and then heated in the reactor. In some embodiments, the reactants are pre-heated before entering the reactor.

In some embodiments, the carbonylation reactor(s) can operate at a pressure of about 600-1200 psig, about 700-1100 psig, about 800-1000 psig, about 850-950 psig, or about 900 psig. In some embodiments, the reaction pressure can range from between about 50 psig to about 5000 psig. In some embodiments, the reaction pressure is about 100 psig, about 200 psig, about 300 psig, about 400 psig, about 500 psig, about 600 psig, about 700 psig, about 800 psig, about 900 psig, or about 1000 psig. In some embodiments, the pressure ranges from about 50 psig to about 2000 psig. In some embodiments, the pressure ranges from about 100 psig to 1000 psig. In some embodiments, the pressure ranges from about 200 psig to about 800 psig. In some embodiments, the pressure ranges from about 800 psig to about 1600 psig. In some embodiments, the pressure ranges from about 1500 psig to about 3500 psig. In some embodiments, the pressure ranges from about 3000 psig to about 5500 psig. In some embodiments, the reaction pressure is supplied entirely by the carbon monoxide. For example, carbon monoxide is added to the reactor at high pressure to increase pressure to the reaction pressure. In some embodiments, all reactants, solvent and catalyst are supplied to the reactor at reaction pressure.

In some embodiments, the reaction is maintained for a period of time sufficient to allow complete, near complete reaction of the ethylene oxide to carbonylation products or as complete as possible based on the reaction kinetics and or reaction conditions. In some embodiments, the reaction time is a residence time in the carbonylation reactor in step (a). In certain embodiments, the residence time is about 12 hours, about 8 hours, about 6 hours, about 3 hours, about 2 hours or about 1 hour. In certain embodiments, the residence time is about 30 minutes, about 20 minutes, about 15 minutes, about 10 minutes, about 5 minutes, about 3 minutes, about 2 minutes, or about 1 minute. In certain embodiments, the residence time is less than 1 minute.

The chemistry involved in a carbonylation reaction system can include, but are not limited to, the following three reactions: (1) CO+EO→bPL; (2) EO→acetaldehyde; (3) bPL→succinic anhydride. The conversions for the three reactions may vary depending on many factors including amount of reactants, amount of catalyst, temperature, pressure, flow rate, etc. However, the first reaction can have an EO conversion of about 0.2-0.999, about 0.5-0.95, about 0.6-0.9, about 0.7-0.8, or about 0.75. The second reaction can have an EO conversion of about 0-0.1, about 0.001-0.02, about 0.002-0.01, or about 0.005. The third reaction can have a bPL conversion of about 0.0002-0.02, about 0.0005-0.01, about 0.001-0.003, or about 0.002.

Figure 15:
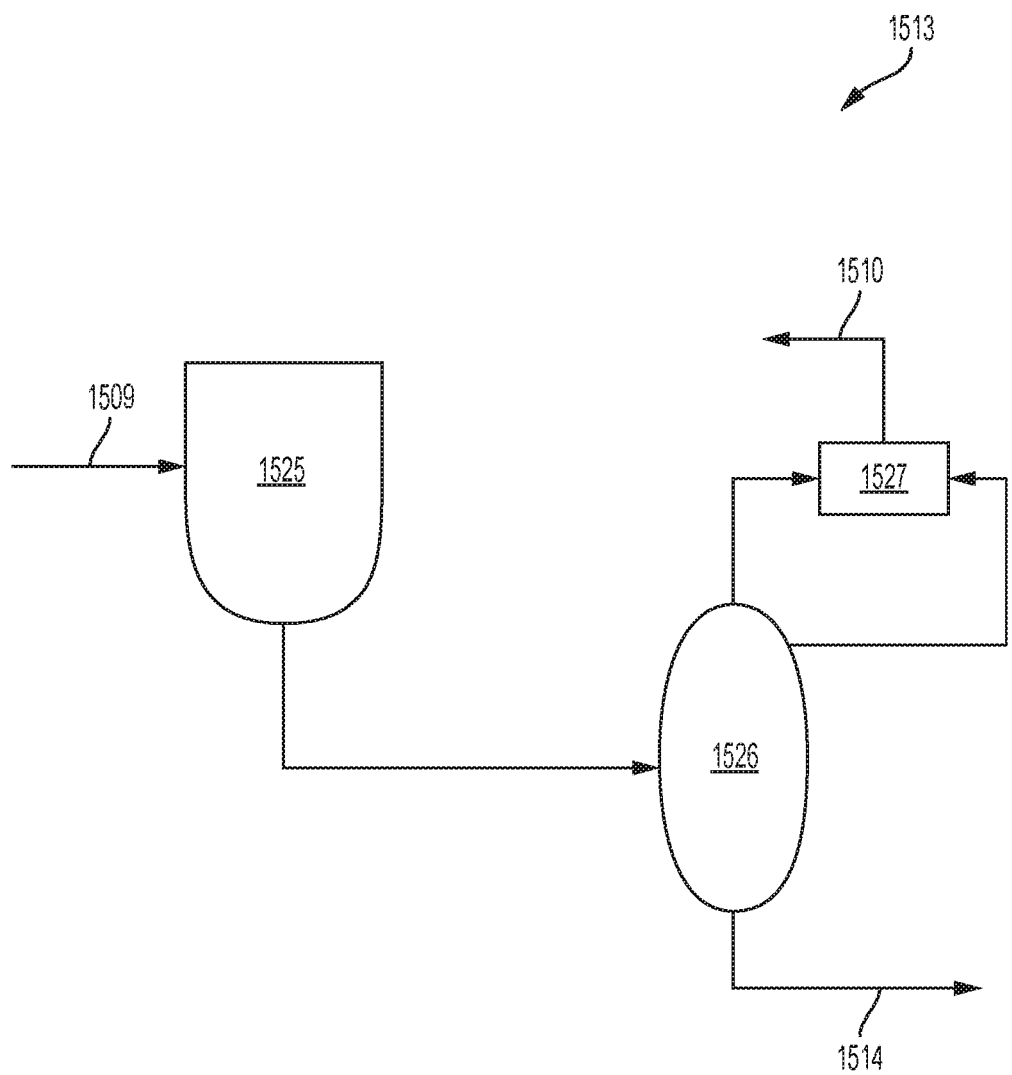
FIG. 15 illustrates an embodiment of a carbonylation reaction system described herein.

FIG. 15 illustrates an exemplary embodiment of a carbonylation reaction system disclosed herein. Carbonylation reaction system 1513 can include carbonylation reaction system inlet 1509 for carbonylation reactor 1525. As previously described, the inlet can be made up of multiple inlets or feeds into the reaction system. In addition, carbonylation reaction system 1513 includes flash tank 1526 with condenser 1527. Flash tank 1526 and condenser 1527 separate the reactor product stream into recycled carbon monoxide stream 1510 and carbonylation product stream 1514.

Carbonylation Product Stream (i.e., BPL Product Stream)

In some embodiments, the carbonylation product stream includes at least about 2000 kg/hr bPL, at least about 2500 kg/hr bPL, at least about 3000 kg/hr bPL, at least about 3500 kg/hr bPL, at least about 3638 kg/hr bPL, at least about 4000 kg/hr bPL, at least about 8000 kg/hr bPL, at least about 12000 kg/hr bPL, at least about 16000 kg/hr bPL, at least about 20000 kg/hr bPL, at least about 25000 kg/hr bPL, at least about 30000 kg/hr bPL, at least about 35000 kg/hr bPL, at least about 36380 kg/hr bPL, or at least about 40000 kg/hr bPL. In some embodiments, the carbonylation product stream includes between about 2000 kg/hr bPL and about 4000 kg/hr bPL, about 2500 kg/hr bPL and about 4000 kg/hr bPL, about 3000 kg/hr bPL and about 4000 kg/hr bPL, about 3500 kg/hr bPL and about 4000 kg/hr bPL, about 3638 kg/hr bPL and about 4000 kg/hr bPL, between about 2000 kg/hr bPL and about 40000 kg/hr bPL, about 2500 kg/hr bPL and about 40000 kg/hr bPL, about 3000 kg/hr bPL and about 40000 kg/hr bPL, about 3500 kg/hr bPL and about 40000 kg/hr bPL, about 3638 kg/hr bPL and about 40000 kg/hr bPL, about 4000 kg/hr bPL and about 40000 kg/hr bPL, about 8000 kg/hr bPL and about 40000 kg/hr bPL, about 12000 kg/hr bPL and about 40000 kg/hr bPL, about 16000 kg/hr bPL and about 40000 kg/hr bPL, about 20000 kg/hr bPL and about 40000 kg/hr bPL, about 25000 kg/hr bPL and about 40000 kg/hr bPL, about 30000 kg/hr bPL and about 40000 kg/hr bPL, or about 35000 kg/hr bPL and about 40000 kg/hr bPL.

In some embodiments, the carbonylation product stream includes at least about 30 kmol/hr bPL, at least about 40 kmol/hr bPL, at least about 45 kmol/hr bPL, at least about 50 kmol/hr bPL, at least about 55 kmol/hr bPL, at least about 100 kmol/hr bPL, at least about 200 kmol/hr bPL, at least about 300 kmol/hr bPL, at least about 400 kmol/hr bPL, at least about 450 kmol/hr bPL, at least about 500 kmol/hr bPL, or at least about 550 kmol/hr bPL. In some embodiments, the mass fraction of bPL in the carbonylation product stream can be about 0.1-0.4, about 0.15-0.3, about 0.18-0.25, about 0.2-0.23, at least about 0.15, at least about 0.2, or at least about 0.224. In some embodiments, the mole fraction of bPL in the carbonylation product stream can be about 0.1-0.4, about 0.15-0.3, about 0.18-0.25, about 0.21-0.23, at least about 0.15, at least about 0.2, or at least about 0.22. The carbonylation product stream can also include other components including unreacted ethylene oxide (in mass fraction of about 0.005-0.05, about 0.02-0.045, about 0.04, at most about 0.014, at most about 0.02, or at most about 0.05), unreacted carbon monoxide (in mass fraction of about 0.0005-0.01, at most about 0.01, or at most about 0.02), acetaldehyde (in mass fraction of about 0.0005-0.001, at most about 0.001, or at most about 0.002), succinic anhydride (in mass fraction of about 0.0005-0.001, at most about 0.001, or at most about 0.002), carbonylation catalyst (in about 40-640 kg/hr, about 45-600 kg/hr, about 50-600 kg/hr, about 50-300 kg/hr, about 50-100 kg/hr, about 40-64 kg/hr, about 45-60 kg/hr, about 50-60 kg/hr, at most 54.8 kg/hr, at most about 60 kg/hr, at most about 300 kg/hr, or at most about 600 kg/hr or a mass fraction of about 0.001-0.005, about 0.002-0.004, at most about 0.003, or at most about 0.004), and the remainder solvent. In some embodiments, the carbonylation product stream can include sufficient ethylene oxide so as to prevent anhydride formation.

In some embodiments, the carbonylation product stream from the carbonylation reaction system can have a temperature of about 50-100° C., about 60-90° C., about 65-75° C., or about 70° C. In some embodiments, the carbonylation product stream can have a pressure of about 1-5 bar, about 2-4 bar, or about 3 bar.

In some embodiments, the carbonylation reaction system has a selectivity of at least about 95%, at least about 97%, at least about 99%, at least about 99.5%, or at least about 99.8%. In some embodiments, the carbonylation reaction system has a yield of at least about 90%, at least about 95%, at least about 98%, at least about 99%, or at least about 99.5%. In some embodiments, the selectivity of bPL is the ratio of bPL yield to ethylene oxide conversion, wherein the bPL yield is measured relative to ethylene oxide. In other embodiments, the selectivity of bPL is the ratio of bPL yield to carbon monoxide conversion, wherein the bPL yield is measured relative to carbon monoxide.

Carbonylation Catalyst Recycle System

With reference again to FIG. 1, the carbonylation catalyst recycle system may be employed to recover at least a portion of the carbonylation catalyst, or components thereof, present in the β-propiolactone product stream. Such recovered carbonylation catalyst may be recycled and reused in the β-propiolactone production system/production process.

Carbonylation catalyst components may include, for example, compounds produced by degradation of the catalyst, compounds used to produce the catalyst, metals or metal ions which were part of the catalyst, any organic compounds which were part of the catalyst, metal carbonyls or metal complexes which were part of the catalyst. For example, in some embodiments, carbonylation catalyst components are carbonyl cobaltate, aluminum salen compounds, aluminum porphyrin compounds, aluminum salophen compounds, cobalt or cobalt ions, or aluminum or aluminum ions, or any combinations thereof.

Any suitable methods and techniques known in the art may be used to recover at least a portion of the carbonylation catalyst present in the β-propiolactone product stream. Such methods and techniques may include, for example, nanofiltration (as depicted in FIG. 1), distillation, liquid-liquid extraction, ionic liquids, and ion exchange, or adsorption. Combinations of methods and techniques described herein may also be employed.

Nanofiltration

In some embodiments, the carbonylation catalyst recycle system involves the use of nanofiltration. For example, a nanofiltration membrane may be used. In some variations, the nanofiltration membrane is an organic solvent-stable nanofiltration membrane. Although any nanofiltration membrane may be used in combination with any organic solvent or organic solvent system compatible with the carbonylation reaction, the nanofiltration membrane may be selected in combination with the organic solvent or solvents such that the process achieves predetermined levels of lactone formation and catalyst-lactone separation. In some variations, the nanofiltration membrane is a polymeric nanofiltration membrane, while in other variations, the nanofiltration membrane is a ceramic nanofiltration membrane.

In some embodiments, the nanofiltration membrane is a polymeric membrane. Any suitable polymeric membranes may be used in the methods described herein. For example, in some variations, the polymeric membrane comprises polyimides, polyamide-imides, silicone-coated polyamide composites, polyacrylonitriles, polydimethylsiloxane films on polyacrylonitrile supports, silcones, polyphosphazenes, polyphenylene sulfide, polyetheretherketone, or polybenzimidazol. In certain variations, the polymeric membrane has a silicone backbone.

In certain variations, the polymeric membrane is selected from polyimides, including those marketed under the trademark STARMEM by Membrane Extraction Technology Ltd (Wembley, UK) and integrally skinned asymmetric membranes made from polyimides, polyamide-imides, silicone-coated polyamide composites, polyacrylonitriles, polydimethylsiloxane films on polyacrylonitrile supports, silcones, polyphosphazenes, polyphenylene sulfide, polyetheretherketone, and polybenzimidazol. In some embodiments, the organic solvent is tetrahydrofuran and the nanofiltration membrane is an integrally skinned asymmetric polyimide membrane made from Lenzing P84 or a ST ARMEM® polyimide membrane. In some embodiments, the organic solvent is diethyl ether and the nanomembrane is a silicone-coated polyamide composite. In some embodiments, the nanofiltration membrane is a commercially available membrane. In other embodiments, the nanofiltration membrane is an integrally skinned asymmetric polyimide membrane made from Lenzing P84 and manufactured by GMT Membrantechnik GmbH (Rheinfelden, Germany). In some other embodiments, the nanofiltration membrane is a STARMEM® polyimide membrane from Membrane Extraction Technology Ltd (Wembley, UK) and the nanofiltration step is performed at a temperature under 50° C. and a pressure under 60 bar. In still other embodiments, the nanofiltration membrane is a silicone-coated organic solvent resistant polyamide composite nanofiltration membrane as disclosed in U.S. Pat. No. 6,887,380, incorporated herein by reference.

In other variations, the nanofiltration membrane is a ceramic membrane comprising inorganic materials.

Figure 3:
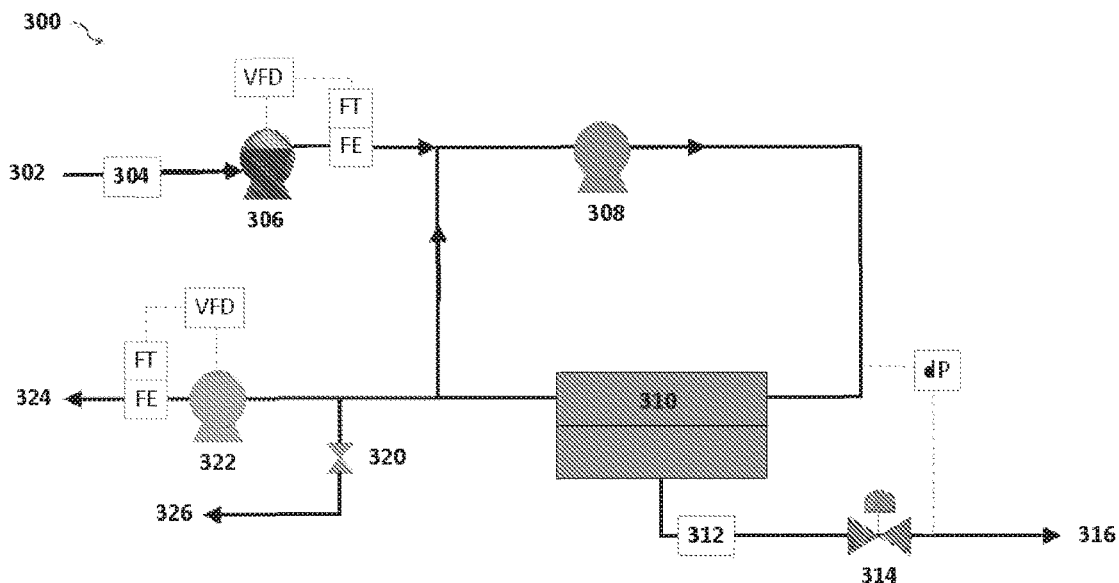
FIG. 3 is a schematic illustration of a carbonylation catalyst recycle system that employs membranes, configured to isolate residual carbonylation catalyst from a β-propiolactone product stream.

Nanofiltration membranes of various configurations may be employed in the carbonylation catalyst recycling system. For example, in some embodiments, the membrane is a plate-and-frame membrane. With reference to FIG. 3, exemplary carbonylation catalyst recycle system 300 that uses membrane 310 is depicted. Feed 302 may include, for example, β-propiolactone, carbonylation solvent, small amounts of ethylene oxide and carbon monoxide, carbonylation catalyst, and by-products (such as acetaldehyde and succinic anhydride). Feed 302 is transferred to membrane via pumps 306 and 308. Sensor 304 is positioned before pump 306 to regulate the rate at which feed 302 is pumped through membrane 310. In some variations, sensor 304 may be a ultra-violet (UV) sensor. Other suitable sensors may also be employed. Feed 302 passes through membrane 310 by way of the transmembrane pressure, varied according to the pump set points. In some variations, membrane 310 is a plate-and-frame membrane, as depicted in FIG. 3. However, in other variations, other suitable membranes may be used. For example, in other variation, membrane 310 of carbonylation catalyst recycle system 300 may be a spiral wound membrane or a tubular membrane, and such alternative configurations are discussed in further detail below.

With reference again to FIG. 3, membrane 310 produces permeate stream 316 and retentate stream 324. Permeate stream 316 may include, for example, β-propiolactone, carbonylation solvent, small amounts of ethylene oxide and carbon monoxide, by-products (such as acetaldehyde and succinic anhydride), and trace amounts of carbonylation catalyst. Further, permeate stream 316 may have a permeability of at least 0.5 $L/m^2$ hr bar, at least 0.6 $L/m^2$ hr bar, at least 0.7 $L/m^2$ hr bar, at least 0.8 $L/m^2$ hr bar, at least 0.9 $L/m^2$ hr bar, at least 1.0 $L/m^2$ hr bar, at least 1.1 $L/m^2$ hr bar, at least 1.2 $L/m^2$ hr bar, at least 1.3 $L/m^2$ hr bar, at least 1.4 $L/m^2$ hr bar, at least 1.5 $L/m^2$ hr bar, at least 1.6 $L/m^2$ hr bar, at least 1.7 $L/m^2$ hr bar, at least 1.8 $L/m^2$ hr bar, at least 1.9 $L/m^2$ hr bar, at least 2 $L/m^2$ hr bar, at least 2.5 $L/m^2$ hr bar, at least 3 $L/m^2$ hr bar, at least 3.5 $L/m^2$ hr bar, or at least 4 $L/m^2$ hr bar; or between 0.5 $L/m^2$ hr bar and 5 $L/m^2$ hr bar, or between 3 $L/m^2$ hr bar and 4.5 $L/m^2$ hr bar; or between 0.5 $L/m^2$ hr bar and 10 $L/m^2$ hr bar, or between 3 $L/m^2$ hr bar and 10 $L/m^2$ hr bar. In some variations, permeability (or membrane permeability) refers to volumetric flow rate of material that permeates through a specified surface area at a specified transmembrane pressure (TMP). In some variations, the transmembrane pressure is the pressure difference between the retentate side of the membrane and the permeate side of the membrane. In some embodiments, the relationship can be expressed as Permeability=Volumetric flow rate/(Surface Area×TMP). In some embodiments, permeability may be determined by measuring the flow rate of material which permeates across a membrane sample of known surface area at a known TMP.

Sensor 312 is positioned after membrane 310 to analyze the contents of permeate stream 316. In some variations, sensor 312 may be a UV sensor. Other suitable sensors may also be employed.

Carbonylation catalyst recycle system 300 is configured to achieve a catalyst rejection of at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%, or 100%. In some variations, catalyst rejection refers to the percentage (by mass) of catalyst which permeates through the membrane compared to that which does not and is retained on the retentate side of the membrane. Catalyst rejection may be determined by any suitable method in the art, including, for example, using analytical instruments to detect catalyst concentrations at the membrane feed, permeate and retentate.

With reference again to FIG. 3, pressure control valve 314 is positioned after sensor 312 and biased to upstream flash units. In some embodiments, pressure control valve (PCV) 314 can be used to control transmembrane pressure (TMP) which may affect performance of the membrane. Sensor 312 may detect catalyst rejection and provide a feedback signal to PCV 314 to make adjustments for system performance. PCV 314 may in some embodiments detect the pressure of the upstream flash tank and prevent volatile species (for example, carbon monoxide) from vaporizing as pressure changes across the membrane. Vaporization or flashing across the membrane may affect the durability of the membrane.

Retentate stream 324 may include, for example, carbonylation solvent, β-propiolactone, and carbonylation catalyst. Pump 322 may be used to transfer retentate stream 324 to the β-propiolactone production system/production process described herein (e.g., to a carbonylation reactor of the β-propiolactone production system/production process). In some embodiments, catalyst may deactivate as it is circulated through the membrane system on the retentate side (for example, with exposure to oxygen or water). In certain embodiments, a portion of the retentate stream is purged for a period of time to avoid accumulation of deactivated catalyst within the system. Valve 320 is configured to purge the system and bleed 326.

As discussed above, while FIG. 3 depicts the use of a plate-and-frame membrane, other membrane configurations may be employed. For example, in other embodiments, the membrane is a spiral wound membrane. In yet other embodiments, the membrane is a tubular membrane. In still other embodiments, the membrane is a pleated sheet membrane.

In one variation, the membrane is a polymeric membrane in a plate and frame configuration. In another variation, the membrane is a polymeric membrane in a spiral wound configuration. In yet another variation, the membrane is a ceramic membrane in a tubular configuration.

While FIG. 3 depicts the use of one membrane, in other variations, a plurality of membranes may be used. For example, at least two membranes connected in series may be used. In one variation, a plurality of plate-and-frame membranes connected in series may be used. In other variations, a plurality of spiral wound membranes connected in series may be used. In other variations, a plate-and-frame membrane may be connected in series with a spiral wound membrane. It should be understood that the membrane configurations may be in series, in parallel, or in a combination of series and parallel. For example, in some embodiments, the membranes are configured in a "Christmas tree" configuration.

In one embodiment, the nanofiltration membrane is a polymeric, spiral wound membrane with a silicone backbone, carbonylation catalyst rejection rate of at least 99%, and permeability of at least 1 L/m$^2$ hr bar.

Distillation

In other embodiments, the carbonylation catalyst recycle system involves a distillation apparatus.

In some variations, the distillation apparatus recover at least a portion of the carbonylation catalyst present in the β-propiolactone product stream using a multi-solvent system. For example, in one variation, a two-solvent system may be used, wherein the first solvent has a boiling point above 166° C. and may serve as the carrier of the catalyst, and the second solvent is selected to facilitate the carbonylation reaction.

In other variations, the distillation may include heating the β-propiolactone product stream to volatilize at least a portion of the β-propiolactone and/or the solvent to form a distillate, removing the distillate, and condensing the distillate. In other embodiments, the distillation is a vacuum distillation, wherein the distillate is formed by reducing the pressure of the β-propiolactone product stream. In certain embodiments, vacuum distillation allows at least a portion of the carbonylation catalyst to be removed from the β-propiolactone product stream without degradation of the catalyst at higher temperatures. In other variations, the distillation is performed by both increasing the temperature and decreasing the pressure of the β-propiolactone product stream. The carbonylation catalyst remaining the in the retained mixture after distillation can then be isolated for reuse in the carbonylation reaction using any methods known in the art, including, for example, solvent-solvent extraction, nanofiltration, ionic liquids, or adsorption.

Liquid-Liquid Extraction

In other embodiments, the carbonylation catalyst recycle system involves a liquid-liquid extraction apparatus.

In some variations, the liquid-liquid extraction apparatus employs an extraction solvent in which the catalyst (or a component of the catalyst) is soluble or at least partially soluble. In other variations, the extraction solvent is one in which the β-propiolactone is soluble or at least partially soluble, but which has little tendency to dissolve the carbonylation catalyst (or one or more components of the carbonylation catalyst). In either case, the use of the extraction solvent results in the formation of two phases. In certain embodiments, the extraction solvent is a highly polar solvent such as water or an ionic liquid. In certain embodiments, the extraction solvent is supercritical $CO_2$. In certain embodiments, the extraction solvent is water or an aqueous solution. In certain embodiments, the extraction solvent is an ionic liquid. In certain embodiments where the solvent is an ionic liquid, the ionic liquid has a formula [Cat$^+$][X"] wherein [Cat$^+$] refers to one or more organic cationic species; and [X"] refers to one or more anions. In certain embodiments, [Cat$^+$] is selected from the group consisting of: ammonium, tetraalkylammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium, uronium, and any combination of two or more of these. In accordance with the present invention, [X"] may comprise an anion selected from halides, sulphates, sulfonates, sulfonimides, phosphates, phosphonates, carboxylates, $CN^-$, $NO_3^-$, $NO_2^-$, $BF_4^-$ and $PF_6^-$.

In some embodiments, the extraction solvent includes pentane, cyclohexane, hexane, heptane, tetrahydrofuran, p-dioxane, 4-methyl-1,3-dioxolan-2-one, N,N-dimethylformamide, 1-methyl-2-pyrrolidinone, or sulfolane, or any combinations thereof. In one embodiment, the extraction solvent includes sulfolane and hexane. In another embodiment, the liquid-liquid extraction solvent includes sulfolane, hexane, and dioxane.

Precipitation

In certain embodiments, the carbonylation catalyst recycle system is configured to precipitate the carbonylation catalyst. Precipitation of the carbonylation catalyst may be accomplished by any known methods and techniques. Suitable means of precipitating the catalyst will be apparent to the skilled chemist and may include, but are not limited to: adding a solvent to the β-propiolactone product stream in which the catalyst (or a component thereof) is poorly soluble, cooling the β-propiolactone product stream, adding a material that interacts with the catalyst (or a component thereof) to form an insoluble adduct, removing solvent, excess feedstock, or carbon monoxide from the β-propiolactone product stream, and combinations of any two or more of these. In certain embodiments where the step of treating the β-propiolactone product stream to separate a portion of the carbonylation catalyst entails precipitation, the precipitation step comprises adding a solvent in which the catalyst (or a component of the catalyst) is poorly soluble. In certain embodiments, a non-polar solvent such as an aliphatic hydrocarbon, an aromatic hydrocarbon, or condensed phase $CO_2$ is added to precipitate the catalyst. In certain embodiments, a solvent selected from butane, pentane, hexane, heptane, octane, cyclopentane, cyclohexane, decalin, higher alkanes, and mixtures of two or more alkanes is added to the β-propiolactone product stream to precipitate the catalyst or a catalyst component. In certain embodiments, a solvent selected from benzene, toluene, xylene, mesitylene, chlorobenzene, or other substituted benzene compounds is added to the β-propiolactone product stream to precipitate the catalyst or a catalyst component. In certain embodiments, supercritical $CO_2$ is added to the β-propiolactone product stream to precipitate the catalyst or a catalyst component. In certain embodiments where the carbonylation catalyst comprises the combination of a Lewis acidic metal complex and a metal carbonyl compound and a non-polar solvent is added to the β-propiolactone product stream, this causes precipitation of the Lewis acidic metal complex but leaves at least a portion of the metal carbonyl component of the catalyst behind in the β-propiolactone product stream. In embodiments where the catalyst is precipitated, the step of separating the carbonylation catalyst typically includes further steps to remove the precipitate from the product stream, such isolation steps are well known in the art and can include, but are not limited to filtration, sedimentation, centrifugation, coagulation, and combinations of two or more of these.

Adsorption

In certain embodiments, the carbonylation catalyst recycle system is configured to separate the carbonylation catalyst by adsorbing the carbonylation catalyst or components thereof. In some variations, adsorption can entail treating the product streams containing carbonylation catalyst with a solid adsorbing material. Suitable solid adsorbing materials may include inorganic substances, activated carbon, polymers, resins, or any combination of two or more of these. Suitable inorganic adsorbing materials may include silica gel, silicate minerals, clays, diatomaceous earth, Fuller's earth, ceramics, zirconias, molecular sieves and the like. Suitable polymers may include polystyrenes, polyacrylonitrile, polyimides, polyolefins, polyesters, polyethers, polycarbonates, polyisocyanates, and the like. Such polymers may optionally include additional chemical functional groups to enhance their ability to adsorb carbonylation catalysts or catalyst components. Such functional groups may include acids (e.g., sulfonic or carboxylic acids), coordinating groups (e.g., amine, thiol, phosphine, nitrile, or boron groups), and/or bases, (e.g., amine groups or nitrogen heterocycles). In certain cases, the adsorbing materials (e.g., whether inorganic or polymeric) are acidic, basic, or have undergone chemical treatments to enhance the affinity of the catalyst. In embodiments where carbonylation catalyst is removed from the product streams containing carbonylation catalyst by adsorption, the adsorbent can be contacted with the product stream by any conventional method. This includes, but is not limited to: flowing the product streams containing carbonylation catalyst through a fixed bed of adsorbent; flowing the product streams containing carbonylation catalyst through a fluidized bed of adsorbent; flowing the product streams containing carbonylation catalyst through fabrics, meshes, or filtration plates comprising the adsorbent material; or slurrying the product streams containing carbonylation catalyst with the adsorbent material (typically followed by filtration, centrifugation, sedimentation or the like to remove the adsorbent from the product stream).

In embodiments where the β-propiolactone product stream is flowed through a column of adsorbent, it may be desirable to provide a plurality of such columns in parallel with a provision to switch the flow from one column to another. Thus when one column of adsorbent becomes saturated with catalyst, it can be switched out of the flow path and the flow diverted to a fresh column—in certain embodiments, the interval of time from when a column is placed in the flow path to when it is switched out of the flow path corresponds to the "first time interval" recited in the methods described herein. Where an adsorbent is used to remove catalyst from the β-propiolactone product stream, the inventive methods will typically include a step of desorbing the catalyst or catalyst component(s) from the adsorbent. Such desorption methods are well known in the art and will vary depending on the identity of the adsorbant and the catalyst. Desorption can include treating with a polar solvent or solute which displaces the catalyst or catalyst component, or can comprise a reactive process where a reagent is added to the adsorbed catalyst to regenerate it or form a species which is less adhered to the adsorbing solid.

Ion Exchange

In certain embodiments, the carbonylation catalyst recycle system may be configured to separate the carbonylation catalyst by ion exchange of the carbonylation catalyst or components thereof. In certain embodiments, the carbonylation catalyst recycle system is configured to separate the carbonylation catalyst by treating the β-propiolactone product stream with ion exchange materials. The ion exchange materials may be, for example, cationic, anionic, amphoteric, Lewis basic, Lewis acidic, or may comprise chelating groups. In certain embodiments, the ion exchange material may be a cation exchanger. In certain embodiments, functional groups on the cation exchange materials may be selected from: $-SO_3$, $PO_3^{2-}$, $-COOH$, $-C_6H_4OH$, $-SH$, $-AsO_3$, or $-SeO_3$, or combinations of two or more of these. In certain embodiments, functional groups on the cation exchange materials comprise $-SO_3$ In certain embodiments, the ion exchange material may be an anion exchanger. In certain embodiments, functional groups on the anion exchange materials may be selected from: $-N^+(alkyl)_3$, $-N^+(CH_3)_3$, $-N^+(CH_3)_2C_2H_4OH$, $-N^+(CH_3)_2C_2H_5$, $-P^+(alkyl)_3$, $-P^+(aryl)_3$, $-P^+(C_4H_9)_3$, or $-P^+(Ph)_3$, or combinations of two or more of these. In certain embodiments, functional groups on the anion exchange materials comprise $-N^+(alkyl)_3$. In certain embodiments, functional groups on the anion exchange materials comprise $-P^+(alkyl)_3$. In certain embodiments, functional groups on the anion exchange materials comprise $-P^+(aryl)_3$.

In certain embodiments, the carbonylation catalyst recycle system is configured to separate the carbonylation catalyst by anion exchange and cation exchange. In certain embodiments, where the carbonylation catalyst comprises the combination of a cationic Lewis acid and an anionic metal carbonyl, each is removed separately and the method comprises treating the β-propiolactone product stream with a cation exchange material to remove the Lewis acid and an anion exchange material to remove the metal carbonyl. In certain embodiments the anion and cation exchange are performed concomitantly. In certain embodiments, the anion and cation exchange are performed sequentially. In certain embodiments, the anion exchange is performed first followed by cation exchange. In certain embodiments, the cation exchange is performed first followed by anion exchange. In certain embodiments, an ion exchange material used in the separation step comprising an organic ion exchange resin may prove useful. Organic ion exchange resins generally possess a three dimensional structure, the matrix. Functional groups maybe attached to the structure, or directly incorporated in the polymeric chains. The matrix may be constructed from linear polymeric chains cross-linked with each other by relatively short links. By way of example, in various aspects, the present disclosure includes the use of ion exchange materials comprised of sulphonated polystyrene cross-linked with divinylbenzene:

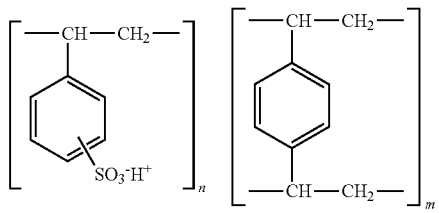

In various aspects, ion exchange materials may take the form of gels, or gel resins, distributed across a bead, or other support substrate. In various aspects, ion exchange materials may take the form of macroporous resins which have a heterogeneous structure consisting of two phases, a gel region comprised of polymers and macroscopic permanent pores. In various embodiments of the present disclosure, the ion exchange materials comprise macroreticular resins which are additionally macroporous resins in which the gel regions consist of a plurality of bead micro-grains. Ion exchange materials may comprise a wide variety of morphologies and forms, including variations in porosity and other surface properties. In various aspects, materials can be formed into, but not limited to beads, pellets, spheres, spheroids, rings, hollow cylinders, blocks, fibers, meshes, membranes, textiles.

In various aspects, the bead size may be widely distributed, or may be very narrow, so-called mono-disperse resins. In embodiments where catalyst is removed from the β-propiolactone product stream by ion exchange, the ion exchange material can be contacted with the product stream by any conventional method. This includes, but is not limited to: flowing the β-propiolactone product stream through a fixed bed of a solid ion exchange material (i.e. in the form of beads, granules or other particles); flowing the β-propiolactone product stream through a fluidized bed of adsorbent, flowing the β-propiolactone product stream through fabrics, meshes, or filtration plates comprising the ion exchange material, or slurrying the β-propiolactone product stream with the ion exchange material (typically followed by filtration, centrifugation, sedimentation or the like to remove the ion exchange material from the product stream). In embodiments where the β-propiolactone product stream is flowed through a packed column of ion exchange material, it may be desirable to provide a plurality of such columns in parallel with a provision to switch the flow from one to another periodically. Thus when one column of ion exchange material becomes saturated with catalyst, it can be switched out of the flow path and the flow diverted to a fresh column. In certain embodiments, the interval of time from when a column is placed in the flow path to when it is switched out of the flow path corresponds to the "first time interval" recited in the methods described herein.

Where an ion exchange material is used to remove catalyst from the β-propiolactone product stream, the inventive methods will typically include a subsequent step of removing the catalyst or catalyst component(s) from the ion exchange material. Such removal methods are well known in the art and typically involve contacting the ion exchange resin with a strong solution of a salt, the anion or cation of which will displace the catalyst component from the ion exchange material. The specifics of this removal step may vary depending on the identity of the adsorbent and the catalyst, but suitable methods are known to those skilled in the art.

Ionic Liquids

In certain embodiments, the carbonylation catalyst recycle system is configured to separate the carbonylation catalyst by using ionic liquids. For example, in some embodiments, In certain embodiments, the carbonylation catalyst recycle system is configured to separate the carbonylation catalyst using an ionic liquid to form a biphasic system comprising an ionic liquid phase and a β-propiolactone product stream. At least a portion of the catalyst (or a component thereof) is extracted into the ionic liquid phase, such that the concentration of catalyst is reduced in the reaction product phase. The ionic liquid phase comprising at least a portion of the carbonylation catalyst is then removed, the carbonylation catalyst is isolated from the ionic liquid phase using any suitable methods known in the art, and the isolated carbonylation catalyst is recycled back into the carbonylation reactor. For example, in some embodiments the carbonylation catalyst is isolated from the ionic liquid phase using, nanofiltration or precipitation. It may also be possible at times to use an ion exchange resin for such separation.

Any suitable ionic liquid known in the art may be used. In some embodiments, a mixture of ionic liquids is used.

Materials of Construction

The materials of construction suitable for the carbonylation catalyst recycling system may use any materials that are compatible with, for example, the membrane used. In some variations, the carbonylation catalyst recycling system has inert, metal surfaces, for example, to reduce or eliminate polymer nucleation sites.

In other variations, the carbonylation catalyst recycling system may use elastomer seals that are compatible with ethylene oxide, carbon monoxide and/or β-propiolactone, and has little to no permeability to atmosphere. Examples may include: Kalrez 6375, Chemraz 505, PTFE encapsulated Viton, and PEEK.

In yet other variations, the materials of construction of external parts of the carbonylation catalyst recycling system may be compatible with the environment, including, for example, sand and salty water, and is not heat absorbing. Further, safety interlocks and safe operating parameters may be employed. For example, the carbonylation catalyst recycling system may be configured to mitigate polypropiolactone formation prior to the polypropiolactone production system/production process, and/or to avoid catalyst decomposition (e.g., by addition of CO pressure on permeate or retentate side).

β-Propiolactone Product Stream Entering Carbonylation Catalyst Recycling System

With reference again to FIG. 1, the β-propiolactone product stream from the β-propiolactone production system/production process is transferred to the carbonylation catalyst recycling system. In some embodiments, the β-propiolactone product stream includes at least about 2000 kg/hr bPL, at least about 2500 kg/hr bPL, at least about 3000 kg/hr bPL, at least about 3500 kg/hr bPL, at least about 3638 kg/hr bPL, at least about 4000 kg/hr bPL, at least about 5000 kg/hr bPL, at least about 1000 kg/hr bPL, at least about 20000 kg/hr bPL, at least about 35000 kg/hr bPL, at least about 36380 kg/hr bPL, or at least about 40000 kg/hr bPL. In some embodiments, the β-propiolactone product stream includes about 2000 kg/hr bPL, about 2500 kg/hr bPL, about 3000 kg/hr bPL, about 3500 kg/hr bPL, about 3638 kg/hr bPL, about 4000 kg/hr bPL, about 5000 kg/hr bPL, about 1000 kg/hr bPL, about 20000 kg/hr bPL, about 35000 kg/hr bPL, about 36380 kg/hr bPL, or about 40000 kg/hr bPL. In some embodiments, the β-propiolactone product stream includes between about 2000 kg/hr bPL and 4000 kg/hr bPL, between about 2500 kg/hr bPL and 4000 kg/hr bPL, between about 3000 kg/hr bPL and 4000 kg/hr bPL, between about 3500 kg/hr bPL and 4000 kg/hr bPL, between about 3638 kg/hr bPL and 4000 kg/hr bPL, between about 2000 kg/hr bPL and 40000 kg/hr bPL, between about 2500 kg/hr bPL and 40000 kg/hr bPL, between about 3000 kg/hr bPL and 40000 kg/hr bPL, between about 3500 kg/hr bPL and 40000 kg/hr bPL, between about 3638 kg/hr bPL and 40000 kg/hr bPL, between about 4000 kg/hr bPL and 40000 kg/hr bPL, between about 5000 kg/hr bPL and 40000 kg/hr bPL, between about 1000 kg/hr bPL and 40000 kg/hr bPL, between about 20000 kg/hr bPL and 40000 kg/hr bPL, between about 35000 kg/hr bPL and 40000 kg/hr bPL, between about 36380 kg/hr bPL and 40000 kg/hr bPL, or between about 40000 kg/hr bPL and 40000 kg/hr bPL. In some embodiments, the β-propiolactone product stream includes at least about 30 kmol/hr bPL, at least about 40 kmol/hr bPL, at least about 45 kmol/hr bPL, at least about 50 kmol/hr bPL, at least about 55 kmol/hr bPL, at least about 100 kmol/hr bPL, at least about 200 kmol/hr bPL, at least about 300 kmol/hr bPL, at least about 400 kmol/hr bPL, at least about 450 kmol/hr bPL, at least about 500 kmol/hr bPL, or at least about 550 kmol/hr bPL. In some embodiments, the mass fraction of bPL in the β-propiolactone product stream can be about 0.1-0.4, about 0.15-0.3, about 0.18-0.25, about 0.2-0.23, at least about 0.15, at least about 0.2, or at least about 0.224. In some embodiments, the mole fraction of bPL in the β-propiolactone product stream can be about 0.1-0.4, about 0.15-0.3, about 0.18-0.25, about 0.21-0.23, at least about 0.15, at least about 0.2, or at least about 0.22. The β-propiolactone product stream can also include other components including unreacted ethylene oxide (in mass fraction of about 0.005-0.05, about 0.01-0.045, about 0.04, at most about 0.014, at most about 0.02, or at most about 0.05), unreacted carbon monoxide (in mass fraction of about 0.0005-0.01, at most about 0.01, or at most about 0.02), acetaldehyde (in mass fraction of about 0.0005-0.005, at most about 0.005, or at most about 0.01), succinic anhydride (in mass fraction of about 0.0005-0.005, at most about 0.005, or at most about 0.001), carbonylation catalyst (in about 40-640 kg/hr, 300-640 kg/hr, 40-300 kg/hr, 40-64 kg/hr, about 45-60 kg/hr, about 50-60 kg/hr, at most 54.8 kg/hr, at most 60 kg/hr, at most 100 kg/hr, at most 300 kg/hr, or at most about 600 kg/hr or a mass fraction of about 0.001-0.005, about 0.002-0.004, at most about 0.003, or at most about 0.004), and the remainder solvent. In some embodiments, the β-propiolactone product stream includes carbonylation catalyst components (in about 40-640 kg/hr, 300-640 kg/hr, 40-300 kg/hr, 40-64 kg/hr, about 45-60 kg/hr, about 50-60 kg/hr, at most 54.8 kg/hr, at most 60 kg/hr, at most 100 kg/hr, at most 300 kg/hr, or at most about 600 kg/hr or a mass fraction of about 0.001-0.005, about 0.002-0.004, at most about 0.003, or at most about 0.004).

In some embodiments, the β-propiolactone product stream from the β-propiolactone production system/production process can have a temperature of about 40-100° C., about 50-90° C., about 65-75° C., or about 70° C. In some embodiments, the β-propiolactone product stream can have a pressure of about 1-15 bar, about 2-10 bar, or about 7 bar.

β-Propiolactone Product Stream Exiting Carbonylation Catalyst Recycling System

In some embodiments, the β-propiolactone product stream exiting the carbonylation catalyst recycling system includes at least about 2000 kg/hr bPL, at least about 2500 kg/hr bPL, at least about 3000 kg/hr bPL, at least about 3100 kg/hr bPL, at least about 3200 kg/hr bPL, at least about 3500 kg/hr bPL, at least about 3638 kg/hr bPL, at least about 4000 kg/hr bPL, at least about 5000 kg/hr bPL, at least about 1000 kg/hr bPL, at least about 20000 kg/hr bPL, or at least about 35000 kg/hr bPL. In some embodiments, the β-propiolactone product stream includes about 2000 kg/hr bPL, about 2500 kg/hr bPL, about 3000 kg/hr bPL, about 3500 kg/hr bPL, about 3638 kg/hr bPL, about 4000 kg/hr bPL, about 5000 kg/hr bPL, about 1000 kg/hr bPL, about 20000 kg/hr bPL, about 35000 kg/hr bPL, about 36380 kg/hr bPL, or about 40000 kg/hr bPL. In some embodiments, the β-propiolactone product stream exiting the carbonylation catalyst recycling system includes between about 2000 kg/hr bPL and 3500 kg/hr bPL, between about 2500 kg/hr bPL and 3500 kg/hr bPL, between about 3000 kg/hr bPL and 3500 kg/hr bPL, between about 2000 kg/hr bPL and 35000 kg/hr bPL, between about 2500 kg/hr bPL and 35000 kg/hr bPL, between about 3000 kg/hr bPL and 35000 kg/hr bPL, between about 3500 kg/hr bPL and 35000 kg/hr bPL, between about 3638 kg/hr bPL and 35000 kg/hr bPL, between about 4000 kg/hr bPL and 35000 kg/hr bPL, between about 5000 kg/hr bPL and 35000 kg/hr bPL, between about 1000 kg/hr bPL and 35000 kg/hr bPL, or between about 20000 kg/hr bPL and 35000 kg/hr bPL. In some embodiments, the post-isolation β-propiolactone product stream includes at least about 30 kmol/hr bPL, at least about 35 kmol/hr bPL, at least about 40 kmol/hr bPL, at least about 43 kmol/hr bPL, at least about 45 kmol/hr bPL, at least about 100 kmol/hr bPL, at least about 200 kmol/hr bPL, at least about 300 kmol/hr bPL, or at least about 350 kmol/hr bPL In some embodiments, the mass fraction of bPL in the post-isolation β-propiolactone product stream can be about 0.1-0.4, about 0.15-0.3, about 0.18-0.25, about 0.2-0.24, at least about 0.15, at least about 0.2, or at least about 0.225. In some embodiments, the mole fraction of bPL in the post-isolation β-propiolactone product stream can be about 0.1-0.4, about 0.15-0.3, about 0.18-0.25, about 0.21-0.23, at least about 0.15, at least about 0.2, or at least about 0.22. The post-isolation β-propiolactone product stream can also include other components including unreacted ethylene oxide (in mass fraction of about 0.005-0.05, about 0.01-0.04, about 0.044, at most about 0.014, at most about 0.02, or at most about 0.05), unreacted carbon monoxide (in mass fraction of about 0.0005-0.001, at most about 0.001, or at most about 0.002), acetaldehyde (in mass fraction of about 0.0005-0.005, at most about 0.005, or at most about 0.01), succinic anhydride (in mass fraction of about 0.0005-0.0051, at most about 0.005, or at most about 0.01), carbonylation catalyst (in about 0-50 kg/hr, about 0.5-20 kg/hr, about 1-15 kg/hr, about 0-5 kg/hr, about 0.5-2 kg/hr, about 1-1.5 kg/hr, at most 1.4 kg/hr, at most about 2 kg/hr, at most 10 kg/hr, or at most 20 kg/hr), and the remainder solvent. In some variations, the post-isolation β-propiolactone product stream can includes carbonylation catalyst components (in about 0-50 kg/hr, about 0.5-20 kg/hr, about 1-15 kg/hr, about 0-5 kg/hr, about 0.5-2 kg/hr, about 1-1.5 kg/hr, at most 1.4 kg/hr, at most about 2 kg/hr, at most 10 kg/hr, or at most 20 kg/hr).

In some embodiments, the β-propiolactone product stream exiting the carbonylation catalyst recycling system can have a temperature of about 20-60° C., about 30-50° C., about 35-45° C., or about 40° C. In some embodiments, the β-propiolactone product stream exiting the carbonylation catalyst recycling system can have a pressure of about 1-15 bar, about 2-10 bar, or about 7 bar.

Carbonylation Catalyst Regeneration and Accumulation

The carbonylation catalyst may be recovered from the catalyst recycling system in a form other than as active catalyst. Thus, with reference to FIG. 3, in some variations, retentate stream 324 may require further processing by one or more additional steps to regenerate the carbonylation catalyst for use in the β-propiolactone production system/production process.

Further, the carbonylation catalyst (or a component thereof) separated from the β-propiolactone product stream may be accumulated through some interval of time. The accumulated catalyst (or component) forms a spent catalyst batch that is eventually reused (either in whole or in part) in a carbonylation process. The process for which the catalyst is re-used may or may not be the same process from which the catalyst was isolated. Likewise it may be reused for the same process but on another day or in a different reactor. This is in contrast to methods wherein the separated catalyst is treated as a stream within the reaction process which is returned to the reactor within a relatively short period.

In certain embodiments where the carbonylation catalyst comprises a cationic Lewis acid in combination with an anionic metal carbonyl, the cationic Lewis acid portion of the catalyst is captured from the β-propiolactone product stream without the associated metal carbonyl. In certain embodiments, the cationic Lewis acid is accumulated in a form with a counterion other than the anionic metal carbonyl. In such embodiments, the methods may include a further step of treating the accumulated batch of cationic Lewis acid under conditions to swap a non-metal carbonyl anion associated with the accumulated Lewis acid with a metal carbonyl anion.

In certain embodiments where the carbonylation catalyst comprises a cationic Lewis acid in combination with an anionic metal carbonyl, the metal carbonyl portion of the catalyst is captured from the β-propiolactone product stream without the associated Lewis acid. The metal carbonyl thus accumulated may be captured as an anionic metal carbonyl (for example by anion exchange) or it may be accumulated in another form such as a reduced metal species, a metal salt, a neutral metal carbonyl, a mixed metal carbonyl complex, or some other form. In such embodiments, the methods may include a further step of treating the accumulated species to regenerate a catalytically active metal carbonyl compound. In the case where an intact metal carbonyl anion is accumulated (for example by capture on an anion exchange resin), such steps may include metathesis to free the metal carbonyl anion from the resin. This will typically entail flooding the resin with another anion (such as sodium chloride) to displace the metal carbonyl. The metal carbonyl may then be obtained as its sodium salt and utilized to produce active catalyst according to known catalyst synthesis procedures. Therefore, in certain embodiments, systems and methods described herein comprise further steps of freeing accumulated metal carbonyl anion from a resin. In certain embodiments, such steps entail further steps of utilizing accumulated metal carbonyl anion to regenerate active catalyst by combining the accumulated metal carbonyl with a suitable Lewis acid.

In certain embodiments, the metal carbonyl may be accumulated in a form other than as an intact metal carbonyl anion. For example, in CO-deficient atmospheres, the metal carbonyl may lose one or more CO ligands to form multinuclear metal carbonyl species, salts, or precipitate in elemental form. In other embodiments, a strong ligand may be utilized to displace one or more CO ligands and aid in capture of the metal carbonyl as a new complex. It is known that such species can be utilized to regenerate well defined metal carbonyl compounds by treatment under CO pressure. Therefore, in certain embodiments, systems and methods described herein include further steps of regenerating the catalytically active metal carbonyl species from a non-catalytically active material accumulated from the β-propiolactone product stream. In certain embodiments, such steps entail further steps of treating accumulated residue derived from a catalytically active metal carbonyl compound under conditions to regenerate a catalytically active metal carbonyl suitable for reuse. In certain embodiments, such steps include a step of treating the accumulated residue under high CO pressure. In certain embodiments, methods include the step of treating a cobalt-containing residue accumulated from the β-propiolactone product stream under conditions of high CO pressure to convert it to dicobalt octacarbonyl.

In certain embodiments where the accumulation of catalyst separated from the β-propiolactone product stream comprises steps of recovering two or more separate catalyst components in separate recovered catalyst batches, additional steps of recombining recovered catalyst components may be needed to produce active carbonylation catalyst. In some cases the recovered catalyst components may be combined directly while in other steps one or more of the components may require processing as described above prior to step of combining. In certain embodiments such steps entail a metathesis to recombine a recovered cationic Lewis acid with a recovered metal carbonyl anion such as a carbonyl cobaltate.

The time interval required to accumulate a batch is dependent on the mode of accumulation, and the scale and economics of any processes required to transform the accumulated catalyst residue into active catalyst. In some embodiments, the time interval for accumulation of the catalyst or residue is on the order of hours to days, but may be weeks. Therefore, in certain embodiments of any of the methods described above, the first time interval is in the range from about 1 hour to about 200 hours. In certain embodiments, the first time interval is from about 2 hours to about 8 hours, from about 4 hours to about 16 hours, from about 12 hours to about 24 hours, or from about 16 hours to about 36 hours. In certain embodiments, the first time interval is from about 1 day to about 20 days, from about 1 day to about 3 days, from about 2 days to about 5 days, from about 5 days to about 10 days, or from about 10 days to about 20 days.

During this time, the carbonylation reactor may be fed from a reservoir of catalyst which is depleted as the amount of accumulated catalyst (or catalyst residue) increases on the back end of the process. Additional time may be required to process the accumulated catalyst or catalyst residue to remanufacture active catalyst. Therefore, in some variations, some multiple of the first time interval have elapsed from the first time interval when the catalyst was accumulated to the later time at which the carbonylation reactor is fed with a catalyst feed stream containing catalyst derived from the catalyst accumulated during the first time interval. In certain embodiments the length of time between the second time interval (during with catalyst recovered is fed to reactor), and the first time interval (during which the catalyst was accumulated) is on the order of about 1 to about 100 times the length of the first time interval. In other words, if the first time interval is 10 hours, the second time interval would occur from about 10 hours to about 2000 hours after the completion of the accumulation step. In certain embodiments, the length of time between the second time interval and the first time interval is from about 1 to about 10 times the length of the first time interval. In certain embodiments, the length of time between the second time interval and the first time interval is from about 1 to about 3 times, from about 2 to about 5 times, from about 4 to about 10 times, from about 10 to about 50 times, from about 40 to about 80 times, or from about 50 to about 100 times, the length of the first time interval. In certain embodiments, the length of time between the second time interval and the first time interval is greater than 100 times the first time interval.

Continuous Replacement of Catalyst at Predetermined Rate

In certain variations, the carbonylation catalyst recycling system may be configured to continuously or intermittently introduce to the carbonylation reactor a catalyst replacement component that is different from the carbonylation catalyst (e.g., from the carbonylation catalyst source) and may comprise a species selected from the group consisting of the Lewis acid, a precursor to the Lewis acid, the metal carbonyl, and a precursor to the metal carbonyl.

In some embodiments, the catalyst replacement component comprises the Lewis acid. In some embodiments, the catalyst replacement component comprises a precursor to the Lewis acid. In some embodiments, the catalyst replacement component comprises the metal carbonyl. In some embodiments, the catalyst replacement component comprises a precursor to the metal carbonyl.

In some embodiments, the catalyst replacement component is introduced at a rate that results in less than 10% variation in the rate of the carbonylation reaction over a period of one hour. In some embodiments, the catalyst replacement component is introduced at a rate that results in less than 5% variation in the rate of the carbonylation reaction over a period of one hour.

In some embodiments, the rate at which the catalyst replacement component is added to the carbonylation reactor is determined by the rate at which the carbonylation reaction rate has been observed to decrease. In some embodiments, the rate at which the one or more catalyst replacement components are added to the carbonylation reactor is directly proportional to the rate at which the carbonylation reaction rate has been observed to decrease.

In some embodiments, the one or more catalyst replacement components are introduced continuously to the carbonylation reactor at the same rate that the carbonylation reaction rate is observed to decrease. In some embodiments, the one or more catalyst replacement components are introduced intermittently to the carbonylation reactor to produce an average rate which matches the rate at which the carbonylation reaction rate has been observed to decrease.

Thus, if the carbonylation reaction rate has been observed to decrease 5% over the course of a time period, the catalyst replacement component may either be added continuously or intermittently at such a rate that 5% of the initial amount of Lewis acid or metal carbonyl present in the carbonylation reactor is added over that same time period. In some embodiments, the catalyst replacement component is added continuously. In some embodiments, the catalyst replacement component is added every hour. In some embodiments, the catalyst replacement component is added every 30 minutes. In some embodiments, the catalyst replacement component is added every 15 minutes. In some embodiments, the catalyst replacement component is added every 10 minutes. In some embodiments, the catalyst replacement component is added every 5 minutes. In some embodiments, the catalyst replacement component is added every minute.

One of skill in the art will appreciate that the shorter the intervals at which the one or more catalyst replacement components are added, the less variation in the overall carbonylation reaction rate will be observed. It should be recognized, however, that this must be balanced against other considerations such as the complexity of making multiple additions.

Recycling to BPL Production System/Production Process

In some embodiments, the carbonylation catalyst and/or solvent stream may be recycled to the feed stream or to the carbonylation reactor. In some embodiments, the portion of the solvent and/or catalyst from the β-propiolactone product stream recycled to the carbonylation reactor or feed stream ranges from about 0% to about 100%. In some embodiments, the portion of the solvent and/or catalyst from the β-propiolactone product stream recycled to the carbonylation reactor or feed stream is about 100%, about 90%, about 80%, about 70%, about 60%, about 50%, about 40%, about 30%, about 20%, about 10%, or about 0%. In some embodiments, a different percentage of the catalyst, as compared to the solvent is recycled, i.e., the proportions of either the catalyst or solvent component do not need to be equal.

BPL Purification System (and Solvent Recycle)

After the catalyst isolation system, the post-isolation carbonylation stream (i.e., post-isolation β-propiolactone product stream) can be fed to the BPL Purification system. The BPL purification system can separate bPL into a BPL purified stream from low-boiling impurities before it enters the polymerization reaction system, where high purity bPL can be required. In some embodiments, the BPL purified stream can have at least about 90 wt % bPL, at least about 95 wt % bPL, at least about 98 wt % bPL, at least about 99 wt % bPL, at least about 99.3 wt % bPL, at least about 99.5 wt % bPL, at least about 99.8 wt %, or at least about 99.9 wt %. In some embodiments, the BPL purified stream can have at most about 1 wt % solvent, at most about 0.5 wt % solvent, or at most about 0.1 wt % solvent. In some embodiments, the BPL purification system can also create a solvent recycle stream. In some embodiments, the BPL purification system can separate the bPL from the other components in the post-isolation carbonylation stream such as solvent, unreacted ethylene oxide, unreacted carbon monoxide, secondary reaction product acetaldehyde, secondary reaction product succinic anhydride, and carbonylation catalyst or components thereof that was not isolated in the catalyst isolation system. The separation of bPL from the other components in the post-isolation carbonylation stream can be accomplished by various methods known to those of ordinary skill in the art.

Carbonylation catalyst components may include, for example, compounds produced by degradation of the catalyst, compounds used to produce the catalyst, metals or metal ions which were part of the catalyst, any organic compounds which were part of the catalyst, metal carbonyls or metal complexes which were part of the catalyst. For example, in some embodiments, carbonylation catalyst components are carbonyl cobaltate, aluminum salen compounds, aluminum porphyrin compounds, aluminum salophen compounds, cobalt or cobalt ions, or aluminum or aluminum ions, or any combinations thereof.

In some embodiments, the temperature in the BPL purification system can be at most about 150° C., at most about 125° C., at most about 115° C., at most about 105° C., or at most about 100° C. When bPL is exposed to temperatures greater than 100° C., the bPL can potentially decompose or be partially polymerized. Accordingly, the bPL can be purified without being exposed to temperatures of about 150° C., 125° C., 115° C., 105° C., or 100° C.

In some embodiments, the separation is performed by exploiting the boiling point differential between the beta-propiolactone and the other components of the carbonylation product stream, primarily the solvent. In some embodiments, the boiling point of the solvent is lower than the boiling point of the beta-propiolactone. In some embodiments, the solvent is volatilized (e.g., evaporated) from the BPL purification feed along with other lighter components (e.g., ethylene oxide & acetaldehyde), leaving behind bPL, other heavier compounds (e.g., catalyst and succinic anhydride) and some leftover solvent from the BPL purification feed. In some embodiments, this includes exposing the BPL purification feed to reduced pressure. In some embodiments, this includes exposing BPL purification feed to increased temperature. In some embodiments, this includes exposing the BPL purification feed to both reduced pressure and increased temperature.

In some embodiments, the pressure is selected so that the boiling point of the solvent is reduced by about 5° C. as compared to the boiling point at atmospheric pressure. In some embodiments, the pressure is selected so the boiling point of the solvent is reduced by about 10° C. as compared to the boiling point at atmospheric pressure. In some embodiments, the pressure is selected so the boiling point of the solvent is reduced by about 20° C. as compared to the boiling point at atmospheric pressure. In some embodiments, the pressure is selected so the boiling point of the solvent is reduced by about 50° C. as compared to the boiling point at atmospheric pressure.

In some embodiments, the increased temperature is above the boiling point of the solvent but below the boiling point of the beta-propiolactone, at the selected pressure. In some embodiments, the temperature is at least about 20° C. below the boiling point of the beta-propiolactone. In some embodiments, the temperature is at least about 30° C. below the boiling point of the beta-propiolactone. In some embodiments, the temperature is at least about 50° C. below the boiling point of the beta-propiolactone.

In some embodiments, the reduced pressure is in the range from about 1 Torr to about 760 Torr. In some embodiments, the pressure is in the range of about 1 Torr to about 400 Torr. In some embodiments, the pressure is in the range of about 5 Torr to about 200 Torr. In some embodiments, the pressure is in the range of about 10 Torr to about 100 Torr. In some embodiments, the pressure is in the range of about 20 Torr to about 50 Torr. In some embodiments, the pressure is about 50 Torr, about 100 Torr, about 150 Torr, about 200 Torr, about 250 Torr, about 300 Torr, about 400 Torr about 500 Torr, about 600 Torr or about 700 Torr.

In some embodiments, the separation step is performed at a pressure below about 100 Torr and at a temperature above about 120° C. In some embodiments, the separation step is performed at a pressure below about 50 Torr and at a temperature above about 100° C. In some embodiments, the separation step is performed at a pressure below about 50 Torr and at a temperature above about 50° C. In some embodiments, the separation step is performed at a pressure below about 50 Torr and at a temperature above about 110° C. In some embodiments, the separation step is performed at a pressure below about 50 Torr and at a temperature above about 90° C. In some embodiments, the separation step is performed at a pressure below about 20 Torr and at a temperature above about 60° C. In some embodiments, the separation step is performed at a pressure below about 10 Torr and at a temperature above about 50° C.

In some embodiments, the separation may be effected in a sequence of steps, each operating at an independent temperature and pressure. For example, in one embodiment, two steps may be used to obtain a more effective separation of beta-propiolactone, or a separate separation step may be used to isolate certain reaction by-products. In some embodiments, when a mixture of solvents is used, multiple separation steps may be required to remove particular solvents, individually or as a group, and effectively isolate the beta-propiolactone.

In certain embodiments, the separation of the beta-propiolactone from the BPL purification feed is performed in two stages. In some embodiments the process includes a preliminary separation step to remove one or more components of the BPL purification feed having boiling points below that of the beta-propiolactone product.

In some embodiments, the preliminary separation step includes separating the BPL purification feed into a gas stream comprising ethylene oxide, solvent, and bPL (and potentially carbon monoxide, acetaldehyde, and/or bPL); and a liquid stream comprising beta-propiolactone, carbonylation catalyst (and potentially succinic anhydride and/or solvent). In the second step of separation, the liquid stream is further separated into a beta-propiolactone stream comprising beta-propiolactone, a solvent stream comprising solvent, and potentially a catalyst and succinic anhydride purge stream. The gas stream can also be further separated into a solvent stream comprising solvent, a light gases stream comprising solvent and ethylene oxide (and potentially acetaldehyde), and a liquid bPL stream comprising bPL and solvent. The liquid bPL stream can join with the liquid stream prior to separation of the liquid stream and form a combined feed to the second separation step. In some embodiments, the solvent stream from the second separation step and/or the solvent stream from the gas stream separation can form the solvent recycle stream which can be fed to the carbonylation reaction system or to a solvent reservoir.

In some embodiments where one or more solvents with a boiling point lower than that of the beta-propiolactone are present, the lower boiling solvent may be volatilized (e.g., evaporated) from the BPL purification feed in a preliminary separation step, leaving behind a mixture comprising catalyst, beta-propiolactone, other solvents (if any) and other compounds in the BPL purification stream which is then further treated to separate the beta-propiolactone stream.

In certain embodiments where the separation is performed in two stages, the first step of separation comprises exposing the reaction stream to mildly reduced pressure to produce the gas stream and the liquid stream. In certain embodiments where the separation is performed in two stages, the gas stream can be returned to the carbonylation step.

In certain embodiments, the separation of the beta-propiolactone from the BPL purification feed is performed in three stages. In the first step of separation, the BPL purification feed is separated into a gaseous stream comprising ethylene oxide, solvent, and bPL (and potentially carbon monoxide and/or acetalhydride); and a liquid stream comprising solvent, beta-propiolactone, and carbonylation catalyst (and potentially succinic anhydride). In the second step of separation, the gaseous stream is separated into a solvent side stream comprising solvent; a light gas stream comprising ethylene oxide and solvent (and potentially carbon monoxide and/or acetaldehyde); and second liquid stream comprising solvent and bPL. In the third step of separation, the second liquid stream and the first liquid stream are combined and separated into a gaseous solvent stream comprising solvent, a purified BPL stream comprising bPL, and potentially a catalyst and succinic anhydride purge stream. In some embodiments, the solvent side stream and/or the gaseous solvent stream can be used as the solvent recycle stream for use in the carbonylation reaction system or can be stored in a solvent storage tank.

In certain embodiments where the separation is performed in three stages, the first step of separation comprises exposing the BPL purification feed to atmospheric pressure. In certain embodiments where the separation is performed in three stages, the second step of separation comprises exposing the gaseous stream to atmospheric pressure. In certain embodiments where the separation is performed in three stages, the third step of separation comprises exposing the gaseous stream to a vacuum or reduced pressure. In certain embodiments, the reduced pressure is between about 0.05-0.25 bara. In certain embodiments, the reduced pressure is between about 0.1-0.2 bara or about 0.15 bara.

In certain embodiments, the separation of the beta-propiolactone from the BPL purification feed is performed in four stages. In the first step of separation, the BPL purification feed is separated into a gaseous stream comprising ethylene oxide, solvent, and bPL (and potentially carbon monoxide and/or acetalhydride); and a liquid stream comprising solvent, beta-propiolactone, and carbonylation catalyst (and potentially succinic anhydride). In the second step of separation, the gaseous stream is separated into a solvent side stream comprising solvent; a light gas stream comprising ethylene oxide and solvent (and potentially carbon monoxide and/or acetaldehyde); and second liquid stream comprising solvent and bPL. In the third step of separation, the second liquid stream and the first liquid stream are combined and separated into a gaseous solvent stream comprising solvent, a purified BPL stream comprising bPL, and potentially a catalyst and succinic anhydride purge stream. In the fourth step of separation, the light gas stream is separated into a third solvent stream comprising solvent and a second light gas stream comprising ethylene oxide (and potentially carbon monoxide and/or acetaldehyde). In some embodiments, the solvent side stream, the gaseous solvent stream, and/or the third solvent stream can be used as the solvent recycle stream for use in the carbonylation reaction system or can be stored in a solvent storage tank.

In certain embodiments where the separation is performed in four stages, the first step of separation comprises exposing the BPL purification feed to atmospheric pressure. In certain embodiments where the separation is performed in four stages, the second step of separation comprises exposing the gaseous stream to atmospheric pressure. In certain embodiments where the separation is performed in four stages, the third step of separation comprises exposing the combined liquid stream to a vacuum or reduced pressure. In certain embodiments, the reduced pressure is between about 0.05-0.25 bara. In certain embodiments, the reduced pressure is between about 0.1-0.2 bara or about 0.15 bara. In certain embodiments where the separation is performed in four stages, the fourth step of separation comprises exposing the light gas stream to atmospheric pressure.

In some embodiments, the BPL purification system can include at least one distillation column to separate bPL from the other components in the post-isolation carbonylation stream. In some embodiments, the BPL purification system includes at least two distillation columns. In some embodiments, the BPL purification system includes at least three distillation columns. In some embodiments, at least one of the distillation columns is a stripping column (i.e., stripper). In some embodiments, at least one of the distillation columns is a vacuum column. In some embodiments, the BPL purification system can include an initial evaporator, wherein the post-isolation carbonylation stream is first fed to an evaporator in the BPL purification system. The evaporator can perform a simple separation between the solvent and the bPL in the post-isolation carbonylation stream. The evaporator can reduce loads on subsequent distillation columns making them smaller. In some embodiments, the evaporator can reduce loads on subsequent distillation columns making them smaller by evaporating solvent in the post-isolation carbonylation stream at about atmospheric pressure and about 100° C.

Figure 16:
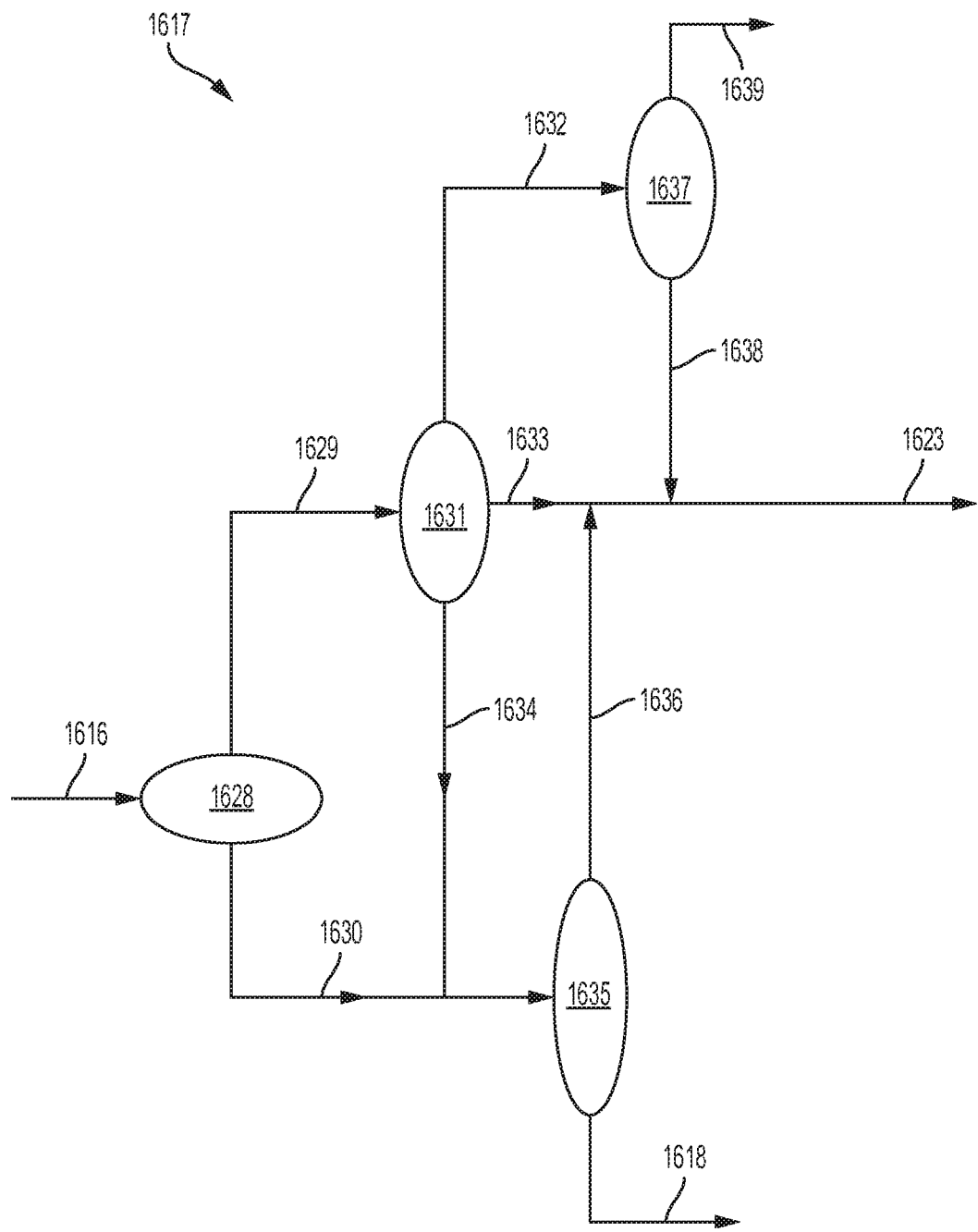
FIG. 16 illustrates an embodiment of a BPL purification system described herein.

FIG. 16 illustrates an exemplary embodiment of the BPL Purification system disclosed herein.

Feed Stream

As depicted in FIG. 16, in some embodiments of the exemplary system, feed 1616 to BPL purification system 1617 can be the post-isolation carbonylation product stream (i.e., post-isolation β-propiolactone product stream). In other embodiments, the feed to the BPL purification system can be the carbonylation product stream. In some embodiments, the feed to BPL purification system is at least about 10000 kg/hr, at least about 11000 kg/hr, at least about 12000 kg/hr, at least about 13000 kg/hr, at least about 13777 kg/hr, at least about 20000 kg/hr, at least about 50000 kg/hr, at least about 100000 kg/hr, at least about 110000 kg/hr, at least about 120000 kg/hr, at least about 130000 kg/hr, or at least about 137770 kg/hr. In some embodiments, the feed to BPL purification system is about 10000 kg/hr, about 11000 kg/hr, about 12000 kg/hr, about 13000 kg/hr, about 13777 kg/hr, about 20000 kg/hr, about 50000 kg/hr, about 100000 kg/hr, about 110000 kg/hr, about 120000 kg/hr, about 130000 kg/hr, or about 137770 kg/hr. In some embodiments, the feed to BPL purification system is between about 10000 kg/hr and about 13777 kg/hr, between about 11000 kg/hr and about 13777 kg/hr, between about 12000 kg/hr and about 13777 kg/hr, between about 13000 kg/hr and about 13777 kg/hr, between about 10000 kg/hr and 137770 kg/hr, between about 11000 kg/hr and about 137770 kg/hr, between about 12000 kg/hr and about 137770 kg/hr, between about 13000 kg/hr and about 137770 kg/hr, between about 13777 kg/hr and about 137770 kg/hr, between about 20000 kg/hr and about 137770 kg/hr, between about 50000 kg/hr and about 137770 kg/hr, between about 100000 kg/hr and about 137770 kg/hr, between about 110000 kg/hr and about 137770 kg/hr, between about 120000 kg/hr and about 137770 kg/hr, or between about 130000 kg/hr and about 137770 kg/hr. In some embodiments, the feed to BPL purification system has a bPL wt % between about 10-30, about 15-28, about 18-25, about 20-25, about 22-23, about 22.5, or at least 22.5. In some embodiments, the feed to BPL purification system has solvent (e.g., THF) wt % between 60-90, about 65-85, about 70-80, about 72-78, about 74-76, about 75, about 75.8, or at least about 75. In some embodiments, the feed to BPL purification system has a CO wt % between about 0-0.2, about 0.05-0.15, about 0.1, or at most about 0.2. In some embodiments, the feed to BPL purification system has an acetaldehyde wt. % between about 0-0.2, about 0.05-0.15, about 0.1, at most about 0.1, or at most about 0.2. In some embodiments, the feed to BPL purification system has a succinic anhydride wt. % between about 0-0.2, about 0.05-0.15, about 0.1, at most about 0.1, or at most about 0.2. In some embodiments, the feed to BPL purification system has an EO wt % between about 0-3, about 0.5-2, about 1-2, about 1.4, at most about 1.4, or at most about 2. In some embodiments, the feed to the BPL purification system has trace amounts of carbonylation catalyst. In some embodiments, the feed to the BPL purification system has trace amounts of carbonylation catalyst components.

Evaporator

In some embodiments, the feed to the BPL purification system can be fed to evaporator 1628. In some embodiments, the evaporator can operate at most about 5 bara, at most about 4 bara, at most about 3 bara, at most about 2 bara, at most about atmospheric pressure (i.e., 1 bara), or at about atmospheric pressure. In some embodiments, the evaporator can operate at a temperature between about 80-120° C., between about 90-100° C., between about 95-105° C., at about 100° C., at most about 100° C., at most about 105° C., at most about 110° C., or at most about 120° C. In some embodiments, the evaporator is a flash tank. Referring again to FIG. 16, in the exemplary system evaporator 1628 can separate the feed into overhead stream 1629 and bottoms stream 1630. Overhead stream 1629 can comprise mainly of THF with low boiling point components (e.g., CO, EO, acetaldehyde) and a small amount of bPL. In some embodiments, overhead stream 1629 can have a mass flow rate of at least about 9000 kg/hr, at least about 10000 kg/hr, at least about 11000 kg/hr, at least about 11500 kg/hr, or at least about 12000 kg/hr. In some embodiments, overhead stream 1629 can have a solvent (e.g., THF) wt % of about 75-95, about 80-90, about 85, about 86.7, at least about 75, at least about 80, at least about 85, or at least about 90. In some embodiments, overhead stream 1629 can have a bPL wt % of about 0-20, about 5-20, about 8-15, about 10, about 11.5, at most about 25, at most about 20, at most about 15, at most about 11.5, at most about 10, or at most about 5. In some embodiments, overhead stream 1629 can have a carbon monoxide wt % of about 0-0.2, about 0.05-0.15, about 0.1, at most about 0.2, or at most about 0.1. In some embodiments, overhead stream 1629 can have an ethylene oxide wt % of about 0-5, about 0.5-3, about 1-2, about 1.6, at most 5, at most 3, at most 2, at most 1.6. In some embodiments, overhead stream 1629 can have an acetaldehyde wt % of about 0-0.4, about 0.1-0.3, about 0.2, at most about 0.4, or at most about 0.2.

In some embodiments, bottoms stream 1630 can have a mass flow rate of at least about 500 kg/hr, at least about 1000 kg/hr, at least about 1500 kg/hr, at least about 2000 kg/hr, at least about 2200 kg/hr, at least about 3000 kg/hr, at least about 4000 kg/hr, at least about 5000 kg/hr, at least about 10000 kg/hr, at least about 15000 kg/hr, at least about 20000 kg/hr, at least about 22000 kg/hr, at least about 30000 kg/hr. In some embodiments, bottoms stream 1630 can have a mass flow rate of between about 500 kg/hr and about 3000 kg/hr, between about 1000 kg/hr and about 3000 kg/hr, between about 1500 kg/hr and about 3000 kg/hr, between about 2000 kg/hr and about 3000 kg/hr, between about 2200 kg/hr and about 3000 kg/hr, between about 500 kg/hr and about 30000 kg/hr, between about 1000 kg/hr and about 30000 kg/hr, between about 1500 kg/hr and about 30000 kg/hr, between about 2000 kg/hr and about 30000 kg/hr, between about 2200 kg/hr and about 30000 kg/hr, between about 3000 kg/hr and about 30000 kg/hr, between about 4000 kg/hr and about 30000 kg/hr, between about 5000 kg/hr and about 30000 kg/hr, between about 10000 kg/hr and about 30000 kg/hr, between about 15000 kg/hr and about 30000 kg/hr, between about 20000 kg/hr and about 30000 kg/hr, between about 22000 kg/hr and about 30000 kg/hr. In some embodiments, bottoms stream 1630 can have a bPL wt % of about 60-95, about 65-90, about 70-85, about 75-85, about 79.7, about 80, at least about 65, at least about 70, at least about 75, at least about 79.7, at least about 85. In some embodiments, bottoms stream 1630 can have a solvent wt % of about 5-40, about 10-30, about 15-25, about 18-20, about 19.2, about 20, at most 40, at most 30, at most 25, at most 20, at most 19.2, at most 15, or at most 10. In some embodiments, bottoms stream 1630 can have an ethylene oxide wt % of about 0-0.4, about 0.1-0.3, about 0.2, at most about 0.4, or at most about 0.2. In some embodiments, bottoms stream 1630 can have a succinic anhydride wt % of about 0-2, about 0.2-1.6, about 0.4-1.2, about 0.6-1, about 0.7-0.9, at most about 2, at most about 1, at most about 0.8. In some embodiments, the bottoms stream 1630 can have a carbonylation catalyst wt % of about 0-0.2, about 0.05-0.15, about 0.1, at most about 0.2, or at most about 0.1. In some embodiments, the bottoms stream 1630 can have a carbonylation catalyst component wt % of about 0-0.2, about 0.05-0.15, about 0.1, at most about 0.2, or at most about 0.1.

Solvent Purification Column

Referring again to FIG. 16, in the exemplary system depicted overhead stream 1629 can be sent to solvent purification column 1631. The solvent purification column can be a distillation column. In some embodiments, the solvent purification column can be a stripping column or stripper. In some embodiments, the solvent purification column can operate at most about 5 bara, at most about 4 bara, at most about 3 bara, at most about 2 bara, at most about atmospheric pressure (i.e., 1 bara), or at about atmospheric pressure. In some embodiments, the evaporator can operate at a temperature of at most about 100° C., at most about 105° C., at most about 110° C., or at most about 120° C. In some embodiments, an overhead temperature is maintained at about 20-60° C., about 30-50° C., about 40-50° C., about 44° C. In some embodiments, the solvent purification column can prevent bPL from getting into any vent streams. In some embodiments, solvent purification column can have at least 12 stages with a condenser as stage 1. In some embodiments, solvent purification column can have an internal cooler which can create a side stream. In some embodiments, solvent purification column can have an internal cooler above the side stream withdrawal. In some embodiments, internal cooler can be between stages in the middle of the column. In some embodiments, internal cooler can be between stages 5 and 6 of the solvent purification column. In some embodiments, solvent purification column can separate overhead stream 1629 into overhead stream 1632, bottoms stream 1634, and side stream 1633. Overhead stream 1632 can comprise low boiling components (e.g., EO, CO, acetaldehyde) and around half solvent. Bottoms stream 1634 can comprise mainly bPL and solvent. In some embodiments, solvent purification column can recover at least 90 wt %, at least 95 wt %, at least 98 wt %, at least 99 wt %, or at least 99.5 wt % of bPL from overhead stream 1629 in bottoms stream 1634.

In some embodiments, overhead stream 1632 can have a mass flowrate of at least 200 kg/hr, at least 300 kg/hr, at least 400 kg/hr, at least 411 kg/hr, at least 500 kg/hr, at least 1000 kg/hr, at least 1500 kg/hr, at least 2000 kg/hr, at least 3000 kg/hr, at least 4000 kg/hr, at least 4110 kg/hr, or at least 5000 kg/hr. In some embodiments, overhead stream 1632 can have a mass flowrate of between 200 kg/hr and 500 kg/hr, between 300 kg/hr and 500 kg/hr, between 400 kg/hr and 500 kg/hr, between 411 kg/hr and 500 kgr/hr, between 200 kg/hr and 5000 kg/hr, between 300 kg/hr and 5000 kg/hr, between 400 kg/hr and 5000 kg/hr, between 411 kg/hr and 5000 kgr/hr. In some embodiments, overhead stream 1632 can have a solvent (e.g., THF) wt % of about 30-70, about 40-60, about 45-55, about 50-55, about 50, about 53.9, at most 75, at most 65, at most 60, at most 55, at most 53.9, at most 50, at most 45. In some embodiments, overhead stream 1632 can have an ethylene oxide wt % of about 20-60, about 30-50, about 35-45, about 37-43, about 40.6, at least about 20, at least about 25, at least about 30, at least about 35, at least about 40, at least about 40.6, at least about 45, or at least about 50. In some embodiments, overhead stream 1632 can have a carbon monoxide wt % of about 0-5, about 0.5-3, about 1-2, about 1.5-2, about 1.7, at most about 5, at most about 3, at most about 2, at most about 1.7, at most about 1. In some embodiments, overhead stream 1632 can have a acetaldehyde wt % of about 0-10, about 1-7, about 2-5, about 3-4.5, about 3.5-4, about 3.8, at most about 10, at most about 7, at most about 5, at most about 4, at most about 3.8, at most about 3.

In some embodiments, bottoms stream 1634 can have a mass flowrate of at least about 1000 kg/hr, at least about 1200 kg/hr, at least about 1400 kg/hr, at least about 1600 kg/hr, at least about 1643 kg/hr, at least about 1800 kg/hr, at least about 4000 kg/hr, at least about 7500 kg/hr, at least about 10000 kg/hr, at least about 12000 kg/hr, at least about 14000 kg/hr, at least about 16000 kg/hr, at least about 16430 kg/hr, or at least about 18000 kg/hr. In some embodiments, bottoms stream 1634 can have a mass flowrate of about 1000 kg/hr, about 1200 kg/hr, about 1400 kg/hr, about 1600 kg/hr, about 1643 kg/hr, about 1800 kg/hr, about 4000 kg/hr, about 7500 kg/hr, about 10000 kg/hr, about 12000 kg/hr, about 14000 kg/hr, about 16000 kg/hr, about 16430 kg/hr, or about 18000 kg/hr. In some embodiments, bottoms stream 1634 can have a mass flowrate of between 1000 kg/hr and 1800 kg/hr, between 1200 kg/hr and 1800 kg/hr, between 1400 kg/hr and 1800 kg/hr, between 1600 kg/hr and 1800 kg/hr, between 1643 kg/hr and 1800 kg/hr, between 1000 kg/hr and 18000 kg/hr, between 1200 kg/hr and 18000 kg/hr, between 14000 kg/hr and 18000 kg/hr, between 16000 kg/hr and 18000 kg/hr, between 1643 kg/hr and 18000 kg/hr, between 4000 kg/hr and 18000 kg/hr, between 10000 kg/hr and 18000 kg/hr, or between 16000 kg/hr and 18000 kg/hr. In some embodiments, bottoms stream 1634 can have a bPL wt % of about 60-95, about 70-90, about 75-85, about 80, about 80.4, at least 60, at least 70, at least 75, at least 80, at least 80.4, at least 85, at least 90, or at least 95. In some embodiments, bottoms stream 1634 can have a solvent wt % of about 5-40, about 10-30, about 15-25, about 20, about 19.5, at most 40, at most 30, at most 25, at most 20, at most 19.5, at most 15, or at most 10. In some embodiments, bottoms stream 1634 can have an ethylene oxide wt % of about 0-0.4, about 0.1-0.3, about 0.2, at most about 0.4, or at most about 0.2.

In some embodiments, side stream 1633 can have a mass flow rate of at least about 6000 kg/hr, at least about 7000 kg/hr, at least about 8000 kg/hr, at least about 9000 kg/hr, at least about 9500 kg/hr, at least about 9508 kg/hr, at least about 10000 kg/hr, at least about 20000 kg/hr, at least about 40000 kg/hr, at least about 60000 kg/hr, at least about 70000 kg/hr, at least about 80000 kg/hr, at least about 90000 kg/hr, at least about 95000 kg/hr, at least about 95080 kg/hr, or at least about 100000 kg/hr. In some embodiments, side stream 1633 can have a mass flow rate of about 6000 kg/hr, about 7000 kg/hr, about 8000 kg/hr, about 9000 kg/hr, about 9500 kg/hr, about 9508 kg/hr, about 10000 kg/hr, about 20000 kg/hr, about 40000 kg/hr, about 60000 kg/hr, about 70000 kg/hr, about 80000 kg/hr, about 90000 kg/hr, about 95000 kg/hr, about 95080 kg/hr, or about 100000 kg/hr. In some embodiments, side stream 1633 can have a mass flow rate of between 6000 kg/hr and 10000 kg/hr, between 7000 kg/hr and 10000 kg/hr, between 8000 kg/hr and 10000 kg/hr, between 9000 kg/hr and 10000 kg/hr, between 9500 kg/hr and 10000 kg/hr, between 9508 kg/hr and 10000 kg/hr, between 6000 kg/hr and 100000 kg/hr, between 10000 kg/hr and 100000 kg/hr, between 20000 kg/hr and 100000 kg/hr, between 40000 kg/hr and 100000 kg/hr, between 60000 kg/hr and 100000 kg/hr, between 70000 kg/hr and 100000 kg/hr, between 80000 kg/hr and 100000 kg/hr, or between 90000 kg/hr and 100000 kg/hr, between. In some embodiments, side stream 1633 can have a solvent wt % of at least 95, at least 98, at least 99, at least 99.7. In some embodiments, side stream 1633 can have an ethylene oxide wt. % of about 0-0.4, about 0.1-0.3, about 0.2, at most about 0.4, or at most about 0.2. In some embodiments, side stream 1633 can have a bPL wt % of about 0-0.2, about 0.05-0.15, about 0.1, at most about 0.1, or at most about 0.2.

BPL Purification Column

Bottoms stream 1630 and bottoms stream 1634 can be combined and sent to BPL purification column 1635. BPL purification column can be a distillation column. In some embodiments, BPL purification column can be a vacuum column or a column operating under reduced pressure. In some embodiments, the operating pressure of the BPL purification column can be less than atmospheric pressure (1 bara), less than about 0.5 bara, less than about 0.25 bara less than 0.2 bara, less than 0.15 bara, or about 0.15 bara. In some embodiments, the BPL purification column can include a reboiler that can be maintained at most about 120° C., at most about 110° C., at most about 100° C., or about 100° C. In some embodiments, an overhead temperature is maintained at about 5-30° C., about 10-20° C., about 12-16° C., about 14° C.

In some embodiments, BPL purification column can separate the combined bottoms streams 1630 and 1634 into overhead stream 1636 and bottoms stream 1618 (i.e., BPL purified stream 1618). Bottoms stream 1618 can be substantially pure bPL with minimal solvent. In some embodiments, bottoms stream 1618 can also include some heavy components such as residual carbonylation catalyst and succinic anhydride. The carbonylation catalyst can be considered to be non-volatile and can accumulate in the BPL purification column's sump. Accumulated catalyst can be removed periodically by purging sump when the catalyst wt % reaches a predefined value (e.g., at least 1 wt %, 2 wt %, 3 wt %, 4 wt %, or 5 wt %). In contrast to the carbonylation catalyst, succinic anhydride can have some volatility and if accumulated in the sump can produce an undesirable rise in boiling temperature in the reboiler. In some embodiments, succinic anhydride can also accumulate in the sump and can be purged in the same manner the accumulated catalyst can be purged. In some embodiments, overhead stream 1636 can have a mass flow rate of about at least about 500 kg/hr, at least about 600 kg/hr, at least about 700 kg/hr, at least about 750 kg/hr at least about 800 kg/hr, or at least about 850 kg/hr. In some embodiments, overhead stream 1636 can have a solvent wt % of at least about 95, at least about 98, at least about 99, at least about 99.1, or at least about 99.5. In some embodiments, overhead stream 1636 can have an ethylene oxide wt % of about 0-3, about 0.2-2, about 0.2-1.5, about 0.5-1, about 0.8, at most about 3, at most about 2, at most about 1, at most about 0.8, at most about 0.5. In some embodiments, overhead stream 1638 can have an acetaldehyde wt % of about 0-0.2, about 0.05-0.15, about 0.1, at most about 0.1, or at most about 0.2.

In some embodiments, bottoms stream 1618 can have a mass flow rate of at least about 1000 kg/hr, at least about 2000 kg/hr, at least about 2500 kg/hr, at least about 3000 kg/hr, at least about 3100 kg/hr, at least about 3500 kg/hr, at least about 4000 kg/hr, at least about 5000 kg/hr, at least about 1000 kg/hr, at least about 20000 kg/hr, at least about 35000 kg/hr, at least about 36380 kg/hr, or at least about 40000 kg/hr. In some embodiments, bottoms stream 1618 can have a mass flow rate of about 2000 kg/hr, about 2500 kg/hr, about 3000 kg/hr, about 3500 kg/hr, about 3638 kg/hr, about 4000 kg/hr, about 5000 kg/hr, about 1000 kg/hr, about 20000 kg/hr, about 35000 kg/hr, about 36380 kg/hr, or about 40000 kg/hr. In some embodiments, bottoms stream 1618 can have a mass flow rate of between 1000 kg/hr and 4000 kg/hr, or between 1000 kg/hr and 40000 kg/hr. In some embodiments, bottoms stream 1618 can have a bPL wt % of at least about 95, at least about 98, at least about 99, at least about 99.3, or at least about 99.5. In some embodiments, bottoms stream 1618 can have a solvent wt. % of about 0-0.2, about 0.05-0.15, about 0.1, at most about 0.1, or at most about 0.2. In some embodiments, bottoms stream 1618 can have a succinic anhydride wt % of about 0-3, about 0.1-2, about 0.2-1, about 0.5-1, about 0.6, at most about 3, at most about 2, at most about 1, at most about 0.6, at most about 0.5. In some embodiments, bottoms stream 1618 can have trace amounts of carbonylation catalyst. In some embodiments, BPL purification column can have a purge for the carbonylation catalyst and/or succinic anhydride in the bottoms stream 1618. In some embodiments, the purge can be a valve.

Light Gas Column

Overhead stream 1632 can be sent to light gas column 1637 to be separated into overhead stream 1639 and bottoms stream 1638. The light gas column can be a distillation column. In some embodiments, the light gas column can operate at most about 5 bara, at most about 4 bara, at most about 3 bara, at most about 2 bara, at most about atmospheric pressure (i.e., 1 bara), or at about atmospheric pressure. In some embodiments, light gas column can include a partial condenser. In some embodiments, the partial condenser operates at a temperature of at about 0-20° C., about 5-15° C., about 10-15° C., about 10-13° C. In some embodiments, the temperature maintained at the bottom of light gas column is about 20-70° C., about 40-60° C., about 45-55° C., or about 50° C. In some embodiments, the overhead temperature maintained in light gas column can be about −10-10° C., about −5-5° C., about −2-3° C., or about 1° C. Overhead stream 1639 can comprise mostly of the acetaldehyde produced in the carbonylation reaction system as well as low boiling point ethylene oxide. In some embodiments, overhead stream 1639 can be disposed of (e.g., incinerator, flare, etc.) so acetaldehyde does not accumulate in the overall production system/production process.

In some embodiments, overhead stream 1639 can have a mass flow rate of about 50 kg/hr, about 100 kg/hr, about 150 kg/hr, about 175 kg/hr, about 200 kg/hr, about 250 kg/hr, at least 500 kg/hr, at least 1000 kg/hr, at least 1500 kg/hr, at least 2000 kg/hr, or at least 2500 kg/hr. In some embodiments, overhead stream 1639 can have a mass flow rate of between 50 kg/hr and 250 kg/hr, between 100 kg/hr and 250 kg/hr, between 200 kg/hr and 250 kg/hr, or between 50 kg/hr and 2000 kg/hr. In some embodiments, overhead stream 1639 can have an ethylene oxide wt % of at least about 70, at least about 75, at least about 80, at least about 85, at least about 89.5, at least about 90, or at least about 95. In some embodiments, overhead stream 1639 can have an acetaldehyde wt % of about 0-15, about 1-10, about 2-8, about 6.1, at most about 15, at most about 10, at most about 6.1, at most about 5, or at most about 2. In some embodiments, overhead stream 1639 can have a carbon monoxide wt % of about 0-12, about 1-10, about 2-6, about 4.10, at most about 12, at most about 10, at most about 6, at most about 5, at most about 4.1, or at most about 2.

In some embodiments, overhead stream 1639 can have a solvent wt. % of about 0-2, about 0.1-1, about 0.2-0.6, about 0.4, at most about 2, at most about 1, at most about 0.5, at most about 0.4, or at most about 0.2.

In some embodiments, bottoms stream 1638 can have a mass flow rate of about 50 kg/hr, about 150 kg/hr, about 200 kg/hr, about 235 kg/hr, about 250 kg/hr, about 300 kg/hr or about 350 kg/hr. In some embodiments, bottoms stream 1638 has a solvent wt % of at least about 75, at least about 80, at least about 85, at least about 90, at least about 93.9, at least about 95, at least about 98, or at least about 99. In some embodiments, bottoms stream 1638 has an ethylene oxide wt % of about 0-12, about 1-10, about 2-6, about 4, at most about 12, at most about 10, at most about 8, at most about 5, at most about 4, or at most about 2. In some embodiments, bottoms stream 1638 has an acetaldehyde wt % of about 0-10, about 0.5-5, about 1-4, about 1-3, about 2.2, at most about 10, at most about 5, at most about 2.2, at most about 2, at most about 1.

Solvent Recycle Stream

In some embodiments, side stream 1633, bottoms stream 1638, overhead stream 1636 or combinations thereof can form solvent recycle stream 1623. In some embodiments, side stream 1633, bottoms stream 1638, and overhead stream 1636 can be combined to form solvent recycle stream 1623. In some embodiment, side stream 1633, bottoms stream 1638, and/or overhead stream 1636 can be sent to a solvent recycle tank or storage. In some embodiments, the solvent recycle stream is fed back to the carbonylation reaction system. In some embodiments, the solvent recycle stream fed to the carbonylation reaction system is from the solvent recycle tank or storage. In some embodiments, the solvent streams entering and/or exiting the solvent recycle tank or storage can be purified for example by passing the stream through an absorber to remove potential oxygen and/or moisture from the stream. In some embodiments, the solvent recycle tank or storage can be equipped with sensors to determine the water and/or oxygen content in the storage tank.

Preferred Distillation System

In preferred embodiment, distillation sub-system consists of 3 distillation columns: (1) Lights Removal column, (2) THF Solvent Recovery column, and (3) bPL Purification column.

1. Lights Removal Column

The purpose of this column is to recover Ethylene Oxide (EO) for recycle back to the Carbonylation Reactor as well as to separate low-boiling impurities such as Acetaldehyde (ACH). Distillate stream from this column may contain THF, EO, ACH or only EO and ACH. This column receives a permeate stream from a carbonylation catalyst recovery zone and in a highly preferred form has the following component with representative compositions of THF (about 75.2 wt %), bPL (about 20.5 wt %), Ethylene Oxide (about 4.1 wt %), Acetaldehyde (about 0.07 wt %), Succinic Anhydride (about 0.02 wt %), traces of low and high boiling impurities, and trace residual carbonylation catalyst is fed to Lights Removal distillation column. The distillation column is operated at the pressure of about 1.3 bara (column is operated at atmospheric pressure or slightly above atmospheric pressure). The reboiler temperature is maintained at or below 105° C. Lights column distillate stream consisting essentially of THF (about 93.4 wt %), EO (about 6.5 wt %), ACH (0.1 wt %), and traces of low boiling impurities is fed back to the carbonylation reactor or to optional ACH removal system. The lights column in a highly preferred form produces a bottoms stream consisting essentially of bPL (about 54.9 wt %), THF (about 45.0 wt %), Succinic Anhydride (about 0.05 wt %), trace amounts of low- and high-boiling impurities, and trace residual carbonylation catalyst and high-boiling impurities is fed forward to THF Solvent Recovery column (2).

In some embodiments Lights Removal column can be operated in such a way that Distillate stream consists of only Ethylene Oxide and Acetaldehyde and all THF is exiting the column with the Bottoms stream. If the lights removal column is operated in this configuration the distillate consists essentially of EO (about 98.8 wt %), ACH (about 1.2 wt %), and trace of low boiling impurities. The bottoms stream in this column configuration consists essentially of THF (about 78.5 wt %), bPL (about 21.5 wt %), SAH (about 0.02 wt %), trace amounts of residual carbonylation catalyst, trace amounts of low- and high-boiling impurities.

Accumulation of Acetaldehyde within carbonylation/distillation system can be avoided by implementing a small purge from distillate stream or removed from the distillate stream using an absorbent such as molecular sieves (non-limiting examples are Molecular Sieve 3A, 4A, 5A, 13X, etc.). Optionally, ACH is separated from EO using distillation or extractive distillation.

2. THF Solvent Recovery Column

The purpose of this column is to recover THF solvent for recycle back to the carbonylation reactor. Due to the high boiling point of bPL (162° C. at atmospheric pressure) this column is operated at pressures below atmospheric to limit the reboiler temperature below 105° C. and avoid autopolymerization of bPL. Distillate stream from this column contains essentially pure THF and bottoms stream of this column contains bPL, SAH, residual carbonylation catalyst, and trace amounts of high boiling impurities.

Lights Column Bottom stream containing THF, bPL, SAH, residual carbonylation catalyst, and trace amounts of low and high boiling impurities is fed to THF Solvent Recovery distillation column (the composition of this stream is presented in the section above). Optionally, the THF solvent make-up stream may be fed to this column—this allows removal of O2, H2O, and BHT inhibitor from make-up THF.

The distillation column is operated at the absolute pressure of about 100 Torrs (column is operated under vacuum) and the reboiler temperature is maintained at or below 105° C. The column is designed to minimize air intrusion into the column simplifying removal of O2 and H2O contaminants from recycled THF Solvent stream in downstream unit operation.

The distillate stream from this column consisting of essentially pure THF (purity greater than 99.9 wt %) with trace amounts of low- and high-boiling impurities is recycled back to the carbonylation reactor. Optionally and before it is recycled, this stream may be passed through purification system for removal of contaminants such as O2 and H2O. These impurities can be removed by any means known in the art such as absorption, adsorption, extractive distillation, azeotropic distillation, etc.

The bottoms stream consists of bPL (about 99.8 wt %), SAH (about 0.1 wt %), small amounts of residual carbonylation catalyst, and traces of low- and high-boiling impurities. This stream is fed forward to bPL Purification column.

3. bPL Purification Column

The purpose of this column is to recover purified bPL for subsequent production of PPL (poly-propiolactone). Due to high boiling point of bPL (162° C. at atmospheric pressure) this column is operated at pressures below atmospheric to limit the reboiler temperature below 105° C. and avoid autopolymerization of bPL. The distillate stream from this column contains essentially pure bPL. The bottoms stream of this column contains residual bPL, SAH, residual carbonylation catalyst, and trace amounts of high boiling impurities. The Purified bPL stream is fed forward to Polymerization Reactor and bottoms stream is sent for disposal or recovery of residual bPL and SAH. The bottoms stream from THF recovery column containing bPL (about 99.8 wt %), SAH (about 0.1 wt %), residual carbonylation catalyst, and traces of low- and high-boiling impurities is fed to bPL Purification column.

The bPL purification column is in preferred form operated at the absolute pressure of about 60 Torrs (column is operated under vacuum) and the reboiler temperature is maintained at or below 105° C. The distillate stream consisting of essentially pure bPL (purity greater than 99.9 wt %) with trace amounts of low- and high-boiling impurities is fed forward to bPL Polymerization reactor.

The Bottoms stream of this column consists of bPL (about 88.9 wt %), SAH (about 9.7 wt %), carbonylation catalyst (about 1.4 wt %), and trace high-boiling impurities. The amount of bPL in this bottoms stream is selected to avoid crystallization of SAH at the temperatures below its melting point of 119° C. and to limit the reboiler temperature to below 105° C.

Polypropiolactone Production System/Production Process

Figure 2:
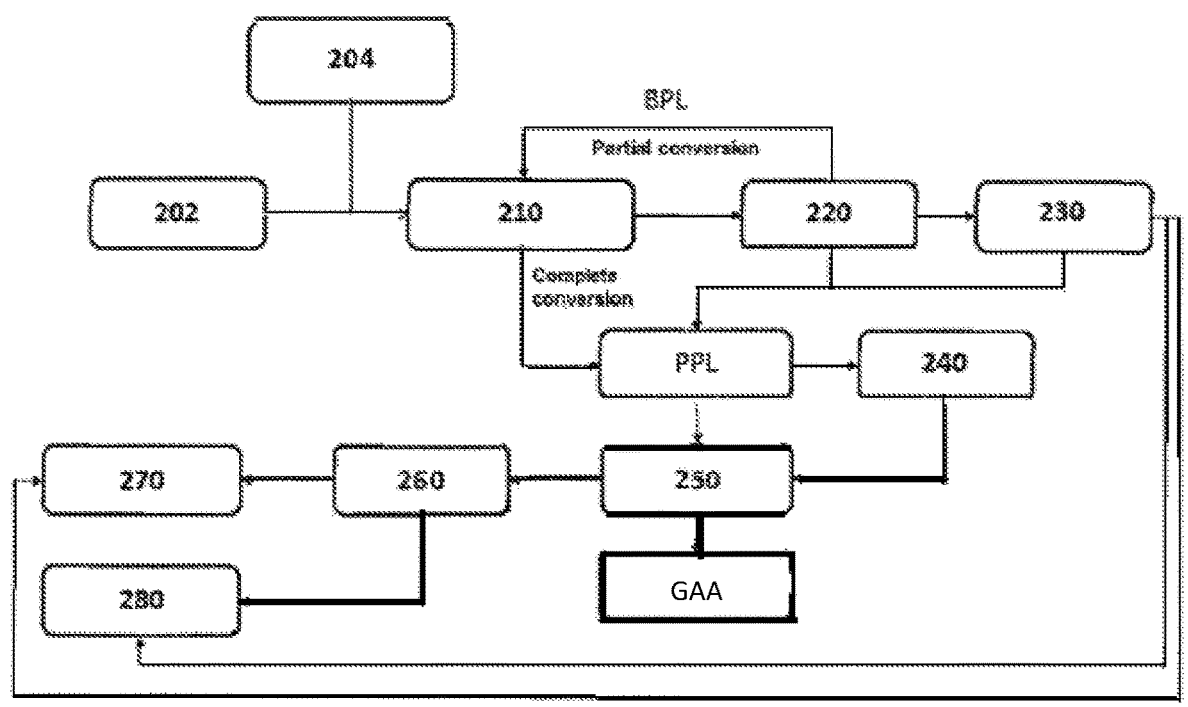
FIG. 2 is a schematic illustration of the unit operations to produce polypropiolactone from β-propiolactone, and glacial acrylic acid from polypropiolactone.

With reference to FIG. 2, the relationship of the polypropiolactone production system/production process with other unit operations, such as the β-propiolactone purification system, the ion removal unit, and the glacial acrylic acid production system/production process, is depicted.

β-Propiolactone purification system 202 is configured to feed a β-propiolactone product stream into polypropiolactone production system/production process 210. Homogeneous catalyst delivery system 204 is configured to feed a homogeneous polymerization catalyst into the polymerization reactor of polypropiolactone production system/production process 210. Polypropiolactone production system/production process 210 is configured to polymerize β-propiolactone to produce polypropiolactone. Depending on the type of polymerization reactors selected and the configuration of such reactors, as well as the operating conditions (e.g., operating temperature, operating pressure, and residence time) and choice of polymerization catalysts used, the extent of conversion of the β-propiolactone may be controlled. In some variations, operating temperature is the average temperature of the contents of the reactor.

In some variations, partial conversion of β-propiolactone to polypropiolactone is achieved, and bPL recycle unit 220 is configured to recycle at least a portion of unreacted β-propiolactone to polypropiolactone production system/production process 210. In other variations, complete conversion of β-propiolactone to polypropiolactone is achieved. The polypropiolactone product stream produced from polypropiolactone production system/production process 210 is fed glacial acrylic acid production system/production process 250, which is configured to produce glacial acrylic acid from the polypropiolactone. Ion removal units 230 and 260 are present to remove at cationic and/or anionic carbonylation catalyst species that may be carried over from the upstream carbonylation reaction in the β-propiolactone production system/production process (not depicted in FIG. 2). For example, when the carbonylation catalyst is a cobalt-aluminum compound, cobalt and aluminum species may be removed by ion removal units 230 and 260. The ionic species isolated by the ion removal units may be disposed using unit 270, or regenerated in unit 280 to produce an active carbonylation catalyst that may be recycled into the β-propiolactone production system/production process.

In some variations, unit 240 is configured to receive the polypropiolactone product stream (e.g., in liquid form) from polypropiolactone production system/production process 210, and is configured to pelletize, extrude, flake, or granulate the polypropiolactone product stream.

It should be understood, however, that FIG. 2 provides one exemplary configuration of these unit operations. In other variations, one or more of the unit operations depicted in FIG. 2 may be added, combined or omitted, and the order of the unit operations may be varied as well.

With reference again to FIG. 1, the polypropiolactone production system/production process is configured to produce polypropiolactone by polymerizing β-propiolactone in the presence of a polymerization catalyst. While FIG. 1 depicts the use of a single plug flow reactor for the polymerization of β-propiolactone to produce polypropiolactone, other reactor types and reactor configurations may be employed.

In some embodiments, the polypropiolactone production system/production process includes a β-propiolactone, a polymerization initiator or catalyst source, and at least one polymerization reactor.

BPL Source

With reference again to FIGS. 6-13, the bPL entering the polypropiolactone production system/production process may be purified bPL from the bPL purification train or recycled bPL from the polymerization reactor, or a combination thereof.

In some embodiments, the inlet to the polymerization process can include at least about 2000 kg/hr bPL, at least about 2500 kg/hr bPL, at least about 3000 kg/hr bPL, at least about 3086 kg/hr bPL, at least about 3500 kg/hr bPL, at least about 3638 kg/hr bPL, at least about 4000 kg/hr bPL, at least about 5000 kg/hr bPL, at least about 1000 kg/hr bPL, at least about 20000 kg/hr bPL, or at least about 35000 kg/hr bPL. In some embodiments, the inlet to the polymerization process can include about 2000 kg/hr bPL, about 2500 kg/hr bPL, about 3000 kg/hr bPL, about 3500 kg/hr bPL, about 3638 kg/hr bPL, about 4000 kg/hr bPL, about 5000 kg/hr bPL, about 1000 kg/hr bPL, about 20000 kg/hr bPL, or about 35000 kg/hr bPL. In some embodiments, the inlet to the polymerization process can include between about 2000 kg/hr bPL and about 3500 kg/hr bPL, between about 2500 kg/hr bPL and about 3500 kg/hr bPL, between about 3000 kg/hr bPL and about 3500 kg/hr bPL, between about 2000 kg/hr bPL and about 35000 kg/hr bPL, between about 2500 kg/hr bPL and about 35000 kg/hr bPL, or between about 3000 kg/hr bPL and about 35000 kg/hr bPL. In some embodiments, the inlet to the polymerization process can include at least about 25 kmol/hr bPL, at least about 30 kmol/hr bPL, at least about 40 kmol/hr bPL, at least about 42 kmol/hr bPL, or at least about 50 kmol/hr bPL. In some embodiments, the mass fraction of bPL in the inlet to the polymerization process can be at least about 0.90, at least about at least about 0.95, at least about 0.98, at least about 0.99, and at least about 0.993. In some embodiments, the mole fraction of bPL in the inlet to the polymerization process can be at least about 0.90, at least about at least about 0.95, at least about 0.98, at least about 0.99, and at least about 0.995. The remainder of the production stream entering the polymerization process can include secondary reaction products such as succinic anhydride (in mole fraction of at most about 0.015, at most about 0.01, or at most about 0.004) and left over solvent (e.g., THF) and leftover carbonylation catalyst (in at most about 1000 ppm). In some variations, the remainder of the production stream entering the polymerization process can include carbonylation catalyst components (in at most about 1000 ppm).

In some variations, the production stream entering the polymerization process further comprises other compounds, such as carbonylation catalyst or components thereof. For example, in some embodiments, the production stream further comprises cobalt or aluminum, or a combination thereof, from the carbonylation catalyst.

Carbonylation catalyst components may include, for example, compounds produced by degradation of the catalyst, compounds used to produce the catalyst, metals or metal ions which were part of the catalyst, any organic compounds which were part of the catalyst, metal carbonyls or metal complexes which were part of the catalyst. For example, in some embodiments, carbonylation catalyst components are carbonyl cobaltate, aluminum salen compounds, aluminum porphyrin compounds, aluminum salophen compounds, cobalt or cobalt ions, or aluminum or aluminum ions, or any combinations thereof.

In certain variations, the production stream entering the polymerization process comprises cobalt. In some embodiments, the cobalt is $Co^{-1}$, $Co$, $Co^{+}$, $Co^{2+}$, or $Co^{3+}$, or a combination thereof. In some embodiments, the production stream has a cobalt concentration between 0.001 mM and 1 mM, 0.001 mM and 0.5 mM, between 0.001 mM and 0.05 mM, between 0.005 mM and 0.02 mM, or between 0.007 mM and 0.015 mM.

In certain variations, the production stream entering the polymerization process comprises aluminum. In some embodiments, the concentration of aluminum in the production stream is between 0.001 mM and 1 mM, 0.001 mM and 0.5 mM, between 0.001 mM and 0.05 mM, between 0.005 mM and 0.02 mM, or between 0.007 mM and 0.015 mM. In certain variations, the production stream entering the polymerization process contains less than 1 ppm cobalt and less than 1 ppm aluminum.

In some embodiments, the inlet to the polymerization process can also include a polymerization catalyst, for example, if the polymerization reaction is a homogenous polymerization reaction. The production stream entering the polymerization process can be the heavy (i.e., bottoms) stream from the BPL Purification system (e.g., BPL distillation system). In some embodiments, the production stream entering the polymerization process can have a temperature between about 30-120° C., between about 50-110° C., or about 70° C. In some embodiments, the production stream entering the polymerization process can be at a pressure of at least about 0.05 bar, at least about 0.1 bar, at least about 5 bar, at least about 10 bar, at least about 15 bar, or at least about 20 bar. In some embodiments, production stream entering the polymerization process is between 0.05 bar and 20 bar, between 0.1 bar and 20 bar, between 5 bar and 15 bar, or between 10 bar and 20 bar.

In some variations, the mole ratio of bPL feed rate to the polymerization initiator feed rate entering the polymerization process is from 500 to 20,000, from 1,000 to 10,000, from 2,000 to 9,000, from 3,000 to 8,000, from 5,000 to 7,000, from 1,000 to 110,000, from 5,000 to 110,000, from 25,000 to 110,000, from 50,000 to 110,000, or from 75,000 to 110,000. In one embodiment, mole ratio of bPL feed rate to the polymerization catalyst feed rate entering the polymerization process is from 1,000 to 9,000.

In some variations, bPL from the bPL purification process and bPL recycled from the polymerization process both enter the polymerization process. In certain embodiments, the weight ratio of recycled bPL to bPL from the bPL Purification process is from 0 to 0.01:0.99, from 0.4:0.6 to 0.1:0.9, from 0.5:0.5 to 0.15:0.85, from 0.35:0.65 to 0.1:0.9, or from 0.25:0.75 to 0.15:0.85.

Other Feed Sources

The polymerization process may further include other feed sources. For example, in one variation, the polymerization system further includes a polymerization initiator source, and the reactor is configured to receive a polymerization initiator from such source. In some variations, the polymerization initiator is a nucleophile.

Polymerization Conditions

In certain embodiments, conversion of bPL to PPL is performed in a continuous flow format. In certain embodiments, conversion of bPL to PPL is performed in a continuous flow format in the gas phase. In certain embodiments, conversion of bPL to PPL is performed in a continuous flow format in the liquid phase. In certain embodiments, conversion of bPL to PPL is performed in a liquid phase in a batch or semi-batch format. Conversion of bPL to PPL may be performed under a variety of conditions. In certain embodiments, the reaction may be performed in the presence of one or more catalysts that facilitate the transformation of the bPL to PPL.

In some embodiments, the production stream entering the polymerization process is a gas or a liquid. The conversion of bPL to PPL in the polymerization process may be performed in either the gas phase or the liquid phase and may be performed neat, or in the presence of a carrier gas, solvent, or other diluent.

In certain variations, the operating temperature of the polymerization reactor is maintained at or below the pyrolysis temperature of polypropiolactone. In some embodiments, the temperature of the reaction zone is maintained at or below about 150° C. In some embodiments, the operating temperature of the polymerization reactor is maintained at about 0° C. to about 200° C. In some embodiments, the operating temperature of the polymerization reactor is maintained at about 25° C. to about 200° C. In some embodiments, the operating temperature of the polymerization reactor is maintained at about 50° C. to about 150° C. In some embodiments, the operating temperature of the polymerization reactor is maintained at about 70° C. to about 150° C. In some embodiments, the operating temperature of the polymerization reactor is maintained at about 100° C. to about 150° C. In some embodiments, the operating temperature of the polymerization reactor is maintained at about 0° C. to about 100° C. In some embodiments, the operating temperature of the polymerization reactor is maintained at about 50° C. to about 100° C. In some variations, operating temperature is the average temperature of the contents of the reactor.

In some variations, the polymerization reactor is configured to produce PPL with a residence time from 1 second to 10 hours, from 1 second to 3 hours, from 1 min to 2 hours, from 1.5 min to 90 min, from 2 min to 75 min, from 2 min to 60 min, from 2 min to 45 min, from 3 min to 30 min, or from 4 min to 15 min. In one embodiment the residence time of the reaction mixture is from 2 min to 90 min. In certain variations, residence time refers to the length of time a material spends in a vessel (for example, a reaction vessel). It may be calculated by specifying the volumetric flow rate of material and active volume of the vessel which the material is contained.

In some variations, the polymerization reactor is configured to produce PPL at an operating pressure from 0.01 bar to 100 bar, from 0.01 bar to 50 bar, from 0.1 bar to 30 bar, from 1 bar to 20 bar, from 2 bar to 15 bar, from 3 bar to 10 bar, from 0.01 bar to 15 bar, from 0.01 bar to 10 bar, from 0.1 bar to 5 bar, or from 0.1 bar to 2 bar. In some embodiments, the polymerization reactor is a CSTR and operating pressure in the reactor is from 0.1 bar to 5 bar. In other embodiments, the polymerization reactor is a PFR and the operating pressure in the reactor is from 1 bar to about 20 bar. In still other embodiments, the polymerization reactor is a loop reactor and the operating pressure in the reactor is from 1 bar to about 20 bar.

Homogeneous Catalysts and Initiators

Any suitable polymerization initiators and/or catalysts may be used to convert the BPL product stream entering the PPL production system/production process into a PPL product stream. In some embodiments, the polymerization initiator or catalyst is homogenous with the polymerization reaction mixture. Any suitable homogeneous polymerization initiator or catalyst capable of converting the production stream to the PPL product stream may be used in the methods described herein.

Catalysts suitable for the ring-opening polymerization step of the methods disclosed herein are disclosed, for example, in: Journal of the American Chemical Society (2002), 124(51), 15239-15248 *Macromolecules*, vol. 24, No. 20, pp. 5732-5733, *Journal of Polymer Science*, Part A-1, vol. 9, No. 10, pp. 2775-2787; Inoue, S., Y. Tomoi, T. Tsuruta & J. Furukawa; *Macromolecules*, vol. 26, No. 20, pp. 5533-5534; *Macromolecules*, vol. 23, No. 13, pp. 3206-3212; *Polymer Preprints* (1999), 40(1), 508-509; *Macromolecules*, vol. 21, No. 9, pp. 2657-2668; and *Journal of Organometallic Chemistry*, vol. 341, No. 1-3, pp. 83-9; and in U.S. Pat. Nos. 3,678,069, 3,169,945, 6,133,402; 5,648,452; 6,316,590; 6,538,101; and 6,608,170. The entirety of each of which is hereby incorporated herein by reference.

The polymerization process may further comprise a polymerization initiator including but not limited to amines, polyamines, phosphines amongst others. Further, a variety of polymerization initiators may be used in the polymerization process, including by not limited to carbonates of alkali- and alkaline earth metals.

In certain embodiments, suitable polymerization—initiators include carboxylate salts of metal ions or organic cations.

In certain embodiments, a polymerization initiator is combined with the production stream containing bPL. In certain embodiments, the molar ratio of the polymerization initiator to the bPL in the production stream is about 1:15000. In certain embodiments, the molar ratio of polymerization intiator:bPL is about 1:100, 1:10000, 1:1000, 1:20000 or a range including any two of these ratios.

In certain embodiments, where the polymerization initiator comprises a carboxylate salt, the carboxylate has a structure such that upon initiating polymerization of bPL, the polymer chains produced have an acrylate chain end. In certain embodiments, the carboxylate ion on a polymerization initiator is the anionic form of a chain transfer agent used in the polymerization process.

In certain embodiments, the carboxylate salt of the polymerization initiator is a salt of (i.e., the anionic form) a compound of Formula (A):

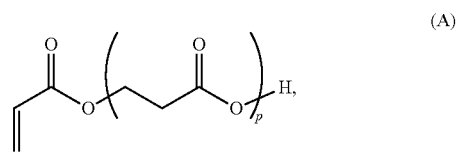

(A)

or a mixture of any two or more of these, where p is from 0 to 9. In certain embodiments, p is from 0 to 5. In certain embodiments, the carboxylate salt of the polymerization initiator is an acrylate salt (i.e. compound of Formula (A) where p=0).

In certain embodiments, the carboxylate salt of the polymerization initiator is a salt of an acrylic acid dimer,

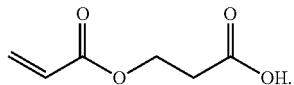

In certain embodiments, the carboxylate salt of the polymerization initiator is a salt of an acrylic acid trimer,

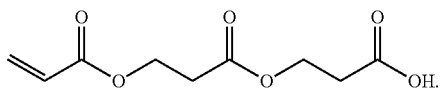

In certain embodiments, where the polymerization initiator comprises a carboxylate salt, the carboxylate is the anionic form of a $C_{1-40}$ carboxylic acid. In certain embodiments, the carboxylate salt can be a salt of a polycarboxylic acid (e.g. a compound having two or more carboxylic acid groups). In certain embodiments, the carboxylate comprises the anion of a $C_{1-20}$ carboxylic acid. In certain embodiments, the carboxylate comprises the anion of a $C_{1-12}$ carboxylic acid. In certain embodiments, the carboxylate comprises the anion of a $C_{1-8}$ carboxylic acid. In certain embodiments, the carboxylate comprises the anion of a $C_{1-4}$ carboxylic acid. In certain embodiments, the carboxylate comprises the anion of an optionally substituted benzoic acid. In certain embodiments, the carboxylate is selected from the group consisting of: formate, acetate, propionate, valerate, butyrate, $C_{5-10}$ aliphatic carboxylate, and $C_{10-20}$ aliphatic carboxylate.

As noted, in certain embodiments, the polymerization initiator comprises a carboxylate salt of an organic cation. In certain embodiments, the polymerization initiator comprises a carboxylate salt of a cation wherein the positive charge is located at least partially on a nitrogen, sulfur, or phosphorus atom. In certain embodiments, the polymerization initiator comprises a carboxylate salt of a nitrogen cation. In certain embodiments, the polymerization initiator comprises a carboxylate salt of a cation selected from the group consisting of: ammonium, amidinium, guanidinium, a cationic form of a nitrogen heterocycle, and any combination of two or more of these. In certain embodiments, the polymerization initiator comprises a carboxylate salt of a phosphorus cation. In certain embodiments, the polymerization initiator comprises a carboxylate salt of a cation selected from the group consisting of: phosphonium and phosphazenium. In certain embodiments, the polymerization initiator comprises a carboxylate salt of a sulfur-containing cation. In certain embodiments, the polymerization initiator comprises a sulfonium salt.

In certain embodiments, the polymerization initiator comprises a carboxylate salt of a protonated amine:

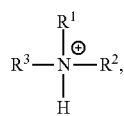

wherein:

each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings.

In certain embodiments where the polymerization initiator comprises a carboxylate salt of a protonated amine, the protonated amine is selected from the group consisting of:

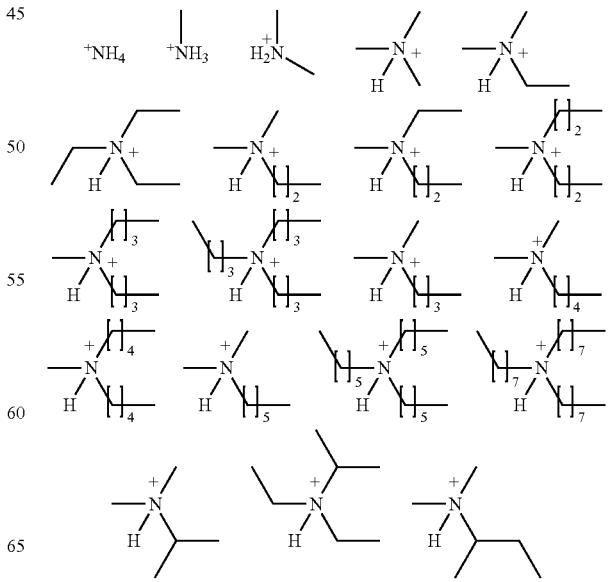

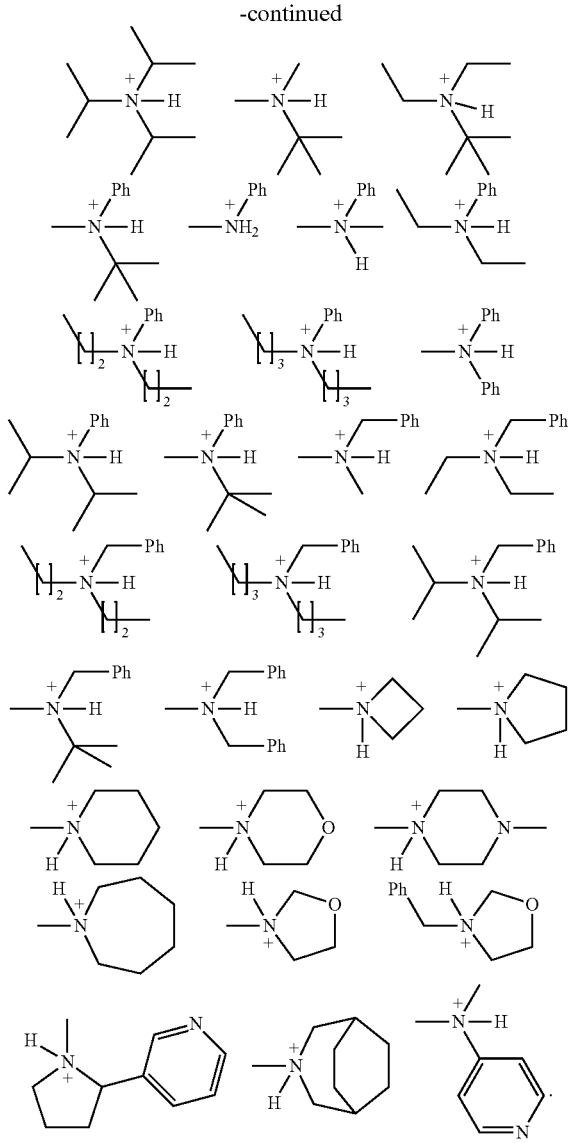

In certain embodiments, the polymerization initiator comprises a carboxylate salt of a quaternary ammonium salt:

$$R^3-\overset{R^1}{\underset{R^4}{\overset{\oplus}{N}}}-R^2,$$

wherein:

each $R^1$, $R^2$ and $R^3$ is described above; and each $R^4$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^4$ group can be taken with an $R^1$, $R^2$ or $R^3$ group to form one or more optionally substituted rings.

In certain embodiments, the polymerization initiator comprises a carboxylate salt of a guanidinium group:

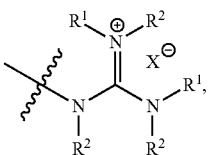

wherein each $R^1$ and $R^2$ is independently as defined above and described in classes and subclasses herein. In certain embodiments, each $R^1$ and $R^2$ is independently hydrogen or $C_{1-20}$ aliphatic. In certain embodiments, each $R^1$ and $R^2$ is independently hydrogen or $C_{1-12}$ aliphatic. In certain embodiments, each $R^1$ and $R^2$ is independently hydrogen or $C_{1-20}$ heteroaliphatic. In certain embodiments, each $R^1$ and $R^2$ is independently hydrogen or phenyl. In certain embodiments, each $R^1$ and $R^2$ is independently hydrogen or 8- to 10-membered aryl. In certain embodiments, each $R^1$ and $R^2$ is independently hydrogen or 5- to 10-membered heteroaryl. In certain embodiments, each $R^1$ and $R^2$ is independently hydrogen or 3- to 7-membered heterocyclic. In certain embodiments, one or more of $R^1$ and $R^2$ is optionally substituted $C_{1-12}$ aliphatic.

In certain embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In certain embodiments, three or more $R^1$ and/or $R^2$ groups are taken together to form an optionally substituted fused ring system.

In certain embodiments, an $R^1$ and $R^2$ group are taken together with intervening atoms to form a compound selected from:

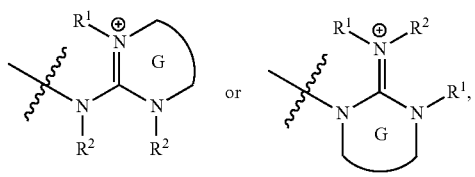

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

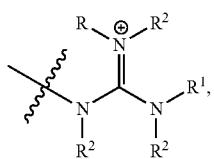

all such resonance forms are contemplated and encompassed by the present disclosure. For example, such groups can also be depicted as

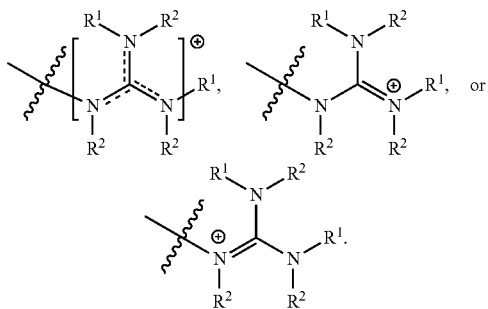

In specific embodiments, a guanidinium cation is selected from the group consisting of:

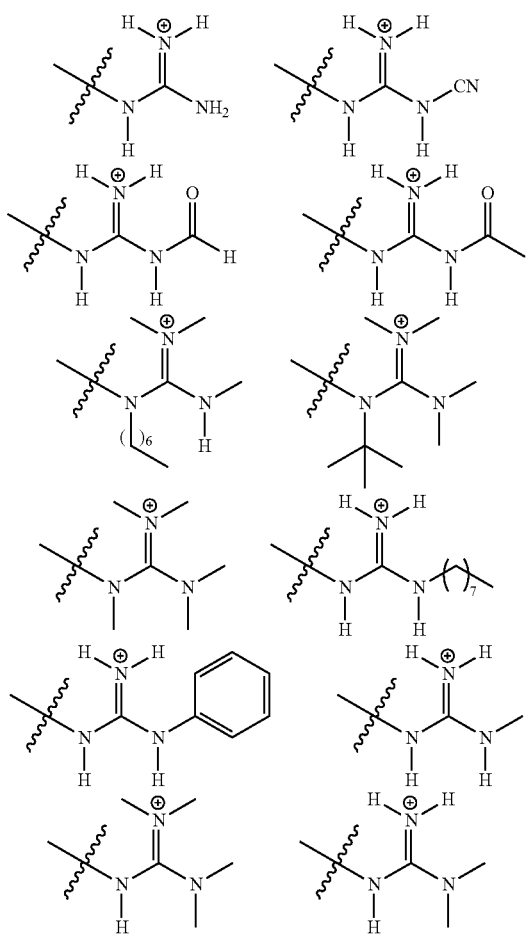

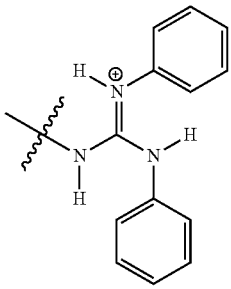

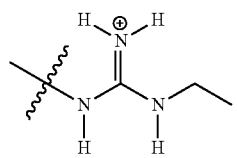

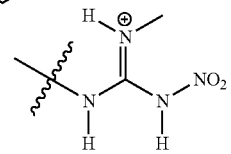

In certain embodiments, a polymerization-initiator comprises a carboxylate salt of a sulfonium group or an arsonium group:

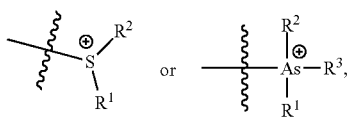

wherein each of $R^1$, $R^2$, and $R^3$ are as defined above and described in classes and subclasses herein.

In specific embodiments, an arsonium cation is selected from the group consisting of:

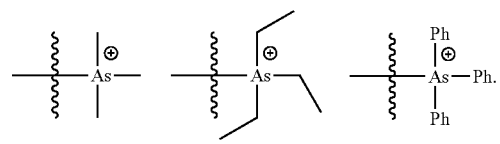

In certain embodiments, a polymerization initiator comprises a carboxylate salt of an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In certain embodiments, a nitrogen-containing heterocycle includes a quaternarized nitrogen atom. In certain embodiments, a nitrogen-containing heterocycle includes an iminium moiety such as

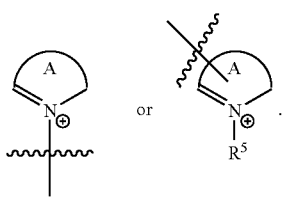

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In certain embodiments, a ring nitrogen to which the attachment is made is thereby quaternized, and In certain embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In certain embodiments, a polymerization initiator comprises a carboxylate salt of

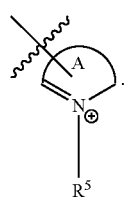

In certain embodiments, ring A is an optionally substituted, 5- to 10-membered heteroaryl group. In certain embodiments, Ring A is an optionally substituted, 6-membered heteroaryl group. In certain embodiments, Ring A is a ring of a fused heterocycle. In certain embodiments, Ring A is an optionally substituted pyridyl group.

In specific embodiments, a nitrogen-containing heterocyclic cation is selected from the group consisting of:

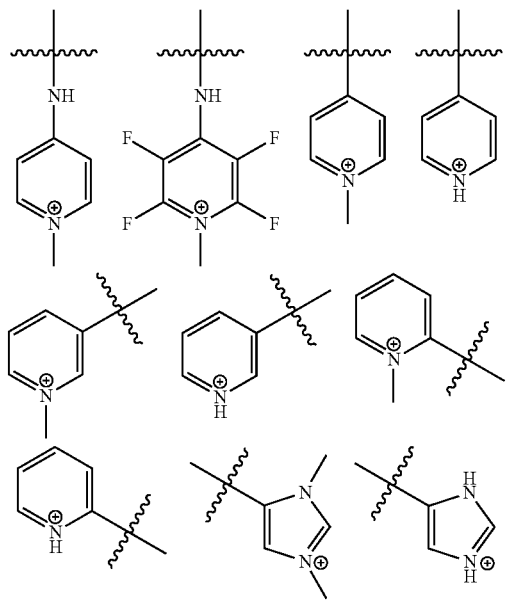

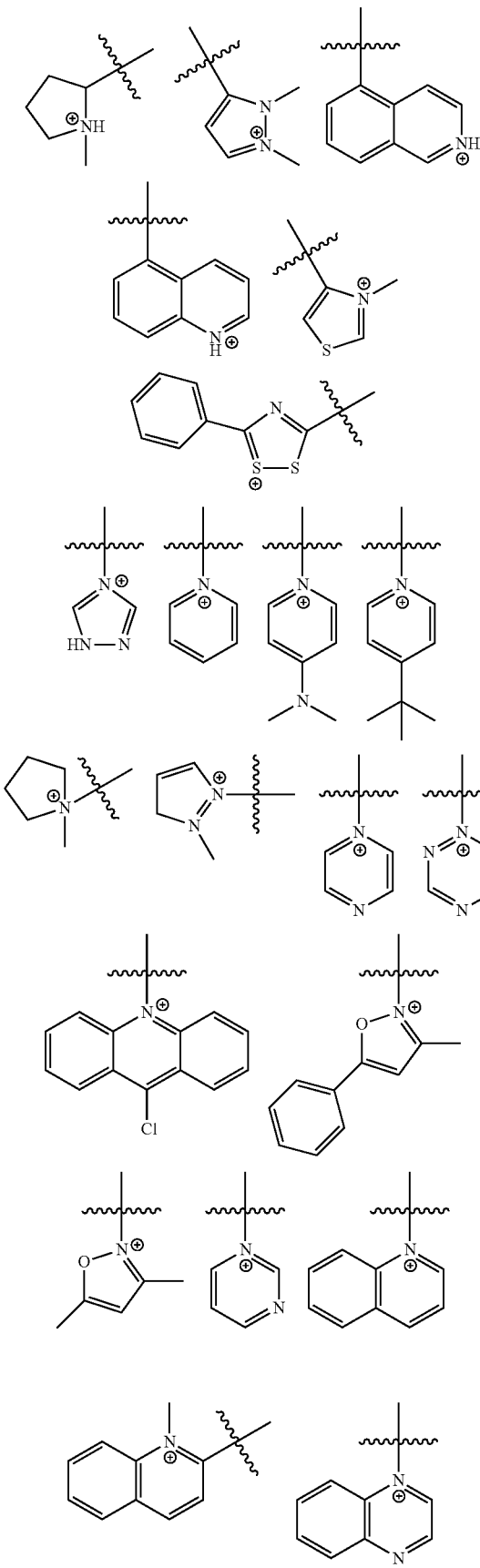

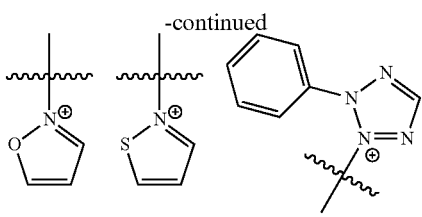

In certain embodiments, a polymerization initiator comprises a carboxylate salt of

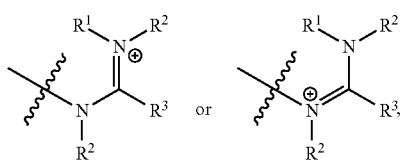

where each $R^1$, $R^2$, and $R^3$ is independently as defined above and described in classes and subclasses herein.

In certain embodiments, a polymerization initiator comprises a carboxylate salt of

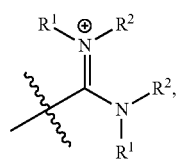

wherein each $R^1$ and $R^2$ is independently as defined above and described in classes and subclasses herein.

In certain embodiments, a polymerization initiator comprises a carboxylate salt of

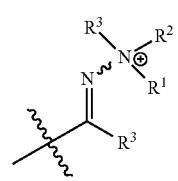

wherein each $R^1$, $R^2$, and $R^3$ is independently as defined above and described in classes and subclasses herein.

In certain embodiments, a polymerization initiator comprises a carboxylate salt of

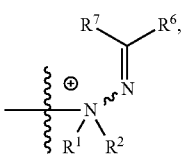

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In certain embodiments, $R^6$ and $R^7$ are each independently an optionally substituted $C_{1-20}$ aliphatic. In certain embodiments, $R^6$ and $R^7$ are each independently an optionally substituted $C_{1-20}$ heteroaliphatic having. In certain embodiments, $R^6$ and $R^7$ are each independently an optionally substituted phenyl or 8-10-membered aryl. In certain embodiments, $R^6$ and $R^7$ are each independently an optionally substituted 5- to 10-membered heteroaryl. In certain embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^6$ and $R^7$ are each independently an optionally substituted $C_{1-6}$ aliphatic. In certain embodiments, each occurrence of $R^6$ and $R^7$ is independently methyl, ethyl, propyl, butyl, pentyl, hexyl, heptyl, octyl, or benzyl. In certain embodiments, each occurrence of $R^6$ and $R^7$ is independently perfluoro. In certain embodiments, each occurrence of $R^6$ and $R^7$ is independently —$CF_2CF_3$.

In certain embodiments, a polymerization initiator comprises a carboxylate salt of

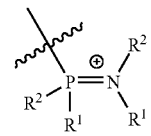

wherein each $R^1$ and $R^2$ is independently as defined above and described in classes and subclasses herein.

In certain embodiments, a polymerization initiator comprises a carboxylate salt of

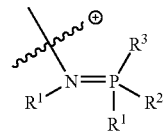

wherein each $R^1$, $R^2$, and $R^3$ is independently as defined above and described in classes and subclasses herein.

In certain embodiments, a cation is

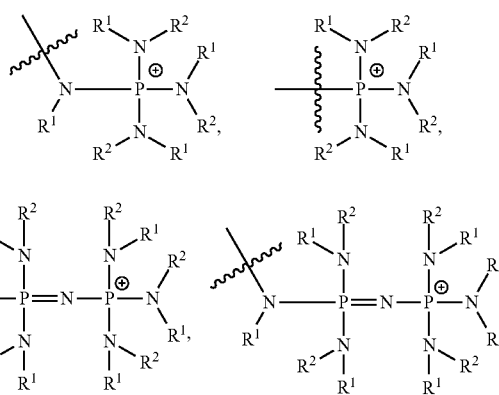

-continued

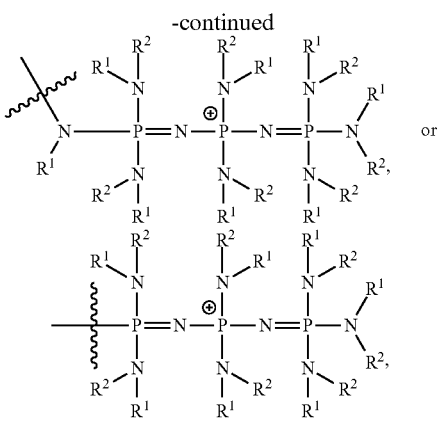

wherein each $R^1$ and $R^2$ is independently as defined above and described in classes and subclasses herein.

In certain embodiments, a polymerization initiator comprises a carboxylate salt of

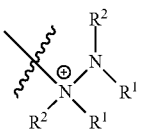

wherein each $R^1$ and $R^2$ is independently as defined above and described in classes and subclasses herein.

In certain embodiments, a polymerization initiator comprises a carboxylate salt of

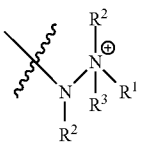

wherein each $R^1$, $R^2$, and $R^3$ is independently as defined above and described in classes and subclasses herein.

In certain embodiments, a polymerization initiator comprises a carboxylate salt of

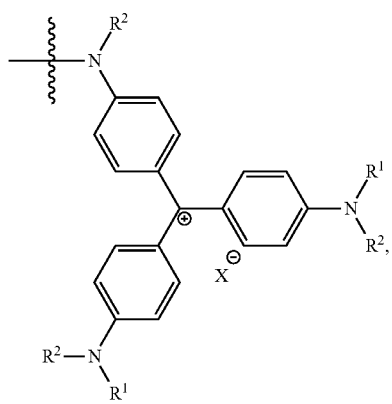

wherein each $R^1$ and $R^2$ is independently as defined above and described in classes and subclasses herein. In certain embodiments, suitable initiator include transition metal compounds. In certain embodiments, suitable catalysts include acid catalysts. In certain embodiments, the catalyst is a heterogeneous catalyst.

In some embodiments, the homogeneous polymerization initiator is a quaternary ammonium salt (for example, tetrabutylammonium (TBA) acrylate, TBA acetate, trimethylphenylammonium acrylate, or trimethylphenylammonium acetate) or a phosphine (for example, tetraphenyl phosphonium acrylate).

In some embodiments, the catalyst is tetrabutylammonium acrylate, sodium acrylate, potassium acrylate, iron chloride, tetrabutylammonium acetate, trimethylphenylammonium acrylate, trimethylphenylammonium acetate, or tetraphenyl phosphonium acrylate.

Figure 4A:
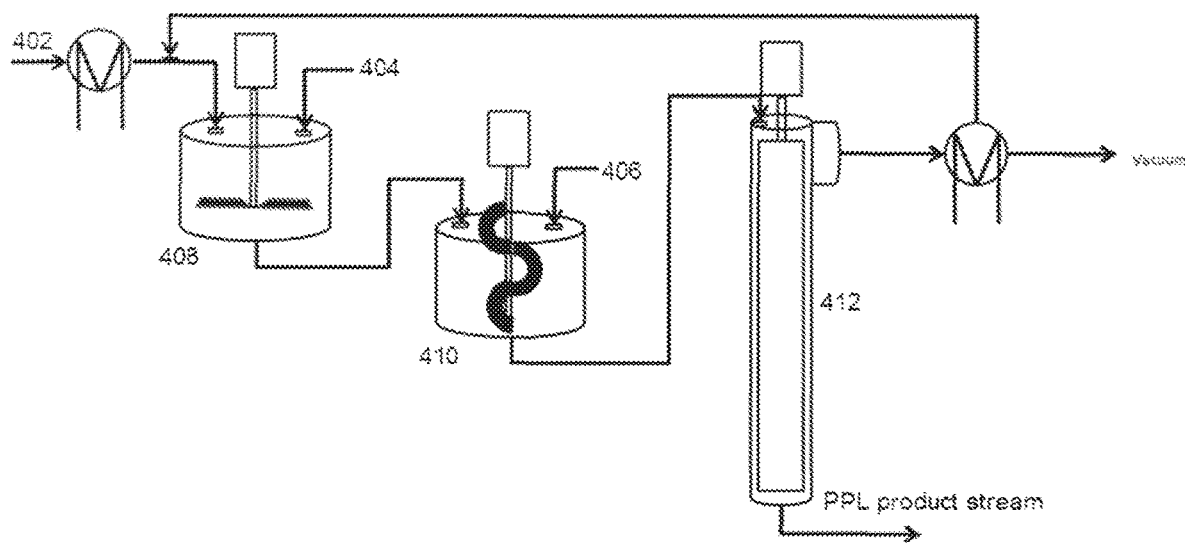
FIG. 4A is a schematic illustration of a system for converting β-propiolactone to polypropiolactone that involves the use of two continuous stirred-tank reactors in series.

With reference to FIG. 4A, the polymerization catalyst in the first reactor (408) and the additional polymerization initiator in the second reactor (410) may be the same or different. For example, in some embodiments, wherein the same initiator is used in both reactors, concentration of initiator is not the same in each reactor.

In some embodiments, the homogeneous polymerization initiator is added to a polymerization reactor as a liquid. In other embodiments it is added as a solid, which then becomes homogeneous in the polymerization reaction. In some embodiments where the polymerization initiator is added as a liquid, the polymerization initiator may be added to the polymerization reactor as a melt or in any suitable solvent. For example, in some variations GAA, molten PPL or bPL is used as a solvent.

In some embodiments, the solvent for the polymerization initiator is selected such that the initiator is soluble, the solvent does not contaminate the product polymer, and the solvent is dry. In some variations, the polymerization initiator solvent is GAA, molten PPL, or bPL. In certain variations, solid PPL is added to a polymerization reactor, heated above room temperature until liquid, and used as the polymerization initiator solvent. In other embodiments, bPL is added to the polymerization reactor, cooled below room temperature until liquid, and used as the polymerization initiator solvent.

In some variations, the solid or liquid polymerization initiator (as a melt or as a solution in a suitable solvent) is prepared in one location, then shipped to a second location where it is used in the polymerization reactor. In other embodiments, the solid or liquid polymerization initiator (as a melt or as a solution in a suitable solvent) is prepared at the location of the polymerization reactor (for example, to reduce exposure to moisture and/or oxygen).

A solid or liquid polymerization initiator (as a melt or as a solution in a suitable solvent) may be pumped into a stirred holding tank or directly into the polymerization reactor.

In some variations, the liquid initiator and/or initiator precursors are dispensed from a shipping vessel/container into an intermediate, inert vessel to be mixed with suitable solvent, and then the initiator solution is fed to the reactor or a pre-mix tank. The initiator preparation system and the connections may be selected in such a way to ensure that the initiator or precursors are not contacted by ambient atmosphere.

In some variations, the polymerization reactor is a PFR, the solid or liquid initiator (as a melt or as a solution in a suitable solvent) and bPL are fed to a small stirred tank and then the mixture is fed to the PFR. In other embodiments, the bPL and the liquid catalyst are fed to a pre-mixer installed at the inlet of the PFR. In yet another embodiment, the PFR has a static mixer, the reaction occurs on the shell side of the reactor, and the solid or liquid initiator and bPL are introduced at the inlet of the reactor and the static mixer elements mix the initiator and bPL. In still another embodiments, the PFR has a static mixer, the reaction occurs on the shell side of the reactor, and the solid or liquid initiator is introduced into the PFR using metering pumps/feeders at multiple locations distributed along the lengths of the reactor.

In some embodiments, the homogeneous polymerization initiator is delivered to the location of the polymerization reactor as a solid (for example, solid Al(TPP)Et, solid sodium acrylate, solid potassium acrylate, solid sodium acetate, solid potassium acetate, or solid TBA acrylate), the solid initiator is unpacked and loaded in hoppers under inert conditions (CO or inert gas), and the solids from hoppers can be fed directly into the polymerization reactor, or be mixed with bPL prior to the reactor, or be metered into a suitable solvent before pumping into the polymerization reactors or mixing tanks.

Heterogeneous System

Any suitable polymerization catalyst may be used in the polymerization process to convert the production stream entering the polymerization process to the PPL product stream. In some embodiments, the polymerization catalyst is heterogeneous with the polymerization reaction mixture. Any suitable heterogeneous polymerization catalyst capable of polymerizing bPL in the production stream to produce the PPL product stream may be used in the methods described herein.

In some embodiments, the heterogeneous polymerization catalyst comprises any of the homogeneous polymerization catalysts described above, supported on a heterogeneous support. Suitable heterogeneous supports may include, for example, amorphous supports, layered supports, or microporous supports, or any combination thereof. Suitable amorphous supports may include, for example, metal oxides (such as aluminas or silicas) or carbon, or any combination thereof. Suitable layered supports may include, for example, clays. Suitable microporous supports may include, for example, zeolites (such as molecular sieves) or cross-linked functionalized polymers. Other suitable supports may include, for example, glass surfaces, silica surfaces, plastic surfaces, metal surfaces including zeolites, surfaces containing a metallic or chemical coating, membranes (comprising, for example, nylon, polysulfone, silica), micro-beads (comprising, for example, latex, polystyrene, or other polymer), and porous polymer matrices (comprising, for example, polyacrylamide, polysaccharide, polymethacrylate).

In some variations, the heterogeneous polymerization catalyst comprises the carboxylate salt of any of the homogeneous polymerization catalysts described above, wherein the carboxylate is heterogeneous. For example, in certain embodiments, the carboxylate of the polymerization catalyst is a compound of Formula (D):

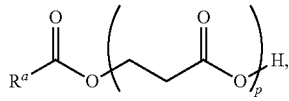

where p is from 0 to 9 and $R^a$ is a non-volatile moiety. The term "non-volatile moiety," as used herein, refers to a moiety or material to which a carboxylate can be attached, and that renders the carboxylate (e.g., when p=0) non-volatile to pyrolysis conditions. In some embodiments, a non-volatile moiety is selected from the group consisting of glass surfaces, silica surfaces, plastic surfaces, metal surfaces including zeolites, surfaces containing a metallic or chemical coating, membranes (comprising, for example, nylon, polysulfone, silica), micro-beads (comprising, for example, latex, polystyrene, or other polymer), and porous polymer matrices (comprising, for example, polyacrylamide, polysaccharide, polymethacrylate). In some embodiments, the non-volatile moiety has a molecular weight above 100, 200, 500, or 1000 g/mol. In some embodiments, the non-volatile moiety is part of a fixed or packed bed system. In some embodiments, the non-volatile moiety is part of a fixed or packed bed system comprising pellets (e.g., zeolite). In certain embodiments, p is from 0 to 5. In certain embodiments, the carboxylate salt of the polymerization catalyst is an acrylate salt (i.e., of compound of Formula (D) where p=0).

In some embodiments, the heterogeneous polymerization catalyst is a solid-supported quaternary ammonium salt (for example, tetrabutylammonium (TBA) acrylate, TBA acetate, trimethylphenylammonium acrylate, or trimethylphenylammonium acetate) or a phosphine (for example, tetraphenyl phosphonium acrylate).

In some embodiments, the catalyst is solid-supported tetrabutylammonium acrylate, iron chloride, TBA acetate, trimethylphenylammonium acrylate, trimethylphenylammonium acetate, or tetraphenyl phosphonium acrylate.

In certain embodiments, conversion of the production stream entering the polymerization process to the PPL product stream utilizes a solid carboxylate catalyst and the conversion is conducted at least partially in the gas phase. In certain embodiments, the solid carboxylate catalyst in the polymerization process comprises a solid acrylic acid catalyst. In certain embodiments, the production stream enters the polymerization process as a liquid and contacted with a solid carboxylate catalyst to form the PPL product stream. In other embodiments, the production stream enters the polymerization process as a gas and contacted with a solid carboxylate catalyst to form the PPL product stream.

In some variations, the polymerization catalyst is a heterogeneous catalyst bed. Any suitable resin may be used for such a heterogeneous catalyst bed. In one embodiment, the polymerization catalyst is a heterogeneous catalyst bed packed in a tubular reactor. In some embodiments, the polymerization reactor system comprises a plurality of heterogeneous catalyst beds, wherein at least one catalyst bed is being used in the polymerization reactor, and at least one catalyst bed is not being used in the polymerization reactor at the same time. For example, the catalyst bed not actively being used may be being regenerated for later use, or may be stored as a back-up catalyst bed in case of catalyst failure of the actively used bed. In one embodiment, the polymerization reactor system comprises three heterogeneous catalyst beds, wherein one catalyst bed is being used in the polymerization reactor, one catalyst bed is being regenerated, and one catalyst bed is being stored as a back-up in case of catalyst failure.

In some variations, the heterogeneous polymerization catalyst is prepared in one location, then shipped to a second location where it is used in the polymerization reactor. In other embodiments, the heterogeneous polymerization catalyst is prepared at the location of the polymerization reactor (for example, to reduce exposure to moisture and/or oxygen).

Solvents

In some embodiments, the polymerization process does not include solvent. In other embodiments, the polymerization process does include one or more solvents. Suitable solvents can include, but are not limited to: hydrocarbons, ethers, esters, ketones, nitriles, amides, sulfones, halogenated hydrocarbons, and the like. In certain embodiments, the solvent is selected such that the PPL product stream is soluble in the reaction medium.

Without wishing to be bound by any particular theory, it is believed that solvents comprising Lewis bases of low to moderate polarity improve the performance of the polymerization reaction. Thus, in certain embodiments, a polymerization solvent comprises a Lewis base and is less polar than 1,3-dioxane ($\varepsilon$=dielectric constant at 20° C.=13.6). In certain embodiments, a polymerization solvent comprises a Lewis base and is less polar than ortho-difluorobenzene ($\varepsilon$=13). In certain embodiments, a polymerization solvent comprises a Lewis base and is less polar than metadifluorobenzene ($\varepsilon$=5). In certain embodiments, a polymerization solvent comprises a Lewis base with substantially the same polarity as 1,4-dioxane ($\varepsilon$=2.2). In some embodiments, a polymerization solvent is less polar than a carbonylation solvent as measured by dielectric constant. In some embodiments, a polymerization solvent has a dielectric constant at 20° C. of less than about 13.6, less than about 13, or less than about 5.

Figure 4B:
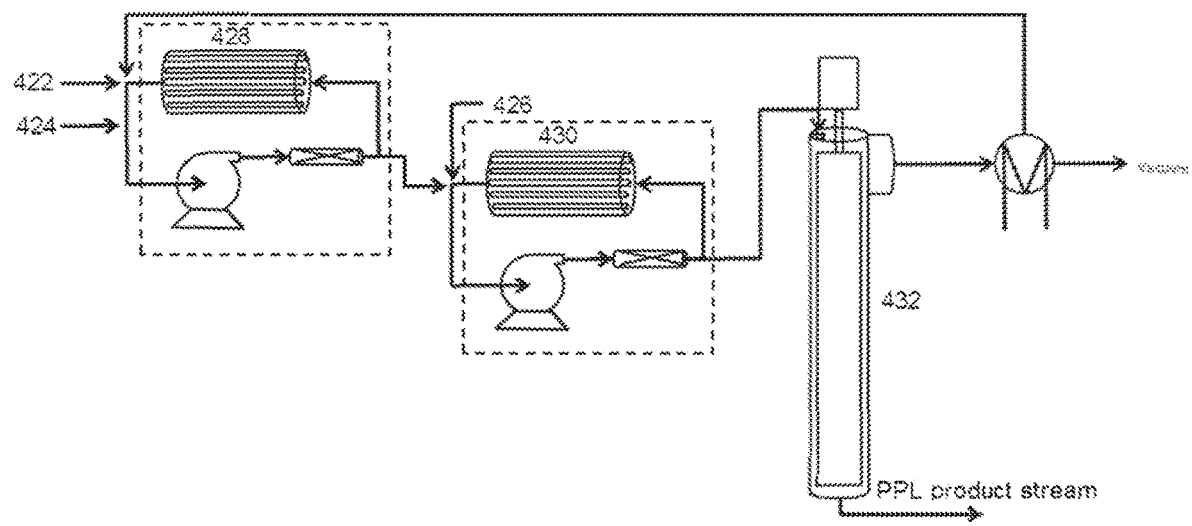
FIG. 4B is a schematic illustration of a system for converting β-propiolactone to polypropiolactone that involves the use of two loop reactors in series.

For example, with reference to polymerization process depicted in FIGS. 4A and 4B, reactors 408 and/or 410 may be configured to receive solvent. For example, in one variation, polymerization process may further include a solvent source configured to feed solvent into reactors 408 and 410. In another variation, the bPL from production stream 402 may be combined with solvent to form the production stream containing bPL fed into reactor 408. In yet another variation, the polymerization catalyst from polymerization catalyst sources 404 and/or 406 may be combined with a solvent to form polymerization catalyst streams fed into the reactors.

Polymerization Reactors

The one or more polymerization reactors in the polymerization process may be any suitable polymerization reactors for the production of the PPL product stream from the production stream entering the polymerization process. For example, the polymerization reactor may be a CSTR, loop reactor, or plug flow reactor, or a combination thereof. In some embodiments, the polymerization process comprises a single reactor, while in other embodiments, the polymerization process comprises a plurality of reactors. In some variations, the bPL is completely converted to PPL in a polymerization reactor. In other variations, the bPL is not completely converted to PPL in a polymerization reactor, and the PPL stream exiting the polymerization reactor comprises unreacted bPL. In certain variations, the PPL stream comprising unreacted bPL is directed to a bPL/PPL separator to remove the bPL from the PPL. The bPL may then be recycled back into the polymerization reactor, as described, for example, in FIGS. 7, 9, 11 and 13 above.

In certain variations, the polymerization process comprises two reactors in series, wherein the purified bPL stream enters the first reactor and undergoes incomplete polymerization to produce a first polymerization stream comprising PPL and unreacted bPL, the first polymerization stream exits the outlet of the first reactor and enters the inlet of the second reactor to undergo additional polymerization. In some variations, the additional polymerization completely converts the bPL to PPL, and the PPL product stream exits the outlet of the second polymerization reactor.

In other variations, the additional polymerization incompletely converts the bPL to PPL, and the PPL product stream exiting the outlet of the second polymerization reactor comprises PPL and unreacted bPL. In certain variations, the PPL product stream enters a BPL/PPL separator to remove unreacted bPL from the PPL product stream. In certain variations, the unreacted bPL is recycled back into the polymerization process. For example, in some variations, the unreacted bPL is recycled to the first polymerization reactor or the second polymerization reactor, or both the first and the second polymerization reactors.

In some embodiments, the polymerization process comprises a series of one or more continuous CSTR reactors followed by a BPL/PPL separator (such as a wiped film evaporator (WFE) or flash tank evaporator operating under vacuum). In other embodiments, the polymerization process comprises a series of one or more loop reactors followed by a BPL/PPL separator (such as a WFE or flash tank evaporator operating under vacuum). In yet other embodiments, the polymerization process comprises a series of one or more in a series of one or more CSTR reactors followed by a polishing plug flow reactor (PFR) or by a BPL/PPL separator (Wiped Film Evaporator or flash tank evaporator operating under vacuum). In still other embodiments, the polymerization process comprises a series of one or more PFR optionally followed by a BPL/PPL separator (such as a WFE or flash tank evaporator operating under vacuum).

In some embodiments, the polymerization process comprises greater than two polymerization reactors. For example, in certain embodiments, the polymerization process comprises three or more polymerization reactors, four or more polymerization reactors, five or more polymerization reactors, six or more polymerization reactors, seven or more polymerization reactors, or eight or more polymerization reactors. In some variations, the reactors are arranged in series, while in other variations, the reactors are arranged in parallel. In certain variations, some of the reactors are arranged in series while others are arranged in parallel.

FIGS. 4A and 4B depict exemplary PPL production system/production process comprising two polymerization reactors connected in series, and a PPL purification and BPL recycle system with a wiped film evaporator (WFE) for recycling of unreacted bPL back into the polymerization reactors. With reference to FIG. 4A, the polymerization process includes bPL source 402 and polymerization catalyst source 404, configured to feed bPL and catalyst, respectively, into reactor 408. Reactor 408 includes a bPL inlet to receive bPL from the bPL source and a polymerization catalyst inlet to receive polymerization catalyst from the polymerization catalyst source. In some variations, the bPL inlet is configured to receive the bPL from the bPL source at a rate of 3100 kg/hr, and the first polymerization catalyst inlet is configured to receive the polymerization catalyst from the polymerization catalyst source at a rate of 0.1 to 5 kg/hr.

With reference again to FIG. 4A, reactor 408 further includes a mixture outlet to output a mixture comprising PPL, unreacted bPL, and residual carbonylation catalyst to reactor 410. Reactor 410 is a second reactor positioned after reactor 408, and is configured to receive the mixture from reactor 408 and additional polymerization catalyst from polymerization catalyst source 406. In some variation, the mixture inlet of the second reactor is configured to receive the mixture from the first reactor at a rate of 4500 kg/hr, and the second polymerization catalyst inlet is configured to receive additional polymerization catalyst from the catalyst source at a rate of 0.1 to 4 kg/hr.

With reference again to FIG. 4A, reactor 408 further includes a mixture outlet to output a mixture comprising PPL, unreacted bPL, and residual carbonylation catalyst to evaporator 412. In some variations, the mixture outlet is configured to output such mixture at a rate of 4500 kg/hr.

With reference to FIG. 4B, the depicted polymerization process includes bPL source 422 and polymerization catalyst source 424, configured to feed bPL and catalyst, respectively, into reactor 428. Reactor 428 includes a bPL inlet to receive bPL from the bPL source and a polymerization catalyst inlet to receive polymerization catalyst from the polymerization catalyst source. In some variations, the bPL inlet is configured to receive the bPL from the bPL source at a rate of 3100 kg/hr, and the first catalyst inlet is configured to receive the catalyst from the catalyst source at a rate of 0.1 to 5 kg/hr.

With reference again to FIG. 4B, reactor 428 further includes a mixture outlet to output a mixture comprising PPL, unreacted bPL, and residual carbonylation catalyst to reactor 430. Reactor 430 is a second reactor positioned after reactor 428, and is configured to receive the mixture from reactor 428 and additional polymerization catalyst from polymerization catalyst source 426. In some variation, the mixture inlet of the second reactor is configured to receive the mixture from the first reactor at a rate of 4500 kg/hr, and the second polymerization catalyst inlet is configured to receive additional polymerization catalyst from the polymerization catalyst source at a rate of 0.1 to 4 kg/hr.

In some variations, the mixture output from reactor 410 (FIG. 4A) and reactor 430 (FIG. 4B) is made up of at least 95% wt PPL.

Such mixture may be output from the second reactor to an evaporator. Evaporator 412 (FIG. 4A) and 432 (FIG. 4B) may be, for example, a wiped film evaporator, thin film evaporator, or falling film evaporator. The evaporator is configured to produce a PPL product stream.

In some variations, the evaporator is configured to produce a PPL product stream having a purity of at least 98%, at least 98.5%, or at least 99%. In other variations, the evaporator is configured to produce a PPL product stream having less 0.6% wt of bPL. In some variations, the PPL stream has trace amounts of carbonylation catalyst. For example, the PPL product stream may have 0.1 mM of cobalt from the carbonylation catalyst. In some variations, the trace amounts of carbonylation catalyst are subsequently removed from the PPL product stream by IER before thermolysis, as described above in FIGS. 6, 7, 10 and 11.

In some variations, the polymerization process further includes one or more heat exchangers. With reference to FIG. 4A, bPL from bPL source 402 may be passed through heat exchanger 414 before such BPL stream is fed into reactor 408.

It should generally be understood that the polymerization is an exothermic reaction. Thus, in other variations, reactors 408 and 410 (FIG. 4A) may further include a connection to at least one heat exchanger. With reference to FIG. 4B, reactors 428 and 430 (FIG. 4B) may further include a connection to at least one heat exchanger.

The reactors of polymerization process may include any suitable reactors, including, for example, continuous reactors or semi-batch reactors. In one variation, with reference to FIG. 4A, the reactors may be continuous-flow stirred-tank reactors. The reactors may also include the same or different stirring devices. For example, in one variation, reactor 408 may include a low velocity impeller, such as a flat blade. In other variation, reactor 410 may include a low shear mixer, such as a curved blade.

A skilled artisan would recognize that the choice for the mixing device in each of the reactors may depend on various factors, including the viscosity of the mixture in the reactor. For example, the mixture in the first reactor may have a viscosity less than 1000 cP. If the viscosity is less than 1000 cP, then a low velocity impeller may be desired. In another example, the mixture in the second reactor may have a viscosity greater than 2000 cP. If the viscosity is greater than 2000 cP, then a low shear mixer may be desired.

In another variation, with reference to FIG. 4B, the reactors may be loop reactors.

It should be understood that while FIGS. 4A and 4B depict the use of two reactors configured in series, other configurations are considered. For example, in other exemplary variations of the polymerization process, three reactors may be employed. In yet other variations where a plurality of reactors is used in the polymerization process, they may be arranged in series or in parallel.

Figure 5:
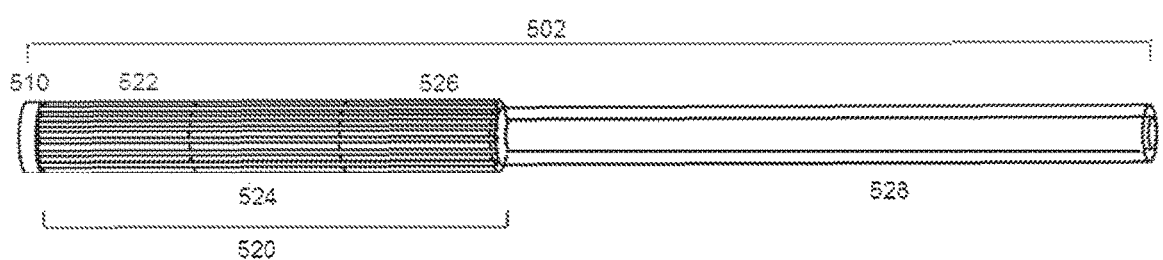
FIG. 5 is a schematic illustration of a system for converting β-propiolactone to polypropiolactone that involves a plug flow reactor with multiple cooling zones.

FIG. 5 depicts yet another exemplary polymerization process, which includes a BPL polymerization reactor. Polymerization reactor 500 includes mixing zone 510 configured to mix the production stream entering the polymerization process and catalyst, and a plurality of cooling zones 520 positioned after the mixing zone. Polymerization reactor 500 has reaction length 502, wherein up to 95% of the bPL in the entering production stream is polymerized in the presence of the catalyst to form PPL in the first 25% of the reaction length. In some variations of the system depicted in FIG. 5, the bPL is completely converted to PPL. Such a system may be used, for example, in the complete conversion of bPL to PPL as described above for FIGS. 6, 8, 10 and 12.

In some variations of a polymerization reactor, the plurality of cooling zones includes at least two cooling zones. In one variation, the plurality of cooling zones includes two cooling zones or three cooling zones.

For example, polymerization reactor 500 as depicted in FIG. 5 has three cooling zones 522, 524 and 526. In one variation, the three cooling zones are connected serially in the first 25% of the reaction length. In another variation, cooling zone 522 is configured to receive a mixture of bPL and the catalyst from the mixing zone at a rate of 3100 kg/hr; cooling zone 524 is configured to receive a mixture of the bPL, the catalyst and PPL produced in cooling zone 522 at a rate of 3100 kg/hr; and cooling zone 526 is configured to receive a mixture of the bPL, the catalyst, the PPL produced in cooling zone 522, and PPL produced in cooling zone 524 at a rate of 3100 kg/hr.

In certain embodiments, the first 25% of the reaction length is a shell and a tube heat exchanger. In one variation, the shell may be configured to circulate a heat transfer fluid to maintain a constant temperature in reaction length 502. In another variation, the tube heat exchanger is configured to remove heat produced in the first reaction zone.

With reference again to FIG. 5, polymerization reactor 500 further includes end conversion zone 528 connected to plurality of cooling zones 520. In some variations, the end conversion zone is configured to receive a mixture of the bPL, the catalyst, and the PPL produced in plurality of cooling zones at a rate of 3100 kg/hr. In one variation, the end conversion zone has no cooling load.

In one variation, the polymerization reactor is a plug flow reactor or a shell-and-tube reactor.

The one or more polymerization reactors used in the methods described herein may be constructed of any suitable material compatible with the polymerization. For example, the polymerization reactor may be constructed from stainless steel or high nickel alloys, or a combination thereof.

In some embodiments, the polymerization process comprises a plurality of polymerization reactors, and the polymerization catalyst is introduced only into the first reactor in the series. In other embodiments, the polymerization catalyst is added separately to each of the reactors in the series. For example, referring again to FIG. 4A, depicted is a polymerization process comprising two CSTR in series, wherein polymerization catalyst is introduced to the first CSTR, and polymerization catalyst is separately introduced to the second CSTR. In other embodiments, a single plug flow reactor (PFR) is used, and polymerization catalyst is introduced at the beginning of the reactor, while in other embodiments polymerization catalyst is introduced separately at a plurality of locations along the length of the PFR. In other embodiments, a plurality of PFR is used, and polymerization catalyst is introduced at the beginning of the first PRF. In other embodiments, polymerization catalyst is introduced at the beginning of each PFR used, while in still other embodiments polymerization catalyst is introduced separately at a plurality of locations along the length of each PFR.

The polymerization reactor may comprise any suitable mixing device to mix the polymerization reaction mixture. Suitable mixing devices may include, for example, axial mixers, radial mixers, helical blades, high-shear mixers, or static mixers. Suitable mixing devices may comprise single or multiple blades, and may be top, bottom, or side mounted. The polymerization reactor may comprise a single mixing device, or multiple mixing devices. In some embodiments, a plurality of polymerization reactors is used, and each polymerization reactor comprises the same type of mixing device. In other embodiments, each polymerization reactor comprises a different type of mixing device. In yet other embodiments, some polymerization reactors comprise the same mixing device, while others comprise different mixing devices Preferred Embodiments of Polymerization Sub-Systems In the preferred embodiments, distillation sub-system consists of (1) one or more polymerization reactors and (2) PPL purification/BPL recycle system.

Preferred BPL Polymerization Reactor

Polymerization of bPL can be performed in one or more reactors operating in series or parallel and in preferred embodiments the distillate stream consisting of essentially pure bPL (purity greater than 99.9 wt %) with trace amounts of low- and high-boiling impurities (non limiting impurities are THF and Succinic Anhydride) is fed bPL Polymerization reactor. The bPL feed stream can be fed at the temperature of the bPL purification column overhead (50-100° C.) or can be cooled to 20-50° C. before being fed to the polymerization reactor.

The preferred combination of conditions for the polymerization of bPL include temperatures in the range 80-150° C., preferrably 120-145° C. at pressures below or above atmospheric in the presence of polymerization initiator. The preferred initiators are quaternary amine and alkali metal salts of acrylic acid. Non limiting examples of polymerization initiators are Sodium Acrylate, Potassium Acrylate, Tetrabutylammonium Acrylate. The molar ratio of polymerization initiator to bPL is from 1:20000 to 1:100, preferably from 1:15000 to 1:500, preferably from 1:10000 to 1:1000, and most preferably from 1:8000 to 1:1500.

In such preferred embodiments, solid polymerization initiator is mixed with fresh bPL stream before the reactor; a high shear mixer can be used to achieve good mixing of bPL with initiator. In another embodiment, solid polymerization initiator is mixed with recycled bPL stream before the reactor; a high shear mixer can be used to achieve good mixing of bPL with initiator. In another embodiment, polymerization reactor if fed directly into the polymerization reactor; optionally, an educator can be used to effectively mix solid initiator with all or part of bPL feed at the inlet to the reactor.

During polymerization of bPL to form PPL Acrylic Acid that acts as chain transfer agent can be formed in-situ. In some embodiments small amounts of acrylic acid can be fed to polymerization reactor to control molecular weight of PPL. To avoid radical polymerization of acrylic acid, radical polymerization inhibitors such as phenothiazine (PTZ) can be fed to the polymerization reactor. The concentration of radical polymerization inhibitor in the reactor is maintained at 50-500 ppm (by weight); preferred inhibitor concentration is in the range from 150 to 250 ppm.

If the plurality of polymerization reactors are operating in series, bPL can be fed to the first reactor only or bPL feed can be split between reactors in series. If the plurality of polymerization reactors are operating in series, a polymerization initiator can be fed to the first reactor only or initiator can be fed to each of the reactors in series.

In one of the preferred embodiments, polymerization of bPL can be conducted in one or more Continuous Stirred Tank Reactors (CSTR) operating in series. The polymerization reaction is exothermic and heat of the reaction can be removed by means known in the art such as an internal heat exchanger or jacket, an external heat exchanger (reaction mixture is circulated through external heat exchanger and cooled stream is returned to the reactor), evaporative cooling (reactor is equipped with attached condenser: bPL is evaporated from the reactor, condensed in the condenser, and cooled bPL stream is returned to the reactor). The reactors can be operated at atmospheric pressure, below atmospheric pressure, above atmospheric pressure.

In another preferred embodiment, polymerization of bPL can be conducted in one or more Loop Reactors operating in series. The reactors can be operated at or above atmospheric pressure. The temperatures of the surfaces in contact with the reaction mixture containing bPL and PPL are kept at temperatures that prevent precipitation of PPL (PPL melting point is at about 70-80° C.)

In another preferred embodiment, polymerization of bPL is conducted in the reactor system consisting of one or more CSTR or Loop Reactors followed by one or more Plug Flow Reactors (PFR). The temperatures of the surfaces in contact with the reaction mixture containing bPL and PPL are kept at temperatures that prevent precipitation of PPL (PPL melting point is at about 70-80° C.)

The concentration of PPL in the stream exiting the reaction system (bPL conversion) is greater than 40 wt %, preferably greater than 60 wt %, preferably greater than 75 wt %. The conversion of bPL can be greater than 80%, greater than 90%, greater than 95%, or greater than 99%. The stream exiting bPL polymerization system is fed forward to PPL purification and bPL recycle system. In one embodiment, polymerization reactor product stream consists of about 80 wt % PPL, about 20 wt % bPL, and polymerization initiator incorporated into PPL molecules.

Preferred PPL Purification/BPL Recycle System

The polymerization reactor product consisting of PPL product and unreacted bPL is fed forward to PPL purification and bPL recycle system. In preferred embodiments bPL can be separated from PPL in one or more flash evaporators operating under vacuum, or one or more Wiped Film Evaporators (WFE) operating under vacuum, or a combination thereof. To avoid decomposition of bPL within this system, surface temperatures in contact with bPL are kept below 200° C., preferably below 180° C., most preferably below 160° C. Recovered bPL is fed back to the polymerization reactor. Purified PPL contains less than 0.5 wt % bPL, preferably less than 0.25 wt % bPL, preferably less than 0.1 wt % bPL, and preferably concentration of bPL in PPL product is less than 100 ppm. Most preferably PPL is fed forward to thermolysis reaction system for production of Acrylic Acid or pelletized for storage or shipment.

BPL Conversion

In some variations, between 5% and 100%, between 10% and 100%, between 20% and 100%, between 30% and 100%, between 40% and 100%, between 50% and 100%, between 60% and 100%, between 70% and 100%, between 80% and 100%, between 90% and 100, or between 95% and 100% of the bPL is converted to PPL in the polymerization process.

In some variations, bPL is partially converted to PPL in the polymerization process. For example, in some variations, complete conversion of bPL to PPL is greater than or equal to 75%, and partial conversion of bPL to PPL is less than 75%. In other variations, complete conversion of bPL to PPL is greater than or equal to 80%, and partial conversion of bPL to PPL is less than 80%. In other variations, complete conversion of bPL to PPL is greater than or equal to 85%, and partial conversion of bPL to PPL is less than 85%. In yet other variations, complete conversion of bPL to PPL is greater than or equal to 90%, and partial conversion of bPL to PPL is less than 90%. In yet other variations, complete conversion of bPL to PPL is greater than or equal to 95%, and partial conversion of bPL to PPL is less than 95%. In one variation, complete conversion of bPL to PPL is greater than or equal to 99%, and partial conversion of bPL to PPL is less than 99%.

In other variations, partial conversion is between 30% and 90%; between 40% and 90%, between 50% and 90%; or between 60% and 90%.

In some variations, the polymerization process comprises a plurality of polymerization reactors, and the conversion of bPL to PPL in each reactor is between 5% and 100%, between 10% and 100%, between 20% and 100%, between 30% and 100%, between 40% and 100%, between 50% and 100%, between 60% and 100%, between 70% and 100%, between 80% and 100%, between 90% and 100, or between 95% and 100% of the bPL is converted to PPL.

In some variations, the polymerization process comprises a plurality of polymerization reactors, and the conversion of bPL to PPL over the entire polymerization process is between 5% and 100%, between 10% and 100%, between 20% and 100%, between 30% and 100%, between 40% and 100%, between 50% and 100%, between 60% and 100%, between 70% and 100%, between 80% and 100%, between 90% and 100, or between 95% and 100% of the bPL is converted to PPL.

In one variation, two reactors are operated in series, and the conversion of bPL to PPL in each reactor is between 10% and 100%.

As described above in FIGS. 9-13, in some embodiments of the methods to produce PPL as described herein, the bPL is completely converted to PPL. In other embodiments, the bPL is partially converted to PPL.

BPL Conversion

Without wishing to be bound by any theory, the polymerization of bPL to PPL proceeds quickly when the concentration of reactants is high and the concentration of products is low. As the reaction progresses to produce more products, the driving force for conversion is reduced. This phenomenon leads reactors which perform full conversion to be larger than those that perform partial conversion. Thus, in certain embodiments, the polymerization conditions and reactor size are selected such that conversion of bPL to PPL is partial (for example, 70% conversion), and a bPL/PPL separation device (for example, a WFE or distillation column) is used to recycle reactants back to the inlet of the reactor. Without wishing to be bound by any theory, this may avoid the requirements of a relatively large reactor while still generating a relatively pure product. In addition, the unreacted bPL is removed, which may make the handling of PPL easier. In the case where no PPL is isolated, removal of bPL reduces the possibility of other products forming during the thermolysis reaction PPL Product Stream In some embodiments, the production system/production process can produce at least about 2000 kg/hr PPL, at least about 2500 kg/hr PPL, at least about 3000 kg/hr PPL, at least about 3050 kg/hr PPL, or at least about 3500 kg/hr PPL, at least about 3638 kg/hr PPL, at least about 4000 kg/hr PPL, at least about 5000 kg/hr PPL, at least about 1000 kg/hr PPL, at least about 20000 kg/hr PPL, or at least about 35000 kg/hr PPL. In some embodiments, the production system/production process can produce about 2000 kg/hr PPL, about 2500 kg/hr PPL, about 3000 kg/hr PPL, about 3500 kg/hr PPL, about 3638 kg/hr PPL, about 4000 kg/hr PPL, about 5000 kg/hr PPL, about 1000 kg/hr PPL, about 20000 kg/hr PPL, or about 35000 kg/hr PPL. In some embodiments, the production system/production process can produce between 2000 kg/hr PPL and 3500 kg/hr PPL, between 2500 kg/hr PPL and 3500 kg/hr PPL, between bout 3000 kg/hr PPL and 3500 kg/hr PPL, between 2000 kg/hr PPL and 35000 kg/hr PPL, between 2500 kg/hr PPL and 35000 kg/hr PPL, between 3000 kg/hr PPL and 35000 kg/hr PPL, between 3500 kg/hr PPL and 35000 kg/hr PPL, between 3638 kg/hr PPL and 35000 kg/hr PPL, between 4000 kg/hr PPL and 35000 kg/hr PPL, between 5000 kg/hr PPL and 35000 kg/hr PPL, between 1000 kg/hr PPL and 35000 kg/hr PPL, or between 20000 kg/PPL and 35000 kg/hr PPL.

In some embodiments, the production system/production process can produce at least about 25 kmol/hr PPL, at least about 30 kmol/hr PPL, at least about 40 kmol/hr PPL, at least about 42 kmol/hr PPL, or at least about 50 kmol/hr PPL. In some embodiments, the mass fraction of PPL in the PPL product stream in the production system/production process after polymerization can be at least about 0.90, at least about at least about 0.95, at least about 0.98, at least about 0.982, and at least about 0.99. In some embodiments, the mole fraction of PPL in the PPL product stream of the production system/production process after polymerization can be at least about 0.90, at least about at least about 0.95, at least about 0.98, at least about 0.984, and at least about 0.99. The remainder of the PPL product stream can include unreacted bPL (in mole fraction of at most about 0.02, at most about 0.015, or at most about 0.011), secondary reaction products such as succinic anhydride (in mole fraction of at most about 0.01, at most about 0.005, or at most about 0.004,) and left over solvent (e.g., THF) and leftover carbonylation catalyst or components thereof (in at most about 1000 ppm). The PPL product stream can then receive thermolysis processing to form GAA. In some embodiments, the PPL product stream of the production system/production process can have a temperature between about 50-150° C., between about 110-150° C., or about 145° C. In some embodiments, the PPL product stream of the production system/production process can be at a pressure of at least about 0.001 bar, about 0.001-1 bar, or at least about 0.005 bar.

In certain embodiments, a method is provided for the production (e.g., integrated production) of a composition comprising PPL chains of Formula (B):

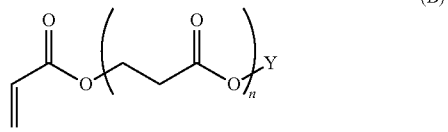

(B)

where n is an integer from 10 to about 1,000 and Y is either —H or a cation, comprising the step of polymerizing bPL in the presence of a chain transfer agent selected from the group consisting of: a compound of Formula (C):

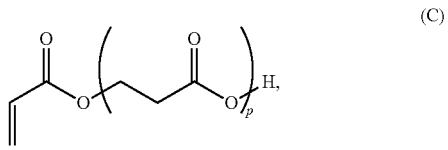

(C)

or a salt thereof, or a mixture of any two or more of these, where p is from 0 to 9. In certain embodiments, the composition further comprises PPL.

In certain embodiments, the PPL composition formed is characterized in that at least 90%, 95%, 99%, 99.5%, 99.8 or 99.9% of the polymer chains in the composition have an acrylate end group.

In certain embodiments, the PPL composition formed is characterized in that at least 90%, 95%, 99%, 99.5%, 99.8 or 99.9% of the polymer chains in the composition are of Formula (B).

In certain embodiments, n is, on average in the polypropiolactone composition, between 10 and 50, or between 50 and 100, or between 100 and 150, or between 150 and 250, or between 250 and 350, or between 350 and 500.

In some embodiments, the system described herein is configured to produce polypropiolactone with an average molecular weight between 800 g/mol and 100000 g/mol, between 500 g/mol and 70000 g/mol, between 1000 g/mol and 60000 g/mol, or between 1500 g/mol and 40000 g/mol. In some embodiments, the molecular weight is number average molecular weight, while in other embodiments, the molecular weight is weight average molecular weight.

In certain embodiments, the PPL composition is characterized in that it has a polydispersity index (PDI) of less than 10.

In certain embodiments, the PPL composition is characterized in that it has a PDI less than 8, or less than 5, or less than 3, or less than 2.5, or less than 2.0.

Cobalt/Ion Removal from PPL

In some embodiments, the PPL product stream is treated to reduce the concentration of cobalt and/or ions. The cobalt may be a cobalt ion or uncharged cobalt, or a combination thereof. The ions may be cobalt ions or non-cobalt ions.

In certain variations, the cobalt is a cobalt ion. The cobalt may be from decomposition of the carbonylation catalyst, residual catalyst components which comprise ions, residual catalyst, or combinations thereof. For example, in some embodiments, the carbonylation catalyst decomposes to produce $Co^{-1}$, Co, $Co^+$, $Co^{2+}$, or $Co^{3+}$, or combinations thereof. Thus, in some embodiments, the cobalt is a cobalt ion, while in other embodiments the cobalt is not a cobalt ion.

In some variations, at least some ions are removed from the PPL product stream. In some variations, the ions comprise metal ions. In other embodiments, the ions comprise non-metal ions. In yet other embodiments, the ions comprise both metal and non-metal ions. As discussed above, in certain variations, the ions comprise cobalt ions. The ions may be from decomposition of the carbonylation catalyst, residual catalyst components which comprise ions, residual catalyst, or ions produced as byproducts of the carbonylation reaction, or combinations thereof. For example in some embodiments, the carbonylation catalyst decomposes to produce $Co^{-1}$, $Co^+$, $Co^{2+}$, $Co^{3+}$, or $Al^{3+}$, or combinations thereof. In other embodiments, ions produced as byproducts of the carbonylation reaction include acetate ($CH_3C(O)O^-$) or acrylate ($CH_2=CHC(O)O^-$), or a combination thereof.

In certain embodiments, the step of treating the PPL product stream to remove at least a portion of cobalt and/or ions comprises ion exchange of cobalt and/or ions using ion exchange materials. In some embodiments, it may be possible to use an ion exchange resin for the ion exchange material. The ion exchange materials may be cationic, anionic, amphoteric, Lewis basic, Lewis acidic, or may comprise chelating groups. In certain embodiments, the ion exchange material may be a cation exchanger. In certain embodiments, functional groups on the cation exchange materials may be selected from: $—SO_3$, $PO_3^{2-}$, —COOH, $—C_6H_4OH$, —SH, $—AsO_3$, or $—SeO_3$, or combinations of two or more of these. In certain embodiments, functional groups on the cation exchange materials comprise $—SO_3$.

In certain embodiments, the ion exchange material may be an anion exchanger. In certain embodiments, functional groups on the anion exchange materials may be selected from: $—N^+(alkyl)_3$, $—N^+(CH_3)_3$, $—N^+(CH_3)_2C_2H_4OH$, $—N^+(CH_3)_2C_2H_5$, $—P^+(alkyl)_3$, $—P^+(aryl)_3$, $—P^+(C_4H_9)_3$, or $—P^+(Ph)_3$, or combinations of two or more of these. In certain embodiments, functional groups on the anion exchange materials comprise $—N^+(alkyl)_3$. In certain embodiments, functional groups on the anion exchange materials comprise $—P^+(alkyl)_3$. In certain embodiments, functional groups on the anion exchange materials comprise $—P^+(aryl)_3$.

In certain embodiments where the step of treating the PPL product stream to separate cobalt and/or ions comprises ion exchange, the process entails both anion exchange and cation exchange. In certain embodiments the anion and cation exchange are performed concomitantly. In certain embodiments, the anion and cation exchange are performed sequentially. In certain embodiments, the anion exchange is performed first followed by cation exchange. In certain embodiments, the cation exchange is performed first followed by anion exchange. In certain embodiments, an organic ion exchange resin may prove useful in the separation step comprises an organic ion exchange resin. The general characteristics and properties of such resins are the same as previously described.

In various aspects, the bead size may be widely distributed, or may be very narrow, so-called mono-disperse resins. In embodiments where catalyst is removed from the PPL product stream by ion exchange, the ion exchange material can be contacted with the PPL product stream by any conventional method. This includes, but is not limited to: flowing the PPL product stream through a fixed bed of a solid ion exchange material (i.e. in the form of beads, granules or other particles); flowing the PPL product stream through a fluidized bed of adsorbent, flowing the PPL product stream through fabrics, meshes, or filtration plates comprising the ion exchange material, or slurrying the PPL product stream with the ion exchange material (typically followed by filtration, centrifugation, sedimentation or the like to remove the ion exchange material from the PPL product stream). In embodiments where the PPL product stream is flowed through a packed column of ion exchange material, it may be desirable to provide a plurality of such columns in parallel with a provision to switch the flow from one to another periodically. Thus when one column of ion exchange material becomes saturated with cobalt and/or ions removed from the PPL product stream, it can be switched out of the flow path and the flow diverted to a fresh column—in certain embodiments, the interval of time from when a column is placed in the flow path to when it is switched out of the flow path corresponds to the "first time interval" recited in the methods described herein.

Where an ion exchange material is used to remove cobalt and/or ions from the PPL product stream, the inventive methods may include a subsequent step of removing the cobalt and/or ions from the ion exchange material. Such removal methods are well known in the art and typically involve contacting the ion exchange resin with a strong solution of a salt, the anion or cation of which will displace the adsorbed component from the ion exchange material.

In certain variations, the cobalt is $Co^{-1}$, Co, $Co^+$, $Co^{2+}$, or $Co^{3+}$, or a combination thereof. In some embodiments, the PPL product stream prior to cobalt removal has a cobalt concentration between 0.001 mM and 5 mM, between 0.01 mM and 3 mM, between 0.01 mM and 2 mM, between 0.01 mM and 1 mM, between 0.05 mM and 0.5 mM, between 0.05 mM and 0.2 mM, or between 0.07 mM and 0.15 mM. In some embodiments, the cobalt concentration of the permeate prior to cobalt removal is about 0.01 mM, about 0.03 mM, about 0.06 mM, about 0.09 mM, about 0.1 mM, about 0.13 mM, about 0.16 mM, about 0.19 mM, about 0.2 mM, about 0.23 mM, about 0.26 mM, about 0.29 mM, or about 0.3 mM. In one embodiment, the cobalt concentration of the PPL before cobalt removal is about 0.1 mM.

Thus, in some embodiments, the concentration of cobalt in the PPL product stream before contacting the ion exchange resin is between 0.001 mM and 5 mM, between 0.01 mM and 3 mM, between 0.01 mM and 2 mM, between 0.01 mM and 1 mM, between 0.05 mM and 0.5 mM, between 0.05 mM and 0.2 mM, or between 0.07 mM and 0.15 mM.

In some embodiments, the concentration of cobalt in the PPL product stream after contacting the ion exchange resin is between 0.001 mM and 1 mM, 0.001 mM and 0.5 mM, between 0.001 mM and 0.05 mM, between 0.005 mM and 0.02 mM, or between 0.007 mM and 0.015 mM. In one variation, the concentration of cobalt in the PPL product stream after contacting the ion exchange resin is 0.01 mM.

In some embodiments, at least some aluminum is removed from the PPL product stream. In certain variations, the aluminum is $Al^{3+}$. In some embodiments, the PPL product stream prior to aluminum removal has an aluminum concentration between 0.001 mM and 5 mM, between 0.01 mM and 3 mM, between 0.01 mM and 2 mM, between 0.01 mM and 1 mM, between 0.05 mM and 0.5 mM, or between 0.09 mM and 0.2 mM. In some embodiments, the PPL product stream prior to aluminum removal has a aluminum concentration of about 0.01 mM, about 0.03 mM, about 0.06 mM, about 0.09 mM, about 0.1 mM, about 0.13 mM, about 0.16 mM, about 0.19 mM, about 0.2 mM, about 0.23 mM, about 0.26 mM, about 0.29 mM, or about 0.3 mM. In one embodiment, the aluminum concentration of the PPL product stream before aluminum removal is about 0.1 mM.

Thus, in some embodiments, the concentration of aluminum in the PPL product stream before contacting the ion exchange resin is between 0.001 mM and 5 mM, between 0.01 mM and 3 mM, between 0.01 mM and 2 mM, between 0.01 mM and 1 mM, between 0.05 mM and 0.5 mM, between 0.05 mM and 0.2 mM, or between 0.07 mM and 0.15 mM.

In some embodiments, the concentration of aluminum in the PPL product stream after contacting the ion exchange resin is between 0.001 mM and 1 mM, 0.001 mM and 0.5 mM, between 0.001 mM and 0.05 mM, between 0.005 mM and 0.02 mM, or between 0.007 mM and 0.015 mM. In one variation, the concentration of aluminum in the PPL product stream after contacting the ion exchange resin is 0.01 mM.

Solid PPL

In some embodiments, the production system/production process described herein further comprises a PPL stream processing system configured to receive the PPL product stream and produce solid PPL. For example, in one embodiment, the PPL product stream is fed into at least one inlet of a PPL stream processing system, and solid PPL exits at least one outlet of the PPL stream processing system. The PPL stream processing system may be configured to produce solid PPL in any suitable form. For example, in some embodiments, the PPL stream processing system is configured to produce solid PPL in pelleted form, flaked form, granulated form, or extruded form, or any combinations thereof. Thus, solid PPL flakes, solid PPL pellets, solid PPL granules, or solid PPL extrudate, or any combinations thereof, may exit the outlet of the PPL stream processing system. The PPL stream processing system may include one or more flaking devices, pelleting devices, extrusion devices, or granulation devices, or any combinations thereof.

Geographic Location

In certain embodiments, the production system/production process described herein produces a PPL product stream at a first location, the PPL product stream is processed to produce solid PPL, and the solid PPL is converted to a GAA product stream in a second location. In some embodiments, the first location and the second location are at least 100 miles apart. In certain embodiments, the first location and the second location are between 100 and 12,000 miles apart. In certain embodiments, the first location and the second location are at least 250 miles, at least 500 miles, at least 1,000 miles, at least 2,000 or at least 3,000 miles apart. In certain embodiments, the first location and the second location are between about 250 and about 1,000 miles apart, between about 500 and about 2,000 miles apart, between about 2,000 and about 5,000 miles apart, or between about 5,000 and about 10,000 miles apart. In certain embodiments, the first location and the second location are in different countries. In certain embodiments, the first location and the second location are on different continents.

In certain embodiments, the solid PPL is transported from the first location to the second location. In some embodiments, the solid PPL is transported a distance of more than 100 miles, more than 500 miles, more than 1,000 miles, more than 2,000 miles or more than 5,000 miles. In certain embodiments, the solid PPL is transported a distance of between 100 and 12,000 miles, between about 250 and about 1000 miles, between about 500 and about 2,000 miles, between about 2,000 and about 5,000 miles, or between about 5,000 and about 10,000 miles. In some embodiments, the solid PPL is transported from a first country to a second country. In certain embodiments, the solid PPL is transported from a first continent to a second continent.

In certain embodiments, the solid PPL is transported from the North America to Europe. In certain embodiments, the solid PPL is transported from the North America to Asia. In certain embodiments, the solid PPL is transported from the US to Europe. In certain embodiments, the solid PPL is transported from the US to Asia. In certain embodiments, the solid PPL is transported from the Middle East to Asia. In certain embodiments, the solid PPL is transported from the Middle East to Europe. The solid PPL may be transported by any suitable means, including, for example, by truck, train, tanker, barge, or ship, or any combinations of these. In some embodiments, the solid PPL is transported by at least two methods selected from truck, train, tanker, barge, and ship. In other embodiments, the solid PPL is transported by at least three methods selected from truck, train, tanker, barge, and ship.

In some embodiments, the solid PPL is in the form of pellets, flakes, granules, or extrudate, or any combination thereof. In some variations, the solid PPL is converted to a GAA product stream using the thermolysis reactor as described herein. In some variations, the solid PPL is fed into an inlet of the thermolysis reactor and is converted to a GAA product stream. In other embodiments, the solid PPL is converted to molten PPL, and the molten PPL is fed into an inlet of the thermolysis reactor as described herein and converted to a GAA product stream.

Acrylic Acid Production System/Production Process

Polypropiolactone (PPL) can generally be converted to acrylic acid (AA) according to the following scheme:

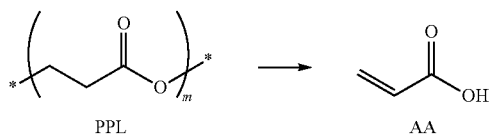

In certain embodiments, the polypropiolactone produced undergoes thermolysis continuously (e.g. in a fed batch reactor or other continuous flow reactor format). In certain embodiments, the continuous thermolysis process is linked to a continuous polymerization process to provide acrylic acid at a rate matched to the consumption rate of the reactor.

Thermolysis Reactors

In some embodiments, the thermolysis reactor is a fluidized bed reactor. Inert gas may be used to fluidize inert solid heat transfer medium (HTM), and polypropiolactone is fed to the reactor. In some variations, the polypropiolactone may be fed to the reactor in molten form, for example, via a spay nozzle. The molten form may help facilitate the dispersion of polypropiolactone inside the reactor.

The reactor may be equipped with a cyclone that returns HTM solid back to the reactor. The inert gas, glacial acrylic acid, and higher boiling impurities (such as succinic anhydride and acrylic acid dimer) are fed from the cyclone to a partial condenser where impurities are separated. For example, the condenser may be used to condense the high boiling impurities, and such impurities can then be purged from the reactor as a residual waste stream.

Glacial acrylic acid with the inert gas may be fed to a second condenser where the glacial acrylic acid and the inert gas are separated. A liquid glacial acrylic acid stream is output from the second condenser, and the inert gas is output as a separate stream that may be returned back to the reactor to fluidize the heat transfer solid. The glacial acrylic acid stream may be used for condensation/absorption and then storage.

The residual waste stream purged from the reactor may include, for example, high boiling organics (or organic heavies), for example, resulting from the polymerization catalyst and succinic anhydride, as well as the cationic and anionic carbonylation catalyst species if carbonylation catalyst was not separated prior to the thermolysis reactor. In some embodiments, the high boiling organics (or organic heavies) may include any compounds which are not acrylic acid. In certain embodiments, the high boiling organics (or organic heavies) may include any compounds which remain in the bottoms stream after condensing the acrylic acid in the glacial acrylic acid production system/production process. In some embodiments, the high boiling organics (or organic heavies) may include succinic anhydride, polymerization catalyst, or carbonylation catalyst or components thereof (for example, organic compounds from the carbonylation catalyst). In some embodiments, the high boiling organics (or organic heavies) have a boiling point higher than acrylic acid.

In other embodiments, the thermolysis reactor is a moving bed reactor. Polypropiolactone is fed into a moving bed reactor as a solid and glacial acrylic acid exits the reactor as a vapor stream and is then condensed.

Conditions

In some variations, the operating temperature in the thermolysis reactor is from about 150° C. to about 300° C., from about 150° C. to about 200° C., from about 150° C. to about 250° C., from about 175° C. to about 300° C., from about 200° C. to about 250° C., from about 225° C. to about 275° C., from about 250° C. to about 300° C., from about 200° C. to about 300° C., from about 200° C. to about 400° C., or from about 200° C. to about 500° C. In some variations, operating temperature is the average temperature of the contents of the reactor.

In some variations, the operating pressure in the thermolysis reactor is from about 0.01 atmospheres to about 500 atmospheres (absolute), from about 0.01 atmospheres to about 10 atmospheres (absolute), from about 0.01 atmospheres to about 50 atmospheres (absolute), from about 1 atmosphere to about 10 atmospheres (absolute), from about 1 atmosphere to about 50 atmospheres (absolute), from about 1 atmosphere to about 100 atmospheres (absolute), from about 10 atmospheres to about 50 atmospheres (absolute), from about 10 atmospheres to about 100 atmospheres (absolute), from about 50 atmospheres to about 100 atmospheres (absolute), from about 50 atmospheres to about 200 atmospheres (absolute), from about 100 atmospheres to about 200 atmospheres (absolute), from about 100 atmospheres to about 250 atmospheres (absolute), from about 200 atmospheres to about 300 atmospheres (absolute), from about 200 atmospheres to about 500 atmospheres (absolute), or from about 250 atmospheres to about 500 atmospheres (absolute).

In a particularly preferred embodiment the PPL stream from a bPL polymerization system enters primary thermolysis reactor, either in solid or liquid phase at a temperature between 100° C. and 320° C., and absolute pressure between 1 mmHg and 5000 mmHg. One of many methods may provide heat transfer input, for example internal coils, external heat exchanger with a pump-around loop from and back to the primary reactor, or a baffled jacket on the walls of the reactor. Alternatively, a high temperature liquid or gas that that does not significantly affect the reaction chemistry may be introduced to maintain desired reaction temperature and separated downstream. Depending upon time and temperature residence time for complete conversion may vary from a few seconds to 24 hours or more. Mixing of the contents of the reactor may also improve mass and heat transfer.

Preferably the thermolysis conditions and arrangement will minimize the loss of PPL. to polyacrylic acid. Representative ways of avoiding polyacrylic acid production include the use of a depolymerization catalyst to decrease required reaction severity to decrease the reaction rate of acrylic acid to polyacrylic acid relative to PPL to acrylic acid; the use of high concentrations of radical polymerization inhibitor; and/or means to minimize the concentration of acrylic acid in the liquid phase.

A continuous PPL thermolysis design (continuous, equal mass flows in and out of the primary reactor) can minimize the concentration of acrylic acid in the liquid phase, which lowers the reaction rate of acrylic acid to polyacrylic acid relative to that of PPL to acrylic acid. Removing vapors from the headspace of the primary reactor will lower the acrylic acid partial pressure in the headspace of the reactor and its liquid contents. Sparging with an inert gas, preferably continuously will further reduce the concentration of acrylic acid in the reactor's liquid contents. Withdrawal of liquid effluent stream and any other nonvolatile components may also be desired to manage accumulation of polyacrylic acid. These may be directed to a second thermolysis reactor, to waste treatment, or to a reactive distillation to convert the considerable PPL in the stream to volatile species such as acrylic acid and short-chain PPL oligomers. The vapor effluent from this distillation operation can flow back to the primary reactor, or be mixed with the vapor effluent from the primary reactor.

The vapor effluent from the various forms and number of suitable thermolysis reactor preferably, before going to product storage, undergoes condensation; passes in vapor phase to a distillation operation to remove higher-boiling and/or lower-boiling impurities before condensation; goes to condensation, then to a distillation in liquid phase to remove higher-boiling and/or lower-boiling impurities and then condensation. In another embodiment the vapor effluent is condensed internally and isolated from the products that are non-volatile before undergoing further purification via distillation before storage or goes directly to product storage. Limiting the temperature of any liquid-phase acrylic acid is known to limit yields to polyacrylic acid. Preferably radical polymerization inhibitor shall be use in all liquid phase acrylic acid. The bottoms from a distillation operation shall optimally be returned to the primary thermolysis reactor for further thermolysis, but may be disposed of as well.

In some variations, the thermolysis process is operated under an oxygen and water free atmosphere. For example, in certain variations, the amount of oxygen present in the thermolysis reactor is less than 1 wt %, less than 0.5 wt %, less than 0.01 wt %, or less than 0.001 wt %. In certain variations, the amount of water present in the thermolysis reactor is less than 1 wt %, less than 0.5 wt %, less than 0.01 wt %, or less than 0.001 wt %.

Glacial Acrylic Acid

In some variations, glacial acrylic acid produced according to the systems and methods described herein has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

In other variations, acrylic acid produced according to the systems and methods described herein is suitable to make high molecular weight polyacrylic acid. In certain variations, acrylic acid produced according to the systems and methods described herein may have a lower purity, such as 95%. Thus, in one variation, the acrylic acid has a purity of at least 95%.

In yet other variations, the glacial acrylic acid has:
 (i) a cobalt level of less than 10 ppm, less than 100 ppm, less than 500 ppm, less than 1 ppb, less than 10 ppb, or less than 100 ppb; or
 (ii) an aluminum level of less than 10 ppm, less than 100 ppm, less than 500 ppm, less than 1 ppb, less than 10 ppb, or less than 100 ppb; or
 (iii) a β-propiolactone level of less than 1 ppm, less than 10 ppm, less than 100 ppm, less than 500 ppm, less than 1 ppb, or less than 10 ppb;
 (iv) an acrylic acid dimer level of less than 2000 ppm, less than 2500 ppm, or less than 5000 ppm; or
 (v) a water content of less than 10 ppm, less than 20 ppm, less than 50 ppm, or less than 100 ppm,
 or any combination of (i) to (v).

Unlike known methods to produce glacial acrylic acid, acetic acid, furfurals and other furans are not produced and thus, are not present in the glacial acrylic acid produced.

Glacial acrylic acid may be used to make polyacrylic acid for superabsorbent polymers (SAPs) in disposable diapers, training pants, adult incontinence undergarments and sanitary napkins. The low levels of impurities present in the glacial acrylic acid produced according to the systems and methods herein help to facilitate a high-degree of polymerization to acrylic acid polymers (PAA) and avoid adverse effects from by-products in end applications. For example, aldehyde impurities in acrylic acid hinder polymerization and may discolor the polymerized acrylic acid. Maleic anhydride impurities form undesirable copolymers which may be detrimental to polymer properties. Carboxylic acids, e.g., saturated carboxylic acids that do not participate in the polymerization, can affect the final odor of PAA or SAP-containing products and/or detract from their use. For example, foul odors may emanate from SAP that contains acetic acid or propionic acid and skin irritation may result from SAP that contains formic acid. The reduction or removal of impurities from petroleum-based acrylic acid is costly, whether to produce petroleum-based crude acrylic acid or petroleum-based glacial acrylic acid. Such costly multistage distillations and/or extraction and/or crystallizations steps are generally employed (e.g., as described in U.S. Pat. Nos. 5,705,688 and 6,541,665).

GAA Production System/Production Process

In some embodiments, the production system/production process can produce at least about 25 kilo tons per annum ("KTA") glacial acrylic acid ("GAA"), at least about 160 KTA GAA, at least about 250 KTA GAA, or at least about 400 KTA GAA for annual production operation of about 8000 hours. In some embodiments, the production system/production process can produce at least about 2000 kg/hr GAA, at least about 2500 kg/hr GAA, at least about 3000 kg/hr GAA, at least about 3025 kg/hr GAA, at least about 3500 kg/hr GAA, at least about 3638 kg/hr GAA, at least about 4000 kg/hr GAA, at least about 5000 kg/hr GAA, at least about 1000 kg/hr GAA, at least about 20000 kg/hr GAA, or at least about 35000 kg/hr GAA. In some embodiments, the production system/production process can produce about 2000 kg/hr GAA, about 2500 kg/hr PPL, about 3000 kg/hr GAA, about 3500 kg/hr GAA, about 3638 kg/hr GAA, about 4000 kg/hr GAA, about 5000 kg/hr GAA, about 1000 kg/hr GAA, about 20000 kg/hr GAA, or about 35000 kg/hr GAA. In some embodiments, the production system/production process can produce between 2000 kg/hr GAA and 3500 kg/hr GAA, between 2500 kg/hr GAA and 3500 kg/hr GAA, between bout 3000 kg/hr GAA and 3500 kg/hr GAA, between 2000 kg/hr GAA and 35000 kg/hr GAA, between 2500 kg/hr GAA and 35000 kg/hr GAA, between 3000 kg/hr GAA and 35000 kg/hr GAA, between 3500 kg/hr GAA and 35000 kg/hr GAA, between 3638 kg/hr GAA and 35000 kg/hr GAA, between 4000 kg/hr GAA and 35000 kg/hr GAA, between 5000 kg/hr GAA and 35000 kg/hr GAA, between 1000 kg/hr GAA and 35000 kg/hr GAA, or between 20000 kg/hr GAA and 35000 kg/hr GAA. In some embodiments, the production system/production process can produce at least about 25 kmol/hr GAA, at least about 30 kmol/hr GAA, at least about 35 kmol/hr GAA, at least about 40 kmol/hr GAA, at least about 42 kmol/hr, or at least about 50 kmol/hr GAA. The remainder of the GAA product stream can include secondary reaction products such as succinic anhydride and left over solvent such as THF. In some embodiments, the GAA product stream of the production system/production process can have a temperature between about 20-60° C., between about 30-50° C., or about 40° C. In some embodiments, the GAA product stream of the production system/production process can be at a pressure of at least about 0.5 bar, about 0.5-1.5 bar, or at least about 1 bar.

POLYMERIZATION EXAMPLES

Example 1

Batch bPL Polymerization Using Sodium Acrylate as Initiator

Figure 17:
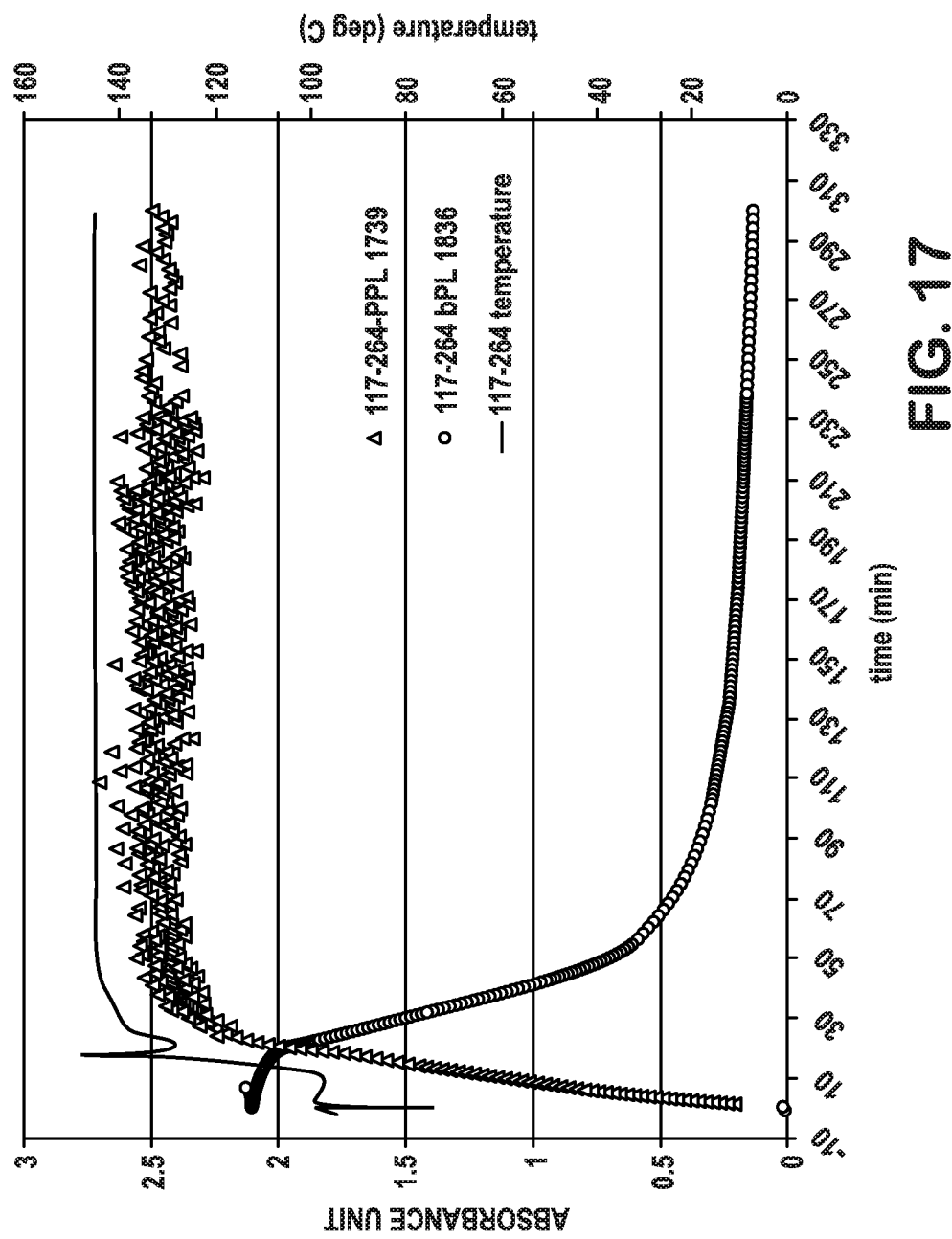
FIGS. 17-20 are plots associated with Example 1 and show a plot of PPL and bPL peak absorbances as a function of time; an $^1$H NMR of the isolated solid; a TGA of the isolated solid; and Melt rheology data of the isolated solid at 120° C.
Figure 18:
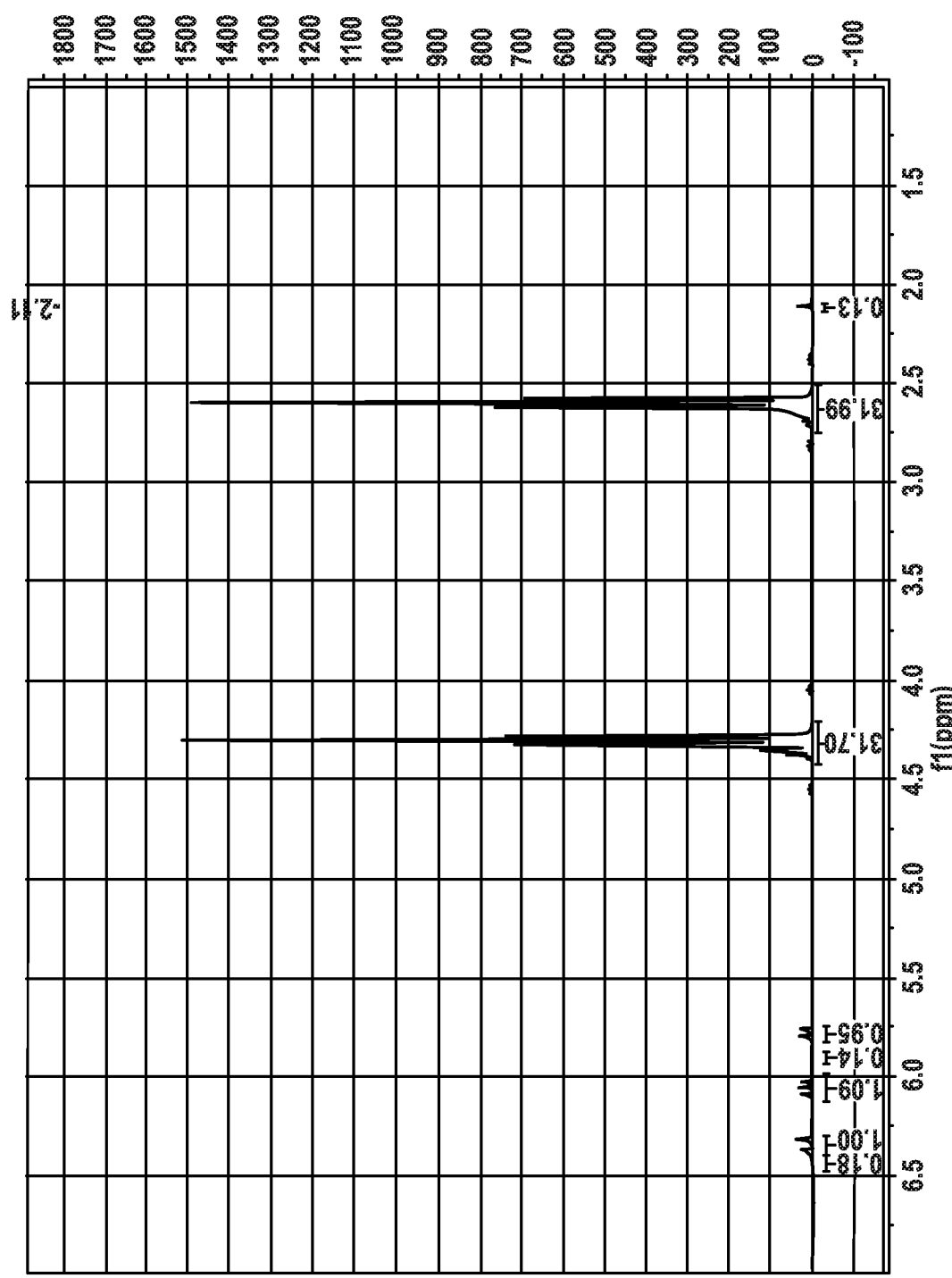
Figure 19:
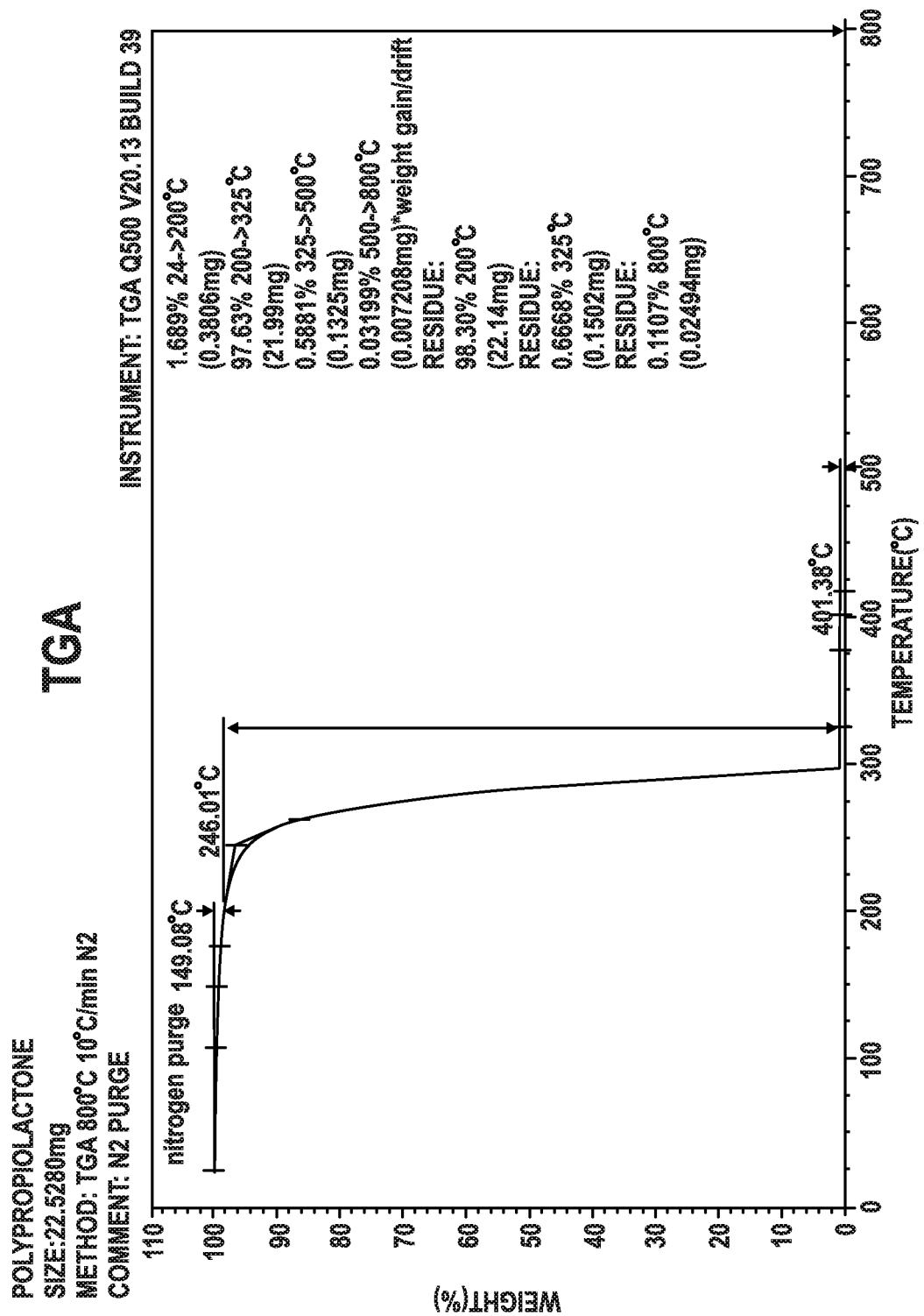
Figure 20:
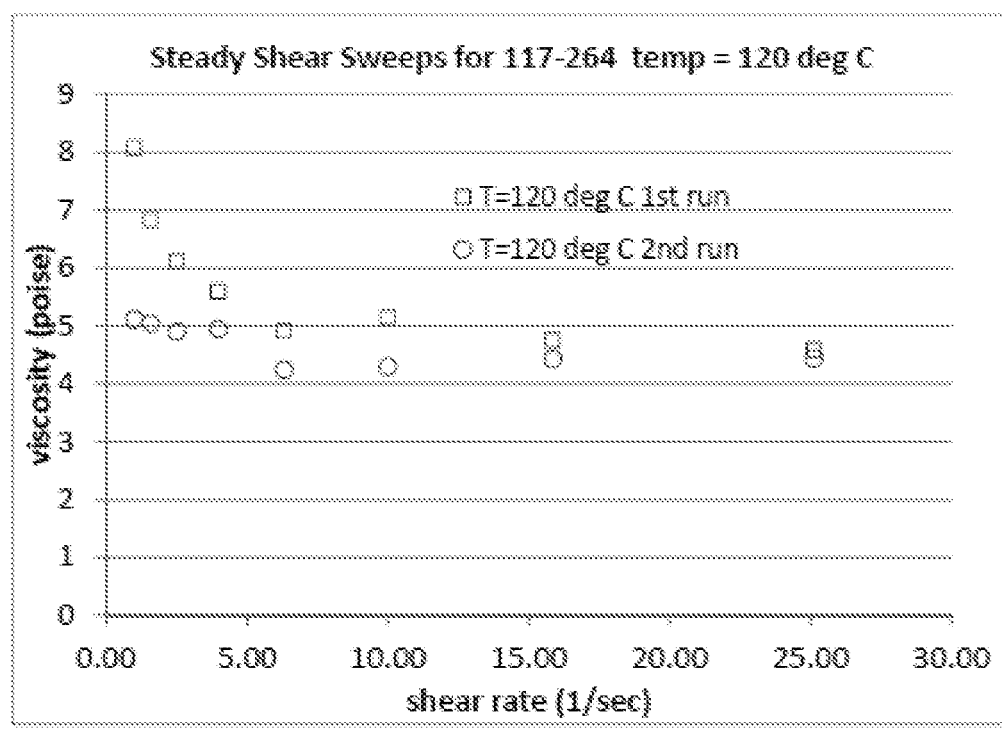

Under nitrogen, a Parr reactor equipped with an ATR-IR sentinel was charged with 16.2 mg of sodium acrylate. The reactor was sealed and heated to 100° C. In a 50 mL stainless vessel, a mixture of 11.8 mg of phenothiazine and 25 g of beta-propiolactone was added under nitrogen. The vessel was sealed and connected to the reactor. The mixture of beta-propiolactone and phenothiazine was injected into the reactor containing sodium acrylate with 50 psi of CO pressure at 100° C. The reaction was agitated to 500 rpm, and monitored by in-line IR. The plot of beta-propionate peak at 1836 cm-1 and poly(propiolactone) peak at 1739 cm-1 as a function of time is shown in FIG. 17. After the temperature was stabilized, the reaction temperature was set to 145° C. And the reaction was run for 5 hours, by which time, the reaction went to completion.

The polymer formed in the reactor was extracted with CHCl3. Volatiles were stripped off by a rotovap. The polymer was further dried under a high vacuum to yield 21.8 g of a white solid. The solid was analyzed by 1H NMR, TGA, SEC, and melt rheology. SEC of the isolated solid gave am Mn of 3710 and an Mw of 8740.

Example 2

Batch bPL Polymerization Using Tetra(Butylammonium) Acrylate as Initiator

Figure 21:
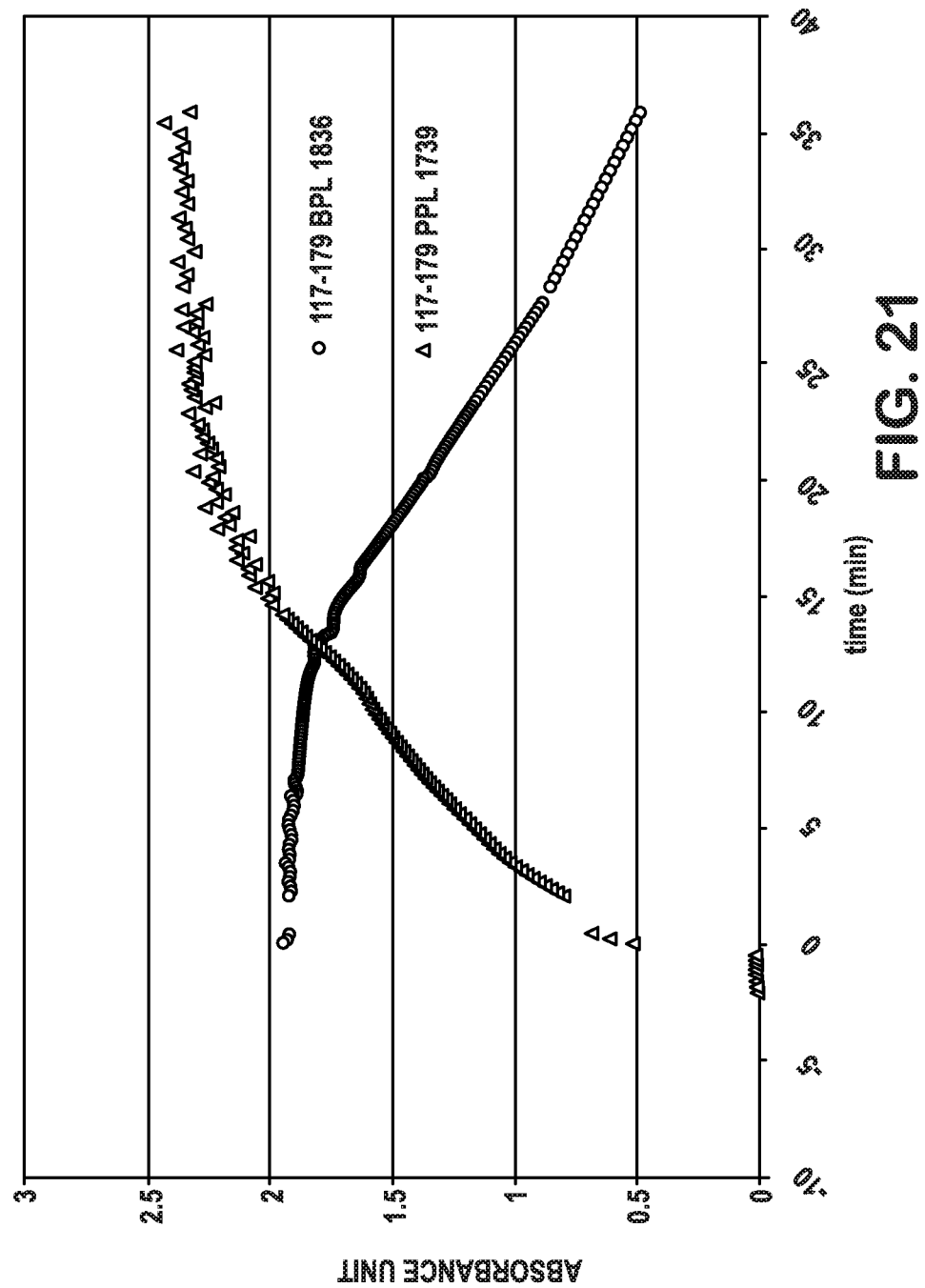
FIGS. 21-24 are plots associated with Example 2 and show a plot of PPL and bPL peak absorbances as a function of time; an $^1$H NMR of the isolated solid; a TGA of the isolated solid; and Melt rheology data of the isolated solid at 120° C.
Figure 22:
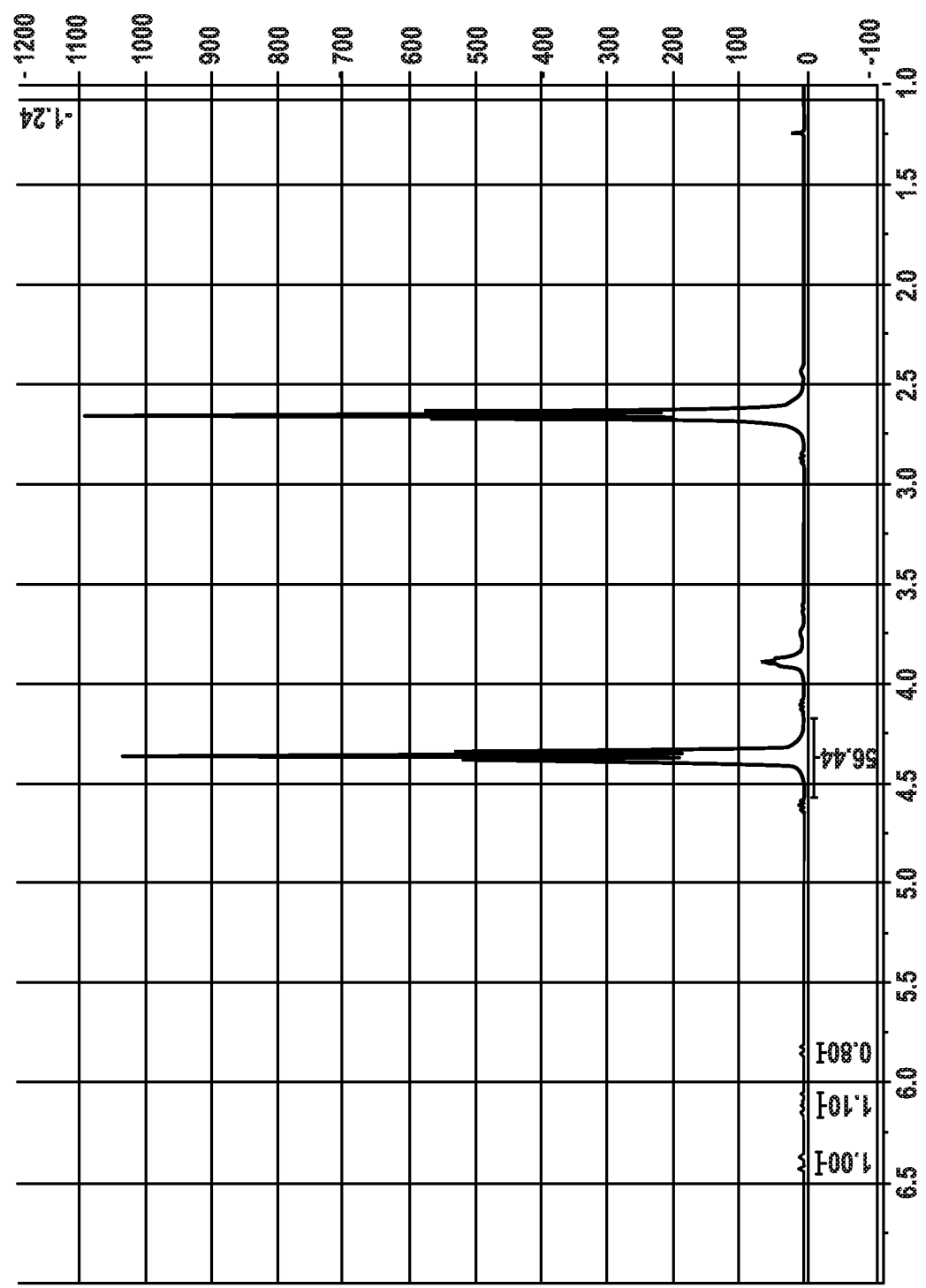
Figure 23:
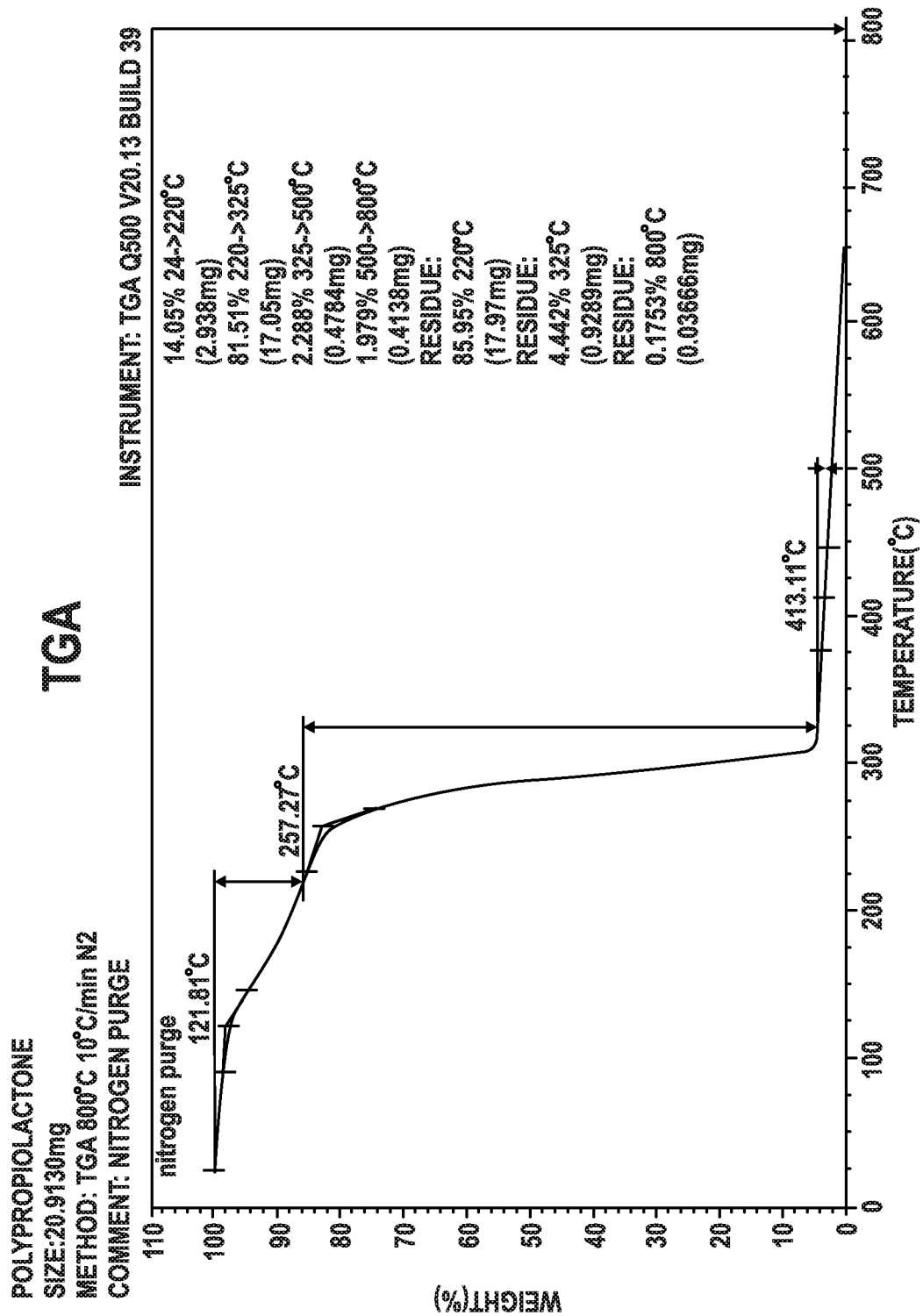
Figure 24:
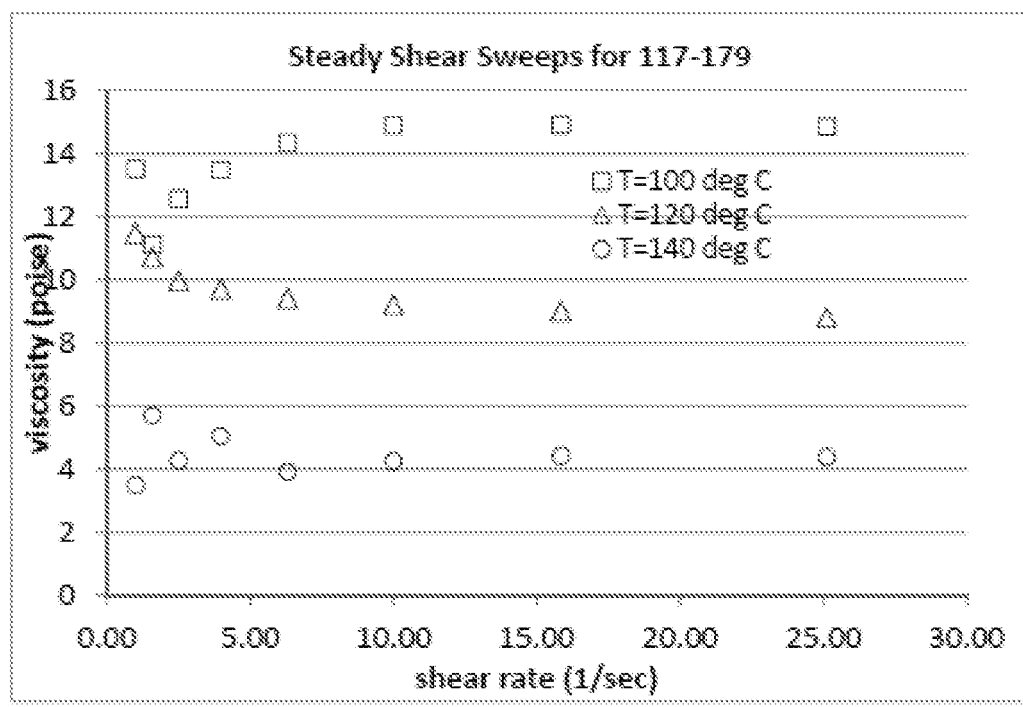
Figure 25:
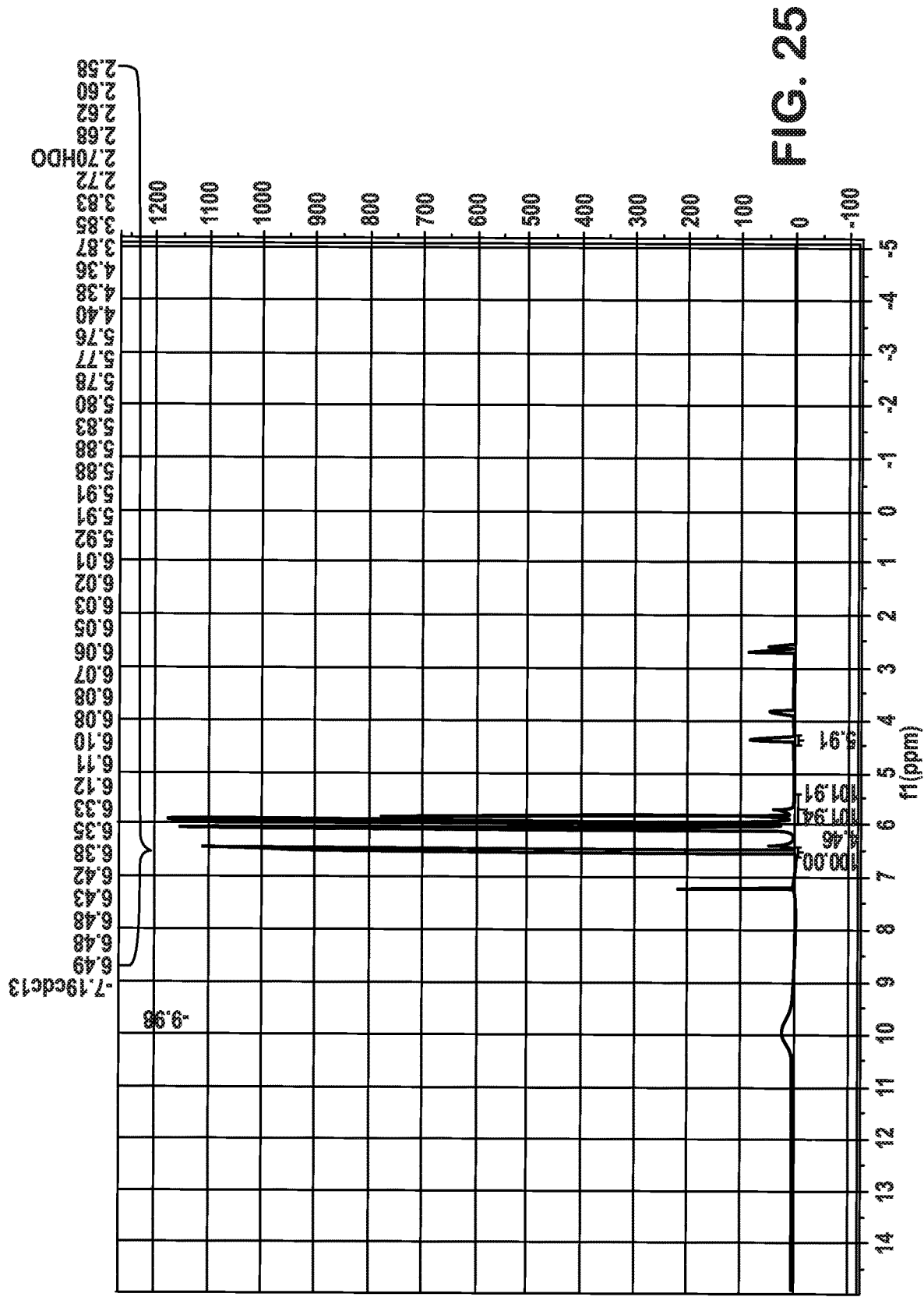
FIGS. 25-28 are plots associated with Example 4 and show $^1$H NMR plots indicating recovery of acrylic acid.
Figure 26:
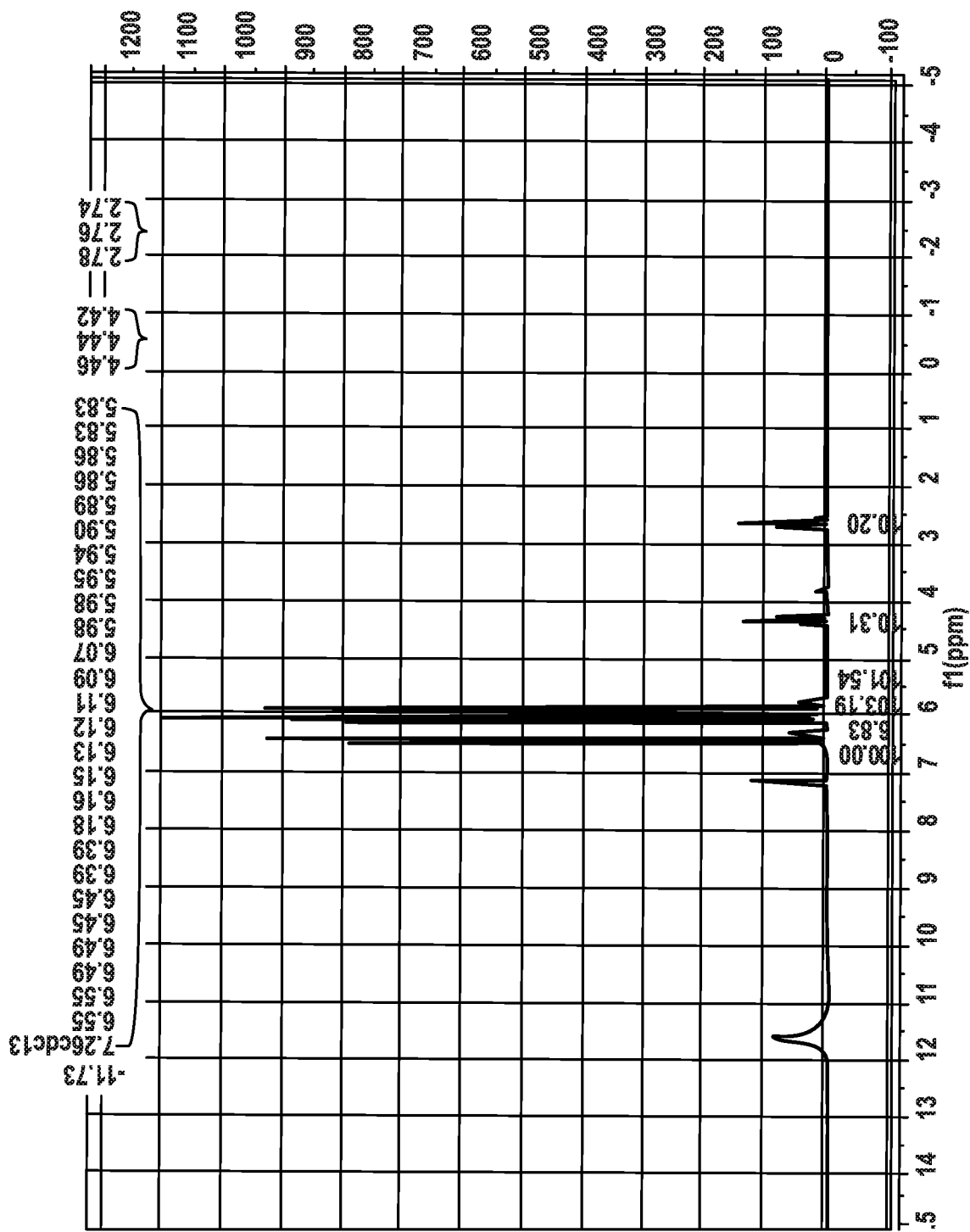
Figure 27:
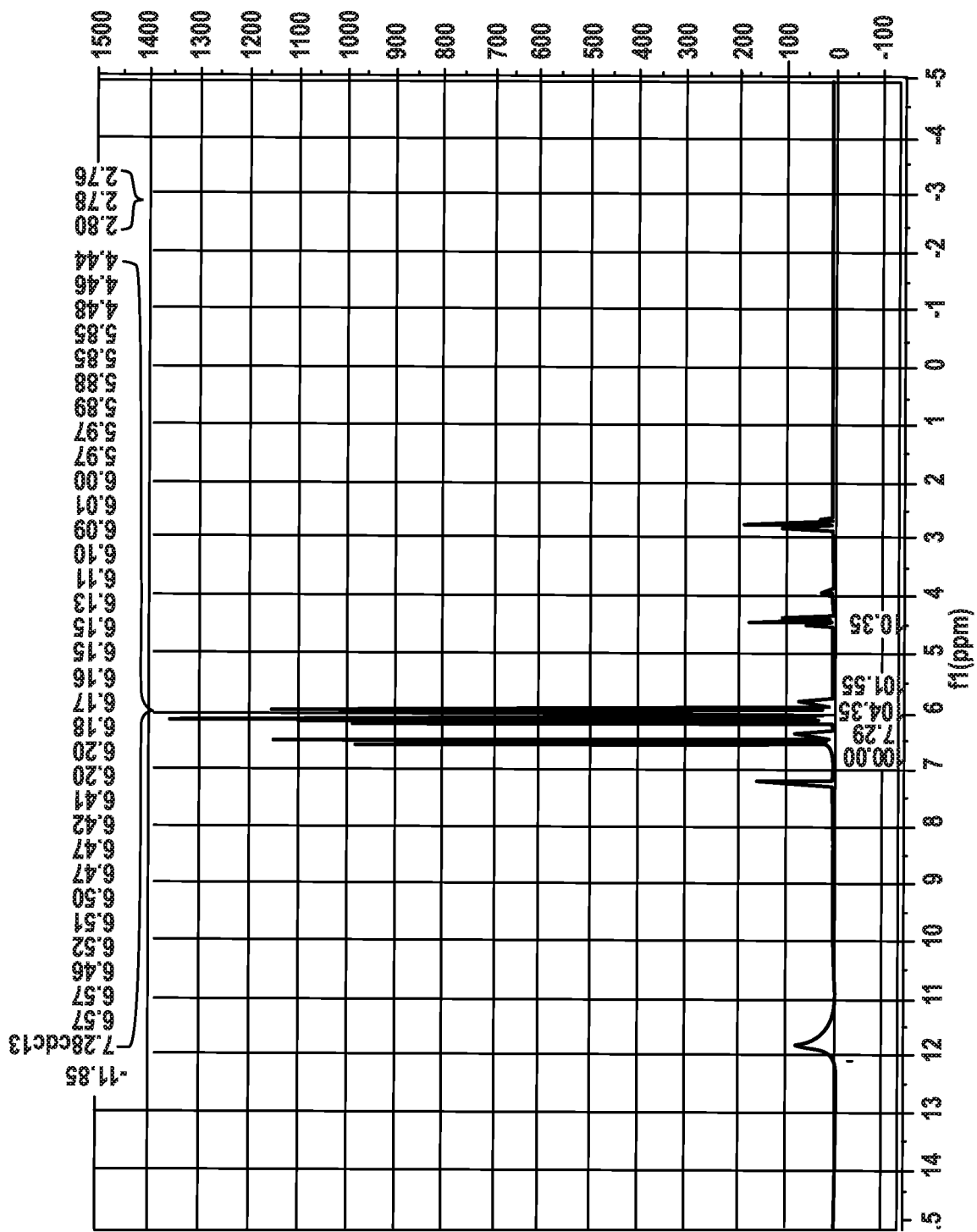
Figure 28:
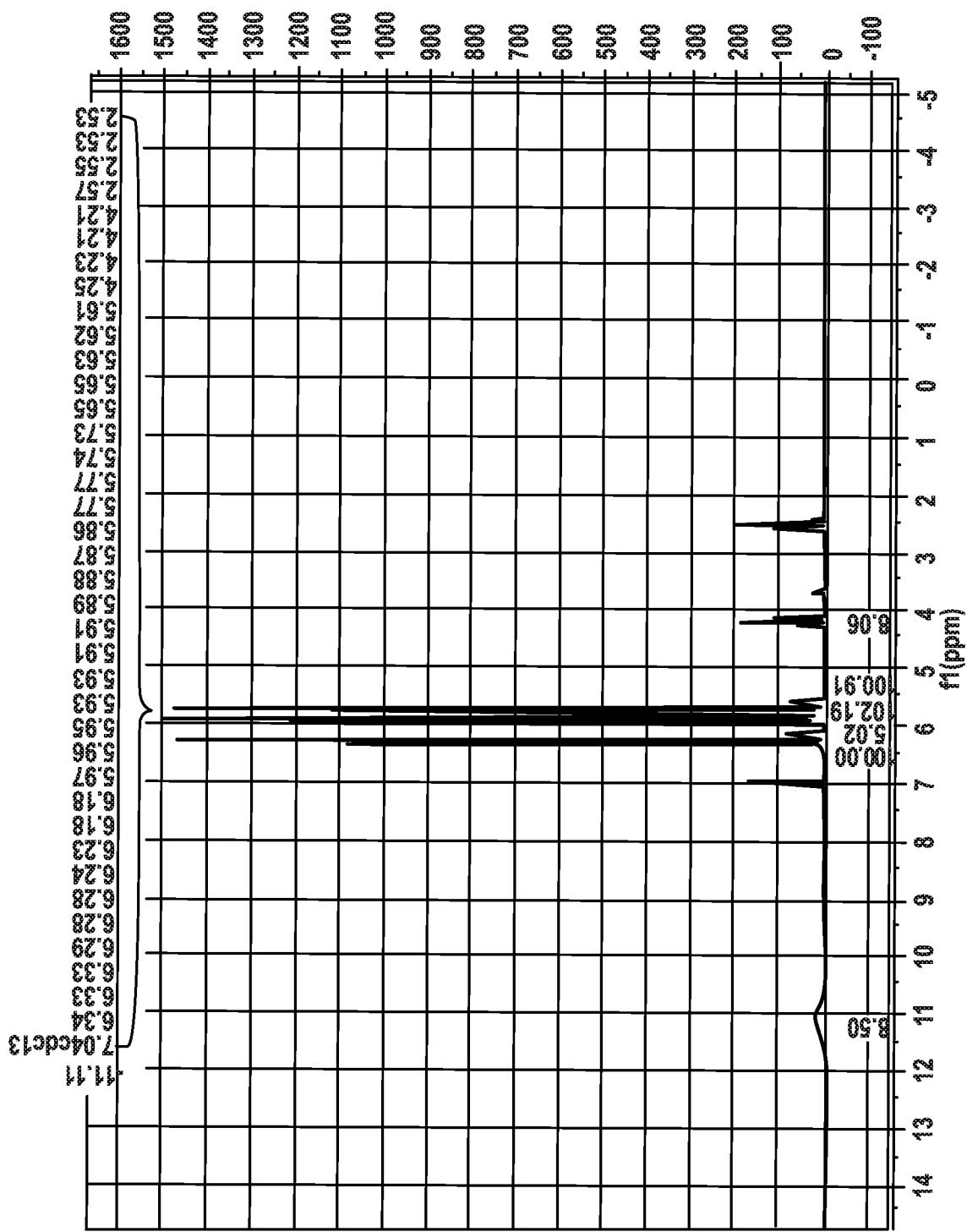

Under nitrogen, a Parr reactor equipped with an ATR-IR sentinel was charged with 12.2 mg of tetrabutylammonium acrylate. The reactor was sealed and heated to 100° C. In a 50 mL stainless vessel, 25 g of beta-propiolactone was added under nitrogen. The vessel was sealed and connected to the reactor. Into the reactor containing tetrabutylammonium acrylate, beta-propiolactone was injected with 50 psi of CO pressure at 100° C. The reaction was agitated to 500 rpm, and monitored by in-line IR. The plot of beta-propionate peak at 1836 cm$^{-1}$ and poly(propiolactone) peak at 1739 cm$^{-1}$ as a function of time is shown in FIG. 21. After the temperature was stabilized, the reaction temperature was set to 140° C. At 36 min after the bPL addition, the reaction reached around 89% conversion, and 25 mL of water was added with 100 psi of CO at 140° C. After hydrolyzing the remaining beta-propiolactone, the polymer was extracted with $CH_2Cl_2$. Volatiles were removed using a rotovap and high vacuum to yield 17.7 g of a white solid. The solid was analyzed by $^1$H NMR, TGA and melt rheology.

Example 2

Polymerization Production Using Plug-Flow Reactor Arrangement

A plug-flow reactor, consisting of two jacketed static mixers of ½" OD×24¾" length and ~60 mL volume, an 3-way nitrogen/feed inlet ball-valve and an outlet with a jacketed viscometer (Cambridge Viscosity ViscoPro 2000 with 372 sensor), type K thermocouple, ATIR IR probe (Mettler-Toledo DS AgX Comp™ and ReactIR™ 15) and a 0-250 psig back-pressure regulator, was heated to 140° C. and purged with nitrogen at ambient pressure. A feed mixture was prepared by combining 0.1670 g of sodium acrylate (milled, sieved to 100 mesh and dried at 130° C. under vacuum, 0.001776 mol), 0.1536 g phenothiazine and 670 mL of □-propiolactone (~760 g, 10.6 mol, chilled to −20° C.) in a one liter, pressure/vacuum rated GL45 bottle equipped with a magnetic stir-bar in a glove-box. The bottle was closed with a three port GL45 cap equipped with a dip-tube and 2-way, ⅛" ball-valve on one port, a ⅛" 2-way-ball valve with a 1 psi cracking-pressure check-valve on the second port and a ⅛" 3-way-ball-valve with one Luer-Lock fitting on the third port. The mixture was stirred briefly to dissolve the phenothiazine and suspend the sodium acrylate. The sealed bottle was removed from the glove-box, transported to the plug-flow reactor, immersed in a water/ice bath on top of a magnetic stirrer and connected via the three ⅛" compression fittings to a feed pump, a vent line (to a scrubber filled with 2% sulfuric acid) and a nitrogen needle-valve, respectively. The mixture was stirred at 400 rpm to keep the sodium acrylate suspended. The 2-way vent-valve was opened followed by switching the 3-way nitrogen/fill valve from closed to nitrogen and adjusting the nitrogen needle-valve to give a steady stream of bubbles in the scrubber. The feed valve was then opened followed by a prime valve on the feed pump (Eldex Optos 2SM, 0.01-10.00 mL/min) and the pump was turned on at a flow rate of 5.00 mL/min and allowed to run until the (Teflon FEP) line from the prime port to the scrubber showed that all bubbles had been ejected. The pump was then turned off, flow set to 0.50 mL/min, prime/feed 3-way ball-valve switched to feed, the reactor inlet 3-way ball-valve switched from nitrogen to feed and the pump turned back on.

After 4 hours, the reactor exit back-pressure regulator was adjusted from ambient pressure to 200 psig and both the viscometer and the ReactIR were turned on. After another hour and a half, the reactor was fully pressurized, the viscometer (70 cP, compensated to 120° C.) and ReactIR (~95% conversion) readings were steady and product was collected into a one liter collection bottle which contained 300 mL of magnetically stirred water. After a further 22.5 hours, the feed mixture was nearly exhausted and a 20 mL portion of chloroform was added to the feed bottle via syringe and the Luer-Lock fitting on the nitrogen/fill 3-way ball-valve. When the feed bottle was nearly empty again, another 20 mL of chloroform was added. When that charge had been consumed, a further 500 mL of chloroform was added. A fresh receiving bottle was placed on the reactor exit and conditions maintained for another 21 hours when feed pump and circulating bath were turned off.

The crude product mixture from the first receiver bottle was transferred to a large blender with an additional 500 mL of water, blended until no particles >5 mm were observed and the solid collected by filtration, air-dried and then vacuum dried at 40° C. for 20 hours to give 562.1 grams of solid PPL product. The mixture of PPL solution in chloroform and aqueous liquid from the second receiver bottle was separated, the chloroform phase washed with water, dried and concentrated to 300 mL by azeotropic distillation and diluted in 600 mL of 2-propanol. The resulting precipitate was collected by filtration, air dried and then dried in vacuo at 40° C. for 2 hours to give 90.5 grams of colorless solid PPL product. The filtrate was stripped of volatiles on a rotary evaporator at 50° C. to give 45.0 g of clear, colorless oil, which separated into liquid and solid upon cooling.

1H NMR analysis suggested that solid from the first receiver was composed of 556 grams of PPL, with a molecular weight of ~1210 g/mol with small amount (6 grams) of 3-hydroxypropionic acid (3-HPA) resulted from the hydrolysis of bPL in water (the GPC results showed Mn=275, Mw=1530 and Mn/Mw=5.56). The isolated solid from the second receiver contained 90 grams of PPL with a molecular weight of 2030 g/mol (the GPC results showed Mn=328, Mw=1900, Mw/Mn=5.79.) and 0.5 grams of 3-HPA.

POLYMERIZATION EXAMPLES

Example 4

Batch Thermolysis of PPL to Acrylic Acid

A lab-scale batch thermolysis system consisting of a two-necked round-bottom glass flask of 25 mL approximate internal volume (the reaction flask) was carried out. The reaction flask was equipped with an internal thermocouple and the top center opening in the flask was equipped with a short-path distillation apparatus. The short-path distillation apparatus consisted of a short path still (similar to Ace Glass item #6554-06) with an additional thermocouple to monitor vapor temperature, followed by a water-cooled condenser, and finally a four-armed "cow" product receiver in a dry ice/acetone-cooled dewar. The reaction flask was set in a fabric heating mantle, the power to which was controlled by a temperature controller that receives feedback from the thermocouple inside the reaction flask. Additional heat was provided with electric heat tape, wrapped around the top of the reaction flask and the distillation apparatus. The top of the reaction flask and the bottom of the distillation apparatus were insulated. The fabric heating mantle was set above a magnetic stir plate, and a PTFE-coated stir bar was added to the reaction flask.

The tared reaction flask was charged with 90 mg dry sodium acrylate, 5 mg PTZ, and 4.995 g of PPL produced from ring-opening polymerization of solvent-free bPL in the presence of sodium acrylate (at a concentration of 1 mol per 6,000 mol of bPL) and phenothiazine (at a concentration of 200 ppmw in bPL). In addition, the tared product receiver was pre-charged with 5 mg PTZ (distributed among the four product arms). After system assembly, the product receiver was attached to a nitrogen and vacuum source, and the air was displaced with nitrogen. Next, the reactor contents were heated to 90 degC to melt and begin stirring. The system was brought under vacuum to an absolute pressure of approximately 700 torr, and the reactor temperature setpoint was set to 210 degC. Internal reflux was observed inside the reaction flask within minutes. It took 8-10 minutes to heat reactor contents up to 210 degC. The moment the reactor contents reached 210 degC is defined as t=0. The reactor contents were held at 210 degC for 10 minutes, at which point the reactor flask was mostly empty, save for a glassy darker solid and the stir bar.

It was later determined that the residual material in the reaction flask weighed 156 mg. Four product samples were obtained—sample 129-098A contained material collected until t=2 minutes, 129-098B contained material collected between t=2 minutes and t=8 minutes, 129-098C contained material between t=8 minutes and t=9 minutes, and 129-098D contained collected material between t=9 minutes and t=10 minutes, when heat sources were shut off. The total product collected weighed 4.7816 g. Next, each sample was pipetted from the cow to labeled vials, and samples were taken for 1H NMR (see FIGS. 25-28). NMR analysis suggests an average acrylic acid content in 129-098A of 94.4%, in 129-098B of 90.7%, in 129-098C of 90.6%, and in 129-098D of 92.5% by mass. The balance consists of di-acrylic acid ester and traces of other PPL oligomers where n>2.

POLYMERIZATION EXAMPLES

Example 4

Batch Thermolysis of PPL to Acrylic Acid

A lab-scale batch thermolysis system consisting of a two-necked round-bottom glass flask of 50 mL approximate internal volume (the reaction flask). The reaction flask was equipped with an internal thermocouple and the top center opening in the flask is equipped with a distillation apparatus. The distillation apparatus consisted of two Vigreux columns in series oriented coaxially (each similar to Ace Glass item #6578-04), followed by an adapter with an additional thermocouple to monitor vapor temperature, followed by a water-cooled condenser, and finally a 50 mL round-bottom product receiver in a dry ice/acetone-cooled dewar. The reaction flask was set in a fabric heating mantle, the power to which is controlled by a temperature controller that receives feedback from the thermocouple inside the reaction flask. Additional heat was provided with electric heat tape, wrapped around the top of the reaction flask and the distillation apparatus. The top of the reaction flask and the bottom of the distillation apparatus are insulated. The fabric heating mantle was set above a magnetic stir plate, and a PTFE-coated stir bar is added to the reaction flask.

The tared reaction flask was charged with 1000 mg dry sodium acrylate, 20 mg PTZ, and 19.162 g of PPL produced from ring-opening polymerization of solvent-free bPL in the presence of sodium acrylate (at a concentration of 1 mol per 6,000 mol of bPL) and phenothiazine (at a concentration of 200 ppmw in bPL). In addition, the tared product receiver was pre-charged with 5 mg PTZ. After system assembly, the product receiver was attached to a nitrogen and vacuum source, and the air was displaced with nitrogen. Next, the reactor contents were heated to 90 degC to melt and begin stirring. The system was brought under vacuum to an absolute pressure of approximately 90 torr, and the reactor temperature setpoint was set to 165 degC. Internal reflux was observed inside the reaction flask within minutes. It took approximately 10 minutes to heat reactor contents up to 165 degC. The moment the reactor contents reached 165 degC is defined as t=0. The reactor contents were held at 165 degC for 40 minutes, at which point the reactor flask was still easily mixed by the stir bar.

Figure 29:
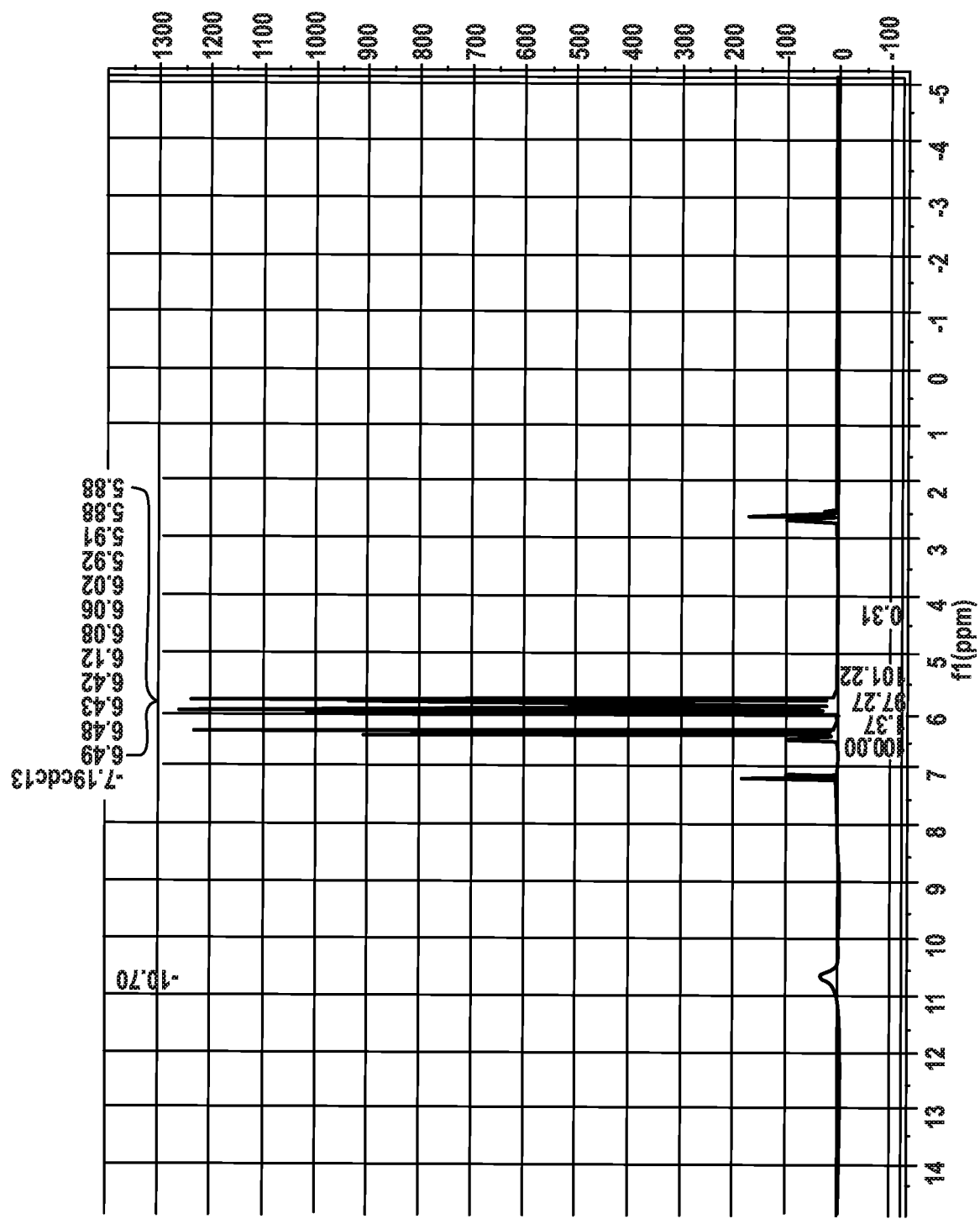
FIG. 29 are plots associated with Example 5 and shows an $^1$H NMR plot indicating recovery of acrylic acid.

It was later determined the residual material in the reaction flask weighed 4.7186 g. Product sample 129-108 consisted of all collected product, and weighed 14.6586 g. Next, a sample was taken for 1H NMR (see FIG. 29). NMR analysis suggests an average acrylic acid content in 129-108_Dist of 99.7%. The balance consists of di-acrylic acid ester and traces of other PPL oligomers where n>2.

This application discloses several numerical ranges in the text and figures. The numerical ranges disclosed inherently support any range or value within the disclosed numerical ranges even though a precise range limitation is not stated verbatim in the specification because this invention can be practiced throughout the disclosed numerical ranges.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, systems and methods described herein are not intended to be limited to the embodiments shown, but are to be accorded the widest scope consistent with the principles and features disclosed herein. Finally, the entire disclosure of the patents and publications referred in this application are hereby incorporated herein by reference.

What is claimed is:

1. A process for producing acrylic acid from a source of β-propiolactone, the process comprising:
    contacting a β-propiolactone feed stream with a polymerization initiator in a polypropiolactone reaction zone having at least one polymerization reactor to produce a polypropiolactone outlet stream comprising polypropiolactone and β-propiolactone, wherein the at least one polymerization reactor is at least one of a continuous reactor or a semi-batch reactor; and
    passing at least a portion of the polypropiolactone outlet stream to an acrylic acid production zone comprising a thermolysis reactor that receives the at least a portion of the polypropiolactone outlet stream to produce an acrylic acid stream comprising acrylic acid.

2. The process of claim 1, wherein the polymerization initiator is selected from the group consisting of quaternary ammonium salts, alkali metal salts of carboxylic acids and phosphonium salts.

3. The process of claim 1, wherein a radical polymerization inhibitor is present in the polypropiolactone reaction zone.

4. The process of claim 3, wherein the radical polymerization inhibitor comprises phenothiazine in a concentration of 50-500 ppm (by weight).

5. The process of claim 1, wherein the polypropiolactone reaction zone comprises a first polymerization reactor and a second polymerization reactor;
    wherein the process further comprises:
    producing a first mixture in the first polymerization reactor, wherein the first mixture comprises a first amount of the polypropiolactone, a first amount of unreacted β-propiolactone and a first amount of residual polymerization initiator; and
    passing the first mixture and an additional amount of the polymerization initiator to the second polymerization reactor to produce at least a portion of the polypropiolactone outlet stream, wherein the at least a portion of the polypropiolactone outlet stream comprises a second amount of the polypropiolactone, a second amount of unreacted β-propiolactone, and a second amount of residual polymerization initiator.

6. The process of claim 5, further comprising separating the second amount of unreacted β-propiolactone from the at least a portion of the polypropiolactone outlet stream in at least one of a flash tank evaporator, a wiped-film evaporator or a distillation apparatus.

7. The process of claim 1, wherein the polypropiolactone outlet stream comprises solid polypropiolactone.

8. The process of claim 1, wherein the acrylic acid production zone comprises at least one of: a thermolysis reactor in a form of a continuous stirred-tank reactor,
    a plug flow reactor, a wiped film evaporator, a moving bed reactor; a kneader reactor; or
    a fluidized bed reactor for receiving molten polypropiolactone.

9. The process of claim 1, further comprising separating at least a portion of the acrylic acid stream into (i) an acrylic acid stream comprising acrylic acid having a purity of at least 90%, and (ii) an organic heavies stream.

10. A process for producing acrylic acid from ethylene oxide and carbon monoxide, comprising:
    contacting input components comprising a carbon monoxide feed, an ethylene oxide feed, and a catalyst recycle stream with a carbonylation catalyst and a solvent in a carbonylation reaction zone and producing a β-propiolactone outlet stream comprising β-propiolactone, ethylene oxide and carbonylation catalyst;
    passing at least a portion of the β-propiolactone outlet stream to a carbonylation catalyst recycling zone and separating said portion into i) a β-propiolactone separation stream comprising a portion of the β-propiolactone outlet stream from which at least some carbonylation catalyst has been removed and ii) the recycle stream, comprising β-propiolactone, solvent, ethylene oxide, carbonylation catalyst, succinic anhydride, and acetaldehyde;
    passing at least a portion of the recycle stream to the carbonylation reaction zone;
    purifying at least a portion of the β-propiolactone separation stream in a β-propiolactone purification zone comprising at least one separator, wherein the β-propiolactone purification zone produces a purified β-propiolactone stream and rejects a portion of at least one of β-propiolactone, solvent, ethylene oxide, carbonylation catalyst, succinic anhydride, and acetaldehyde in one or more rejection streams;
    passing at least a portion of the purified β-propiolactone stream and a polymerization initiator to a polypropiolactone reaction zone having at least one polymerization reactor that produces a polypropiolactone outlet stream comprising polypropiolactone and β-propiolactone; and
    passing at least a portion of the polypropiolactone outlet stream to an acrylic acid production zone comprising a thermolysis reactor that receives the at least a portion of the polypropiolactone outlet stream and produces an acrylic acid stream comprising acrylic acid.

11. The process of claim 10, wherein the β-propiolactone purification zone produces an ethylene oxide rejection stream as one of the rejection streams,
wherein the ethylene oxide rejection stream comprises ethylene oxide, and at least a portion of the ethylene oxide rejection stream is passed to the carbonylation reaction zone.

12. The process of claim 11, wherein the β-propiolactone purification zone produces a solvent recovery stream as one of the rejection streams, wherein the solvent recovery stream comprises solvent, and wherein at least a portion of the solvent recovery stream is passed to the carbonylation reaction zone.

13. The process of claim 10, wherein:
I) the carbonylation catalyst recycling zone comprises one or more membrane systems from which the catalyst recycle stream is recovered as a retentate and β-propiolactone separation stream is recovered as a permeate; and
II) the β-propiolactone purification zone comprises
a.) an ethylene oxide recovery section comprising at least one distillation column that receives at least a portion of the β-propiolactone separation stream and produces an ethylene oxide stream containing ethylene oxide that is passed to the carbonylation reactor and a solvent bottoms stream containing solvent and β-propiolactone,
b.) a solvent recovery section comprising at least one distillation column that receives at least a portion of the solvent bottoms stream and produces an overhead recovered solvent stream comprising solvent that is passed to the carbonylation zone and a β-propiolactone bottoms stream comprising β-propiolactone, and
c.) a β-propiolactone concentration section comprising at least one distillation column that receives the β-propiolactone bottoms stream and produces a bottoms rejection stream and produces the purified β-propiolactone as an overhead stream.

14. The process of claim 10, wherein at least one of the carbon monoxide feed and the ethylene oxide feed have at least one of an oxygen level of less than 5 ppm and a water level of less than 5 ppm.

15. The process of claim 10, wherein the carbonylation catalyst is a cobalt-aluminum catalyst.

16. The process of claim 10, wherein the carbonylation catalyst is at least partially dissolved in a catalyst solvent, and the catalyst solvent comprises an ether, a hydrocarbon, sulfolane, N-methyl pyrrolidone, 1,3 dimethyl-2-imidazolidinone, ethylene carbonate, propylene carbonate, butylene carbonate, dibasic esters, acetonitrile, ethyl acetate, propyl acetate, butyl acetate, 2-butanone, cyclohexanone, difluorobenzene, acetone, or methylethyl ketone, or any combination thereof.

17. The process of claim 10, wherein the carbonylation reactor operates at a temperature from −20° C. to 160° C. and operates at a pressure from 100 psig to 5000 psig, and produces β-propiolactone with a selectivity of at least 90%.

18. The process of claim 10, wherein the carbonylation reaction zone contains at least one reactor selected from the group consisting of a continuous reactor or a semibatch reactor.

19. The process of claim 10, wherein the β-propiolactone outlet stream satisfies on a mass fraction basis the condition of having: at least 0.1 β-propiolactone; at most 0.9 solvent; at most 0.07 ethylene oxide; between 0.0005 to 0.04 of carbon monoxide; at most 0.005 catalyst; at most 0.07 acetaldehyde; or at most 0.07 succinic anhydride.

20. The process of claim 10, wherein the β-propiolactone outlet stream satisfies on a mass fraction basis the condition of having: at least 0.1 and at most 0.4 β-propiolactone; at most 0.9 solvent; at least 0.005 and at most 0.07 ethylene oxide; between 0.0005 to 0.001 of carbon monoxide; at least 0.0001 and at most 0.005 catalyst; at least 0.0001 and at most 0.06 acetaldehyde; or at least 0.0001 and at most 0.06 succinic anhydride.

21. The process of claim 10, wherein the carbonylation catalyst recycling zone comprises a membrane that is a ceramic membrane or a polymeric membrane, wherein the membrane has a carbonylation catalyst rejection rate greater than 95% or a permeability of greater than 1.0 L m−2 hr−1 bar−1.

22. The process of claim 10, wherein the purifying of the β-propiolactone separation stream in the β-propiolactone purification zone is performed using a vacuum column, and the purified β-propiolactone stream is recovered as a vacuum column overhead stream having a β-propiolactone purity of at least 99%.

23. A process for producing acrylic acid from ethylene oxide and carbon monoxide, comprising: contacting carbon monoxide feed, an ethylene oxide feed, a carbon monoxide overhead stream and a β-propiolactone recycle stream with a carbonylation catalyst and a solvent in a carbonylation reaction zone and producing a β-propiolactone outlet stream comprising β-propiolactone, solvent, ethylene oxide, carbon monoxide, carbonylation catalyst, acetaldehyde, and succinic anhydride;

passing at least a portion of the β-propiolactone outlet stream to a carbon monoxide separator and recovering
i.) the carbon monoxide separator overhead stream wherein the carbon monoxide separator overhead stream comprises ethylene oxide and carbon monoxide and ii.) a carbon monoxide separator bottoms stream comprising β-propiolactone, solvent, carbonylation catalyst, acetaldehyde, succinic anhydride, and ethylene oxide;

passing at least a portion of the carbon monoxide separator overhead stream to the carbonylation reaction zone;

passing at least a portion the carbon monoxide separator bottoms stream to a membrane separation section of a carbonylation catalyst recycling zone and separating said at least a portion of the carbon monoxide separator bottoms stream into i) a β-propiolactone recycle stream comprising a retentate containing separated carbonylation catalyst, solvent, and β-propiolactone, and ii) a β-propiolactone separation stream comprising a permeate containing β-propiolactone, solvent, acetaldehyde, succinic anhydride, ethylene oxide and carbonylation catalyst;

passing at least a portion of the β-propiolactone recycle stream to the carbonylation reaction zone;

passing at least a portion of the β-propiolactone separation stream to a β-propiolactone purification zone comprising at least one separation zone that separates the β-propiolactone separation stream into a solvent recycle stream comprising solvent, and a purified β-propiolactone stream comprising β-propiolactone and carbonylation catalyst;

passing at least a portion of the purified β-propiolactone stream and a polymerization initiator to a polypropiolactone reaction zone having at least one polymerization reactor that contacts the at least a portion of the purified β-propiolactone stream with the polymerization initiator and produces a polypropiolactone outlet stream comprising polypropiolactone and β-propiolactone;

passing at least a portion of the polypropiolactone outlet stream to a polypropiolactone/β-propiolactone processing zone having at least one separation zone to produce i) a polypropiolactone/β-propiolactone overhead stream that increases the concentration of β-propiolactone relative to the polypropiolactone outlet stream, and ii) a polypropiolactone/β-propiolactone separator bottoms stream that comprises polypropiolactone;

passing at least a portion of the polypropiolactone/β-propiolactone overhead stream to the polypropiolactone reaction zone;

passing at least a portion of the polypropiolactone/β-propiolactone bottoms stream to an acrylic acid production zone comprising a thermolysis reactor that receives the at least a portion of the a polypropiolactone outlet stream and produces an acrylic acid stream; and separating at least a portion of the acrylic acid stream in a separator into (i) acrylic acid stream comprising acrylic acid having a purity of at least 90%, and (ii) an organic heavies stream.

24. The process of claim 23, wherein the acrylic acid stream has an acrylic acid purity of greater than 99.5% and comprises glacial acrylic acid.

25. The process of claim 23, wherein the at least one polymerization reactor produces polypropiolactone at a polypropiolactone conversion of at least 50%.

26. The process of claim 23, wherein the at least one separation zone in the polypropiolactone/β-propiolactone processing zone comprises at least one flash tank, or at least one evaporator, or a combination thereof.

27. The process of claim 26, wherein the at least one evaporator is at least one wiped film evaporator, thin film evaporator, or falling film evaporator.

28. The process of claim 23, wherein the carbonylation reactor zone operates at a temperature between 30° C. and 160° C., and a pressure between 100 psig and 5000 psig.

29. The process of claim 23, wherein the carbon monoxide separator is a flash tank.

30. The process of claim 23, wherein the membrane separation section comprises at least one membrane selected from the group consisting of ceramic membranes and polymeric membranes, wherein the at least one membrane has a rejection rate of greater than 95% or a permeability of greater than 1.0 1.0 L m–2 hr–1 bar–1.

31. The process of claim 23, wherein the at least one separation zone comprises a distillation column that operates at or below atmospheric pressure and at a temperature of less than 120° C.

32. The process of claim 23, wherein the solvent recycle stream comprises solvent, and the solvent recycle stream has less than 15 wt % of β-propiolactone, ethylene oxide, carbon monoxide, acetaldehyde, or succinic anhydride.

33. The process of claim 23, wherein the purified βpropiolactone stream comprises (i) β-propiolactone and (ii) less than 1 wt % of solvent, ethylene oxide, carbon monoxide, acetaldehyde, or succinic anhydride.

34. A process for producing glacial acrylic acid from ethylene oxide and carbon monoxide, comprising:

contacting carbon monoxide feed, an ethylene oxide feed, a carbon monoxide overhead stream and a β-propiolactone recycle stream with a carbonylation catalyst and a solvent in a carbonylation reaction zone and producing a β-propiolactone outlet stream comprising β-propiolactone, solvent, ethylene oxide, carbon monoxide, carbonylation catalyst, acetaldehyde, and succinic anhydride;

passing at least a portion of the β-propiolactone outlet stream to a carbon monoxide separator and recovering i.) the carbon monoxide overhead stream wherein the carbon monoxide overhead stream comprises ethylene oxide and carbon monoxide and ii.) a carbon monoxide bottoms stream comprising β-propiolactone, solvent, carbonylation catalyst, acetaldehyde, succinic anhydride, ethylene oxide and carbon monoxide;

passing at least a portion of the carbon monoxide overhead stream to the carbonylation reaction zone;

passing at least a portion the carbon monoxide bottoms stream to a membrane separation section of a carbonylation catalyst recycling zone and separating said at least a portion of the carbon monoxide bottoms stream into i) a β-propiolactone recycle stream comprising a retentate containing separated carbonylation catalyst, solvent and β-propiolactone and ii) a β-propiolactone separation stream comprising a permeate containing β-propiolactone, solvent, acetaldehyde, succinic anhydride, ethylene oxide, carbon monoxide, and carbonylation catalyst;

passing at least a portion of the β-propiolactone recycle stream to the carbonylation reaction zone;

purifying the β-propiolactone separation stream in a β-propiolactone purification zone comprising at least one distillation column that further separates the β-propiolactone separation stream into a solvent recycle stream comprising solvent and a purified β-propiolactone stream comprising β-propiolactone;

passing at least a portion of the purified β-propiolactone stream and a polymerization initiator to a polypropiolactone reaction zone having at least one polymerization reactor that contacts the at least a portion of the purified β-propiolactone stream with the polymerization initiator and produces a polypropiolactone outlet stream comprising polypropiolactone and β-propiolactone;

passing at least a portion of the polypropiolactone outlet stream to an acrylic acid production zone comprising a thermolysis reactor that receives the at least a portion of the polypropiolactone outlet stream and produces an acrylic acid stream; and separating at least a portion of the acrylic acid stream in a condenser into (i) an acrylic acid stream comprises acrylic acid having a purity of at least 90%, and (ii) an organic heavies stream.

35. The process of claim 34, wherein the acrylic acid stream has an acrylic acid purity of greater than 99.5%, and wherein the acrylic acid stream comprises glacial acrylic acid.

36. The process of claim 34, wherein the at least a portion of the polypropiolactone outlet stream that passes to the acrylic acid production zone first passes to a polypropiolactone purification zone, wherein the polypropiolactone purification zone comprises a polypropiolactone ion exchange zone comprising a resin column that a.) purifies the at least a portion of the polypropiolactone outlet stream that passes to the acrylic acid production zone so that the polypropiolactone outlet stream comprises at least 90 wt % of polypropiolactone, and b.) removes an ionic species stream comprising cationic carbonylation catalyst species and anionic carbonylation catalyst species.

37. The process of claim 34, wherein at least a portion of the polypropiolactone outlet stream that passes to the acrylic acid production zone from the polypropiolactone purification zone first passes to a polypropiolactone processing zone before passing to the acrylic acid production zone, and the polypropiolactone processing zone converts the at least a portion of the polypropiolactone outlet stream that passes to the acrylic acid production zone to solid form.

38. The process of claim 34, wherein:
a.) at least a portion of the polypropiolactone outlet stream that passes to the acrylic acid production zone passes from the polypropiolactone purification zone to a polypropiolactone/β-propiolactone processing zone before passing to the acrylic acid production zone and the a polypropiolactone/β-propiolactone processing zone has at least one separation zone to produce i.) an overhead stream that increases the concentration of β-propiolactone in the at least a portion of the polypropiolactone outlet stream that passes to the acrylic acid production zone and ii.) a polypropiolactone/β-propiolactone bottoms stream that comprises polypropiolactone; and
b.) a condensate ion exchange zone comprising a resin column receives at least a portion of the organic heavies and separates the organic heavies into a heavies output stream and an ionic species stream comprising cationic carbonylation catalyst species and anionic carbonylation catalyst species.

39. The process of claim 1, wherein the at least one polymerization reactor is at least one plug-flow reactor.

40. The process of claim 1, wherein the at least one polymerization reactor is at least one continuous-flow stirred-tank reactor.

41. The process of claim 1, wherein the at least one polymerization reactor is at least one loop reactor.

42. The process of claim 5, wherein the first polymerization reactor is at least one continuous-flow stirred-tank reactor or loop reactor, and the second polymerization reactor is at least one plug-flow reactor.

43. The process of claim 8, wherein the thermolysis reactor is the fluidized bed reactor for receiving molten polypropiolactone.

44. The process of claim 8, wherein the thermolysis reactor is the moving bed reactor.

45. The process of claim 1, wherein the at least one polymerization reactor is at least one of a continuous-flow stirred-tank reactor, a loop reactor, or a plug-flow reactor.

46. The process of claim 1, wherein the polymerization initiator is selected from the group consisting of ammonium acrylate, ammonium acetate, phosphonium acrylate, sodium acrylate, potassium acrylate, phosphonium acetate, tetra-n-butylammonium acrylate, sodium acetate, potassium acetate, tetra-n-butylammonium acetate, trimethylphenylammonium acrylate, trimethylphenylammonium acetate, and tetraphenyl phosphonium acrylate.

47. The process of claim 10, wherein the carbonylation catalyst is a carbonyl cobaltate in combination with an aluminum porphyrin compound, a carbonyl cobaltate in combination with an aluminum salen compound, a carbonyl cobaltate in combination with an aluminum salophen compound, or Al(TPP)Co(CO)4, or any combination thereof.

48. The process of claim 10, wherein the carbonylation catalyst is at least partially dissolved in a catalyst solvent, and the catalyst solvent comprises tetrahydrofuran, hexane, 2,5-dimethyl tetrahydrofuran, sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, propyl acetate, butyl acetate, 2-butanone, cyclohexanone, toluene, difluorobenzene, dimethoxy ethane, acetone, or methylethyl ketone, or any combination thereof.

49. The process of claim 10, wherein the carbonylation reaction zone contains at least one reactor selected from the group consisting of a continuous-flow stirred-tank reactor, and a loop reactor.

* * * * *

UNITED STATES PATENT AND TRADEMARK OFFICE
CERTIFICATE OF CORRECTION

PATENT NO. : 10,703,702 B2
APPLICATION NO. : 15/223178
DATED : July 7, 2020
INVENTOR(S) : Sadesh H. Sookraj and Jay J. Farmer Page 1 of 1

It is certified that error appears in the above-identified patent and that said Letters Patent is hereby corrected as shown below:

On the Title Page

Item (71) Applicant name should be —Novomer, Inc., Rochester, NY (US)—

In the Claims

Column 140, Claim 34, Line 47, "comprises" should be —comprising—

Signed and Sealed this
Twenty-seventh Day of October, 2020

Andrei Iancu
*Director of the United States Patent and Trademark Office*